United States Patent
Fan et al.

(10) Patent No.: US 12,162,878 B2
(45) Date of Patent: Dec. 10, 2024

(54) BRD4 INHIBITOR AS WELL AS A PREPARATIVE METHOD AND USE THEREOF

(71) Applicant: HINOVA PHARMACEUTICALS INC., Sichuan (CN)

(72) Inventors: Lei Fan, Sichuan (CN); Fei Wang, Sichuan (CN); Xiaoquan Wu, Sichuan (CN); Kexin Xu, Sichuan (CN); Ke Chen, Sichuan (CN); Tongchuan Luo, Sichuan (CN); Shaohua Zhang, Sichuan (CN); Yongxu Huo, Sichuan (CN); Zhilin Tu, Sichuan (CN); Xinghai Li, Sichuan (CN); Yuanwei Chen, Sichuan (CN)

(73) Assignee: HINOVA PHARMACEUTICALS INC., Sichuan (CN)

( * ) Notice: Subject to any disclaimer, the term of this patent is extended or adjusted under 35 U.S.C. 154(b) by 869 days.

(21) Appl. No.: 17/160,302

(22) Filed: Jan. 27, 2021

(65) Prior Publication Data

US 2021/0147419 A1    May 20, 2021

Related U.S. Application Data

(63) Continuation-in-part of application No. PCT/CN2019/097776, filed on Jul. 25, 2019.

(30) Foreign Application Priority Data

Jul. 27, 2018    (CN) ......................... 201810847583.X

(51) Int. Cl.
    C07D 471/04    (2006.01)
    A61K 45/06    (2006.01)
    C07D 519/00    (2006.01)

(52) U.S. Cl.
    CPC ............ *C07D 471/04* (2013.01); *A61K 45/06* (2013.01); *C07D 519/00* (2013.01)

(58) Field of Classification Search
    CPC ........................... C07D 471/04; C07D 519/00
    See application file for complete search history.

(56) References Cited

FOREIGN PATENT DOCUMENTS

| | | |
|---|---|---|
| CN | 104136435 A | 11/2014 |
| CN | 105518007 A | 4/2016 |
| CN | 106414442 A | 2/2017 |
| CN | 106986872 A | 7/2017 |
| CN | 107207493 A | 9/2017 |
| WO | 2015081203 A1 | 6/2015 |
| WO | 2018130174 A1 | 7/2018 |

OTHER PUBLICATIONS

Wang, et al. WO 2013098052 A1 (abstract) Jul. 4, 2013; retrieved from STN; Accession No. 2013:1041440.*

* cited by examiner

*Primary Examiner* — Shawquia Jackson
(74) *Attorney, Agent, or Firm* — NKL Law; Allen Xue

(57) ABSTRACT

The compound of formula (I) has a good inhibitory effect on the proliferation of human prostate cancer cells CWR22RV1 and breast cancer cells; and combined use of the compound with an androgen receptor inhibitor HC-1119 significantly enhances the inhibitory effect on prostate cancer cells, and the inhibitory effect increases with increased concentration. The compound of formula (I) can not only be used independently to prepare an antineoplastic agent but can also be used in combination with other agents having antineoplastic effects, such as an androgen receptor inhibitor, or other targeting drugs etc., to prepare an antineoplastic agent having stronger therapeutic effects, especially an agent for treating prostate cancer and breast cancer.

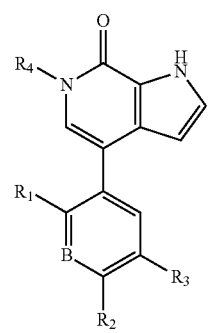

(I)

20 Claims, No Drawings

BRD4 INHIBITOR AS WELL AS A PREPARATIVE METHOD AND USE THEREOF

TECHNICAL FIELD

The present invention belongs to the field of medicinal chemistry, and specifically relates to a BRD4 inhibitor as well as a preparative method and use thereof.

BACKGROUND ART

BRD4 protein in the bromodomain of BET family contains acetylated lysine residues that can bind to histones and other proteins, and plays a key role in regulating gene transcription and controlling cell growth. BRD4 protein is associated with large protein complexes that regulate the transcription of many genes, including mediators, PAFc and super-elongation complexes. The researches by Jang et al. show that the kinase activity of BRD4 can directly phosphorylate and activate RNA polymerase II, and thus regulate gene transcription and expression (Mol. Cell, 2005, 19, 523-534). Devaiah et al. (Rroc. Nat. Acad. Sci., USA 2012, 109, 6927-6932) have reported that the progression of cells lacking BRD4 is shown to be affected when passing the cell cycle.

Researches have shown that many human diseases are closely related to BRD4 protein, such as tumors, autoimmune or inflammatory diseases, and viral infections. Among them, tumors related to BRD4 protein include breast cancer, brain cancer, cervical cancer, colorectal cancer, gastrointestinal cancer, esophageal cancer, liver cancer, lung cancer, pancreatic cancer, endometrial cancer, nasopharyngeal cancer, ovarian cancer, prostate cancer, and hematopoietic system tumors. For hematopoietic tumors, researches have shown that in the models of lymphoma, multiple myeloma, and B-cell polar lymphatic leukemia, the expression of MYC can be inhibited by interfering with the binding of BRD4 to the oncogene MYC.

BRD4 inhibitors, targetting BRD4 and having an inhibitory action on it, have a great value in anti-cancer, anti-inflammatory, and other fields, and have attracted great attention from major pharmaceutical companies and scientific research institutions. For example, in 2013, Dr. Hernando discovered that BRD4 is overexpressed in melanoma cells and maintains the proliferation of tumor cells. The inhibition on the expression of BRD4 will obviously slow down the growth of tumor cells. According to Chen Chong et al (The effect of BRD4 inhibitor GSK525762A on the proliferation and apoptosis of acute B lymphocytic leukemia cells and its possible mechanism, National Lymphatic Tumor Diagnosis and Treatment Progress Seminar, 2014), BRD4 inhibitors can inhibit the proliferation of acute B lymphocytic leukemia cells and promote its apoptosis. According to Ni Ping et al. (The inhibitory effect of BRD4 inhibitor JQ1 on the growth of non-small cell lung cancer, Journal of Nanjing Medical University (Natural Science Edition), issue 8, 2015), BRD4 inhibitors can inhibit the growth of non-small cell lung cancer. Currently, small molecule compounds that can block the specific binding of lysine acetylate and BRD4 have gradually become a research focus.

Therefore, developing new BRD4 inhibitors is of great significance for the treatment of various diseases or symptoms related to BET protein.

SUMMARY OF THE INVENTION

The object of the present invention is to provide a BRD4 inhibitor, as well as a preparative method and use thereof.

The present invention first provides a compound of formula (I), or a pharmaceutically acceptable salt, solvate or hydrate thereof:

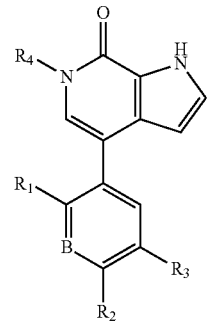

(I)

Wherein, $R_1$ and $R_2$ are each independently selected from H, halogen, $C_1$-$C_8$ alkyl, $C_1$-$C_8$ haloalkyl, $C_1$-$C_8$ alkoxy, substituted aryl, substituted heteroaryl,

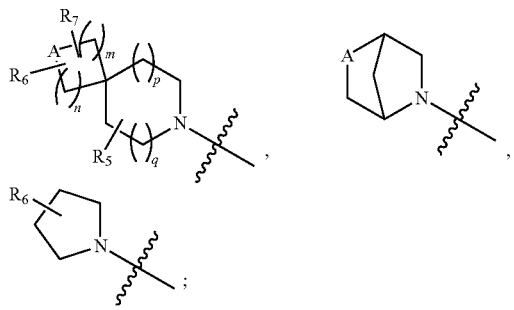

$R_3$ is selected from the group consisting of —$NHSO_2R_8$, —$SO_2R_8$, —$SO_2NR_8R_9$, $C_1$-$C_8$ alkyl, carboxyl, —$CONHR_8$, —$COOR_8$, —$COR_8$, hydroxyl-substituted $C_1$-$C_8$ alkyl, —$NHCOR_8$, —$NHCONHR_8$, amino,

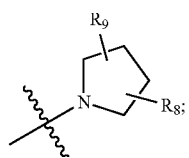

$R_4$ is selected from the group consisting of H, $C_1$-$C_8$ alkyl, $C_1$-$C_8$ haloalkyl, and $C_1$-$C_8$ deuterated alkyl;
A is selected from $CH_2$, NH, O, S, SO, $SO_2$;
B is selected from CH, N;
m, n, p, q=0, 1, 2;
$R_5$, $R_6$, $R_7$, $R_8$, and $R_9$ are each independently selected from the group consisting of H, halogen, hydroxyl, cyano, $CONH_2$, $C_1$-$C_8$ alkyl, $C_1$-$C_8$ alkoxy, $C_3$-$C_8$ cycloalkyl, $C_3$-$C_8$ heterocycloalkyl, hydroxyl or carboxyl-substituted $C_3$-$C_8$ heterocycloalkyl, —$COOR_{10}$, hydroxyl or carboxyl-substituted $C_1$-$C_8$ alkyl, $C_1$-$C_8$ haloalkyl, $C_1$-$C_8$ deuterated alkyl, aryl, heteroaryl;
$R_{10}$ is selected from H and $C_1$-$C_8$ alkyl.
Further, $R_4$ is selected from $C_1$-$C_8$ alkyl and $C_1$-$C_8$ deuterated alkyl.
Further, $R_4$ is selected from methyl and deuterated methyl.
Further, $R_{10}$ is selected from H and ethyl.

Further, said compound of formula (I) has a structure of formula (II):

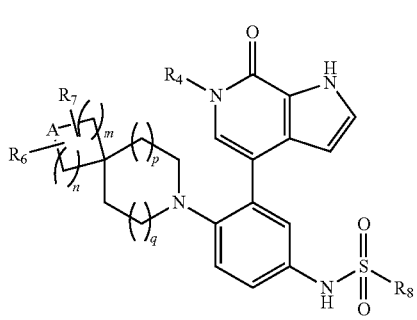

(II)

Wherein, $R_6$ and $R_7$ are each independently selected from the group consisting of H, halogen, $COOR_{10}$; $R_8$ is selected from $C_1$-$C_8$ alkyl, $C_3$-$C_8$ cycloalkyl, and $C_3$-$C_8$ heterocycloalkyl; $R_4$ is selected from methyl and deuterated methyl; A is selected from $CH_2$, O or S; m, n, p, q=0, 1, 2.

Further, said compound of formula (I) has a structure of formula (III)-1 or (III)-2:

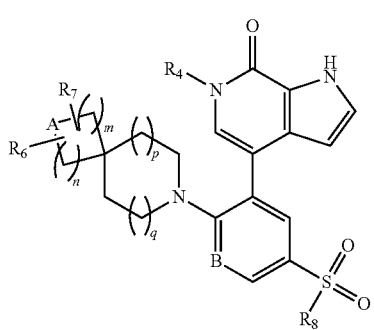

(III)-1

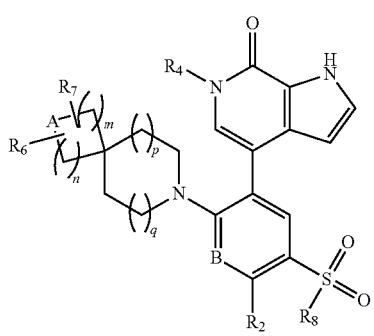

(III)-2

Wherein, B is CH or N; $R_6$ and $R_7$ are each independently selected from H, halogen, cyano, $COOR_{10}$, $CONH_2$, hydroxyl-substituted $C_1$-$C_8$ alkyl; $R_8$ is selected from $C_1$-$C_8$ alkyl, hydroxyl or carboxyl-substituted $C_1$-$C_8$ alkyl, $C_3$-$C_8$ cycloalkyl, $C_3$-$C_8$ heterocycloalkyl, and hydroxyl or carboxyl-substituted $C_3$-$C_8$ heterocycloalkyl; $R_4$ is selected from methyl and deuterated methyl; A is selected from $CH_2$, O or S; m, n, p, q=0, 1, 2; $R_2$ is halogen.

Further, said compound of formula (I) has a structure of formula (IV):

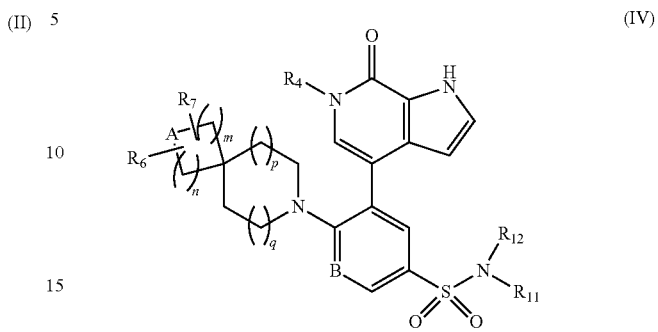

(IV)

Wherein, B is C or N; $R_6$ and $R_7$ are each independently selected from H, halogen;

$R_{12}$ and $R_{11}$ are each independently selected from H, $C_1$-$C_8$ alkyl, hydroxyl or carboxyl-substituted $C_1$-$C_8$ alkyl, $C_1$-$C_8$ deuterated alkyl; or $R_{12}$ and $R_{11}$ are linked to form a five-membered ring; $R_4$ is selected from methyl and deuterated methyl; A is selected from $CH_2$, O or S; m, n, p, q=0, 1, 2.

Further, said compound of formula (I) has a structure of formula (V):

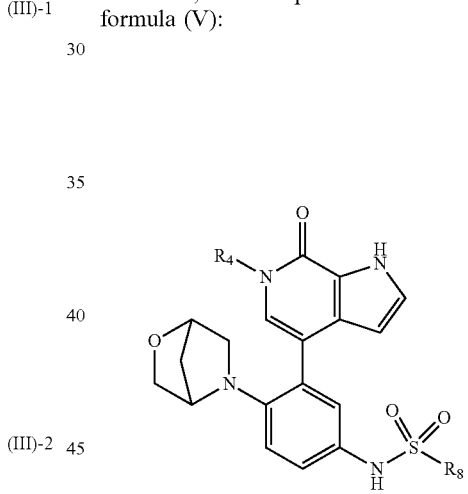

(V)

Wherein, $R_8$ is selected from $C_1$-$C_8$ alkyl; $R_4$ is selected from methyl and deuterated methyl.

Further, said compound of formula (I) is one of the following compounds:

7

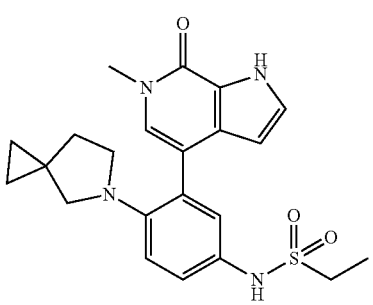

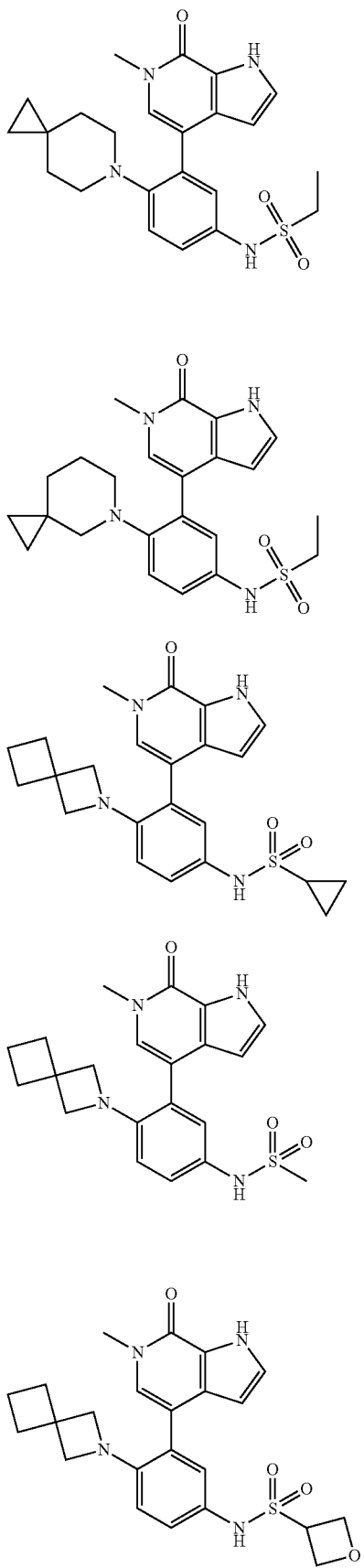
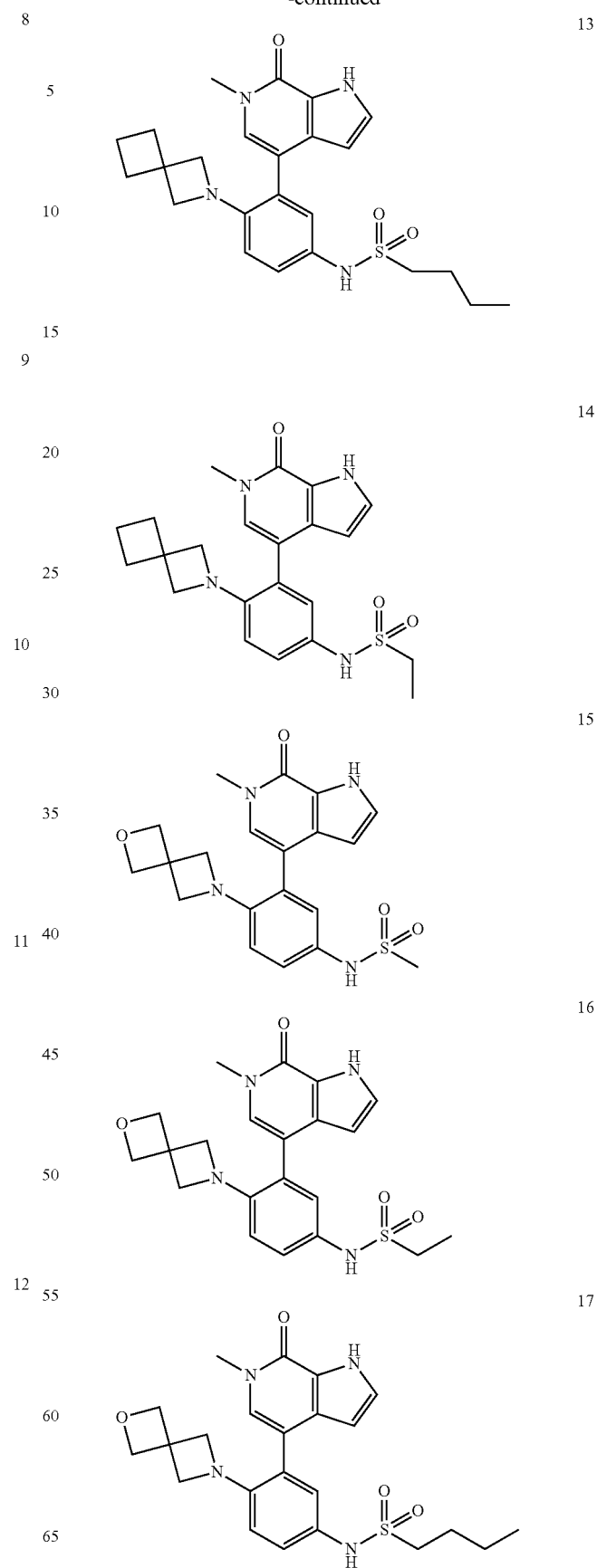

-continued
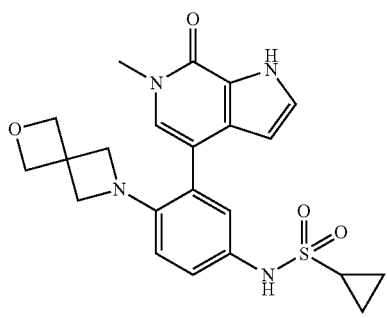
18
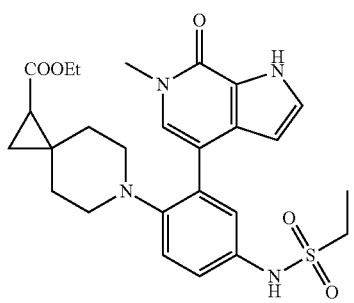
19
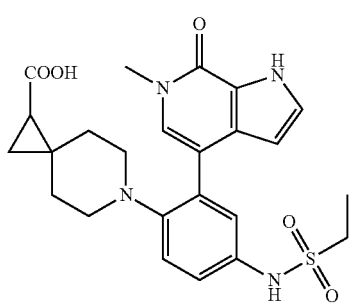
-continued
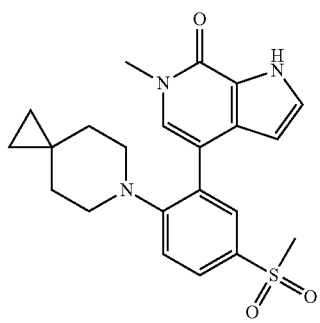
26
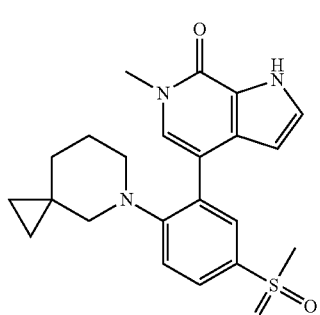
27
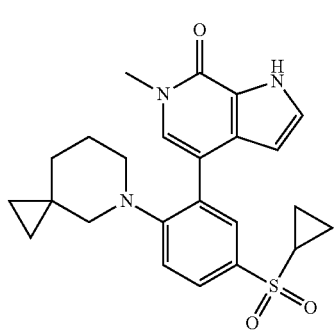
28
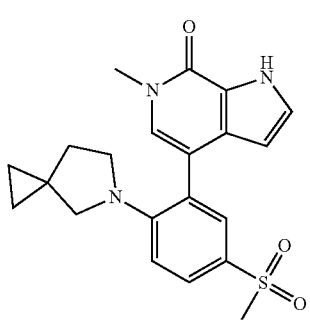
24
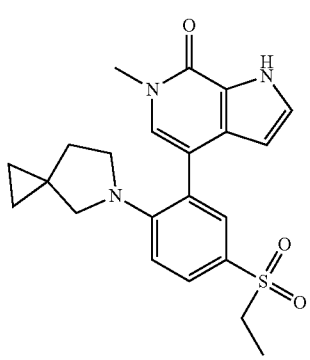
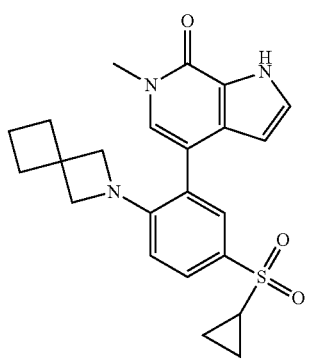
29
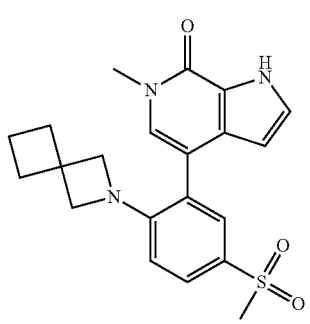
30

31
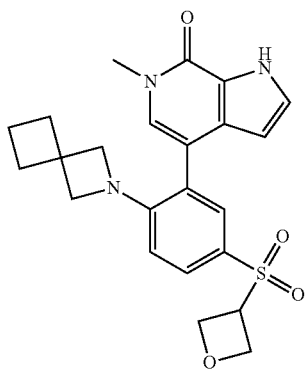
32
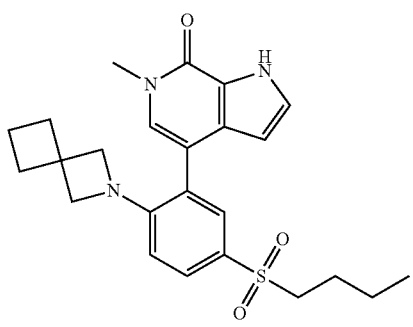
33
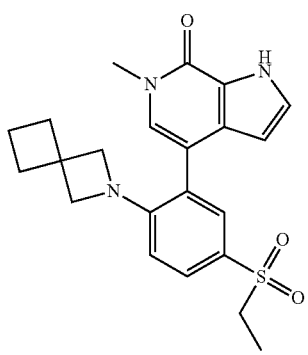
34
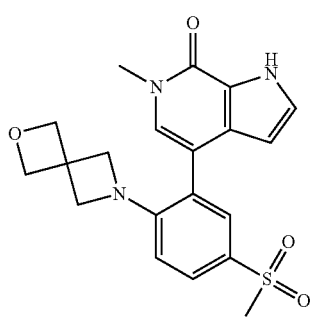
35
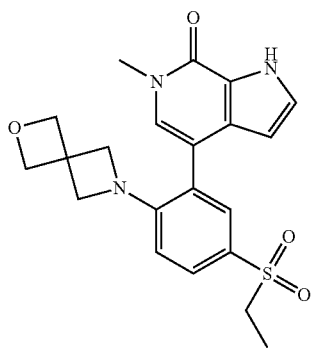
36
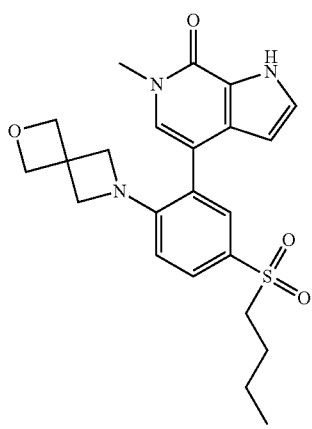
37
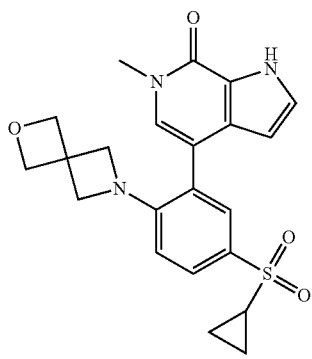
38
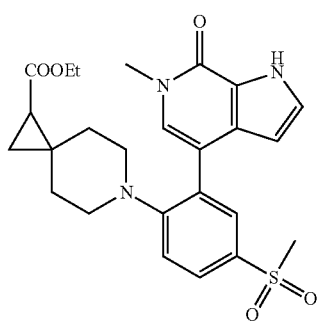

39
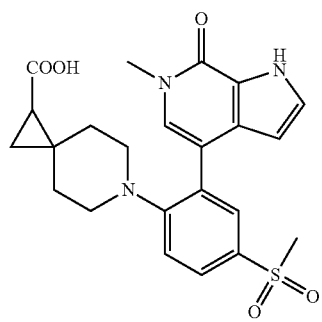
40
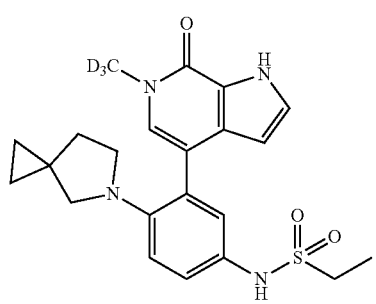
41
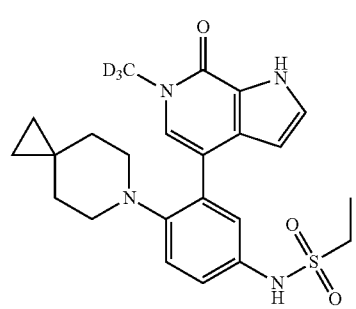
42
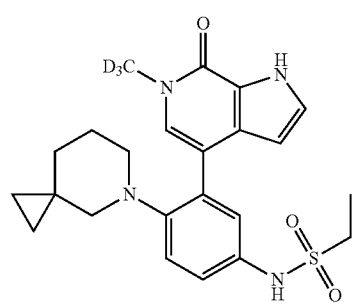
43
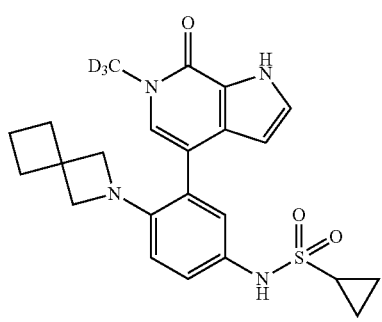
44
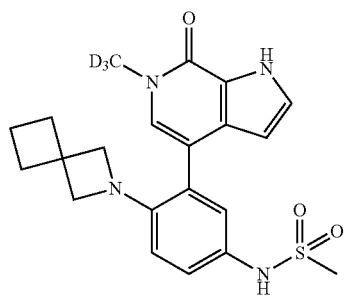
45
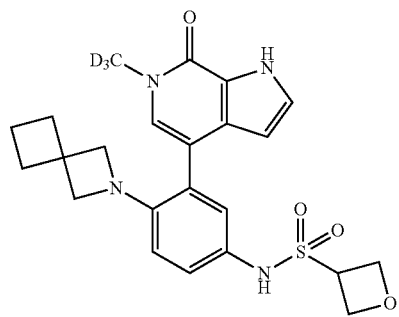
46
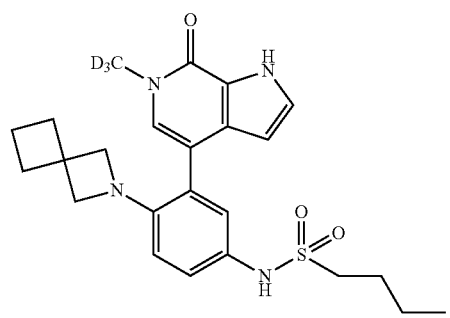
47
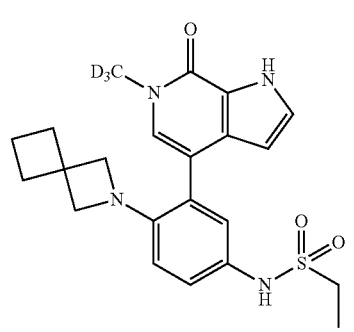
48
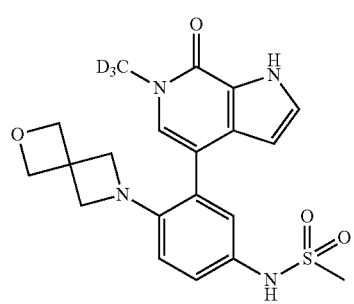

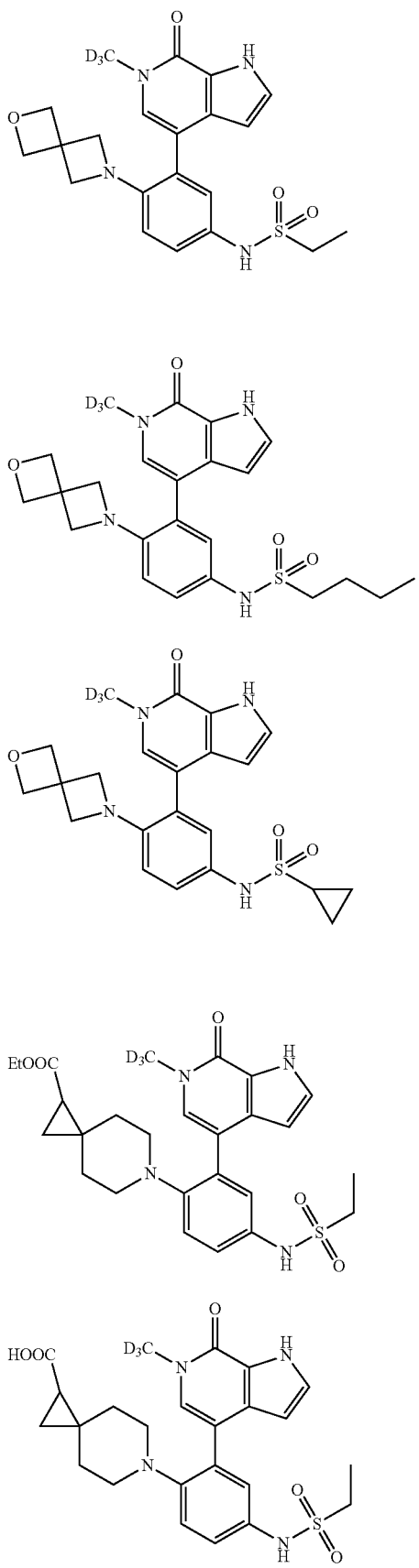

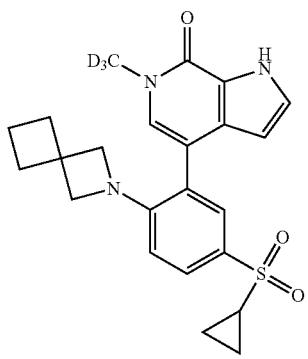
59
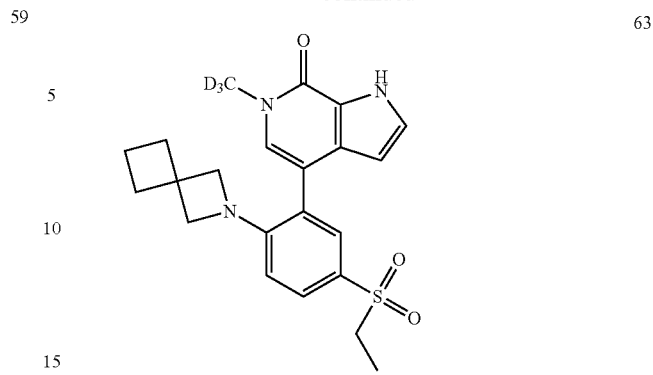
63
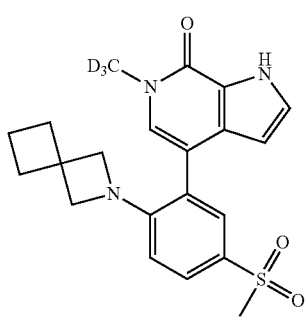
60
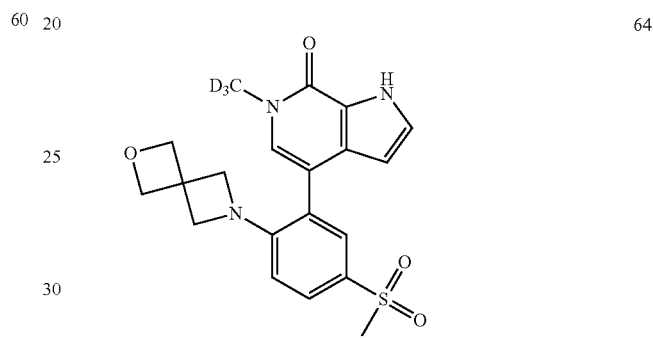
64
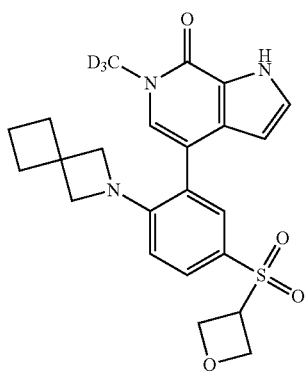
61
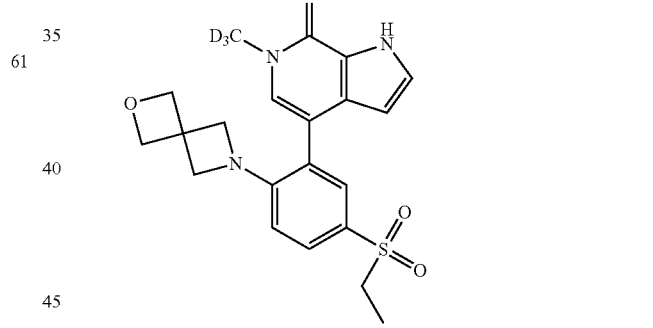
65
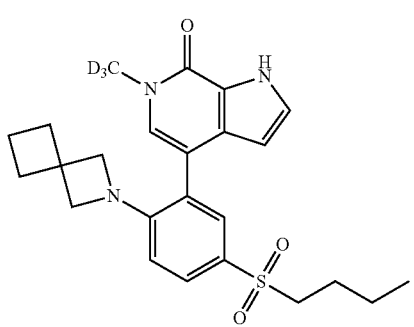
62
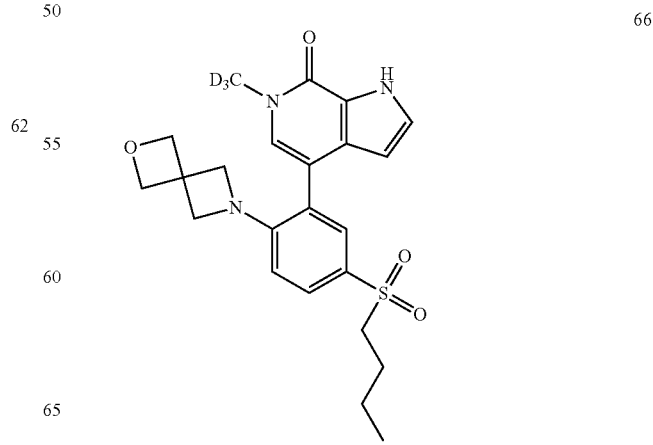
66

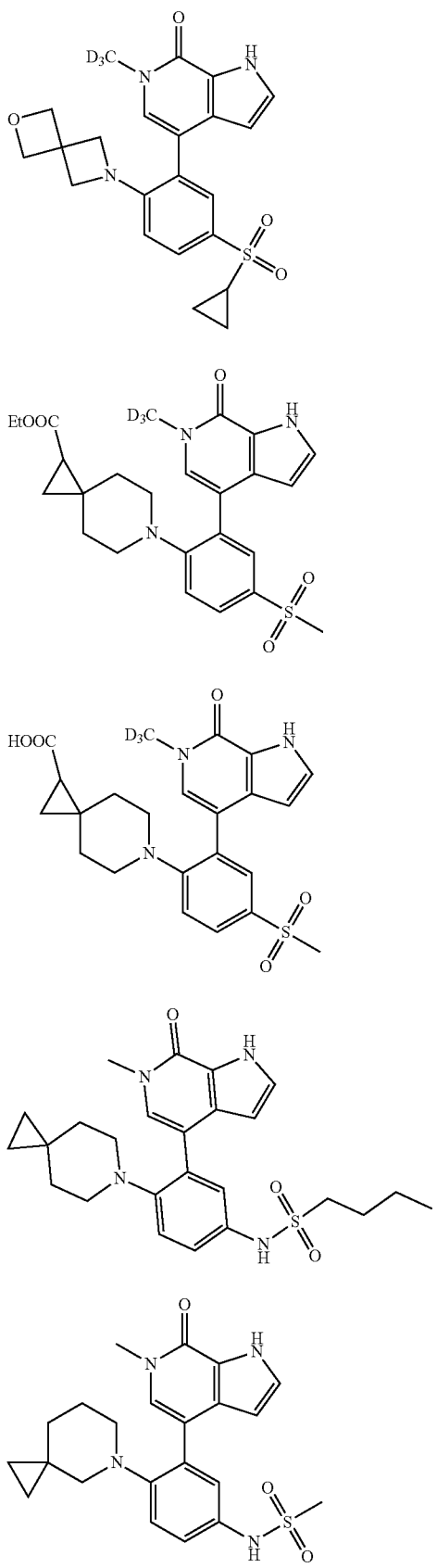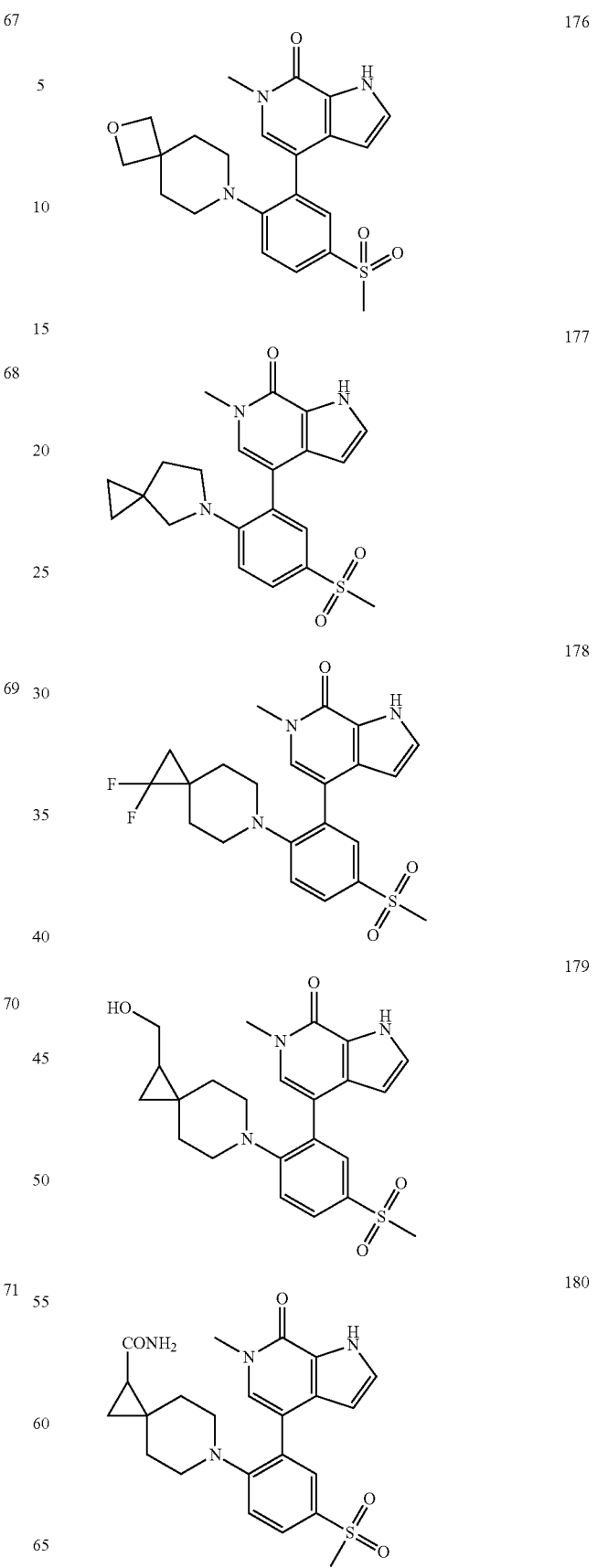

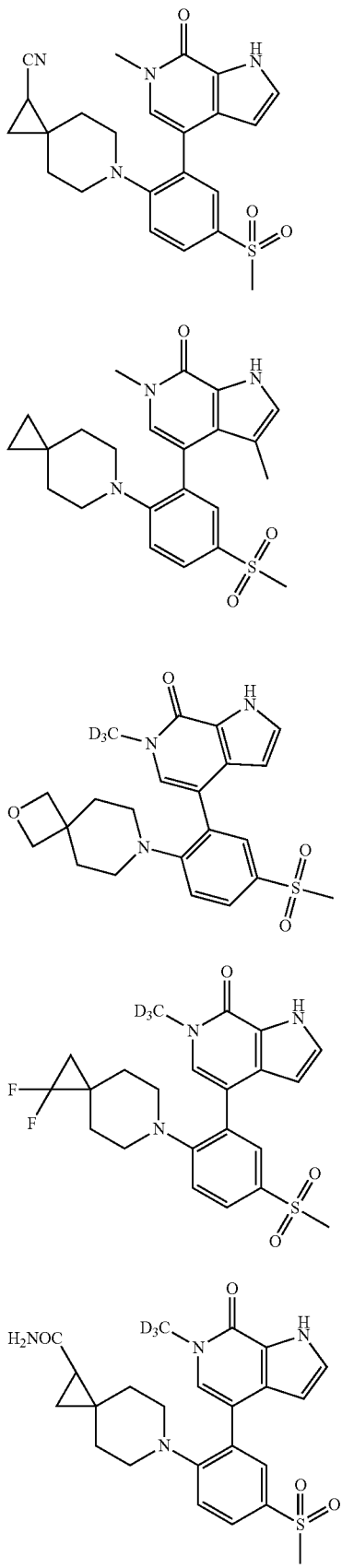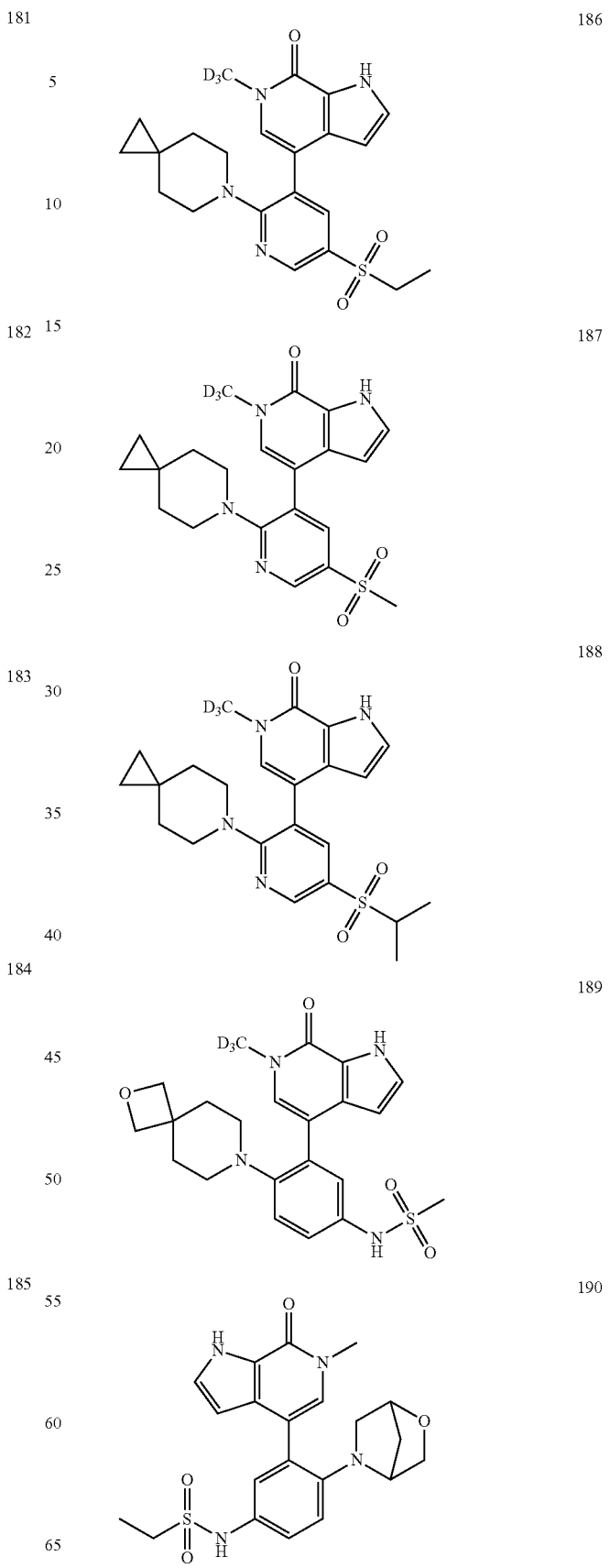

191 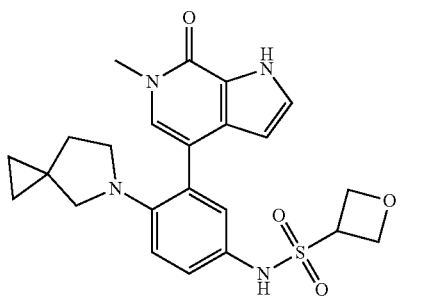
192 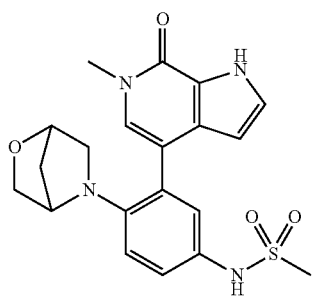
193 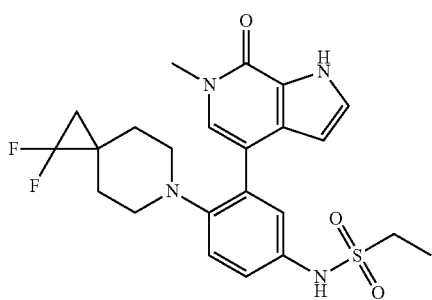
194 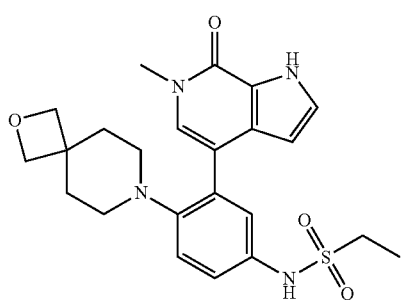
195 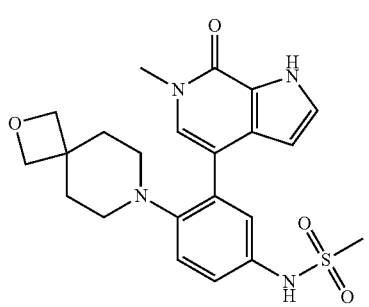
196 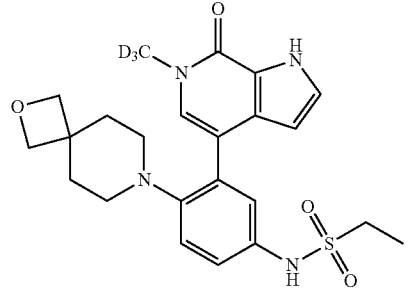
197 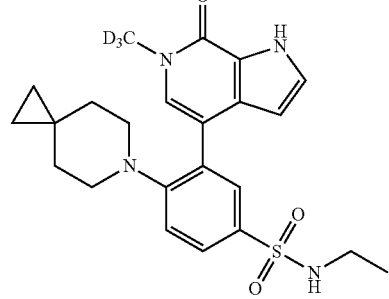
198 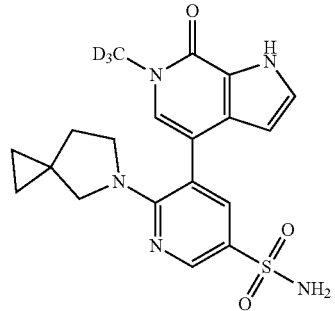
199 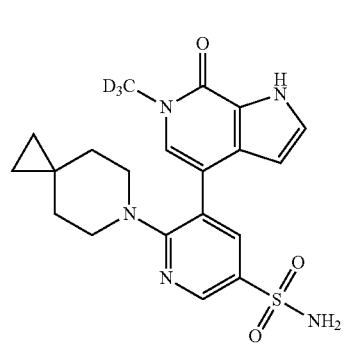
200 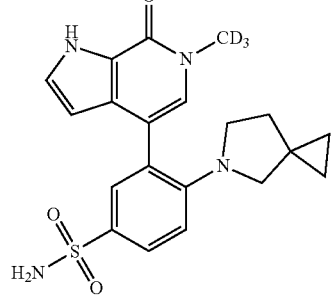

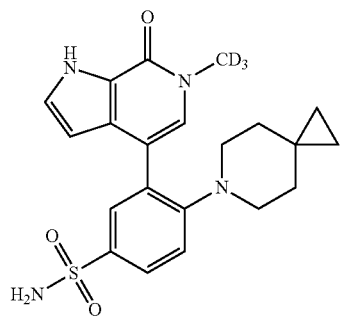
201
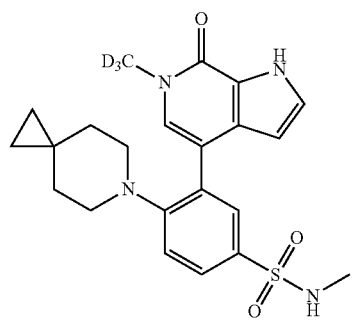
202
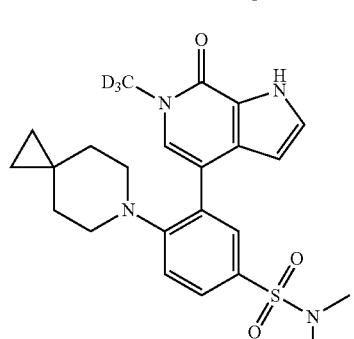
203
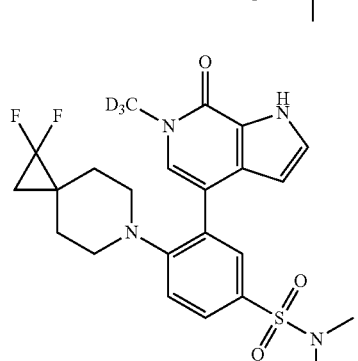
204
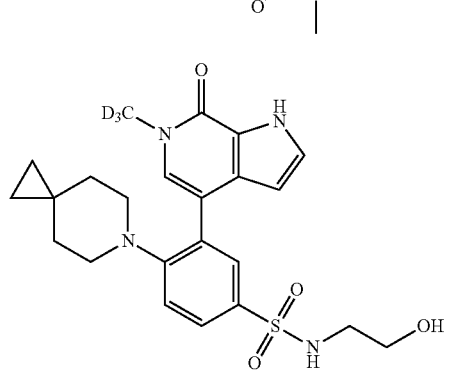
205
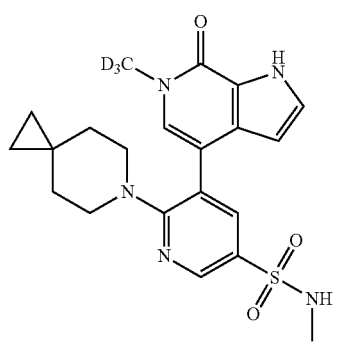
206
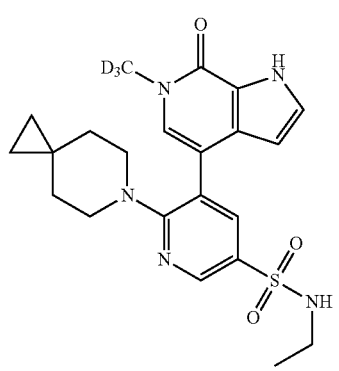
207
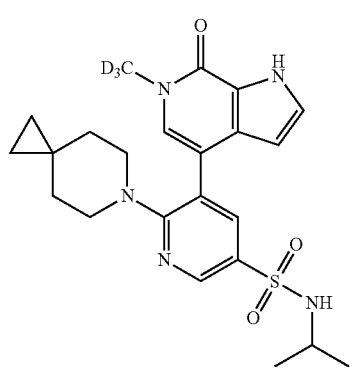
208
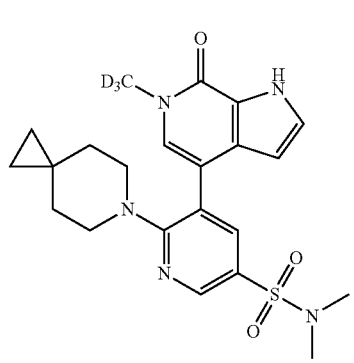
209

210 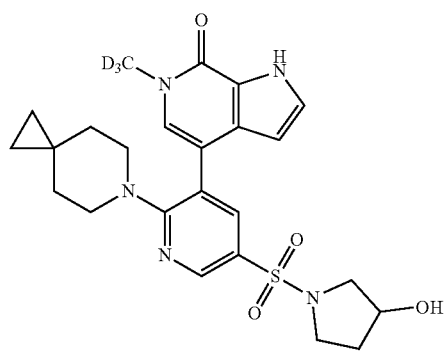
211 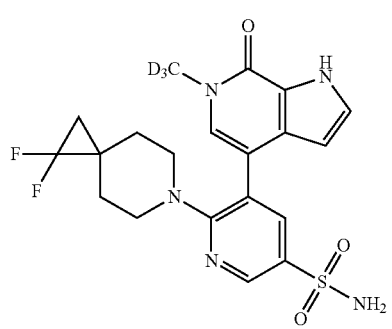
212 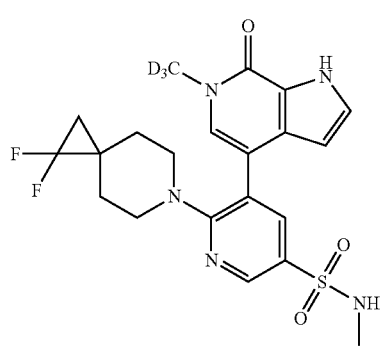
213 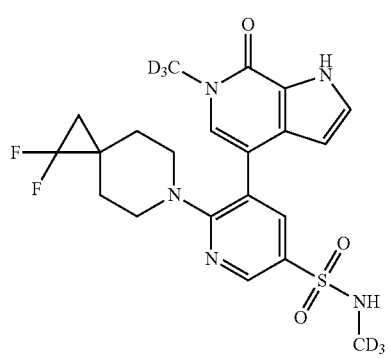
214 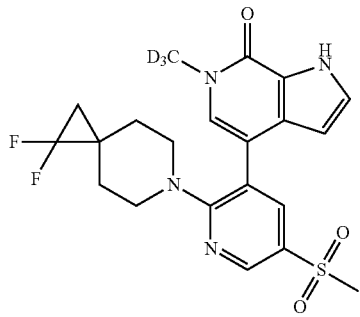
215 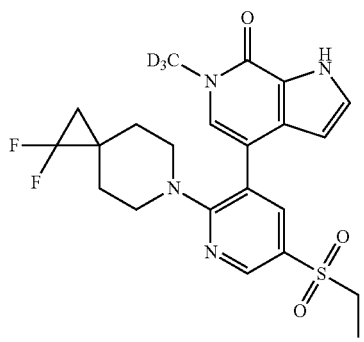
216 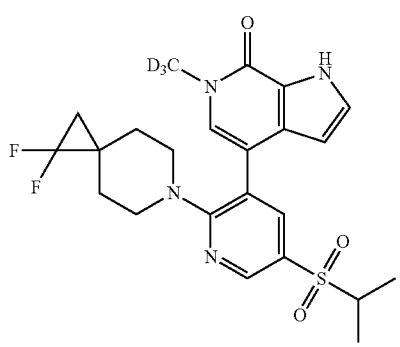
217 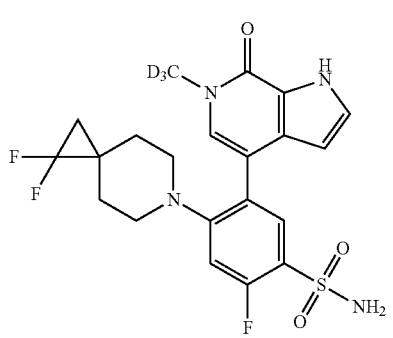

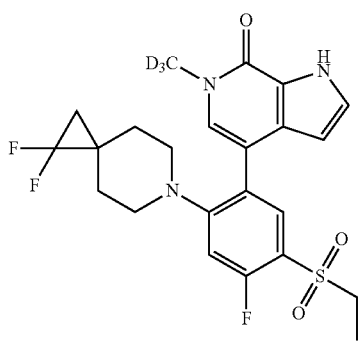
218
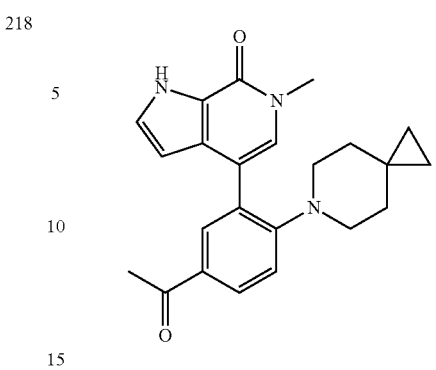
223
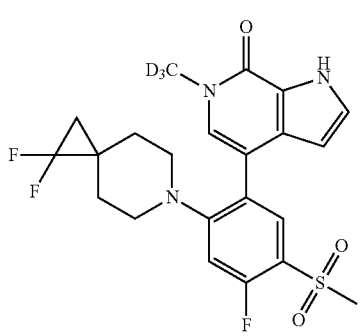
219
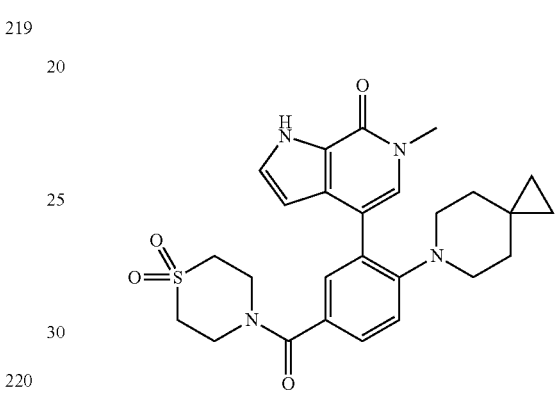
224
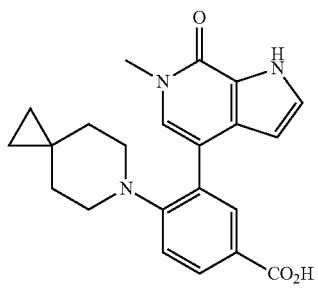
220
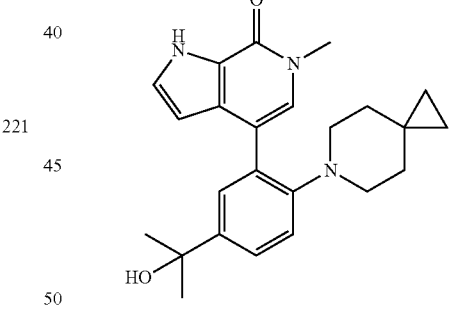
225
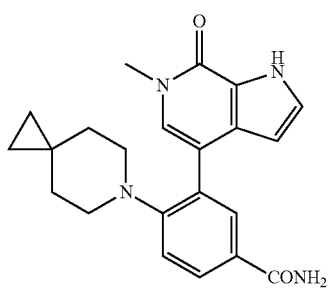
221
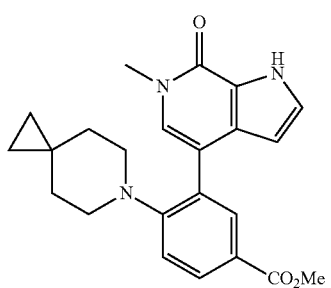
222
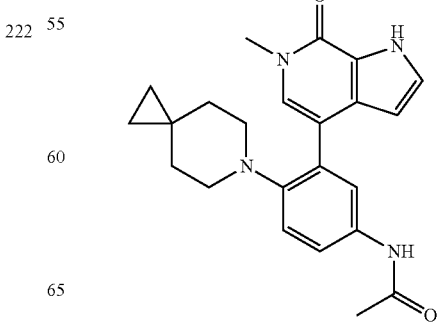
226

227 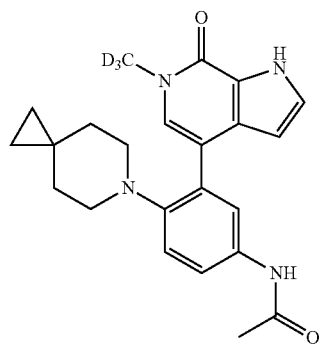
228 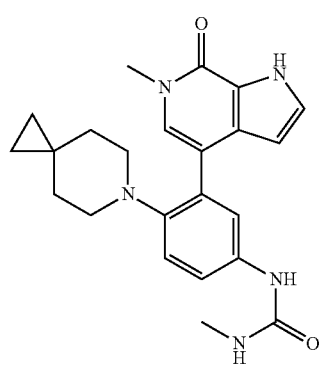
229 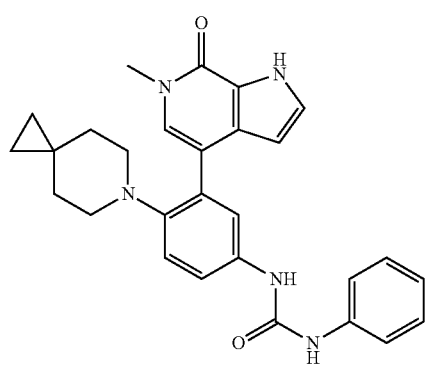
230 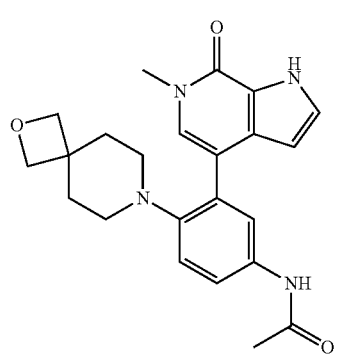
231 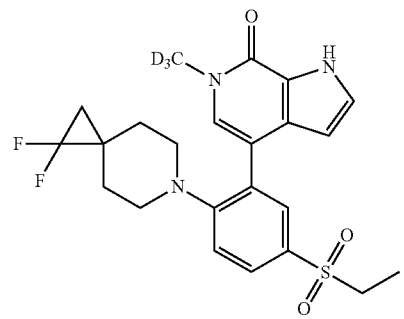
232 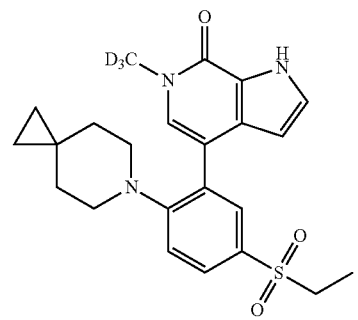
233 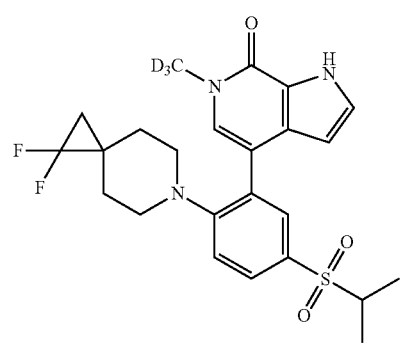
234 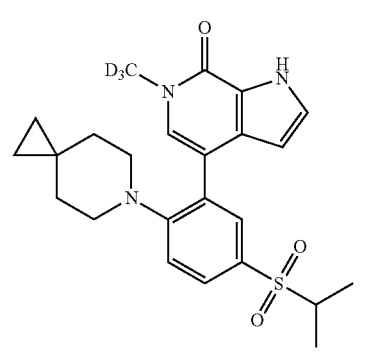
235 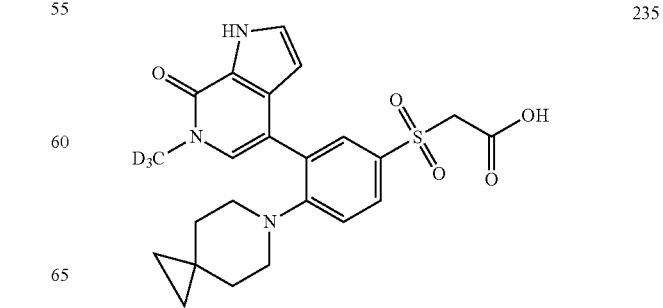

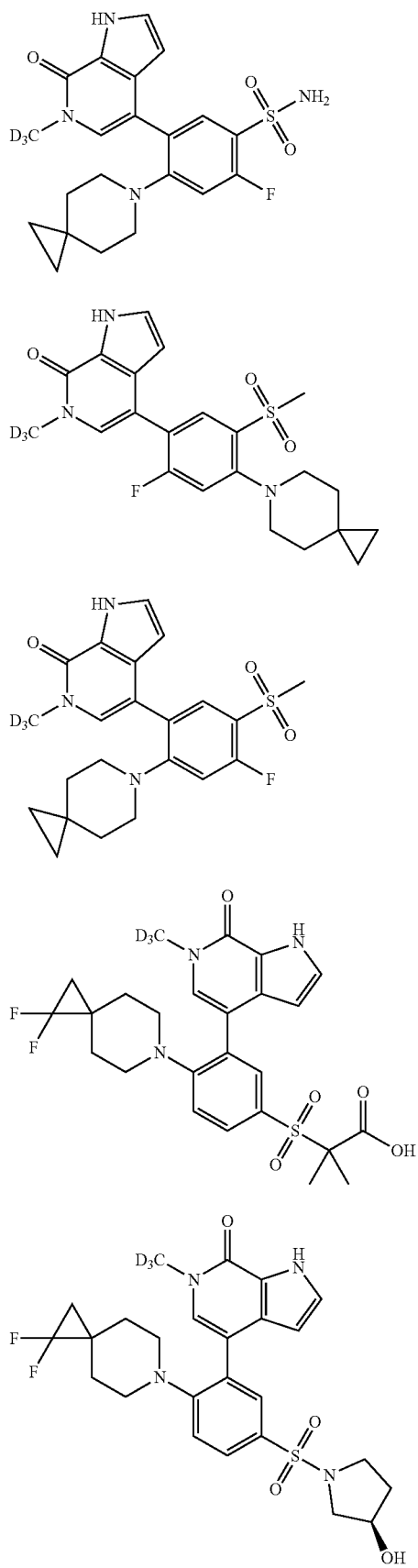
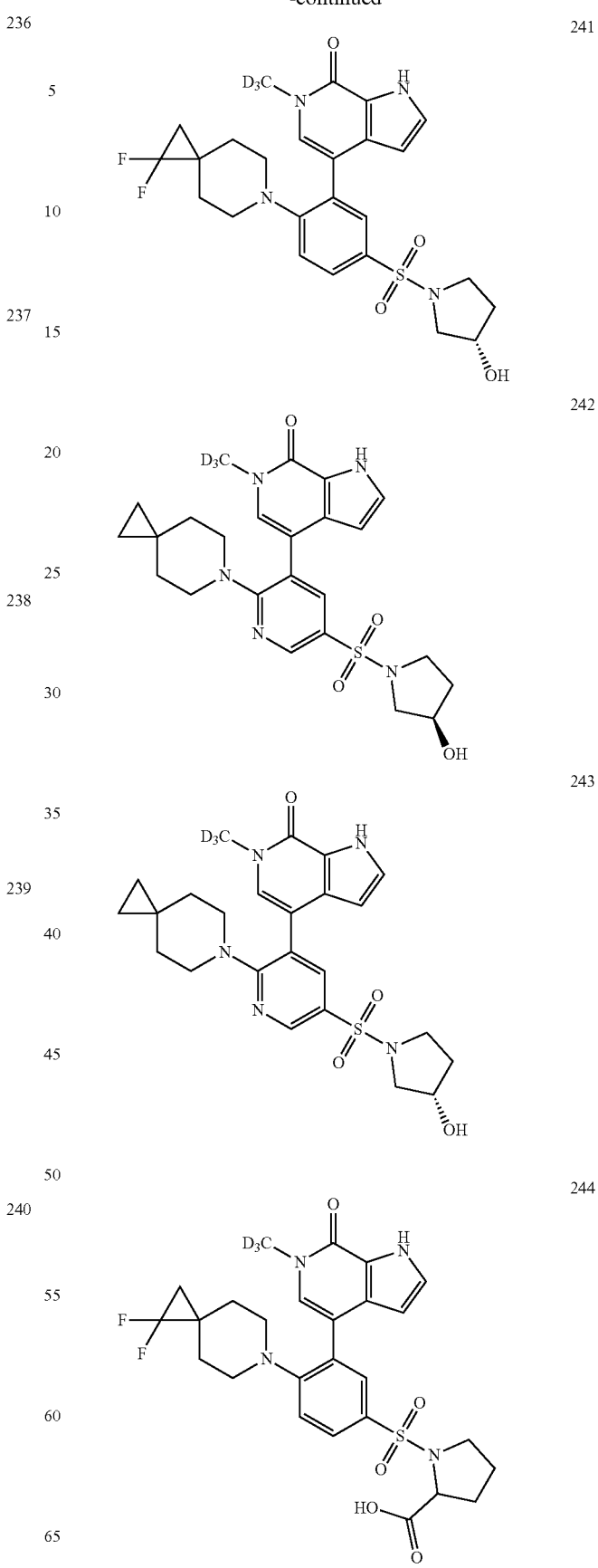

245 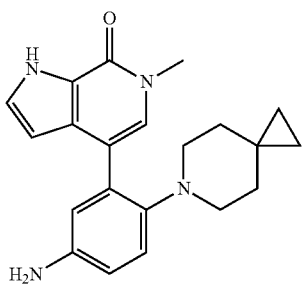
246 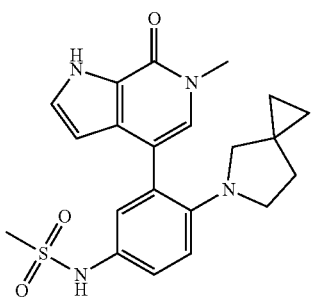
247 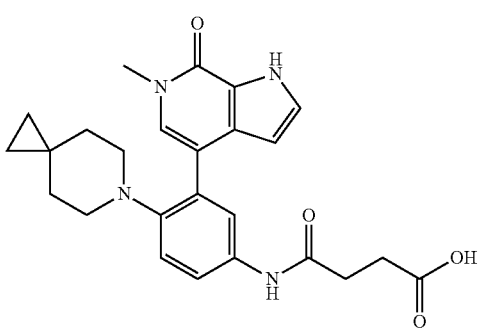
248 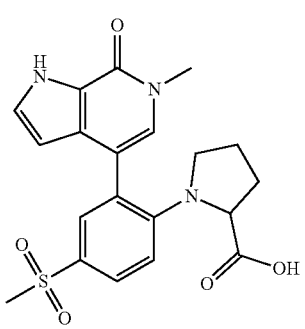
249 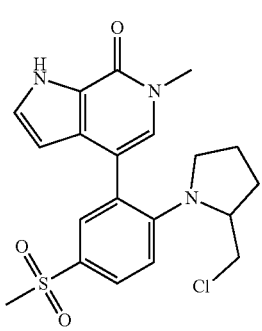
250 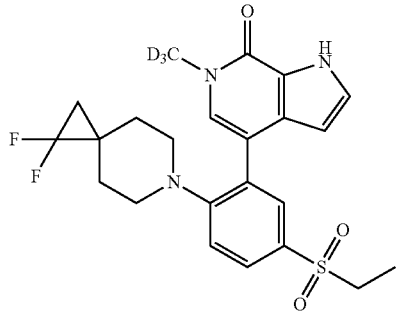
251 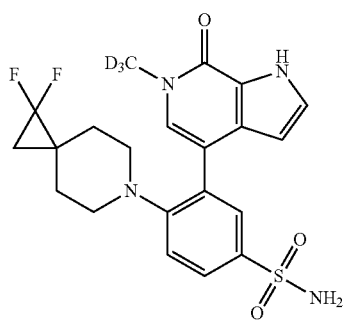
252 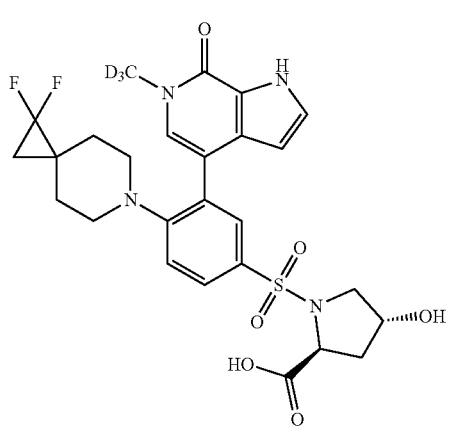
253 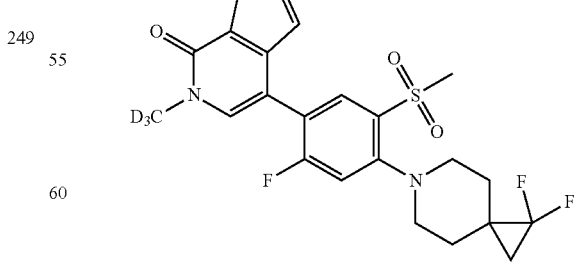
The present invention further provides a method for preparation of the compound mentioned above, characterized in that it comprises the following schemes:

Scheme 1
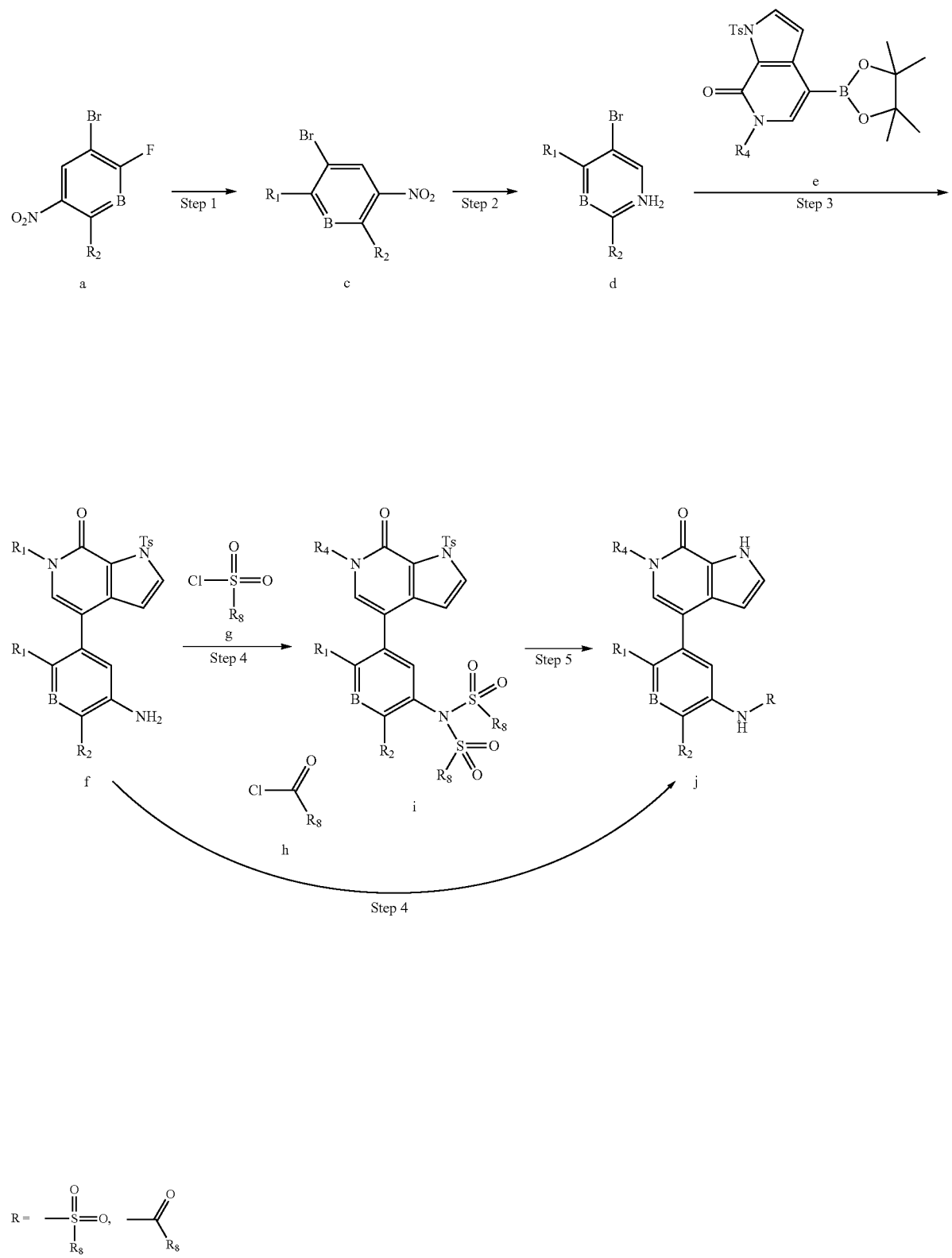

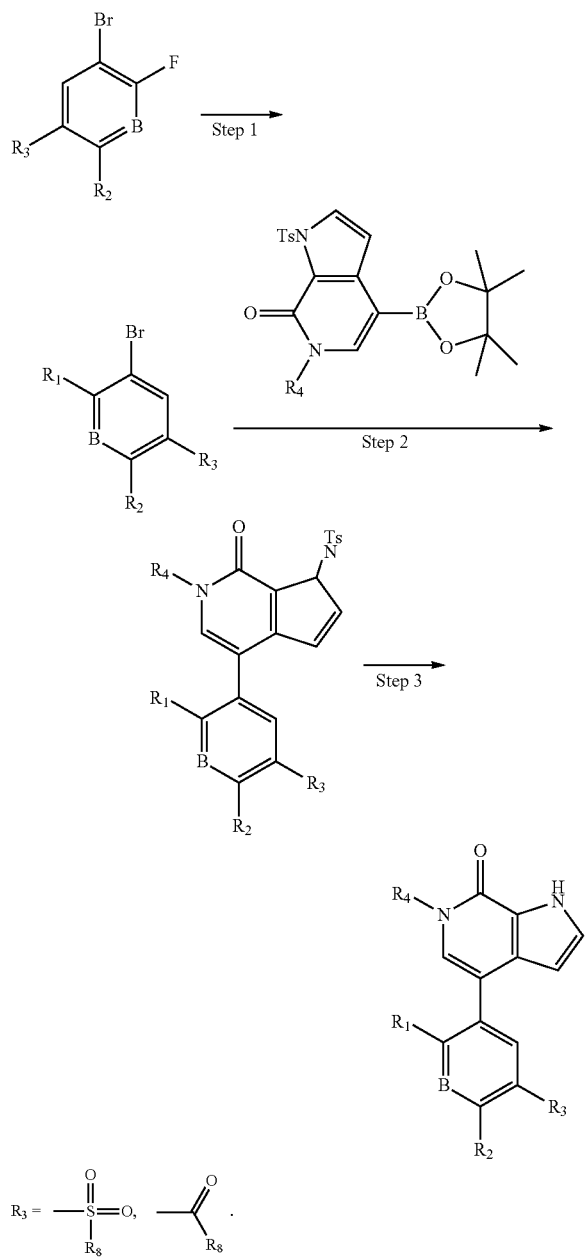

Scheme 2

The present invention further provides the use of the compound mentioned above, or a pharmaceutically acceptable salt, solvate or hydrate thereof in the preparation of drugs for treatment of diseases or symptoms related to BET protein.

Further, the diseases or symptoms related to BET protein are tumors, autoimmune or inflammatory diseases, and viral infections.

Further, the tumor is breast cancer, brain cancer, cervical cancer, colorectal cancer, gastrointestinal cancer, esophageal cancer, liver cancer, lung cancer, pancreatic cancer, endometrial cancer, nasopharyngeal cancer, ovarian cancer, and prostate cancer;

Preferably, the hematopoietic system tumor is selected from lymphoma, multiple myeloma and B-cell polar lymphocytic leukemia.

Further, the tumor is breast cancer and prostate cancer.

Further, the autoimmune or inflammatory disease is allergy, allergic rhinitis, arthritis, asthma, chronic obstructive pulmonary disease, degenerative arthritis, skin disease, organ rejection, eczema, hepatitis, inflammatory bowel disease, multiple sclerosis, myasthenia gravis, psoriasis, sepsis, systemic lupus erythematosus, tissue transplant rejection, and type 1 diabetes.

Further, the viral infection is that infected with the following viruses: adenovirus, hepatitis B virus, hepatitis C virus, herpes virus, human immunodeficiency virus, and human papilloma virus.

The present invention further provides a pharmaceutical composition, that is a commonly used pharmaceutical preparations obtained by using the compound mentioned above or a pharmaceutically acceptable salt, solvate or hydrate thereof as an active ingredient, with addition of pharmaceutically acceptable excipients or auxiliary components.

The present invention further provides a drug combination with anti-tumor efficacy, that contains the compound mentioned above or a pharmaceutically acceptable salt, solvate or hydrate thereof, and other drugs with anti-tumor effects, as well as pharmaceutically acceptable carriers in units of the same or different specifications for simultaneous or separated administration.

Further, said other drugs with anti-tumor effects are chemotherapeutic drugs, and preferably, the chemotherapeutic drugs are targeted drugs.

Further, said targeted drug is selected from one or more of androgen receptor inhibitors or other targeted drugs.

Further, said targeted drug is androgen receptor inhibitors.

"Other drugs with anti-tumor effects" mean those with anti-tumor effects other than the compound of the present invention or a pharmaceutically acceptable salt, solvate or hydrate thereof.

"Other targeted drugs" mean anti-tumor drugs with targeted therapeutic effects other than androgen receptor inhibitors.

The compound provided in the present invention has a good inhibitory effect on the proliferation of various human prostate cancer cells (CWR22RV1 and Vcap) and breast cancer cells (BT474, MCF-7, MDA-MB-231, and MDA-MB-453); moreover, the use of the compound according to the present invention in combination with the androgen receptor inhibitor HC-1119 can significantly improve the inhibitory effect on prostate cancer cells, and the inhibitory effect is enhanced as the increase of the concentration. It is shown that the compound of the present invention can not only be used alone to prepare anti-tumor drugs, but also can be used with other anti-tumor drugs, such as androgen receptor inhibitors, other targeted drugs, etc., to prepare anti-tumor drugs with better therapeutic effects, especially those for treatment of prostate cancer and breast cancer.

For the definition of the term used in the present the invention: unless otherwise specified, the initial definition provided for the group or the term herein is applicable to those in the whole specification; for terms not specifically defined herein, according to the disclosure content and the context, the term should have the meaning commonly given by those skilled in the field.

"Substitution" means that the hydrogen in a molecule is substituted by other different atoms or molecules.

The minimum and the maximum for the content of carbon atoms in hydrocarbon groups are represented by prefixes, for example, the prefix $(C_a\sim C_b)$ alkyl means any alkyl containing "a"~"b" carbon atoms. Therefore, for example, $C_1\sim C_8$ alkyl mean an alkyl containing 1-8 carbon atoms. $C_1\sim C_8$ alkyl means $C_1$, $C_2$, $C_3$, $C_4$, $C_5$, $C_6$, $C_7$, and $C_8$ alkyl, namely a straight or branched alkyl containing 1-8 carbon atoms, such as methyl, ethyl, propyl, butyl, isobutyl, t-butyl, sec-butyl, pentyl, hexyl, heptyl, octyl and so on.

Said cycloalkyl means cyclic alkyls, such as cyclopropyl, cyclobutyl, cyclopentyl, cyclohexyl and so on.

Said halogen is fluorine, chlorine, bromine, and iodine.

The term "pharmaceutically acceptable" denotes a certain carrier, vehicle, diluent, excipient, and/or formed salt, and is usually chemically or physically compatible with other ingredients constituting a certain pharmaceutical dosage form, as well as physiologically compatible with the recipient.

The term "salt" or "pharmaceutically acceptable salt" means acid and/or basic salt that is formed by reaction of above-mentioned compound or its stereoisomer with inorganic and/or organic acid and base, and also includes zwitterionic salts (inner salts), and further includes quaternary ammonium salts, such as alkylammonium salt. These salts can be directly obtained during the final isolation and purification of a compound. The salts can also be obtained by mixing above-mentioned compound or its stereoisomers with a certain amount of acid or base appropriately (for example, in equivalent).

These salts may form a precipitate in the solution, and be collected by filtration, or recovered after evaporation of the solvent, or obtained by freeze-drying after reaction in an aqueous medium.

"$SO_2$" is

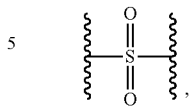

and "SO" is

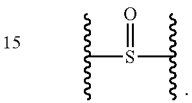

"Other drugs with anti-tumor effects" mean all anti-tumor drugs in the prior art, except for the compound of the present invention or a pharmaceutically acceptable salt, solvate or hydrate thereof.

Obviously, based on above content of the present invention, according to the common technical knowledge and the conventional means in the field, without department from above basic technical spirits, other various modifications, alternations or changes can further be made.

By following specific examples of said embodiments, above content of the present invention is further illustrated. But it should not be construed that the scope of above subject of the present invention is limited to following examples. The techniques realized based on above content of the present invention are all within the scope of the present invention.

EXAMPLES

General reaction scheme 1

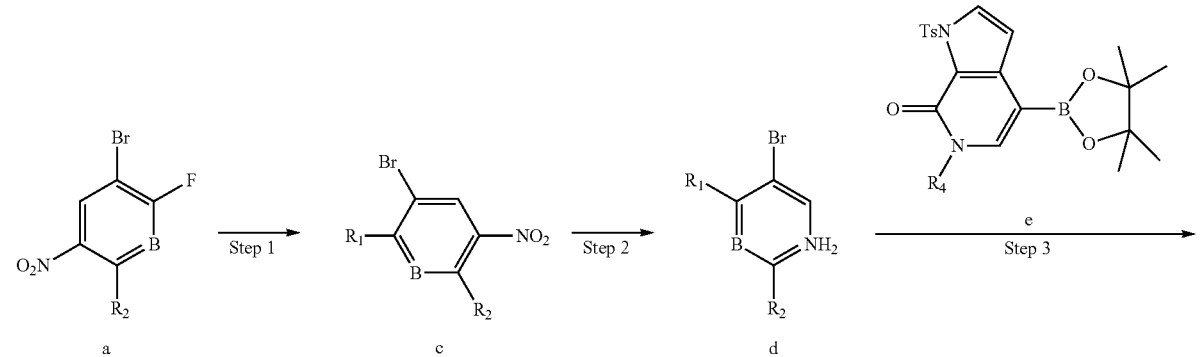

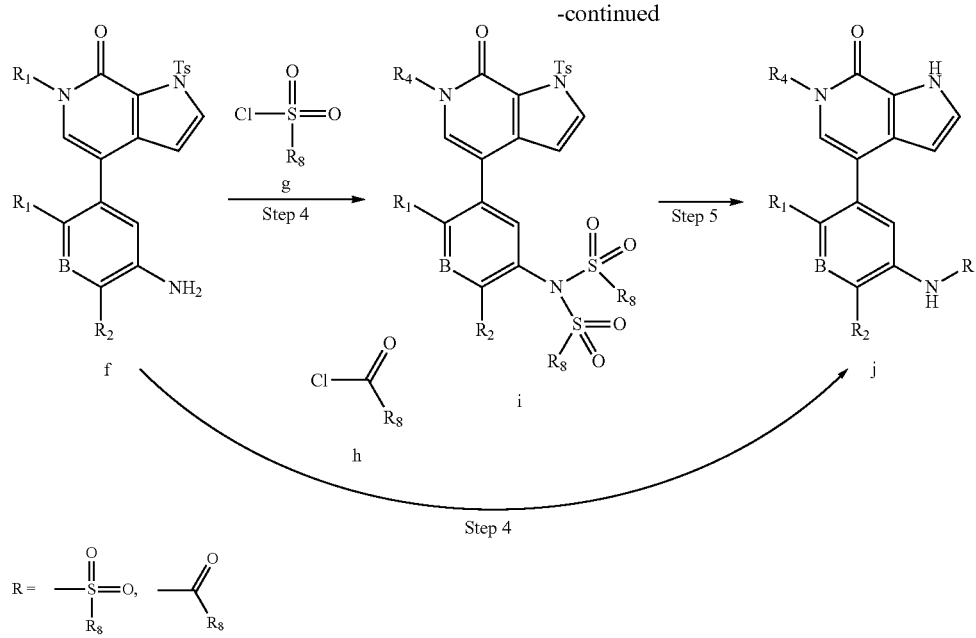
Example 1 Synthesis of Compound 7
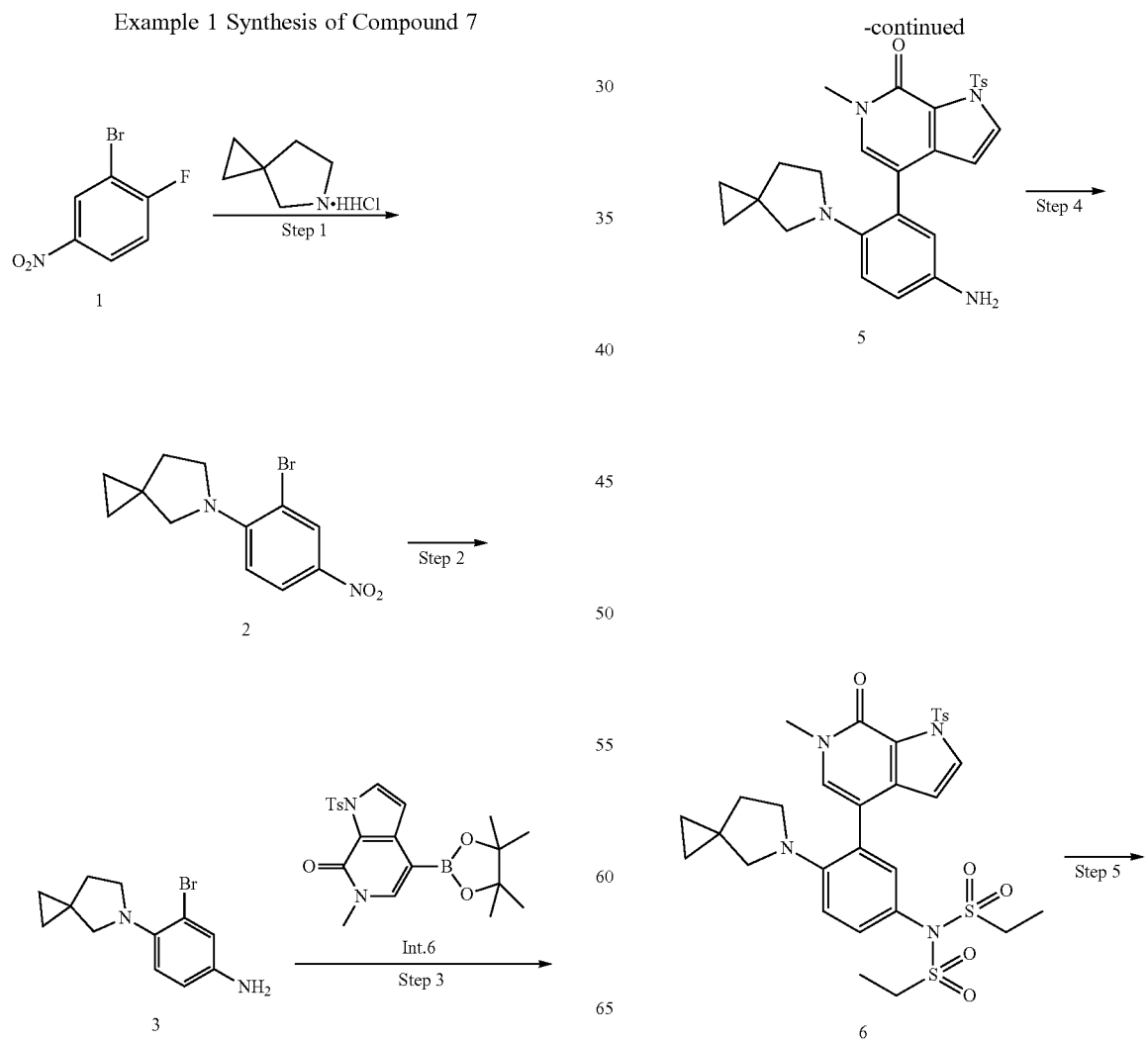

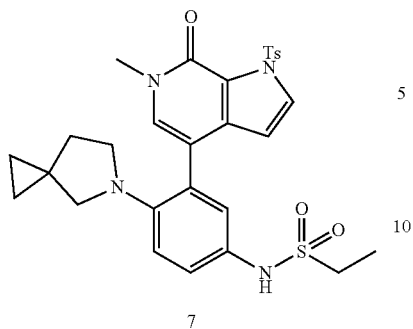

7

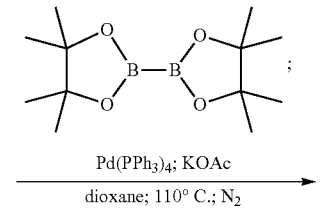

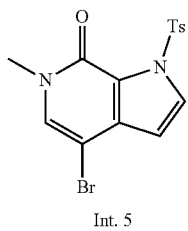

Int. 5

Synthesis of 6-methyl-4-(4,4,5,5-tetramethyl-1,3,2-dioxaborolan-2-yl)-1-tosyl-1H-pyrrolo [2,3-c]pyridin-7(6H)-one (Int. 6)

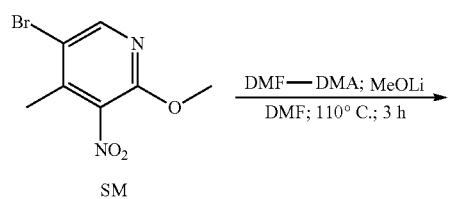

SM

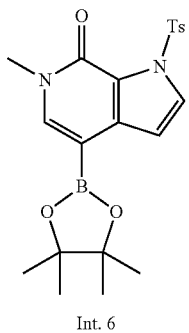 [SMILES: Cc1ccc(S(=O)(=O)n2ccc3c(B4OC(C)(C)C(C)(C)O4)cn(C)c(=O)c32)cc1]

Int. 6

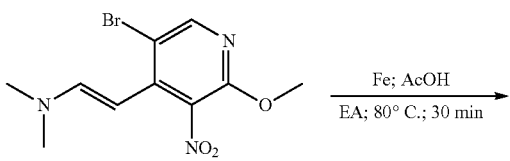

Int. 1

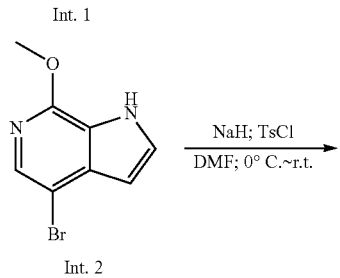

Int. 2

Synthesis of (E)-2-(5-bromo-2-methoxy-3-nitropyridin-4-yl)-N,N-dimethylethylamine (Int. 1)

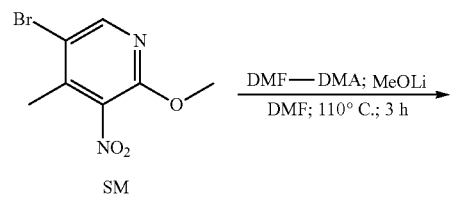

SM

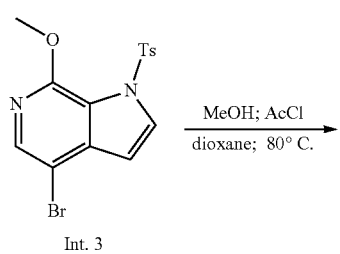

Int. 3

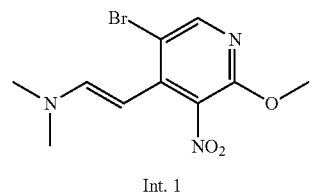

Int. 1

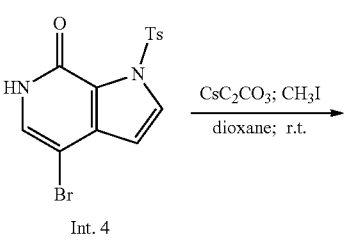

Int. 4

To a 10 L reaction flask containing N,N-dimethylformamide (4 L), were added 5-bromo-2-methoxy-4-methyl-3-nitropyridine (200 g, 0.8 mol), N,N-dimethylformamide dimethyl acetal (571.2 g, 4.8 mol), and lithium methoxide (0.9 g, 0.024 mol), and then the reaction mixture was heated to 110° C. and stirred for 3 h. After it was cooled to room temperature, the reaction solution was added to ice water (12 L), and after the solid was fully precipitated, the mixture was filtered with suction, washed with water (1 L), and dried. Intermediate 1 (240 g) was obtained as brown-red solid powder with a yield of 98%.

Synthesis of 4-bromo-7-methoxy-1H-pyrrolo[2,3-c]pyridin (Int. 2)

Synthesis of 4-bromo-1-tosyl-1H-pyrrolo[2,3-c]pyridin-7(6H)-one (Int. 4)

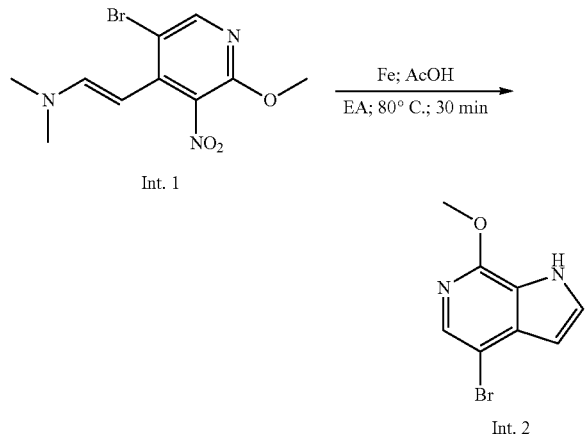

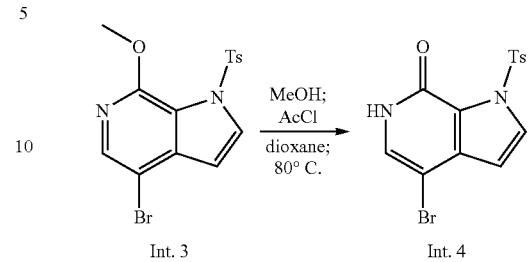

1,4-Dioxane (2 L) and methanol (78 g, 2.45 mol) were added to a 5 L reaction flask. Acetyl chloride (154 g, 1.96 mol) was added to the reaction flask at room temperature. After addition, the reaction was stirred for additional 1 h. Intermediate compound 3 (188 g, 0.49 mol) was added, and the temperature was heated to 80° C., then the reaction was stirred overnight. After completion of the reaction, the solvent was rotatory evaporated, and the residue was triturated with 300 mL methyl tert-butyl ether (300 mL), followed by vacuum filtration, intermediate compound 4 (139 g) was obtained with a yield of 77%.

The solvent ethyl acetate (5 L), reduced iron powder (223 g, 3.97 mol), and acetic acid (2.3 L, 39.7 mol) were added to a 10 L reaction flask. After heating to 80° C., intermediate compound 1 (240 g, 0.79 mol) was add stepwise. After the addition, the reaction was allowed to continue at this temperature for 30 min. Then, the reaction was cooled, filtered with suction, rotatory evaporated, and triturated with a mixed solvent of ethanol (1 L) and water (1 L). After filtration and drying, intermediate compound 2 (140 g) was obtained with a yield of 78%.

Synthesis of 4-bromo-6-methyl-1-tosyl-1H-pyrrolo[2,3-c]pyridin-7(6H)-one (Int. 5)

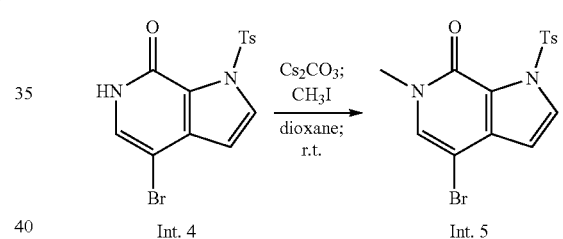

Synthesis of 4-bromo-7-methoxy-1-p-tosyl-1H-pyrrolo[2,3-c]pyridine (Int. 3)

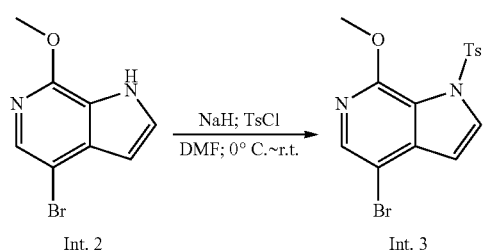 [SMILES: COc1ncc(Br)c2cc[nH]c12 ; COc1ncc(Br)c2ccn(S(=O)(=O)c3ccc(C)cc3)c12]

1,4-Dioxane (2 L), intermediate compound 4 (79 g, 0.21 mol), cesium carbonate (118 g, 0.32 mol), and methyl iodide (92 g, 0.64 mol) were added to a 5 L reaction flask and stirred overnight at room temperature. After completion of the reaction, the solution was filtered and rotatory evaporated to obtain intermediate compound 5 (75 g) with a yield of 94%.

Synthesis of 6-methyl-4-(4,4,5,5-tetramethyl-1,3,2-dioxaborolan-2-yl)-1-tosyl-1H-pyrrolo[2,3-c]pyridin-7(6H)-one (Int. 6)

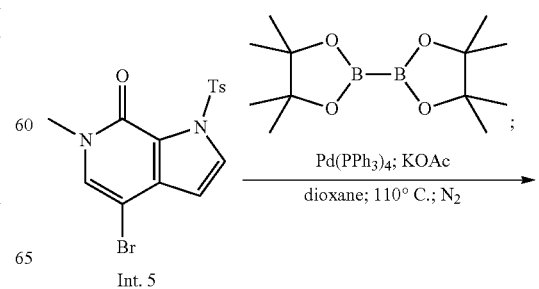

N,N-dimethylformamide (2 L) and intermediate compound 2 (140 g, 0.62 mol) were added to a 5 L reaction flask, and after dissolved, the mixture was cooled to 0° C. in an ice-water bath, then NaH (40 g, 60%, 0.99 mol) was added to the reaction solution under the temperature of the reaction being <10° C. After NaH was added and no bubbling was found, p-toluenesulfonyl chloride (177 g, 0.93 mol) was added, and the reaction mixture was stirred overnight at room temperature. After completion of the reaction, the reaction solution was poured into 6 L water to precipitate the solid, and then filtered with suction. The solid was dissolved in 200 mL ethyl acetate by heating, and then 600 mL n-hexane was added to precipitate the solid. After vacuum filtration, intermediate compound 3 (188 g) was obtained, with a yield of 80%.

47

-continued

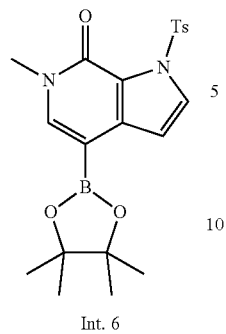

Int. 6

1,4-Dioxane (800 mL), intermediate compound 5 (38 g, 0.1 mol), bis(pinacolato)diboron (102 g, 0.4 mol), and potassium acetate (20.4 g, 0.2 mol) were added to a 2 L reaction flask, and after purging $N_2$ three times, tetrakis (triphenylphosphine)palladium (12 g, 0.01 mol) was added. Followed by purging $N_2$ three times, the reaction was warmed up to 110° C., and stirred overnight. After completion of the reaction, the reaction mixture was purified by filtration and column chromatography, to provide intermediate compound 6 (40 g) with a yield of 93%.

Synthesis of 5-(2-bromo-4-nitrophenyl)-5-aza-spiro [2.4]heptane (Compound 2)

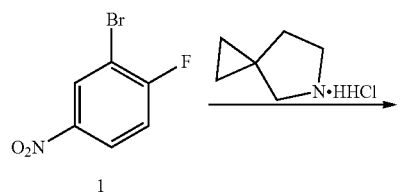

1

Compound 1 (1.1 g, 5 mmol), 5-aza-spiro[2.4]heptane hydrochloride (798 mg, 6 mmol), sodium carbonate (1.27 g, 12 mmol), and DMSO (15 mL) were added to a 50 mL reaction flask, and the system was reacted at 80° C. for 10 h. After completion of the reaction, the reaction solution was poured into 50 mL water, and extracted with 45 mL dichloromethane (15 mL×3). The organic phases were combined, dried over anhydrous sodium sulfate, and purified by column chromatography to obtain compound 2 (1.15 g) with a yield of 78%. MS: m/z 297.3 [M+H]⁺.

48

Synthesis of 3-bromo-4-(5-aza-spiro[2.4]heptane-5-yl)phenylamine (Compound 3)

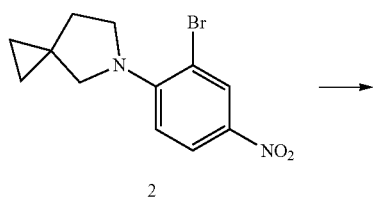

2

3

Compound 2 (888 mg, 3 mmol), methanol (10 mL), and Raney nickel (50 mg) were added to a 50 mL reaction flask, then hydrazine hydrate (3 mL) was added at 0° C., and the system was reacted at 20° C. for 3 h. After completion of the reaction, the reaction solution was poured into 50 mL water, and extracted with 30 mL dichloromethane (15 mL×3). The organic phases were combined, dried over anhydrous sodium sulfate, and purified by column chromatography to obtain compound 3 (678 mg) with a yield of 85%. MS: m/z 267.3 [M+H]⁺.

Synthesis of 4-(5-amino-2-(5-aza-spiro[2.4]heptan-5-yl)phenyl)-6-methyl-1-tosyl-1H-pyrrolo [2,3-c] pyridin-7(6H)-one (Compound 5)

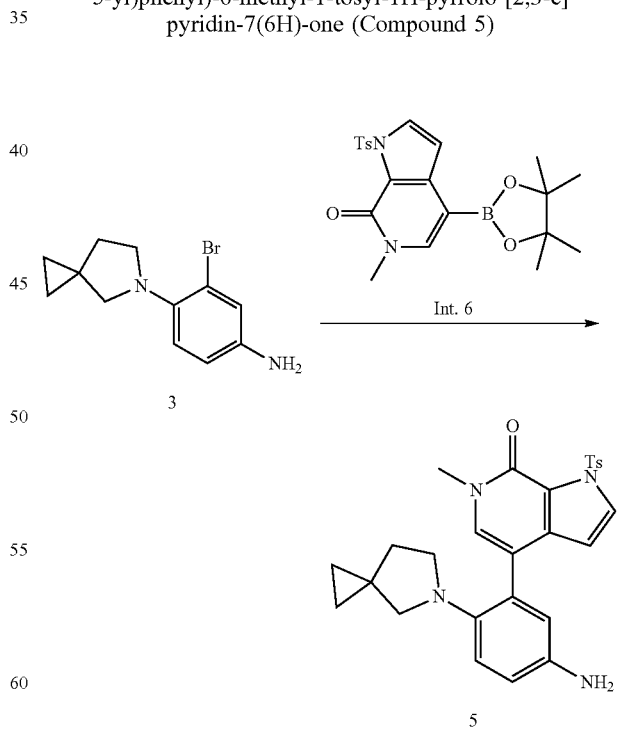

Compound 3 (266 mg, 1 mmol), compound Int. 8 (556 mg, 1.3 mmol), Pd(PPh₃)₄ (69.2 mg, 0.06 mmol), Na₂CO₃ (212 mg, 2 mmol), and DMF/H₂O (5 mL/0.3 mL) were added to a 30 mL reaction flask, and the system was reacted at 100° C. for 10 h under protection of nitrogen. After completion of the reaction, the reaction solution was poured into 30 mL water, and extracted with 30 mL dichloromethane (10 mL×3). The organic phases were combined, dried over anhydrous sodium sulfate, and purified by prep-TLC to obtain compound 5 (219 mg) with a yield of 45%. MS: m/z 489.2 [M+H]⁺.

Synthesis of N-(ethylsulfonyl)-N-(3-(6-methyl-7-oxo-1-(p-toly)sulfonyl-6,7-dihydro-1H-pyrrolo[2,3-c] pyridin-4-yl)-4-(5-aza-spiro[2.4]heptan-5-yl)phenyl)ethylsulfonamide (Compound 6)

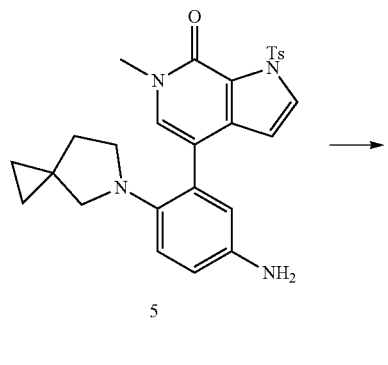

5

Synthesis of N-(3-(6-methyl-7-oxo-6,7-dihydro-1H-pyrrolo[2,3-c]pyridin-4-yl)-4-(5-aza-spiro[2.4]heptan-5-yl)phenyl)ethylsulfonamide (Compound 7)

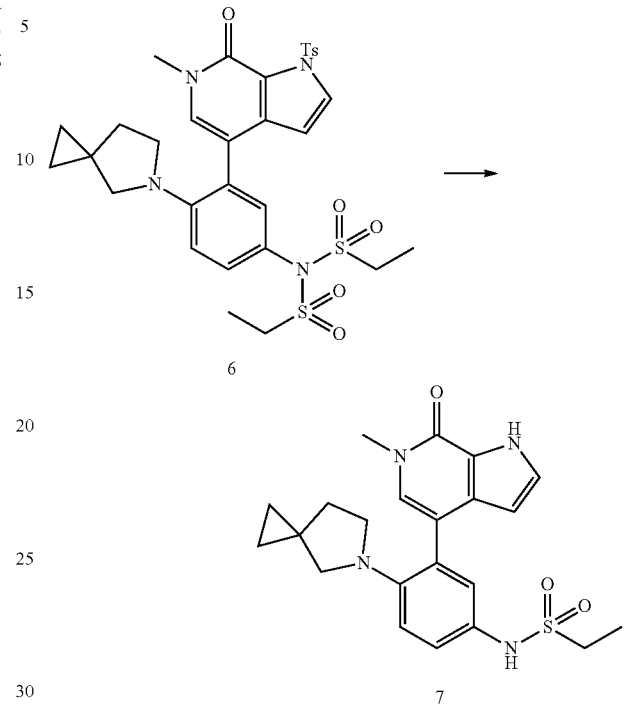

Compound 6 (120 mg, 0.18 mmol), THF (1 mL), and KOH (4 mL, 4M) were added to a 30 mL reaction flask, and the system was reacted at 80° C. for 3 h. After completion of the reaction, the reaction solution was poured into 30 mL water, and extracted with 30 mL dichloromethane (10 mL×3). The organic phases were combined, dried over anhydrous sodium sulfate, and purified by prep-TLC to obtain compound 7 (58 mg) with a yield of 76%. MS: m/z 427 [M+H]⁺.

¹H NMR (400 MHz, DMSO) δ 12.02 (s, 1H), 9.31 (s, 1H), 7.75-7.46 (m, 1H), 7.26 (t, J=2.7 Hz, 1H), 7.16 (s, 1H), 7.13-6.99 (m, 2H), 6.83 (d, J=8.8 Hz, 1H), 3.55 (s, 3H), 3.09 (t, J=6.6 Hz, 2H), 2.98 (q, J=7.3 Hz, 2H), 2.79 (s, 2H), 1.61 (t, J=6.6 Hz, 2H), 1.20 (t, J=7.3 Hz, 3H), 0.38 (m, 4H).

Synthesis of N-(3-(6-methyl-7-oxo-6,7-dihydro-1H-pyrrolo[2,3-c]pyridin-4-yl)-4-(6-aza-spiro[2.5]octan-5-yl)phenyl)ethylsulfonamide (Compound 8)

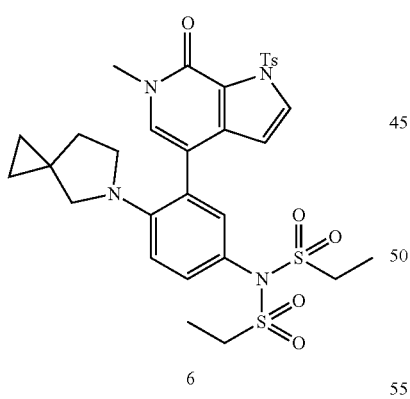

6

Compound 5 (146 mg, 0.3 mmol), dichloromethane (5 mL), and DIPEA (143 mg, 1.2 mmol) were added to a 30 mL reaction flask, and then ethanesulfonyl chloride (88 mg, 0.7 mmol) was added at 0° C. The system was reacted at 20° C. for 3 h. After completion of the reaction, the reaction solution was poured into 30 mL water, and extracted with 30 mL dichloromethane (10 mL×3). The organic phases were combined, dried over anhydrous sodium sulfate, and purified by prep-TLC to obtain compound 6 (120 mg) with a yield of 60%. MS: m/z 673.6 [M+H]⁺.

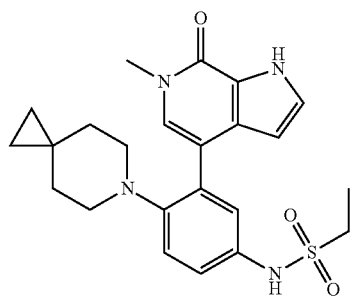

By the synthetic method and procedure of compound 7, the synthesis of compound 8 could be carried out with corresponding reagents. Among them, 6-aza-spiro[2.5]octane hydrochloride was used to replace 5-aza-spiro[2.4]heptane hydrochloride in the first step of the reaction, while other reaction reagents and conditions were completely consistent with those for synthesis of compound 7, and thus compound 8 was prepared.

MS: 441.0 [M+H]⁺

¹H NMR (400 MHz, DMSO) δ ppm 11.98 (s, 1H), 9.54 (s, 1H), 7.44 (s, 1H), 7.28 (s, 1H), 7.17-7.05 (m, 3H), 6.16 (s, 1H), 3.57 (s, 3H), 3.07-3.01 (m, 2H), 2.78 (s, 4H), 1.23-1.13 (m, 7H), 0.19 (s, 4H).

Synthesis of N-(3-(6-methyl-7-oxo-6,7-dihydro-1H-pyrrolo[2,3-c]pyridin-4-yl)-4-(5-aza-spiro[2.5]octan-5-yl)phenyl)ethylsulfonamide (Compound 9)

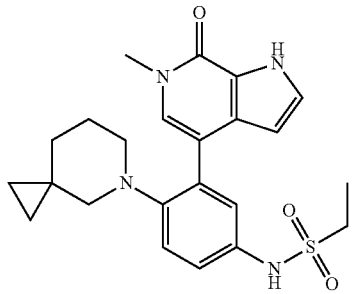

By the synthetic method and procedure of compound 7, the synthesis of compound 9 could be carried out with corresponding reagents. Among them, 5-aza-spiro[2.5]octane hydrochloride was used to replace 5-aza-spiro[2.4]heptane hydrochloride in the first step of the reaction, while other reaction reagents and conditions were completely consistent with those for synthesis of compound 7, and thus compound 9 was prepared.

MS: 441.0 [M+H]⁺

¹H NMR (400 MHz, DMSO) δ 12.01 (s, 1H), 9.55 (s, 1H), 7.46 (s, 1H), 7.29 (m, 1H), 7.19 (m, 1H), 7.15-7.09 (m, 1H), 7.03 (d, J=8.6 Hz, 1H), 6.22-6.12 (m, 1H), 3.57 (s, 3H), 3.32 (m, 1H), 3.04 (m, 2H), 2.97 (m, 1H), 2.77 (m, 1H), 2.47 (m, 1H), 1.51-1.34 (m, 2H), 1.32-1.08 (m, 5H), 0.85 (m, 1H), 0.71 (m, 1H), 0.14 (m, 1H), 0.04 (m, 1H).

Synthesis of N-(3-(6-methyl-7-oxo-6,7-dihydro-1H-pyrrolo[2,3-c]pyridin-4-yl)-4-(2-aza-spiro[3.3]heptan-2-yl)phenyl)cyclopropanesulfonamide (Compound 10)

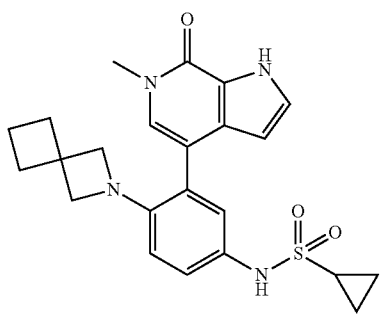

By the synthetic method and procedure of compound 7, the synthesis of compound 10 could be carried out with corresponding reagents. Among them, 2-aza-spiro[3.3]heptane hydrochloride was used to replace 5-aza-spiro[2.4]heptane hydrochloride in the first step of the reaction, and cyclopropanesulfonyl chloride was used to replace ethanesulfonyl chloride in the fourth step, while other reaction reagents and conditions were completely consistent with those for synthesis of compound 7, and thus compound 10 was prepared.

MS: m/z 439.5 [M+H]⁺

¹H NMR (400 MHz, DMSO-d₆) δ 12.05 (s, 1H), 9.20 (s, 1H), 7.27 (t, J=2.4, 1H), 7.01 (s, 1H), 7.08 (dd, J₁=2.4 Hz, J₂=8.8 Hz, 1H), 6.98 (d, J=2.4, 1H), 6.51 (d, J=8.8 Hz, 1H), 6.08 (t, J=1.6 Hz, 1H), 3.56 (s, 3H), 3.40 (s, 4H), 2.45 (m, 1H), 1.95 (t, J=7.6 Hz, 4H), 1.68-1.63 (m, 2H), 0.95-0.80 (m, 4H).

Synthesis of N-(3-(6-methyl-7-oxo-6,7-dihydro-1H-pyrrolo[2,3-c]pyridin-4-yl)-4-(2-aza-spiro[3.3]heptan-2-yl)phenyl)methanesulfonamide (Compound 11)

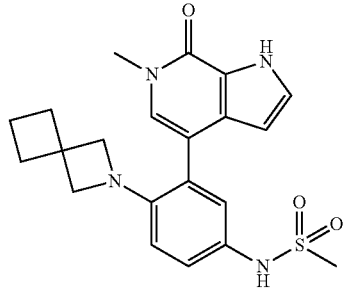

By the synthetic method and procedure of compound 7, the synthesis of compound 11 could be carried out with corresponding reagents. Among them, 2-aza-spiro[3.3]heptane hydrochloride was used to replace 5-aza-spiro[2.4]heptane hydrochloride in the first step of the reaction, and methanesulfonyl chloride was used to replace ethanesulfonyl chloride in the fourth step, while other reaction reagents and conditions were completely consistent with those for synthesis of compound 7, and thus compound 11 was prepared.

MS: m/z 413.5 [M+H]⁺

¹H NMR (400 MHz, DMSO-d₆) δ 12.05 (s, 1H), 9.20 (s, 1H), 7.27 (t, J=2.4, 1H), 7.01 (s, 1H), 7.08 (dd, J₁=2.4 Hz, J₂=8.8 Hz, 1H), 6.98 (d, J=2.4, 1H), 6.51 (d, J=8.8 Hz, 1H), 6.08 (t, J=1.6 Hz, 1H), 3.56 (s, 3H), 3.40 (s, 4H), 2.88 (s, 3H), 1.95 (t, J=7.6 Hz, 4H), 1.68-1.63 (m, 2H).

Synthesis of N-(3-(6-methyl-7-oxo-6,7-dihydro-1H-pyrrolo[2,3-c]pyridin-4-yl)-4-(2-aza-spiro[3.3]heptan-2-yl)phenyl)oxetane-3-sulfonamide (Compound 12)

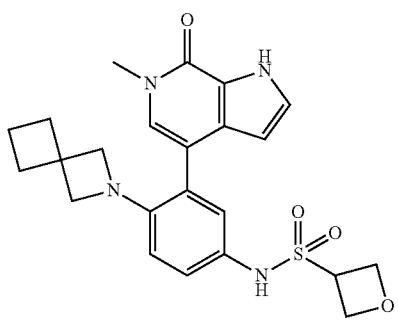

12

By the synthetic method and procedure of compound 7, the synthesis of compound 12 could be carried out with corresponding reagents. Among them, 2-aza-spiro[3.3]heptane hydrochloride was used to replace 5-aza-spiro[2.4]heptane hydrochloride in the first step of the reaction, and oxetanesulfonyl chloride was used to replace ethanesulfonyl chloride in the fourth step, while other reaction reagents and conditions were completely consistent with those for synthesis of compound 7, and thus compound 12 was prepared.

MS: m/z 455.5 [M+H]$^+$ $^1$H NMR (400 MHz, DMSO-d$_6$) δ 12.05 (s, 1H), 9.20 (s, 1H), 7.27 (t, J=2.4, 1H), 7.01 (s, 1H), 7.08 (dd, J$_1$=2.4 Hz, J$_2$=8.8 Hz, 1H), 6.98 (d, J=2.4 Hz, 1H), 6.51 (d, J=8.8 Hz, 1H), 6.08 (t, J=1.6 Hz, 1H), 4.90-4.60 (m, 4H), 4.60-4.48 (m, 1H), 3.56 (s, 3H), 3.40 (s, 4H), 1.95 (t, J=7.6 Hz, 4H), 1.68-1.63 (m, 2H).

Synthesis of N-(3-(6-methyl-7-oxo-6,7-dihydro-1H-pyrrolo[2,3-c]pyridin-4-yl)-4-(2-aza-spiro[3.3]heptan-2-yl)phenyl)butane-1-sulfonamide (Compound 13)

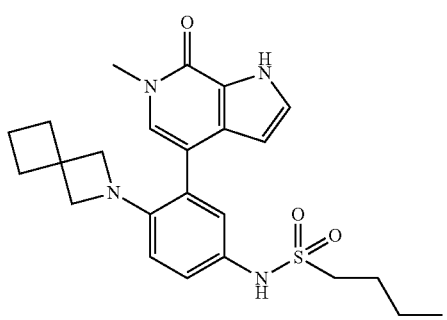

13

By the synthetic method and procedure of compound 7, the synthesis of compound 13 could be carried out with corresponding reagents. Among them, 2-aza-spiro[3.3]heptane hydrochloride was used to replace 5-aza-spiro[2.4]heptane hydrochloride in the first step of the reaction, and butanesulfonyl chloride was used to replace ethanesulfonyl chloride in the fourth step, while other reaction reagents and conditions were completely consistent with those for synthesis of compound 7, and thus compound 13 was prepared.

MS: m/z 455.6 [M+H]$^+$ $^1$H NMR (400 MHz, DMSO): 12.07 (s, 1H), 9.29 (s, 1H), 7.29 (t, J=2.6 Hz, 1H), 7.09 (s, 1H), 7.05 (dd, J=8.5, 2.3 Hz, 1H), 6.96 (d, J=2.5 Hz, 1H), 6.49 (d, J=8.7 Hz, 1H), 6.12-6.03 (m, 1H), 3.56 (s, 3H), 3.40 (s, 4H), 2.98-2.89 (m, 2H), 1.96 (t, J=7.6 Hz, 4H), 1.65 (dq, J=15.1, 7.5 Hz, 4H), 1.36 (dq, J=14.8, 7.4 Hz, 2H), 0.85 (t, J=7.3 Hz, 3H).

Synthesis of N-(3-(6-methyl-7-oxo-6,7-dihydro-1H-pyrrolo[2,3-c]pyridin-4-yl)-4-(2-aza-spiro[3.3]heptan-2-yl)phenyl)ethanesulfonamide (Compound 14)

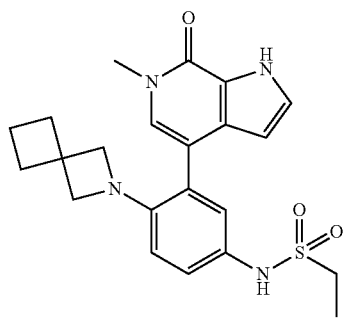

14

By the synthetic method and procedure of compound 7, the synthesis of compound 14 could be carried out with corresponding reagents. Among them, 2-aza-spiro[3.3]heptane hydrochloride was used to replace 5-aza-spiro[2.4]heptane hydrochloride in the first step of the reaction, while other reaction reagents and conditions were completely consistent with those for synthesis of compound 7, and thus compound 14 was prepared.

MS: m/z 426.6 [M+H]$^+$ $^1$H NMR (400 MHz, DMSO-d$_6$) δ 12.05 (s, 1H), 9.20 (s, 1H), 7.27 (t, J=2.4, 1H), 7.01 (s, 1H), 7.08 (dd, J$_1$=2.4 Hz, J$_2$=8.8 Hz, 1H), 6.98 (d, J=2.4 Hz, 1H), 6.51 (d, J=8.8 Hz, 1H), 6.08 (t, J=1.6 Hz, 1H), 3.56 (s, 3H), 3.40 (s, 4H), 2.92 (t, J=8 Hz, 2H), 1.95 (t, J=7.6 Hz, 4H), 1.68-1.63 (m, 2H), 0.83 (t, J=8 Hz, 3H).

Synthesis of N-(3-(6-methyl-7-oxo-6,7-dihydro-1H-pyrrolo[2,3-c]pyridin-4-yl)-4-(2-oxa-6-aza-spiro[3.3]heptan-6-yl)phenyl)methanesulfonamide (Compound 15)

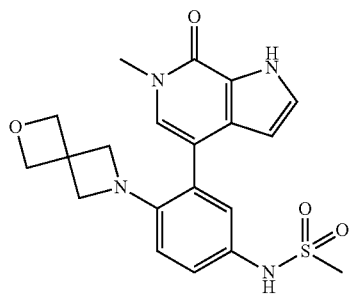

15

By the synthetic method and procedure of compound 7, the synthesis of compound 15 could be carried out with corresponding reagents. Among them, 2-oxa-6-aza-spiro[3.3]heptane hydrochloride was used to replace 5-aza-spiro[2.4]heptane hydrochloride in the first step of the reaction, and methanesulfonyl chloride was used to replace ethanesulfonyl chloride in the fourth step, while other reaction reagents and conditions were completely consistent with those for synthesis of compound 7, and thus compound 15 was prepared.

MS: m/z 415.5 [M+H]⁺

¹H NMR (400 MHz, DMSO): δ 12.10 (s, 1H), 9.21 (s, 1H), 7.29 (t, J=2.5 Hz, 1H), 7.14-7.06 (m, 2H), 7.02 (d, J=2.5 Hz, 1H), 6.57 (d, J=8.7 Hz, 1H), 6.08 (s, 1H), 4.52 (s, 4H), 3.62 (s, 4H), 3.58 (s, 3H), 2.89 (s, 3H).

Synthesis of N-(3-(6-methyl-7-oxo-6,7-dihydro-1H-pyrrolo[2,3-c]pyridin-4-yl)-4-(2-oxa-6-aza-spiro[3.3]heptan-6-yl)phenyl)ethanesulfonamide (Compound 16)

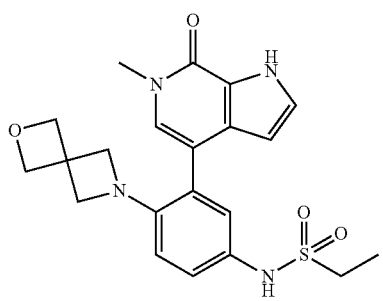

16

By the synthetic method and procedure of compound 7, the synthesis of compound 16 could be carried out with corresponding reagents. Among them, 2-oxa-6-aza-spiro[3.3]heptane hydrochloride was used to replace 5-aza-spiro[2.4]heptane hydrochloride in the first step of the reaction, while other reaction reagents and conditions were completely consistent with those for synthesis of compound 7, and thus compound 16 was prepared.

MS: m/z 429.5 [M+H]⁺

¹H NMR (400 MHz, DMSO): δ 12.11 (s, 1H), 9.35 (s, 1H), 7.30 (t, J=2.7 Hz, 1H), 7.10 (dd, J=8.5, 2.6 Hz, 2H), 7.02 (d, J=2.5 Hz, 1H), 6.56 (d, J=8.7 Hz, 1H), 6.07 (s, 1H), 4.52 (s, 4H), 3.61 (s, 4H), 3.58 (s, 3H), 2.98 (q, J=7.3 Hz, 2H), 1.21 (t, J=7.3 Hz, 3H).

Synthesis of N-(3-(6-methyl-7-oxo-6,7-dihydro-1H-pyrrolo[2,3-c]pyridin-4-yl)-4-(2-oxa-6-aza-spiro[3.3]heptan-6-yl)phenyl)butan-1-sulfonamide (Compound 17)

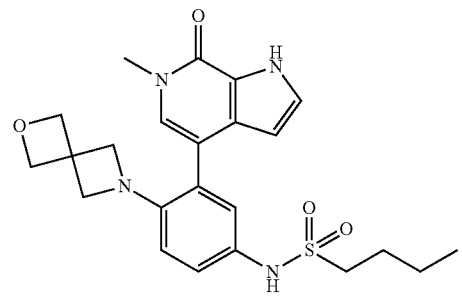

17

By the synthetic method and procedure of compound 7, the synthesis of compound 17 could be carried out with corresponding reagents. Among them, 2-oxa-6-aza-spiro[3.3]heptane hydrochloride was used to replace 5-aza-spiro[2.4]heptane hydrochloride in the first step of the reaction, and butanesulfonyl chloride was used to replace ethanesulfonyl chloride in the fourth step, while other reaction reagents and conditions were completely consistent with those for synthesis of compound 7, and thus compound 17 was prepared.

MS: m/z 457.5 [M+H]⁺

¹H NMR (400 MHz, DMSO): δ 12.11 (s, 1H), 9.34 (s, 1H), 7.29 (t, J=2.7 Hz, 1H), 7.11 (d, J=2.5 Hz, 1H), 7.09 (s, 1H), 7.00 (d, J=2.5 Hz, 1H), 6.56 (d, J=8.7 Hz, 1H), 6.06 (s, 1H), 4.52 (s, 4H), 3.61 (s, 4H), 3.57 (s, 3H), 3.02-2.90 (m, 2H), 1.65 (dt, J=15.2, 7.6 Hz, 2H), 1.36 (dq, J=14.7, 7.4 Hz, 2H), 0.85 (t, J=7.3 Hz, 3H).

Synthesis of N-(3-(6-methyl-7-oxo-6,7-dihydro-1H-pyrrolo[2,3-c]pyridin-4-yl)-4-(2-oxa-6-aza-spiro[3.3]heptan-6-yl)phenyl)cyclopropanesulfonamide (Compound 18)

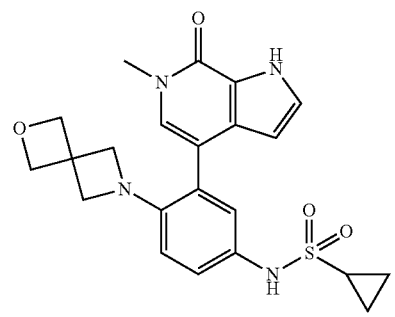

18

By the synthetic method and procedure of compound 7, the synthesis of compound 18 could be carried out with corresponding reagents. Among them, 2-oxa-6-aza-spiro[3.3]heptane hydrochloride was used to replace 5-aza-spiro[2.4]heptane hydrochloride in the first step of the reaction, and cyclopropanesulfonyl chloride was used to replace ethanesulfonyl chloride in the fourth step, while other reaction reagents and conditions were completely consistent with those for synthesis of compound 7, and thus compound 18 was prepared.

MS: m/z 441.5 [M+H]⁺

¹H NMR (400 MHz, DMSO): δ 12.10 (s, 1H), 9.25 (s, 1H), 7.29 (t, J=2.7 Hz, 1H), 7.17-7.07 (m, 2H), 7.03 (d, J=2.5 Hz, 1H), 6.55 (d, J=8.6 Hz, 1H), 6.06 (d, J=2.2 Hz, 1H), 4.52 (s, 4H), 3.61 (s, 4H), 3.58 (s, 3H), 2.45 (m, 1H), 0.95-0.80 (m, 4H).

ethyl 6-(4-(ethylsulfonamide)-6-(6-methyl-7-oxo-6,7-dihydro-1H-pyrrolo [2,3-c]pyridin-4-yl)cyclohexane-1,3-diene-1-yl)-6-aza-spiro[2.5]octan-1-carboxylate (Compound 19)

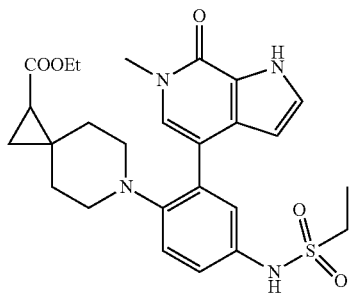

19

By the synthetic method and procedure of compound 7, the synthesis of compound 19 could be carried out with corresponding reagents. Among them, 1-ethyl formate-6-aza-spiro[2.5]octane hydrochloride was used to replace 5-aza-spiro[2.4]heptane hydrochloride in the first step of the reaction, while other reaction reagents and conditions were completely consistent with those for synthesis of compound 7, and thus compound 19 was prepared.

MS: m/z 513.2 [M+H]⁺

¹H NMR (400 MHz, DMSO): δ 12.03 (s, 1H), 9.54 (s, 1H), 7.78 (dd, J=8.5, 2.3 Hz, 1H), 7.71 (d, J=2.3 Hz, 1H), 7.44 (s, 1H), 7.29 (t, J=2.7 Hz, 1H), 7.24 (d, J=8.6 Hz, 1H), 6.14 (t, J=2.3 Hz, 1H), 4.05 (m, 2H), 3.58 (s, 3H), 3.05-2.82 (m, 6H), 1.50-1.36 (m, 3H), 1.23-1.09 (m, 8H), 0.93-0.73 (m, 2H).

Synthesis of 6-(4-(ethylsulfonamide)-2-(6-methyl-7-oxo-6,7-dihydro-1H-pyrrolo[2,3-c]pyridin-4-yl)phenyl)-6-aza-spiro[2.5]octan-1-carboxylic acid (Compound 20)

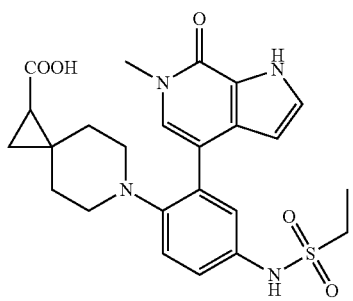

20

By the synthetic method and procedure of compound 7, the synthesis of compound 20 could be carried out with corresponding reagents. Among them, 1-formic acid-6-aza-spiro[2.5]octane hydrochloride was used to replace 5-aza-spiro[2.4]heptane hydrochloride in the first step of the reaction, while other reaction reagents and conditions were completely consistent with those for synthesis of compound 7, and thus compound 20 was prepared.

MS: m/z 486.6 [M+H]⁺

¹H NMR (400 MHz, DMSO): δ 12.03 (s, 1H), 9.54 (s, 1H), 7.78 (dd, J=8.5, 2.3 Hz, 1H), 7.71 (d, J=2.3 Hz, 1H), 7.44 (s, 1H), 7.29 (t, J=2.7 Hz, 1H), 7.24 (d, J=8.6 Hz, 1H), 6.14 (t, J=2.3 Hz, 1H), 3.58 (s, 3H), 3.05-2.82 (m, 6H), 1.50-1.36 (m, 3H), 1.23-1.09 (m, 5H), 0.93-0.73 (m, 2H).

General reaction scheme 2

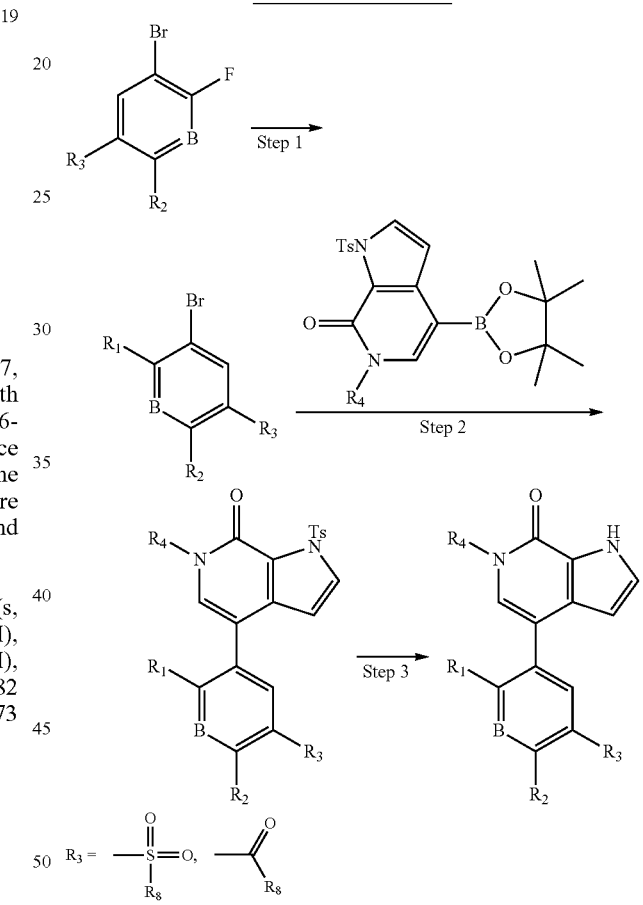

Example 2 Synthesis of Compound 24

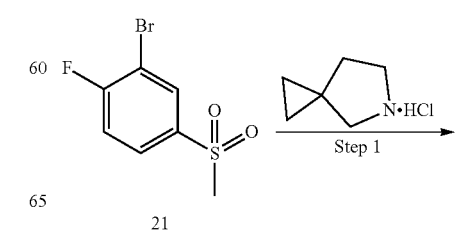

21

-continued

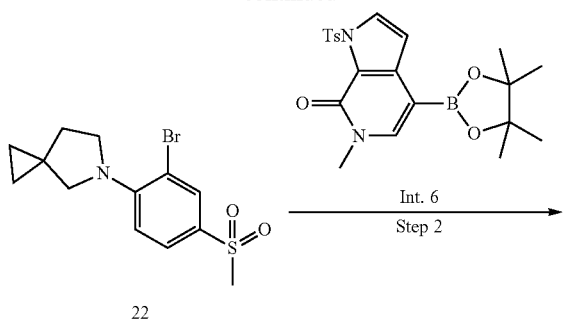

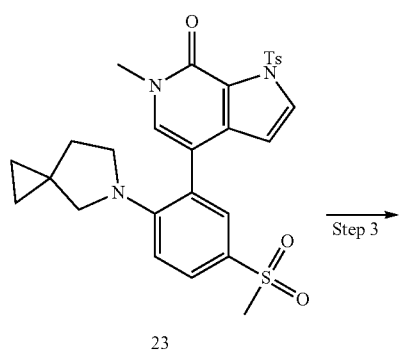

1. Synthesis of 5-(2-bromo-4-(methylsulfuryl)phenyl)-5-aza-spiro[2.4]heptane (compound 22)

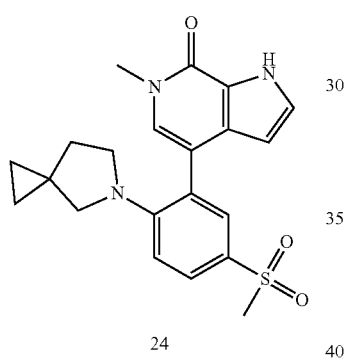

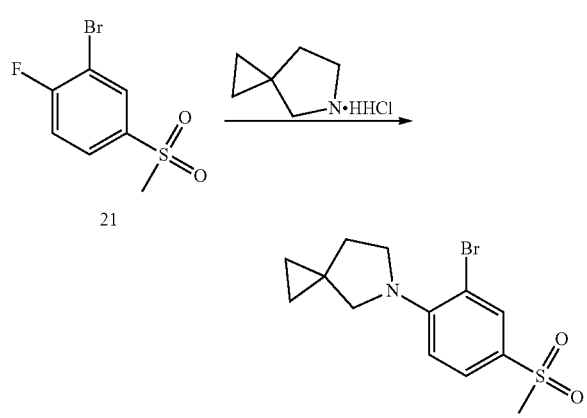

To a 50 mL reaction flask, were added compound 21 (1.26 g, 5 mmol), 5-azaspiro[2.4]heptane hydrochloride (798 mg, 6 mmol), sodium carbonate (1.27 g, 12 mmol), and DMSO (15 mL), and the system was reacted at 80° C. for 10 h. After completion of the reaction, the reaction solution was poured into 50 mL water, and extracted with 45 mL dichloromethane (15 mL×3). The organic phases were combined, dried over anhydrous sodium sulfate, and purified by column chromatography to obtain compound 22 (1.33 g) with a yield of 81%. MS: m/z 330.03 [M+H]$^+$.

2. Synthesis of 6-methyl-4-(5(methylsulfonyl)-2-(5-aza-spiro[2.4]heptan-5-yl)phenyl)-1-tosyl-1H-pyrrolo[2,3-c]pyridin-7(6H)-one (compound 23)

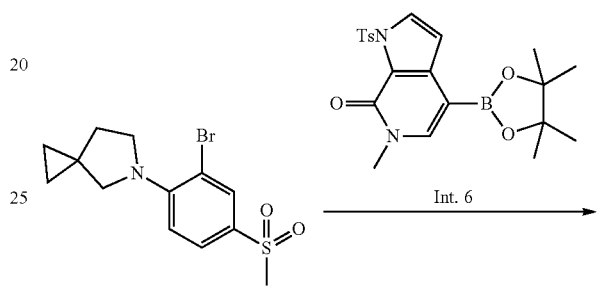

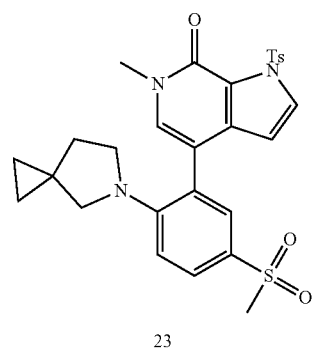

To a 30 mL reaction flask, were added compound 22 (329 mg, 1 mmol), compound 4 (556 mg, 1.3 mmol), Pd(PPh$_3$)$_4$ (69.2 mg, 0.06 mmol), Na$_2$CO$_3$ (212 mg, 2 mmol), and DMF/H$_2$O (5 mL/0.3 mL), and the system was reacted at 100° C. for 10 h under N$_2$ protection. After completion of the reaction, the reaction solution was poured into 30 mL water, and extracted with 30 mL dichloromethane (10 mL×3). The organic phases were combined, dried over anhydrous sodium sulfate, and purified by prep-TLC to obtain compound 23 (264 mg) with a yield of 48%.

MS: m/z 552.5 [M+H]$^+$.

3. Synthesis of 6-methyl-4-(5-(methylsulfonyl)-2-(5-aza-spiro[2.4]heptan-5-yl)phenyl)-1H-pyrrolo[2,3-c]pyridin-7(6H)-one (compound 24)

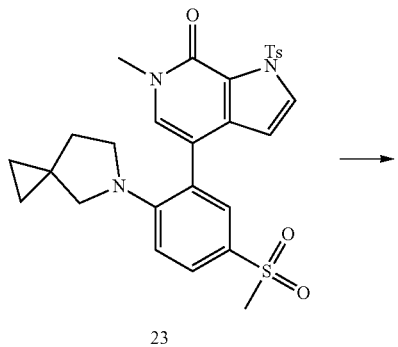

To a 30 mL reaction flask, were added compound 23 (80 mg, 0.15 mmol), THF (1 mL), and KOH (4 mL, 4 M), and the system was reacted at 80° C. for 3 h. After completion of the reaction, the reaction solution was poured into 30 mL water, and extracted with 30 mL dichloromethane (10 mL×3). The organic phases were combined, dried over anhydrous sodium sulfate, and purified by prep-TLC to obtain compound 24 (46 mg) with a yield of 78%. MS: m/z 398.6 [M+H]$^+$.

$^1$H NMR (400 MHz, DMSO) δ 12.22-12.01 (m, 1H), 7.68 (dd, J=8.8, 2.3 Hz, 1H), 7.56 (d, J=2.4 Hz, 1H), 7.34-7.21 (m, 2H), 6.94 (d, J=8.9 Hz, 1H), 6.02 (d, J=2.7 Hz, 1H), 3.68-3.50 (m, 3H), 3.25 (d, J=6.1 Hz, 2H), 3.13 (s, 3H), 2.98 (s, 2H), 1.64 (s, 2H), 0.44 (d, J=8.7 Hz, 4H).

Synthesis of 4-(5(ethylsulfonyl)-2-(5-aza-spiro[2.4]heptan-5-yl)phenyl)-6-methyl-1H-pyrrolo[2,3-c]pyridin-7(6H)-one (Compound 25)

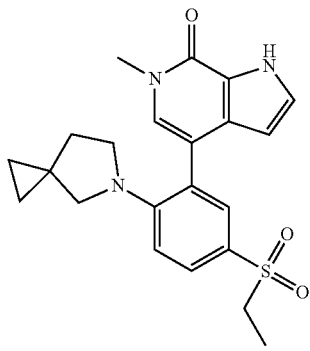

By the synthetic method and procedure of compound 24, the synthesis of compound 25 could be carried out with corresponding reagents. Among them, 2-bromo-1-fluoro-4-ethylsulfurylbenzene was used to replace 2-bromo-1-fluoro-4-methylsulfurylbenzene in the first step of the reaction, while other reaction reagents and conditions were completely consistent with those for synthesis of compound 24, and thus compound 25 was prepared.

MS: m/z 412.6 [M+H]$^+$ $^1$H NMR (400 MHz, DMSO) δ 12.22-12.01 (m, 1H), 7.68 (dd, J=8.8, 2.3 Hz, 1H), 7.56 (d, J=2.4 Hz, 1H), 7.34-7.21 (m, 2H), 6.94 (d, J=8.9 Hz, 1H), 6.02 (d, J=2.7 Hz, 1H), 3.68-3.50 (m, 3H), 3.4 (m, 2H), 3.25 (d, J=6.1 Hz, 2H), 2.98 (s, 2H), 1.64 (s, 2H), 1.2 (m, 3H), 0.44 (d, J=8.7 Hz, 4H).

Synthesis of 6-methyl-4-(5(methylsulfonyl)-2-(6-aza-spiro[2.5]octan-6-yl) phenyl)-1H-pyrrolo[2,3-c]pyridin-7(6H)-one (Compound 26)

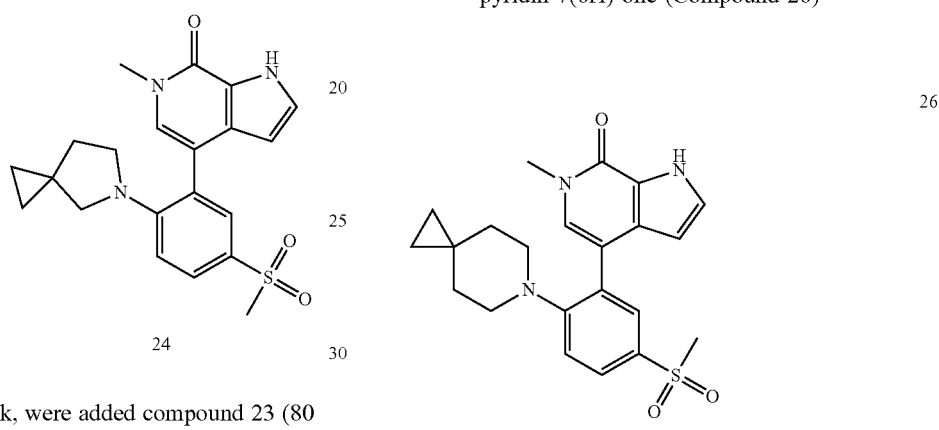

By the synthetic method and procedure of compound 24, the synthesis of compound 26 could be carried out with corresponding reagents. Among them, 6-aza-spiro[2.5]octane hydrochloride was used to replace 5-aza-spiro[2.4]heptane hydrochloride in the first step of the reaction, while other reaction reagents and conditions were completely consistent with those for synthesis of compound 24, and thus compound 26 was prepared.

MS: m/z 412.6 [M+H]$^+$ $^1$H NMR (400 MHz, DMSO) δ 11.98 (s, 1H), 7.44 (s, 1H), 7.28 (s, 1H), 7.17-7.05 (m, 3H), 6.16 (s, 1H), 3.57 (s, 3H), 3.20 (s, 3H), 2.78 (s, 4H), 1.23-1.13 (m, 4H), 0.19 (s, 4H).

Synthesis of 6-methyl-4-(5(methylsulfonyl)-2-(5-aza-spiro[2.5]octan-5-yl) phenyl)-1H-pyrrolo[2,3-c]pyridin-7(6H)-one (Compound 27)

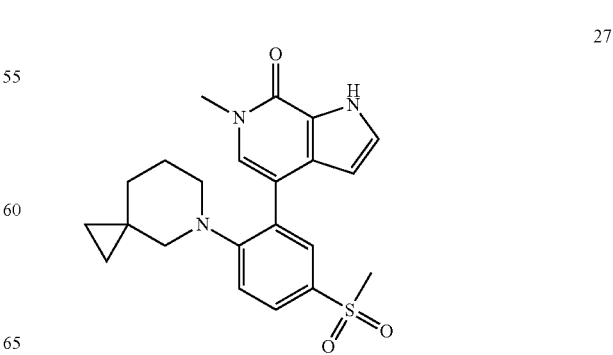

By the synthetic method and procedure of compound 24, the synthesis of compound 27 could be carried out with corresponding reagents. Among them, 5-aza-spiro[2.5]octane hydrochloride was used to replace 5-aza-spiro[2.4]heptane hydrochloride in the first step of the reaction, while other reaction reagents and conditions were completely consistent with those for synthesis of compound 24, and thus compound 27 was prepared.

MS: m/z 412.6 [M+H]+

1H NMR (400 MHz, DMSO) δ 12.01 (s, 1H), 7.46 (s, 1H), 7.29 (m, 1H), 7.19 (m, 1H), 7.15-7.09 (m, 1H), 7.03 (d, J=8.6 Hz, 1H), 6.22-6.12 (m, 1H), 3.57 (s, 3H), 3.32 (m, 1H), 3.20 (s, 3H), 2.97 (m, 1H), 2.77 (m, 1H), 2.47 (m, 1H), 1.51-1.34 (m, 2H), 1.32-1.08 (m, 2H), 0.85 (m, 1H), 0.71 (m, 1H), 0.14 (m, 1H), 0.04 (m, 1H).

Synthesis of 4-(5-(cyclopropylsulfonyl)-2-(5-aza-spiro[2.5]octan-5-yl)phenyl)-6-methyl-1H-pyrrolo[2,3-c]pyridin-7(6H)-one (Compound 28)

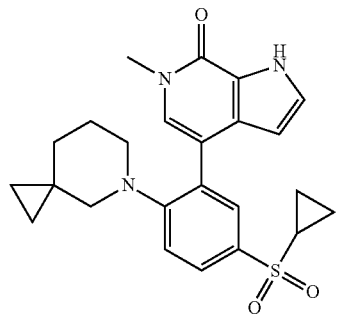

By the synthetic method and procedure of compound 24, the synthesis of compound 28 could be carried out with corresponding reagents. Among them, 5-aza-spiro[2.5]octane hydrochloride was used to replace 5-aza-spiro[2.4]heptane hydrochloride, as well as 2-bromo-1-fluoro-4-cyclopropylsulfurylbenzene was used to replace 2-bromo-1-fluoro-4-methylsulfurylbenzene in the first step of the reaction, while other reaction reagents and conditions were completely consistent with those for synthesis of compound 24, and thus compound 28 was prepared.

MS: m/z 438.6 [M+H]+

1H NMR (400 MHz, DMSO) δ 12.01 (s, 1H), 7.46 (s, 1H), 7.29 (m, 1H), 7.19 (m, 1H), 7.15-7.09 (m, 1H), 7.03 (d, J=8.6 Hz, 1H), 6.22-6.12 (m, 1H), 3.57 (s, 3H), 3.32 (m, 1H), 2.97 (m, 1H), 2.77 (m, 1H), 2.47 (m, 2H), 1.51-1.34 (m, 2H), 1.32-1.08 (m, 2H), 0.85 (m, 5H), 0.71 (m, 1H), 0.14 (m, 1H), 0.04 (m, 1H).

Synthesis of 4-(5-(cyclopropylsulfonyl)-2-(2-aza-spiro[3.3]heptan-2-yl) phenyl)-6-methyl-1H-pyrrolo[2,3-c]pyridin-7(6H)-one (Compound 29)

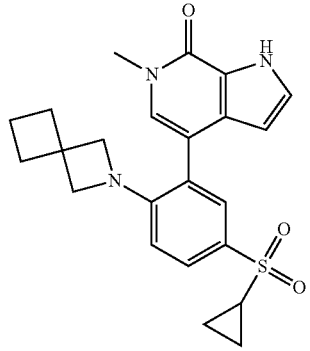

By the synthetic method and procedure of compound 24, the synthesis of compound 29 could be carried out with corresponding reagents. Among them, 2-aza-spiro[3.3]heptane hydrochloride was used to replace 5-aza-spiro[2.4]heptane hydrochloride, as well as 2-bromo-1-fluoro-4-cyclopropylsulfurylbenzene was used to replace 2-bromo-1-fluoro-4-methylsulfurylbenzene in the first step of the reaction, while other reaction reagents and conditions were completely consistent with those for synthesis of compound 24, and thus compound 29 was prepared.

MS: m/z 424.6 [M+H]+

1H NMR (400 MHz, DMSO-d6) δ 12.05 (s, 1H), 7.27 (t, J=2.4, 1H), 7.01 (s, 1H), 7.08 (dd, J1=2.4 Hz, J2=8.8 Hz, 1H), 6.98 (d, J=2.4 Hz, 1H), 6.51 (d, J=8.8 Hz, 1H), 6.08 (t, J=1.6 Hz, 1H), 3.56 (s, 3H), 3.40 (s, 4H), 2.45 (m, 1H), 1.95 (t, J=7.6 Hz, 4H), 1.68-1.63 (m, 2H), 1.01-0.85 (m, 4H).

Synthesis of 6-methyl-4-(5-(methylsulfonyl)-2-(2-aza-spiro[3.3]heptan-2-yl) phenyl)-1H-pyrrolo[2,3-c]pyridin-7(6H)-one (Compound 30)

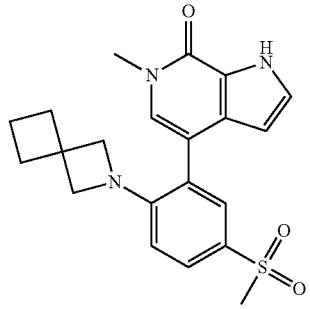

By the synthetic method and procedure of compound 24, the synthesis of compound 30 could be carried out with corresponding reagents. Among them, 2-aza-spiro[3.3]heptane hydrochloride was used to replace 5-aza-spiro[2.4]heptane hydrochloride in the first step of the reaction, while other reaction reagents and conditions were completely consistent with those for synthesis of compound 24, and thus compound 30 was prepared.

MS: m/z 398.6 [M+H]+.

¹H NMR (400 MHz, DMSO-d₆) δ 12.05 (s, 1H), 7.27 (t, J=2.4, 1H), 7.01 (s, 1H), 7.08 (dd, J, =2.4 Hz, J₂=8.8 Hz, 1H), 6.98 (d, J=2.4, 1H), 6.51 (d, J=8.8 Hz, 1H), 6.08 (t, J=1.6 Hz, 1H), 3.56 (s, 3H), 3.40 (s, 4H), 3.20 (s, 3H), 1.95 (t, J=7.6 Hz, 4H), 1.68-1.63 (m, 2H).

Compound 31 Synthesis of 6-methyl-4-(5-(oxetane-3-ylsulfonyl)-2-(2-aza-spiro[3.3]heptan-2-yl)phenyl)-1H-pyrrolo[2,3-c]pyridin-7(6H)-one

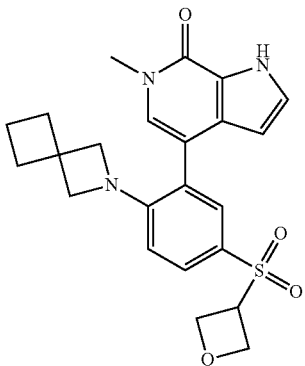

31

By the synthetic method and procedure of compound 24, the synthesis of compound 31 could be carried out with corresponding reagents. Among them, 2-aza-spiro[3.3]heptane hydrochloride was used to replace 5-aza-spiro[2.4]heptane hydrochloride, as well as 3-((3-bromo-4-fluorophenyl)sulfonyl)oxetane was used to replace 2-bromo-1-fluoro-4-methylsulfurylbenzene in the first step of the reaction, while other reaction reagents and conditions were completely consistent with those for synthesis of compound 24, and thus compound 31 was prepared.

MS: m/z 440.6 [M+H]⁺.

¹H NMR (400 MHz, DMSO-d₆) δ 12.05 (s, 1H), 7.27 (t, J=2.4 Hz, 1H), 7.01 (s, 1H), 7.08 (dd, J, =2.4 Hz, J₂=8.8 Hz, 1H), 6.98 (d, J=2.4, 1H), 6.51 (d, J=8.8 Hz, 1H), 6.08 (t, J=1.6 Hz, 1H), 4.95-4.65 (m, 4H), 4.72-4.61 (m, 1H), 3.56 (s, 3H), 3.40 (s, 4H), 1.95 (t, J=7.6 Hz, 4H), 1.68-1.63 (m, 2H).

Synthesis of 4-(5-(methylsulfonyl)-2-(2-aza-spiro[3.3]heptan-2-yl)phenyl)-6-methyl-1H-pyrrolo[2,3-c]pyridin-7(6H)-one (Compound 32)

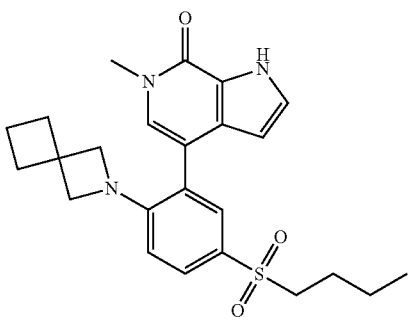

32

By the synthetic method and procedure of compound 24, the synthesis of compound 32 could be carried out with corresponding reagents. Among them, 2-aza-spiro[3.3]heptane hydrochloride was used to replace 5-aza-spiro[2.4]heptane hydrochloride, as well as 2-bromo-1-fluoro-4-butylsulfurylbenzene was used to replace 2-bromo-1-fluoro-4-methylsulfurylbenzene in the first step of the reaction, while other reaction reagents and conditions were completely consistent with those for synthesis of compound 24, and thus compound 32 was prepared.

MS: m/z 440.6 [M+H]⁺.

¹H NMR (400 MHz, DMSO-d₆) δ 12.05 (s, 1H), 7.27 (t, J=2.4, 1H), 7.01 (s, 1H), 7.08 (dd, J₁=2.4 Hz, J₂=8.8 Hz, 1H), 6.98 (d, J=2.4, 1H), 6.51 (d, J=8.8 Hz, 1H), 6.08 (t, J=1.6 Hz, 1H), 3.56 (s, 3H), 3.40 (s, 4H), 3.25 (m, 2H), 1.95 (t, J=7.6 Hz, 4H), 1.68-1.63 (m, 2H), 1.58-1.43 (m, 2H), 1.38-1.23 (m, 2H), 1.08-0.93 (m, 3H).

Synthesis of 4-(5-(ethylsulfonyl)-2-(2-aza-spiro[3.3]heptan-2-yl)phenyl)-6-methyl-1H-pyrrolo[2,3-c]pyridin-7(6H)-one (Compound 33)

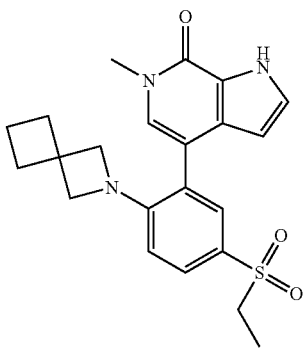

33

By the synthetic method and procedure of compound 24, the synthesis of compound 33 could be carried out with corresponding reagents. Among them, 2-aza-spiro[3.3]heptane hydrochloride was used to replace 5-aza-spiro[2.4]heptane hydrochloride, as well as 2-bromo-1-fluoro-4-ethylsulfurylbenzene was used to replace 2-bromo-1-fluoro-4-methylsulfurylbenzene in the first step of the reaction, while other reaction reagents and conditions were completely consistent with those for synthesis of compound 24, and thus compound 33 was prepared.

MS: m/z 412.6 [M+H]⁺.

¹H NMR (400 MHz, DMSO-d₆) δ 12.05 (s, 1H), 7.27 (t, J=2.4 Hz, 1H), 7.01 (s, 1H), 7.08 (dd, J₁=2.4 Hz, J₂=8.8 Hz, 1H), 6.98 (d, J=2.4, 1H), 6.51 (d, J=8.8 Hz, 1H), 6.08 (t, J=1.6 Hz, 1H), 3.56 (s, 3H), 3.40 (s, 4H), 3.25 (m, 2H), 1.95 (t, J=7.6 Hz, 4H), 1.68-1.63 (m, 2H), 1.25-1.13 (m, 3H).

Synthesis of 6-methyl-4-(5-(methylsulfonyl)-2-(2-oxa-6-aza-spiro[3.3]heptan-6-yl)phenyl)-1H-pyrrolo[2,3-c]pyridin-7(6H)-one (Compound 34)

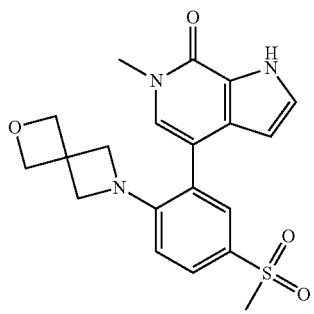

34

By the synthetic method and procedure of compound 24, the synthesis of compound 34 could be carried out with corresponding reagents. Among them, 2-oxa-6-aza-spiro[3.3]heptane hydrochloride was used to replace 5-aza-spiro[2.4]heptane hydrochloride in the first step of the reaction, while other reaction reagents and conditions were completely consistent with those for synthesis of compound 24, and thus compound 34 was prepared.

MS: m/z 400.5 [M+H]$^+$.

$^1$H NMR (400 MHz, DMSO): δ 12.10 (s, 1H), 7.29 (t, J=2.5 Hz, 1H), 7.14-7.06 (m, 2H), 7.02 (d, J=2.5 Hz, 1H), 6.57 (d, J=8.7 Hz, 1H), 6.08 (s, 1H), 4.52 (s, 4H), 3.62 (s, 4H), 3.58 (s, 3H), 3.20 (s, 3H).

Synthesis of 4-(5-(ethylsulfonyl)-2-(2-oxa-6-aza-spiro[3.3]heptan-6-yl) phenyl)-6-methyl-1H-pyrrolo[2,3-c]pyridin-7(6H)-one (Compound 35)

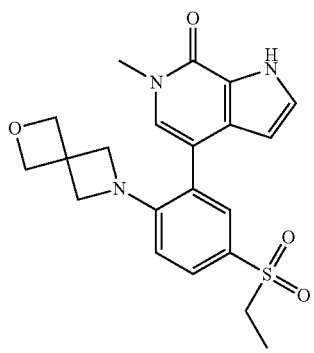

35

By the synthetic method and procedure of compound 24, the synthesis of compound 35 could be carried out with corresponding reagents. Among them, 2-oxa-6-aza-spiro[3.3]heptane hydrochloride was used to replace 5-aza-spiro[2.4]heptane hydrochloride, as well as 2-bromo-1-fluoro-4-ethylsulfurylbenzene was used to replace 2-bromo-1-fluoro-4-methylsulfurylbenzene in the first step of the reaction, while other reaction reagents and conditions were completely consistent with those for synthesis of compound 24, and thus compound 35 was prepared.

MS: m/z 414.5 [M+H]$^+$.

$^1$H NMR (400 MHz, DMSO): δ 12.10 (s, 1H), 7.29 (t, J=2.5 Hz, 1H), 7.14-7.06 (m, 2H), 7.02 (d, J=2.5 Hz, 1H), 6.57 (d, J=8.7 Hz, 1H), 6.08 (s, 1H), 4.52 (s, 4H), 3.62 (s, 4H), 3.58 (s, 3H), 3.25 (m, 2H), 1.25 (m, 3H).

Synthesis of 4-(5-(butylsulfonyl)-2-(2-oxa-6-aza-spiro[3.3]heptan-6-yl) phenyl)-6-methyl-1H-pyrrolo[2,3-c]pyridin-7(6H)-one (Compound 36)

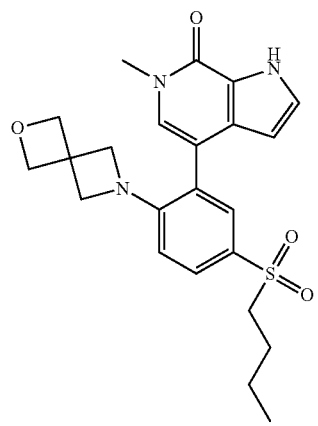

36

By the synthetic method and procedure of compound 24, the synthesis of compound 36 could be carried out with corresponding reagents. Among them, 2-oxa-6-aza-spiro[3.3]heptane hydrochloride was used to replace 5-aza-spiro[2.4]heptane hydrochloride, as well as 2-bromo-1-fluoro-4-butylsulfurylbenzene was used to replace 2-bromo-1-fluoro-4-methylsulfurylbenzene in the first step of the reaction, while other reaction reagents and conditions were completely consistent with those for synthesis of compound 24, and thus compound 36 was prepared.

MS: m/z 442.6 [M+H]$^+$.

$^1$H NMR (400 MHz, DMSO): δ 12.10 (s, 1H), 7.29 (t, J=2.5 Hz, 1H), 7.14-7.06 (m, 2H), 7.02 (d, J=2.5 Hz, 1H), 6.57 (d, J=8.7 Hz, 1H), 6.08 (s, 1H), 4.52 (s, 4H), 3.62 (s, 4H), 3.58 (s, 3H), 3.25 (m, 2H), 1.58-1.43 (m, 2H), 1.38-1.23 (m, 2H), 1.08-0.93 (m, 3H).

Synthesis of 4-(5-(cyclopropylsulfonyl)-2-(2-oxa-6-aza-spiro[3.3]heptan-6-yl) phenyl)-6-methyl-1H-pyrrolo[2,3-c]pyridin-7(6H)-one (Compound 37)

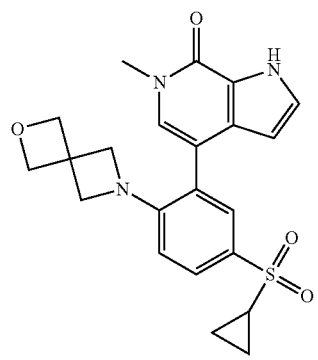

37

By the synthetic method and procedure of compound 24, the synthesis of compound 37 could be carried out with corresponding reagents. Among them, 2-oxa-6-aza-spiro[3.3]heptane hydrochloride was used to replace 5-aza-spiro[2.4]heptane hydrochloride, as well as 2-bromo-1-fluoro-4-cyclopropylsulfurylbenzene was used to replace 2-bromo-1-fluoro-4-methylsulfurylbenzene in the first step of the reaction, while other reaction reagents and conditions were completely consistent with those for synthesis of compound 24, and thus compound 37 was prepared.

MS: m/z 426.5 [M+H]⁺.

¹H NMR (400 MHz, DMSO): δ 12.10 (s, 1H), 7.29 (t, J=2.5 Hz, 1H), 7.14-7.06 (m, 2H), 7.02 (d, J=2.5 Hz, 1H), 6.57 (d, J=8.7 Hz, 1H), 6.08 (s, 1H), 4.52 (s, 4H), 3.65 (s, 4H), 3.58 (s, 3H), 2.45 (m, 1H), 1.01-0.85 (m, 4H).

Synthesis of ethyl 6-(2-(6-methyl-7-oxo-6,7-dihydro-1H-pyrrolo[2,3-c] pyridin-4-yl)-4-(methylsulfonyl)phenyl)-6-azaspiro[2.5]octane-1-carboxylate (Compound 38)

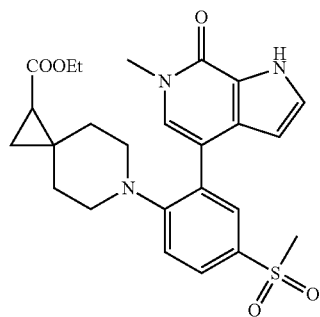

38

By the synthetic method and procedure of compound 24, the synthesis of compound 38 could be carried out with corresponding reagents. Among them, 1-ethyl formate-6-aza-spiro[2.5]octane hydrochloride was used to replace 5-aza-spiro[2.4]heptane in the first step of the reaction, while other reaction reagents and conditions were completely consistent with those for synthesis of compound 24, and thus compound 38 was prepared.

MS: m/z 484.6 [M+H]⁺.

¹H NMR (400 MHz, DMSO) δ 12.03 (s, 1H), 7.78 (dd, J=8.5, 2.3 Hz, 1H), 7.71 (d, J=2.3 Hz, 1H), 7.44 (s, 1H), 7.29 (t, J=2.7 Hz, 1H), 7.24 (d, J=8.6 Hz, 1H), 6.14 (t, J=2.3 Hz, 1H), 4.05 (m, 2H), 3.58 (s, 3H), 3.19 (s, 3H), 3.05-2.82 (m, 4H), 1.50-1.36 (m, 3H), 1.23-1.09 (m, 5H), 0.93-0.73 (m, 2H).

Synthesis of 6-(2-(6-methyl-7-oxo-6,7-dihydro-1H-pyrrolo[2,3-c]pyridin-4-yl)-4-(methylsulfonyl)phenyl)-6-aza-spiro[2.5]octan-1-carboxylic acid (Compound 39)

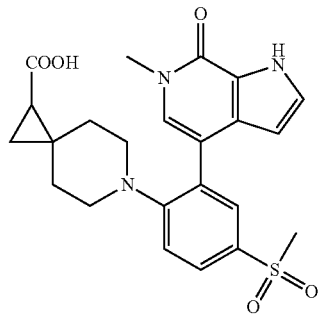

39

By the synthetic method and procedure of compound 24, the synthesis of compound 39 could be carried out with corresponding reagents. Among them, 1-formic acid-6-aza-spiro[2.5]octane hydrochloride was used to replace 5-aza-spiro[2.4]heptane in the first step of the reaction, while other reaction reagents and conditions were completely consistent with those for synthesis of compound 24, and thus compound 39 was prepared.

MS: m/z 456.5 [M+H]⁺.

¹H NMR (400 MHz, DMSO) δ 12.03 (s, 1H), 7.78 (dd, J=8.5, 2.3 Hz, 1H), 7.71 (d, J=2.3 Hz, 1H), 7.44 (s, 1H), 7.29 (t, J=2.7 Hz, 1H), 7.24 (d, J=8.6 Hz, 1H), 6.14 (t, J=2.3 Hz, 1H), 3.58 (s, 3H), 3.19 (s, 3H), 3.05-2.82 (m, 4H), 1.50-1.36 (m, 3H), 1.23-1.09 (m, 2H), 0.93-0.73 (m, 2H).

Synthesis of N-(3-(7-oxo-6-(trideuteromethyl)-6,7-dihydro-1H-pyrrolo[2,3-c] pyridin-4-yl)-4-(5-aza-spiro[2.4]heptan-5-yl)phenyl)ethylsulfonamide (Compound 40)

Synthesis of 4-bromo-6-deuteromethyl-1-tosyl-1H-pyrrolo[2,3-c]pyridin-7(6H)-one (Int. 7)

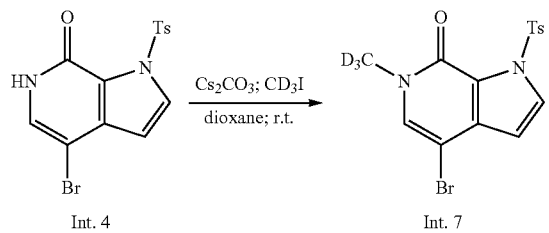 [SMILES: Cc1ccc(S(=O)(=O)n2ccc3c(Br)c[nH]c(=O)c32)cc1 ; [2H]C([2H])([2H])n1cc(Br)c2ccn(S(=O)(=O)c3ccc(C)cc3)c2c1=O]

1,4-Dioxane (2 L), intermediate compound 4 (79 g, 0.21 mol), cesium carbonate (118 g, 0.32 mol), and deuteromethyl iodide (92 g, 0.64 mol) were added to a 5 L reaction flask and stirred overnight at room temperature. After completion of the reaction, the solution was filtered and rotatory evaporated to obtain intermediate compound 7 (75 g) with a yield of 94%.

Synthesis of 6-deuteromethyl-4-(4,4,5,5-tetramethyl-1,3,2-dioxaborolan-2-yl)-1-tosyl-1H-pyrrolo[2,3-c]pyridin-7(6H)-one (Int. 8)

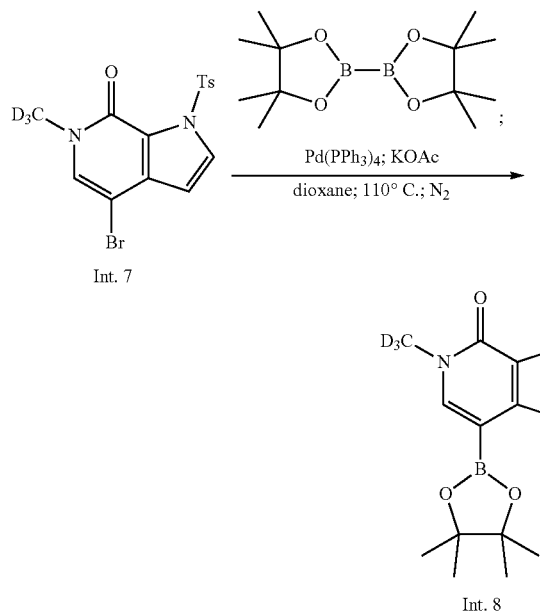

1,4-Dioxane (800 mL), intermediate compound 57 (38.3 g, 0.1 mol), bis(pinacolato)diboron (102 g, 0.4 mol), and potassium acetate (20.4 g, 0.2 mol) were added to a 2 L reaction flask, and after purging N₂ three times, tetrakis(triphenylphosphine)palladium (12 g, 0.01 mol) was added. Followed by purging N₂ three times, the reaction was warmed up to 110° C., and stirred overnight. After completion of the reaction, the reaction mixture was purified by filtration and column chromatography, to provide intermediate compound 8 (40.2 g) with a yield of 93%.

Synthesis of compound 40

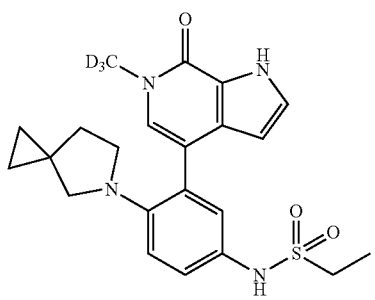

By the synthetic method and procedure of compound 7, the synthesis of compound 40 could be carried out with corresponding reagents. Among them, Int. 8 was used to replace Int. 6 in the third step of the reaction, while other reaction reagents and conditions were completely consistent with those for synthesis of compound 7, and thus compound 40 was prepared.

MS: m/z 430.5 [M+H]⁺.

¹H NMR (400 MHz, DMSO) δ 12.02 (s, 1H), 9.31 (s, 1H), 7.75-7.46 (m, 1H), 7.26 (t, J=2.7 Hz, 1H), 7.16 (s, 1H), 7.13-6.99 (m, 2H), 6.83 (d, J=8.8 Hz, 1H), 3.09 (t, J=6.6 Hz, 2H), 2.98 (q, J=7.3 Hz, 2H), 2.79 (s, 2H), 1.61 (t, J=6.6 Hz, 2H), 1.20 (t, J=7.3 Hz, 3H), 0.38 (m, 4H).

Synthesis of N-(3-(6-trideuteromethyl-7-oxo-6,7-dihydro-1H-pyrrolo[2,3-c] pyridin-4-yl)-4-(6-azaspiro[2.5]octan-5-yl)phenyl)ethylsulfonamide (Compound 41)

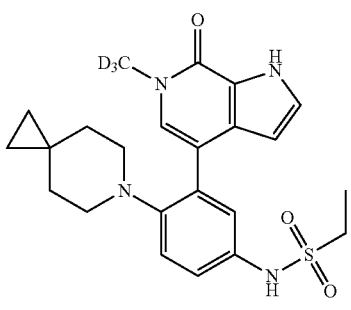

By the synthetic method and procedure of compound 7, the synthesis of compound 41 could be carried out with corresponding reagents. Among them, 6-aza-spiro[2.5]octane hydrochloride was used to substitute 5-aza-spiro[2.4]heptane hydrochloride, and Int. 8 was used to replace Int. 6 in the third step of the reaction, while other reaction reagents and conditions were completely consistent with those for synthesis of compound 7, and thus compound 41 was prepared.

MS: m/z 444.6 [M+H]⁺.

¹H NMR (400 MHz, DMSO) δ 11.98 (s, 1H), 9.54 (s, 1H), 7.44 (s, 1H), 7.28 (s, 1H), 7.17 (s, 1H), 7.13 (d, J=7.8 Hz, 1H), 7.06 (d, J=8.4 Hz, 1H), 6.17 (s, 1H), 3.09-3.02 (m, 2H), 2.78 (s, 4H), 1.23-1.13 (m, 7H), 0.19 (s, 4H).

Synthesis of N-(3-(6-trideuteromethyl-7-oxo-6,7-dihydro-1H-pyrrolo[2,3-c] pyridin-4-yl)-4-(5-azaspiro[2.5]octan-5-yl)phenyl)ethylsulfonamide (Compound 42)

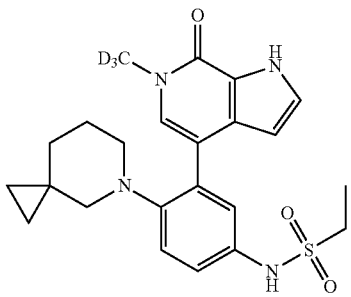

By the synthetic method and procedure of compound 7, the synthesis of compound 42 could be carried out with corresponding reagents. Among them, 5-aza-spiro[2.5]octane hydrochloride was used to substitute 5-aza-spiro[2.4]heptane hydrochloride, and Int. 8 was used to replace Int. 6 in the third step of the reaction, while other reaction reagents and conditions were completely consistent with those for synthesis of compound 7, and thus compound 42 was prepared.

MS: m/z 444.6 [M+H]$^+$.

$^1$H NMR (400 MHz, DMSO) δ 12.01 (s, 1H), 9.55 (s, 1H), 7.46 (s, 1H), 7.29 (m, 1H), 7.19 (m, 1H), 7.15-7.09 (m, 1H), 7.03 (d, J=8.6 Hz, 1H), 6.22-6.12 (m, 1H), 3.32 (m, 1H), 3.04 (m, 2H), 2.97 (m, 1H), 2.77 (m, 1H), 2.47 (m, 1H), 1.51-1.34 (m, 2H), 1.32-1.08 (m, 5H), 0.85 (m, 1H), 0.71 (m, 1H), 0.14 (m, 1H), 0.04 (m, 1H).

Synthesis of N-(3-(6-trideuteromethyl-7-oxo-6,7-dihydro-1H-pyrrolo[2,3-c] pyridin-4-yl)-4-(2-aza-spiro[3.3]heptan-2-yl)phenyl)cyclopropanesulfonamide (Compound 43)

43

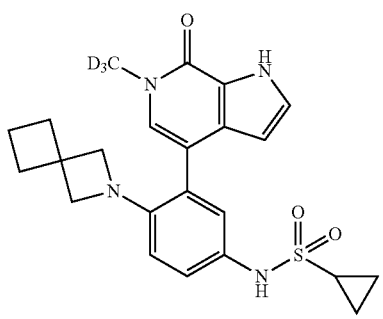

By the synthetic method and procedure of compound 7, the synthesis of compound 43 could be carried out with corresponding reagents. Among them, 2-aza-spiro[3.3]heptane hydrochloride was used to substitute 5-aza-spiro[2.4]heptane hydrochloride in the first step of the reaction, and Int. 8 was used to replace Int. 6 in the third step of the reaction, and cyclopropylsulfonyl chloride was used to substitute ethanesulfonyl chloride in the fourth step of the reaction, while other reaction reagents and conditions were completely consistent with those for synthesis of compound 7, and thus compound 43 was prepared.

MS: m/z 442.6 [M+H]$^+$.

$^1$H NMR (400 MHz, DMSO-d$_6$) δ 12.05 (s, 1H), 9.20 (s, 1H), 7.27 (t, J=2.4, 1H), 7.01 (s, 1H), 7.08 (dd, J$_1$=2.4 Hz, J$_2$=8.8 Hz, 1H), 6.98 (d, J=2.4 Hz, 1H), 6.51 (d, J=8.8 Hz, 1H), 6.08 (t, J=1.6 Hz, 1H), 3.40 (s, 4H), 2.45 (m, 1H), 1.95 (t, J=7.6 Hz, 4H), 1.68-1.63 (m, 2H), 0.95-0.80 (m, 4H).

Synthesis of N-(3-(6-trideuteromethyl-7-oxo-6,7-dihydro-1H-pyrrolo[2,3-c] pyridin-4-yl)-4-(2-aza-spiro[3.3]heptan-2-yl)phenyl)methanesulfonamide (Compound 44)

44

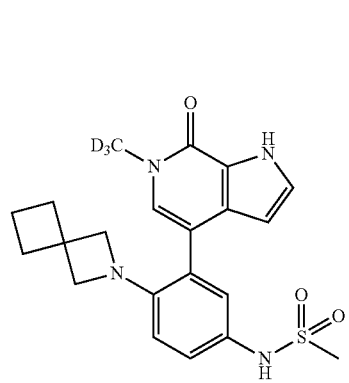

By the synthetic method and procedure of compound 7, the synthesis of compound 44 could be carried out with corresponding reagents. Among them, 2-aza-spiro[3.3]heptane hydrochloride was used to substitute 5-aza-spiro[2.4]heptane hydrochloride in the first step of the reaction, and Int. 8 was used to replace Int. 6 in the third step of the reaction, and methanesulfonyl chloride was used to substitute ethanesulfonyl chloride in the fourth step of the reaction, while other reaction reagents and conditions were completely consistent with those for synthesis of compound 7, and thus compound 44 was prepared.

MS: m/z 415.6 [M+H]$^+$.

$^1$H NMR (400 MHz, DMSO-d$_6$) δ 12.05 (s, 1H), 9.20 (s, 1H), 7.27 (t, J=2.4, 1H), 7.01 (s, 1H), 7.08 (dd, J$_1$=2.4 Hz, J$_2$=8.8 Hz, 1H), 6.98 (d, J=2.4 Hz, 1H), 6.51 (d, J=8.8 Hz, 1H), 6.08 (t, J=1.6 Hz, 1H), 3.40 (s, 4H), 2.88 (s, 3H), 1.95 (t, J=7.6 Hz, 4H), 1.68-1.63 (m, 2H).

Synthesis of N-(3-(6-trideuteromethyl-7-oxo-6,7-dihydro-1H-pyrrolo[2,3-c] pyridin-4-yl)-4-(2-aza-spiro[3.3]heptan-2-yl)phenyl) oxetane-3-sulfonamide (Compound 45)

45

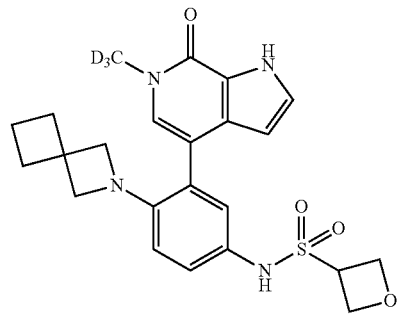

By the synthetic method and procedure of compound 7, the synthesis of compound 45 could be carried out with corresponding reagents. Among them, 2-aza-spiro[3.3]heptane hydrochloride was used to substitute 5-aza-spiro[2.4]heptane hydrochloride in the first step of the reaction, and Int. 8 was used to replace Int. 6 in the third step of the reaction, and oxetane-3-sulfonyl chloride was used to substitute ethanesulfonyl chloride in the fourth step of the reaction, while other reaction reagents and conditions were completely consistent with those for synthesis of compound 7, and thus compound 45 was prepared.

MS: m/z 458.6 [M+H]$^+$.

$^1$H NMR (400 MHz, DMSO-d$_6$) δ 12.05 (s, 1H), 9.20 (s, 1H), 7.27 (t, J=2.4 Hz, 1H), 7.01 (s, 1H), 7.08 (dd, J, =2.4 Hz, J$_2$=8.8 Hz, 1H), 6.98 (d, J=2.4 Hz, 1H), 6.51 (d, J=8.8 Hz, 1H), 6.08 (t, J=1.6 Hz, 1H), 4.90-4.60 (m, 4H), 4.60-4.48 (m, 1H), 3.40 (s, 4H), 1.95 (t, J=7.6 Hz, 4H), 1.68-1.63 (m, 2H).

Synthesis of N-(3-(6-trideuteromethyl-7-oxo-6,7-dihydro-1H-pyrrolo[2,3-c] pyridin-4-yl)-4-(2-aza-spiro[3.3]heptan-2-yl)phenyl)butane-1-sulfonamide (Compound 46)

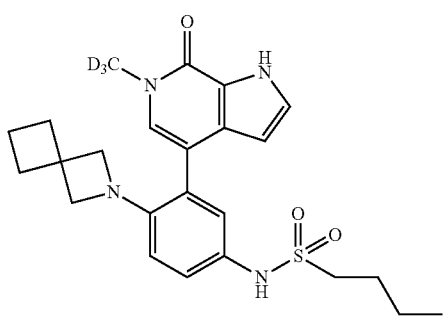

46

By the synthetic method and procedure of compound 7, the synthesis of compound 46 could be carried out with corresponding reagents. Among them, 2-aza-spiro[3.3]heptane hydrochloride was used to substitute 5-aza-spiro[2.4]heptane hydrochloride in the first step of the reaction, and Int. 8 was used to replace Int. 6 in the third step of the reaction, and butanesulfonyl chloride was used to substitute ethanesulfonyl chloride in the fourth step of the reaction, while other reaction reagents and conditions were completely consistent with those for synthesis of compound 7, and thus compound 46 was prepared.

MS: m/z 458.6 [M+H]$^+$.

$^1$H NMR (400 MHz, DMSO): 12.07 (s, 1H), 9.29 (s, 1H), 7.29 (t, J=2.6 Hz, 1H), 7.09 (s, 1H), 7.05 (dd, J=8.5, 2.3 Hz, 1H), 6.96 (d, J=2.5 Hz, 1H), 6.49 (d, J=8.7 Hz, 1H), 6.12-6.03 (m, 1H), 3.40 (s, 4H), 2.98-2.89 (m, 2H), 1.96 (t, J=7.6 Hz, 4H), 1.65 (dq, J=15.1, 7.5 Hz, 4H), 1.36 (dq, J=14.8, 7.4 Hz, 2H), 0.85 (t, J=7.3 Hz, 3H).

Synthesis of N-(3-(6-trideuteromethyl-7-oxo-6,7-dihydro-1H-pyrrolo[2,3-c] pyridin-4-yl)-4-(2-aza-spiro[3.3]heptan-2-yl)phenyl)ethanesulfonamide (Compound 47)

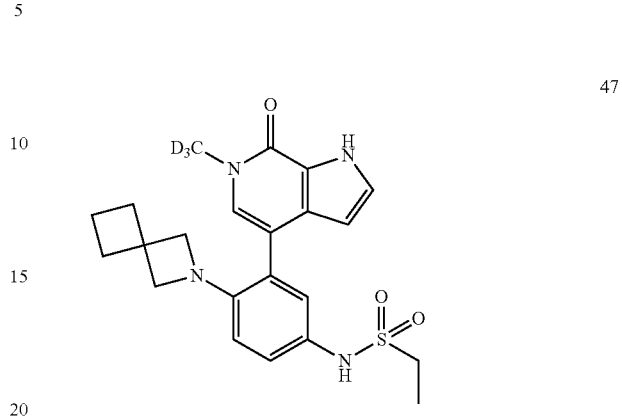

47

By the synthetic method and procedure of compound 7, the synthesis of compound 47 could be carried out with corresponding reagents. Among them, 2-aza-spiro[3.3]heptane hydrochloride was used to substitute 5-aza-spiro[2.4]heptane hydrochloride in the first step of the reaction, and Int. 8 was used to replace Int. 6 in the third step of the reaction, while other reaction reagents and conditions were completely consistent with those for synthesis of compound 7, and thus compound 47 was prepared.

MS: m/z 429.5 [M+H]$^+$.

$^1$H NMR (400 MHz, DMSO-d$_6$) δ 12.05 (s, 1H), 9.20 (s, 1H), 7.27 (t, J=2.4 Hz, 1H), 7.01 (s, 1H), 7.08 (dd, J, =2.4 Hz, J$_2$=8.8 Hz, 1H), 6.98 (d, J=2.4 Hz, 1H), 6.51 (d, J=8.8 Hz, 1H), 6.08 (t, J=1.6 Hz, 1H), 3.40 (s, 4H), 2.92 (t, J=8 Hz, 2H), 1.95 (t, J=7.6 Hz, 4H), 1.68-1.63 (m, 2H), 0.83 (t, J=8 Hz, 3H).

Synthesis of N-(3-(6-trideuteromethyl-7-oxo-6,7-dihydro-1H-pyrrolo[2,3-c] pyridin-4-yl)-4-(2-oxa-6-aza-spiro[3.3]heptan-6-yl)phenyl)methanesulfonamide (Compound 48)

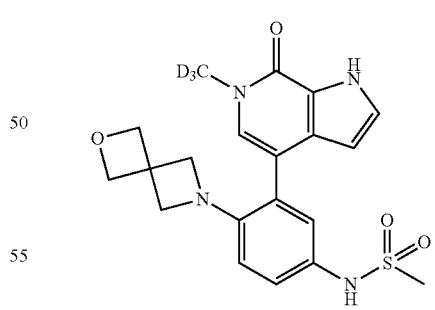

48

By the synthetic method and procedure of compound 7, the synthesis of compound 48 could be carried out with corresponding reagents. Among them, 2-oxa-6-aza-spiro[3.3]heptane hydrochloride was used to substitute 5-aza-spiro[2.4]heptane hydrochloride in the first step of the reaction, and Int. 8 was used to replace Int. 6 in the third step of the reaction, and methanesulfonyl chloride was used to substitute ethanesulfonyl chloride in the fourth step of the reaction, while other reaction reagents and conditions were completely consistent with those for synthesis of compound 7, and thus compound 48 was prepared.

MS: m/z 418.5 [M+H]+.

1H NMR (400 MHz, DMSO): δ 12.10 (s, 1H), 9.21 (s, 1H), 7.29 (t, J=2.5 Hz, 1H), 7.14-7.06 (m, 2H), 7.02 (d, J=2.5 Hz, 1H), 6.57 (d, J=8.7 Hz, 1H), 6.08 (s, 1H), 4.52 (s, 4H), 3.62 (s, 4H), 2.89 (s, 3H).

Synthesis of N-(3-(6-trideuteromethyl-7-oxo-6,7-dihydro-1H-pyrrolo[2,3-c] pyridin-4-yl)-4-(2-oxa-6-aza-spiro[3.3]heptan-6-yl)phenyl)ethanesulfonamide (Compound 49)

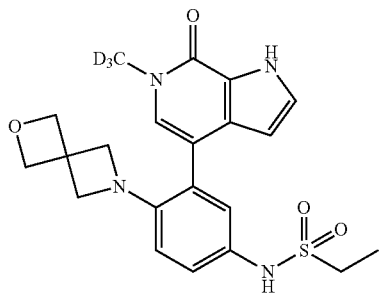

49

By the synthetic method and procedure of compound 7, the synthesis of compound 49 could be carried out with corresponding reagents. Among them, 2-oxa-6-aza-spiro [3.3]heptane hydrochloride was used to substitute 5-aza-spiro[2.4]heptane hydrochloride in the first step of the reaction, and Int. 8 was used to replace Int. 6 in the third step of the reaction, while other reaction reagents and conditions were completely consistent with those for synthesis of compound 7, and thus compound 49 was prepared.

MS: m/z 432.5 [M+H]+.

1H NMR (400 MHz, DMSO): δ 12.11 (s, 1H), 9.35 (s, 1H), 7.30 (t, J=2.7 Hz, 1H), 7.10 (dd, J=8.5, 2.6 Hz, 2H), 7.02 (d, J=2.5 Hz, 1H), 6.56 (d, J=8.7 Hz, 1H), 6.07 (s, 1H), 4.52 (s, 4H), 3.61 (s, 4H), 2.98 (q, J=7.3 Hz, 2H), 1.21 (t, J=7.3 Hz, 3H).

Synthesis of N-(3-(6-trideuteromethyl-7-oxo-6,7-dihydro-1H-pyrrolo[2,3-c] pyridin-4-yl)-4-(2-oxa-6-aza-spiro[3.3]heptan-6-yl)phenyl) butane-1-sulfonamide (Compound 50)

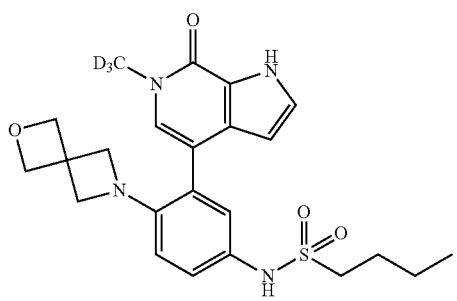

50

By the synthetic method and procedure of compound 7, the synthesis of compound 50 could be carried out with corresponding reagents. Among them, 2-oxa-6-aza-spiro [3.3]heptane hydrochloride was used to substitute 5-aza-spiro[2.4]heptane hydrochloride in the first step of the reaction, and Int. 8 was used to replace Int. 6 in the third step of the reaction, and butanesulfonyl chloride was used to substitute ethanesulfonyl chloride in the fourth step of the reaction, while other reaction reagents and conditions were completely consistent with those for synthesis of compound 7, and thus compound 50 was prepared.

MS: m/z 460.6 [M+H]+.

1H NMR (400 MHz, DMSO): δ 12.11 (s, 1H), 9.34 (s, 1H), 7.29 (t, J=2.7 Hz, 1H), 7.11 (d, J=2.5 Hz, 1H), 7.09 (s, 1H), 7.00 (d, J=2.5 Hz, 1H), 6.56 (d, J=8.7 Hz, 1H), 6.06 (s, 1H), 4.52 (s, 4H), 3.61 (s, 4H), 3.02-2.90 (m, 2H), 1.65 (dt, J=15.2, 7.6 Hz, 2H), 1.36 (dq, J=14.7, 7.4 Hz, 2H), 0.85 (t, J=7.3 Hz, 3H).

Synthesis of N-(3-(6-trideuteromethyl-7-oxo-6,7-dihydro-1H-pyrrolo[2,3-c] pyridin-4-yl)-4-(2-oxa-6-aza-spiro[3.3]heptan-6-yl)phenyl) cyclopropane-sulfonamide (Compound 51)

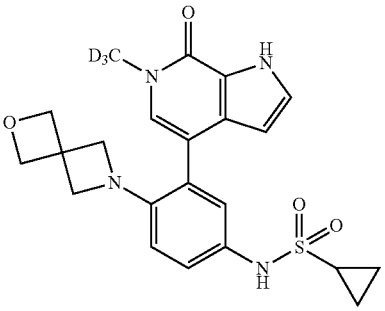

51

By the synthetic method and procedure of compound 7, the synthesis of compound 51 could be carried out with corresponding reagents. Among them, 2-oxa-6-aza-spiro [3.3]heptane hydrochloride was used to substitute 5-aza-spiro[2.4]heptane hydrochloride in the first step of the reaction, and Int. 8 was used to replace Int. 6 in the third step of the reaction, and cyclopropylsulfonyl chloride was used to substitute ethanesulfonyl chloride in the fourth step of the reaction, while other reaction reagents and conditions were completely consistent with those for synthesis of compound 7, and thus compound 51 was prepared.

MS: m/z 444.5 [M+H]+.

1H NMR (400 MHz, DMSO): δ 12.10 (s, 1H), 9.25 (s, 1H), 7.29 (t, J=2.7 Hz, 1H), 7.17-7.07 (m, 2H), 7.03 (d, J=2.5 Hz, 1H), 6.55 (d, J=8.6 Hz, 1H), 6.06 (d, J=2.2 Hz, 1H), 4.52 (s, 4H), 3.61 (s, 4H), 2.45 (m, 1H), 0.95-0.80 (m, 4H).

Synthesis of ethyl 6-(4-(ethylsulfonamide)-6-(6-trideuteromethyl-7-oxo-6,7-dihydro-1H-pyrrolo[2,3-c]pyridin-4-yl)cyclohexane-1,3-diene-1-yl)-6-aza-spiro[2.5]octan-1-carboxylate (Compound 52)

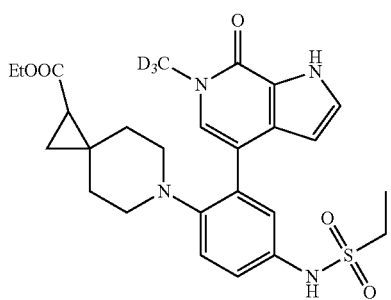

By the synthetic method and procedure of compound 7, the synthesis of compound 52 could be carried out with corresponding reagents. Among them, 1-ethyl formate-6-aza-spiro[2.5]octane hydrochloride was used to substitute 5-aza-spiro[2.4]heptane hydrochloride in the first step of the reaction, and Int. 8 was used to replace Int. 6 in the third step of the reaction, while other reaction reagents and conditions were completely consistent with those for synthesis of compound 7, and thus compound 52 was prepared.

MS: m/z 518.6 [M+H]$^+$.

$^1$H NMR (400 MHz, DMSO): δ 12.03 (s, 1H), 9.54 (s, 1H), 7.78 (dd, J=8.5, 2.3 Hz, 1H), 7.71 (d, J=2.3 Hz, 1H), 7.44 (s, 1H), 7.29 (t, J=2.7 Hz, 1H), 7.24 (d, J=8.6 Hz, 1H), 6.14 (t, J=2.3 Hz, 1H), 4.05 (m, 2H), 3.05-2.82 (m, 6H), 1.50-1.36 (m, 3H), 1.23-1.09 (m, 8H), 0.93-0.73 (m, 2H).

Synthesis of 6-(4-(ethylsulfonamide)-2-(6-trideuteromethyl-7-oxo-6,7-dihydro-1H-pyrrolo[2,3-c]pyridin-4-yl)phenyl)-6-aza-spiro[2.5]octan-1-carboxylic acid (Compound 53)

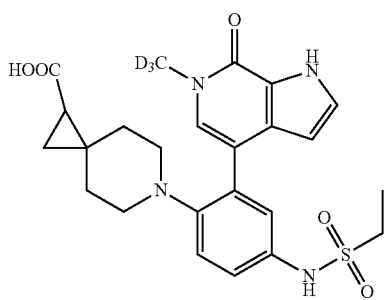

By the synthetic method and procedure of compound 7, the synthesis of compound 53 could be carried out with corresponding reagents. Among them, 1-formic acid-6-aza-spiro[2.5]octane hydrochloride was used to substitute 5-aza-spiro[2.4]heptane hydrochloride in the first step of the reaction, and Int. 8 was used to replace Int. 6 in the third step of the reaction, while other reaction reagents and conditions were completely consistent with those for synthesis of compound 7, and thus compound 53 was prepared.

MS: m/z 490.6 [M+H]$^+$.

$^1$H NMR (400 MHz, DMSO): δ 12.03 (s, 1H), 9.54 (s, 1H), 7.78 (dd, J=8.5, 2.3 Hz, 1H), 7.71 (d, J=2.3 Hz, 1H), 7.44 (s, 1H), 7.29 (t, J=2.7 Hz, 1H), 7.24 (d, J=8.6 Hz, 1H), 6.14 (t, J=2.3 Hz, 1H), 3.05-2.82 (m, 6H), 1.50-1.36 (m, 3H), 1.23-1.09 (m, 5H), 0.93-0.73 (m, 2H).

Synthesis of 6-trideuteromethyl-4-(5(methylsulfonyl)-2-(5-aza-spiro[2.4] heptan-5-yl)phenyl)-1H-pyrrolo[2,3-c]pyridin-7(6H)-one (Compound 54)

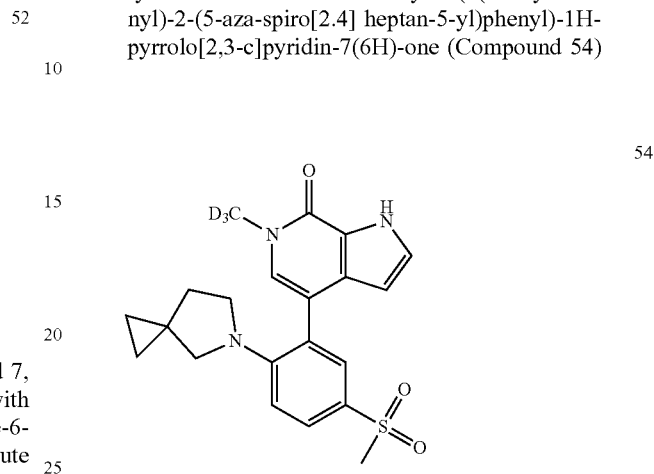

By the synthetic method and procedure of compound 24, the synthesis of compound 54 could be carried out with corresponding reagents. Among them, Int. 8 was used to replace Int. 6 in the second step of the reaction, while other reaction reagents and conditions were completely consistent with those for synthesis of compound 24, and thus compound 54 was prepared.

MS: m/z 401.5 [M+H]$^+$.

$^1$H NMR (400 MHz, DMSO) δ 12.22-12.01 (m, 1H), 7.68 (dd, J=8.8, 2.3 Hz, 1H), 7.56 (d, J=2.4 Hz, 1H), 7.34-7.21 (m, 2H), 6.94 (d, J=8.9 Hz, 1H), 6.02 (d, J=2.7 Hz, 1H), 3.68-3.50 (m, 3H), 3.25 (d, J=6.1 Hz, 2H), 2.98 (s, 2H), 1.64 (s, 2H), 0.44 (d, J=8.7 Hz, 4H).

Synthesis of 4-(5(ethylsulfonyl)-2-(5-aza-spiro[2.4] heptan-5-yl)phenyl)-6-trideuteromethyl-1H-pyrrolo[2,3-c]pyridin-7(6H)-one (Compound 55)

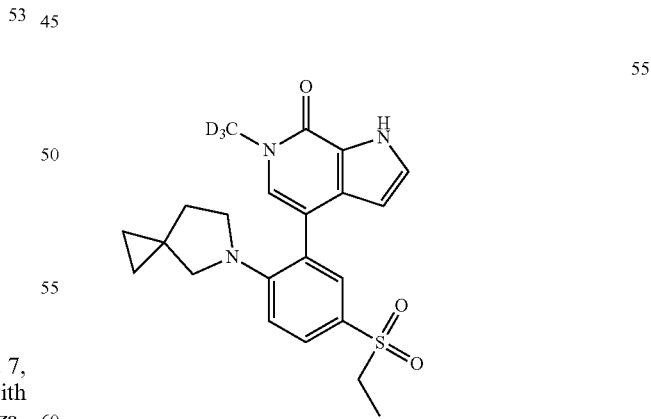

By the synthetic method and procedure of compound 24, the synthesis of compound 55 could be carried out with corresponding reagents. Among them, 2-bromo-1-fluoro-4-ethylsulfurylbenzene was used to substitute 2-bromo-1-fluoro-4-methylsulfonylbenzene in the first step of the reaction, and Int. 8 was used to replace Int. 6 in the second step of the reaction, while other reaction reagents and conditions were completely consistent with those for synthesis of compound 24, and thus compound 55 was prepared.

MS: m/z 415.5 [M+H]⁺.

¹H NMR (400 MHz, DMSO) δ 12.22-12.01 (m, 1H), 7.68 (dd, J=8.8, 2.3 Hz, 1H), 7.56 (d, J=2.4 Hz, 1H), 7.34-7.21 (m, 2H), 6.94 (d, J=8.9 Hz, 1H), 6.02 (d, J=2.7 Hz, 1H), 3.4 (m, 2H), 3.25 (d, J=6.1 Hz, 2H), 2.98 (s, 2H), 1.64 (s, 2H), 1.2 (m, 3H), 0.44 (d, J=8.7 Hz, 4H).

Synthesis of 6-trideuteromethyl-4-(5(methylsulfonyl)-2-(6-aza-spiro[2.5] octan-6-yl)phenyl)-1H-pyrrolo[2,3-c]pyridin-7(6H)-one (Compound 56)

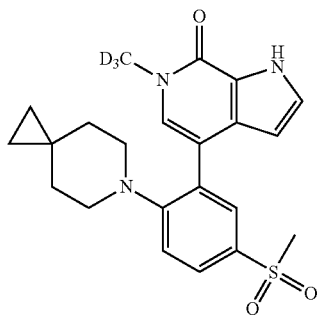

56

By the synthetic method and procedure of compound 24, the synthesis of compound 56 could be carried out with corresponding reagents. Among them, 6-aza-spiro[2.5]octane was used to substitute 5-aza-spiro[2.4]heptane hydrochloride in the first step of the reaction, and Int. 8 was used to replace Int. 6 in the second step of the reaction, while other reaction reagents and conditions were completely consistent with those for synthesis of compound 24, and thus compound 56 was prepared.

MS: m/z 415.5 [M+H]⁺.

¹H NMR (400 MHz, DMSO) δ 12.06 (s, 1H), 7.86-7.67 (m, 2H), 7.46 (s, 1H), 7.35-7.21 (m, 2H), 6.16 (s, 1H), 3.21 (s, 3H), 3.00 (s, 4H), 1.16 (s, 4H), 0.21 (s, 4H).

Synthesis of 6-trideuteromethyl-4-(5(methylsulfonyl)-2-(5-aza-spiro[2.5] octan-5-yl)phenyl)-1H-pyrrolo[2,3-c]pyridin-7(6H)-one (Compound 57)

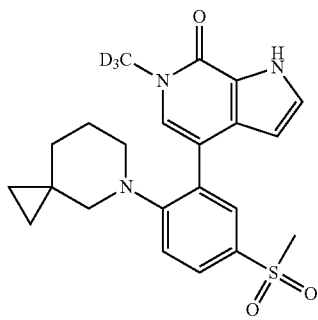

57

By the synthetic method and procedure of compound 24, the synthesis of compound 57 could be carried out with corresponding reagents. Among them, 5-aza-spiro[2.5]octane was used to substitute 5-aza-spiro[2.4]heptane hydrochloride in the first step of the reaction, and Int. 8 was used to replace Int. 6 in the second step of the reaction, while other reaction reagents and conditions were completely consistent with those for synthesis of compound 24, and thus compound 57 was prepared.

MS: m/z 415.5 [M+H]⁺.

¹H NMR (400 MHz, DMSO) δ 12.01 (s, 1H), 7.46 (s, 1H), 7.29 (m, 1H), 7.19 (m, 1H), 7.15-7.09 (m, 1H), 7.03 (d, J=8.6 Hz, 1H), 6.22-6.12 (m, 1H), 3.32 (m, 1H), 3.20 (s, 3H), 2.97 (m, 1H), 2.77 (m, 1H), 2.47 (m, 1H), 1.51-1.34 (m, 2H), 1.32-1.08 (m, 2H), 0.85 (m, 1H), 0.71 (m, 1H), 0.14 (m, 1H), 0.04 (m, 1H).

Synthesis of 4-(5-(cyclopropylsulfonyl)-2-(5-azaspiro[2.5]octan-5-yl)phenyl)-6-trideuteromethyl-1H-pyrrolo[2,3-c]pyridin-7(6H)-one (Compound 58)

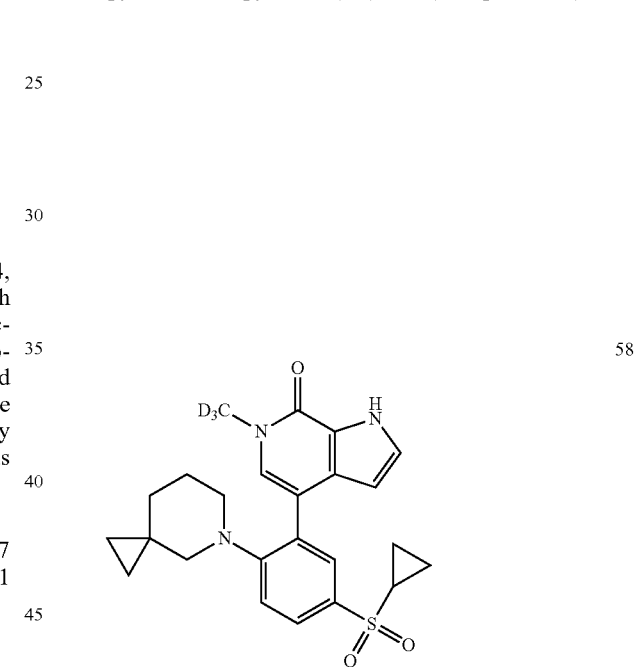

58

By the synthetic method and procedure of compound 24, the synthesis of compound 58 could be carried out with corresponding reagents. Among them, 5-aza-spiro[2.5]octane was used to substitute 5-aza-spiro[2.4]heptane hydrochloride, and 2-bromo-1-fluoro-4-cyclopropylsulfurylbenzene was used to substitute 2-bromo-1-fluoro-4-methylsulfonylbenzene in the first step of the reaction, and Int. 8 was used to replace Int. 6 in the second step of the reaction, while other reaction reagents and conditions were completely consistent with those for synthesis of compound 24, and thus compound 58 was prepared.

MS: m/z 441.6 [M+H]⁺.

¹H NMR (400 MHz, DMSO) δ 12.01 (s, 1H), 7.46 (s, 1H), 7.29 (m, 1H), 7.19 (m, 1H), 7.15-7.09 (m, 1H), 7.03 (d, J=8.6 Hz, 1H), 6.22-6.12 (m, 1H), 3.32 (m, 1H), 2.97 (m, 1H), 2.77 (m, 1H), 2.47 (m, 2H), 1.51-1.34 (m, 2H), 1.32-1.08 (m, 2H), 0.85 (m, 5H), 0.71 (m, 1H), 0.14 (m, 1H), 0.04 (m, 1H).

Synthesis of 4-(5-(cyclopropylsulfonyl)-2-(2-aza-spiro[3.3]heptan-2-yl) phenyl)-6-trideuteromethyl-1H-pyrrolo[2,3-c]pyridin-7(6H)-one (Compound 59)

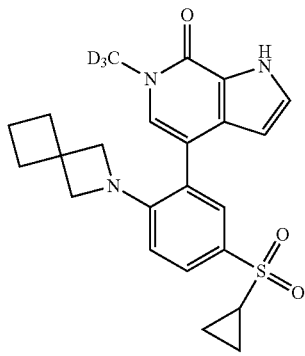

By the synthetic method and procedure of compound 24, the synthesis of compound 59 could be carried out with corresponding reagents. Among them, 2-aza-spiro[3.3]heptane hydrochloride was used to substitute 5-aza-spiro[2.4]heptane hydrochloride, and 2-bromo-1-fluoro-4-cyclopropylsulfurylbenzene was used to substitute 2-bromo-1-fluoro-4-methylsulfonylbenzene in the first step of the reaction, and Int. 8 was used to replace Int. 6 in the second step of the reaction, while other reaction reagents and conditions were completely consistent with those for synthesis of compound 24, and thus compound 59 was prepared.

MS: m/z 426.6 [M+H]$^+$.

$^1$H NMR (400 MHz, DMSO-d$_6$) δ 12.05 (s, 1H), 7.27 (t, J=2.4, 1H), 7.01 (s, 1H), 7.08 (dd, J$_1$=2.4 Hz, J$_2$=8.8 Hz, 1H), 6.98 (d, J=2.4 Hz, 1H), 6.51 (d, J=8.8 Hz, 1H), 6.08 (t, J=1.6 Hz, 1H), 3.40 (s, 4H), 2.45 (m, 1H), 1.95 (t, J=7.6 Hz, 4H), 1.68-1.63 (m, 2H), 1.01-0.85 (m, 4H).

Synthesis of 6-trideuteromethyl-4-(5-(methylsulfonyl)-2-(2-aza-spiro[3.3] heptan-2-yl)phenyl)-1H-pyrrolo[2,3-c]pyridin-7(6H)-one (Compound 60)

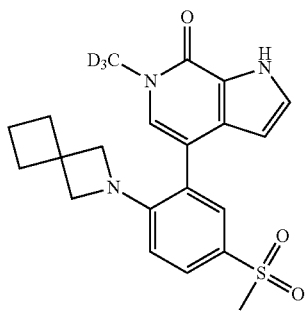

By the synthetic method and procedure of compound 24, the synthesis of compound 60 could be carried out with corresponding reagents. Among them, 2-aza-spiro[3.3]heptane hydrochloride was used to substitute 5-aza-spiro[2.4]heptane hydrochloride in the first step of the reaction, and Int. 8 was used to replace Int. 6 in the second step of the reaction, while other reaction reagents and conditions were completely consistent with those for synthesis of compound 24, and thus compound 60 was prepared.

MS: m/z 400.6 [M+H]$^+$.

$^1$H NMR (400 MHz, DMSO-d$_6$) δ 12.05 (s, 1H), 7.27 (t, J=2.4 Hz, 1H), 7.01 (s, 1H), 7.08 (dd, J$_1$=2.4 Hz, J$_2$=8.8 Hz, 1H), 6.98 (d, J=2.4 Hz, 1H), 6.51 (d, J=8.8 Hz, 1H), 6.08 (t, J=1.6 Hz, 1H), 3.40 (s, 4H), 3.20 (s, 3H), 1.95 (t, J=7.6 Hz, 4H), 1.68-1.63 (m, 2H).

Synthesis of 6-trideuteromethyl-4-(5-(oxetane-3-ylsulfonyl)-2-(2-aza-spiro [3.3]heptan-2-yl)phenyl)-1H-pyrrolo[2,3-c]pyridin-7(6H)-one (Compound 61)

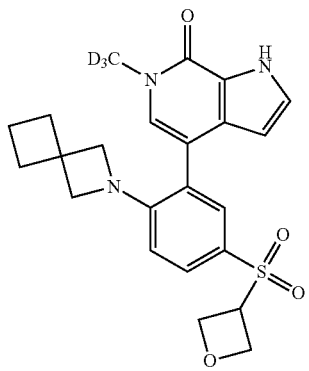

By the synthetic method and procedure of compound 24, the synthesis of compound 61 could be carried out with corresponding reagents. Among them, 3-((3-bromo-4-fluorophenyl)sulfonyl)oxetane was used to substitute 2-bromo-1-fluoro-4-methylsulfonylbenzene, and 2-aza-spiro[3.3]heptane hydrochloride was used to substitute 5-aza-spiro[2.4]heptane hydrochloride in the first step of the reaction, and Int. 8 was used to replace Int. 6 in the second step of the reaction, while other reaction reagents and conditions were completely consistent with those for synthesis of compound 24, and thus compound 61 was prepared.

MS: m/z 443.6 [M+H]$^+$.

$^1$H NMR (400 MHz, DMSO-d$_6$) δ 12.05 (s, 1H), 7.27 (t, J=2.4 Hz, 1H), 7.01 (s, 1H), 7.08 (dd, J$_1$=2.4 Hz, J$_2$=8.8 Hz, 1H), 6.98 (d, J=2.4 Hz, 1H), 6.51 (d, J=8.8 Hz, 1H), 6.08 (t, J=1.6 Hz, 1H), 4.95-4.65 (m, 4H), 4.72-4.61 (m, 1H), 3.40 (s, 4H), 1.95 (t, J=7.6 Hz, 4H), 1.68-1.63 (m, 2H).

Synthesis of 4-(5-(butyl sulfonyl)-2-(2-aza-spiro[3.3]heptan-2-yl)phenyl)-6-trideuteromethyl-1H-pyrrolo[2,3-c]pyridin-7(6H)-one (Compound 62)

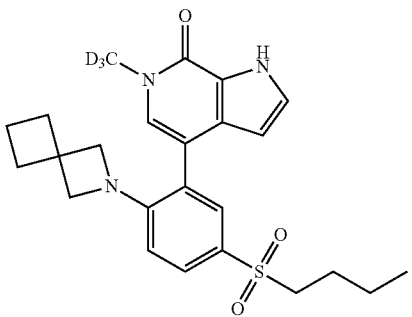

By the synthetic method and procedure of compound 24, the synthesis of compound 61 could be carried out with corresponding reagents. Among them, 2-bromo-1-fluoro-4-butylsulfurylbenzene was used to substitute 2-bromo-1-fluoro-4-methylsulfonylbenzene, and 2-aza-spiro[3.3]heptane hydrochloride was used to substitute 5-aza-spiro[2.4]heptane hydrochloride in the first step of the reaction, and Int. 8 was used to replace Int. 6 in the second step of the reaction, while other reaction reagents and conditions were completely consistent with those for synthesis of compound 24, and thus compound 62 was prepared.

MS: m/z 443.6 [M+H]$^+$.

$^1$H NMR (400 MHz, DMSO-d$_6$) δ 12.05 (s, 1H), 7.27 (t, J=2.4 Hz, 1H), 7.01 (s, 1H), 7.08 (dd, J$_1$=2.4 Hz, J$_2$=8.8 Hz, 1H), 6.98 (d, J=2.4, 1H), 6.51 (d, J=8.8 Hz, 1H), 6.08 (t, J=1.6 Hz, 1H), 3.40 (s, 4H), 3.25 (m, 2H), 1.95 (t, J=7.6 Hz, 4H), 1.68-1.63 (m, 2H), 1.58-1.43 (m, 2H), 1.38-1.23 (m, 2H), 1.08-0.93 (m, 3H).

Synthesis of 4-(5-(ethylsulfonyl)-2-(2-aza-spiro[3.3]heptan-2-yl)phenyl)-6-trideuteromethyl-1H-pyrrolo[2,3-c]pyridin-7(6H)-one (Compound 63)

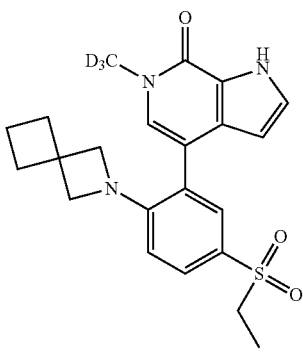

By the synthetic method and procedure of compound 24, the synthesis of compound 63 could be carried out with corresponding reagents. Among them, 2-bromo-1-fluoro-4-ethylsulfurylbenzene was used to substitute 2-bromo-1-fluoro-4-methylsulfonylbenzene, and 2-aza-spiro[3.3]heptane hydrochloride was used to substitute 5-aza-spiro[2.4]heptane hydrochloride in the first step of the reaction, and Int. 8 was used to replace Int. 6 in the second step of the reaction, while other reaction reagents and conditions were completely consistent with those for synthesis of compound 24, and thus compound 63 was prepared.

MS: m/z 415.6 [M+H]$^+$.

$^1$H NMR (400 MHz, DMSO-d$_6$) δ 12.05 (s, 1H), 7.27 (t, J=2.4 Hz, 1H), 7.01 (s, 1H), 7.08 (dd, J$_1$=2.4 Hz, J$_2$=8.8 Hz, 1H), 6.98 (d, J=2.4, 1H), 6.51 (d, J=8.8 Hz, 1H), 6.08 (t, J=1.6 Hz, 1H), 3.40 (s, 4H), 3.25 (m, 2H), 1.95 (t, J=7.6 Hz, 4H), 1.68-1.63 (m, 2H), 1.25-1.13 (m, 3H).

Synthesis of 6-trideuteromethyl-4-(5-(methylsulfonyl)-2-(2-oxa-6-aza-spiro[3.3]heptan-6-yl)phenyl)-1H-pyrrolo[2,3-c]pyridin-7(6H)-one (Compound 64)

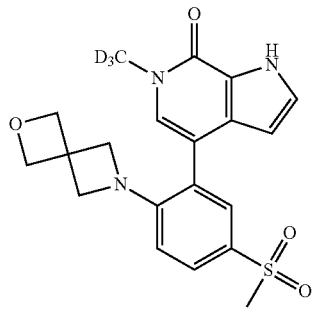

By the synthetic method and procedure of compound 24, the synthesis of compound 64 could be carried out with corresponding reagents. Among them, 2-oxa-6-aza-spiro[3.3]heptane was used to substitute 5-aza-spiro[2.4]heptane hydrochloride in the first step of the reaction, and Int. 8 was used to replace Int. 6 in the second step of the reaction, while other reaction reagents and conditions were completely consistent with those for synthesis of compound 24, and thus compound 64 was prepared.

MS: m/z 403.5 [M+H]$^+$.

$^1$H NMR (400 MHz, DMSO): δ 12.10 (s, 1H), 7.29 (t, J=2.5 Hz, 1H), 7.14-7.06 (m, 2H), 7.02 (d, J=2.5 Hz, 1H), 6.57 (d, J=8.7 Hz, 1H), 6.08 (s, 1H), 4.52 (s, 4H), 3.62 (s, 4H), 3.20 (s, 3H).

Synthesis of 4-(5-(ethylsulfonyl)-2-(2-oxa-6-aza-spiro[3.3]heptan-6-yl) phenyl)-6-trideuteromethyl-1H-pyrrolo[2,3-c]pyridin-7(6H)-one (Compound 65)

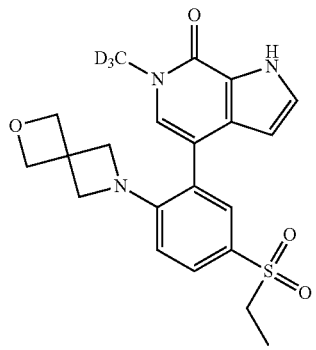

By the synthetic method and procedure of compound 24, the synthesis of compound 65 could be carried out with corresponding reagents. Among them, 2-bromo-1-fluoro-4-ethylsulfurylbenzene was used to substitute 2-bromo-1-fluoro-4-methylsulfonylbenzene, and 2-oxa-6-aza-spiro[3.3] heptane hydrochloride was used to substitute 5-aza-spiro[2.4]heptane hydrochloride in the first step of the reaction, and Int. 8 was used to replace Int. 6 in the second step of the reaction, while other reaction reagents and conditions were completely consistent with those for synthesis of compound 24, and thus compound 65 was prepared.

MS: m/z 417.5 [M+H]$^+$.

$^1$H NMR (400 MHz, DMSO): δ 12.10 (s, 1H), 7.29 (t, J=2.5 Hz, 1H), 7.14-7.06 (m, 2H), 7.02 (d, J=2.5 Hz, 1H), 6.57 (d, J=8.7 Hz, 1H), 6.08 (s, 1H), 4.52 (s, 4H), 3.62 (s, 4H), 3.25 (m, 2H), 1.25 (m, 3H).

Synthesis of 4-(5-(butylsulfonyl)-2-(2-oxa-6-aza-spiro[3.3]heptan-6-yl) phenyl)-6-trideuteromethyl-1H-pyrrolo[2,3-c]pyridin-7(6H)-one (Compound 66)

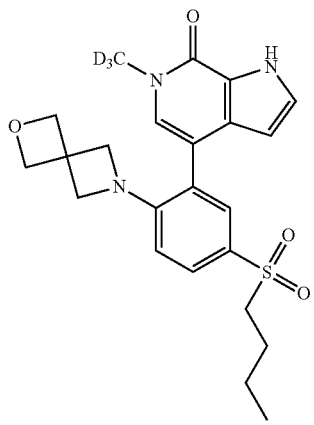

66

By the synthetic method and procedure of compound 24, the synthesis of compound 66 could be carried out with corresponding reagents. Among them, 2-bromo-1-fluoro-4-butylsulfurylbenzene was used to substitute 2-bromo-1-fluoro-4-methylsulfonylbenzene, and 2-oxa-6-aza-spiro[3.3] heptane hydrochloride was used to substitute 5-aza-spiro[2.4]heptane hydrochloride in the first step of the reaction, and Int. 8 was used to replace Int. 6 in the second step of the reaction, while other reaction reagents and conditions were completely consistent with those for synthesis of compound 24, and thus compound 66 was prepared.

MS: m/z 445.5 [M+H]$^+$.

$^1$H NMR (400 MHz, DMSO): δ 12.10 (s, 1H), 7.29 (t, J=2.5 Hz, 1H), 7.14-7.06 (m, 2H), 7.02 (d, J=2.5 Hz, 1H), 6.57 (d, J=8.7 Hz, 1H), 6.08 (s, 1H), 4.52 (s, 4H), 3.62 (s, 4H), 3.25 (m, 2H), 1.58-1.43 (m, 2H), 1.38-1.23 (m, 2H), 1.08-0.93 (m, 3H).

Synthesis of 4-(5-(cyclopropylsulfonyl)-2-(2-oxa-6-aza-spiro[3.3]heptan-6-yl) phenyl)-6-trideuteromethyl-1H-pyrrolo[2,3-c]pyridin-7(6H)-one (Compound 67)

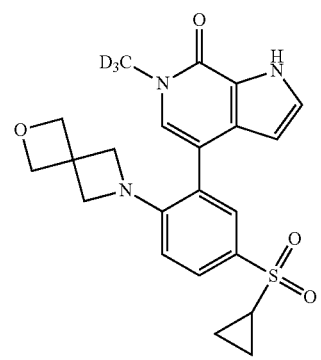

67

By the synthetic method and procedure of compound 24, the synthesis of compound 67 could be carried out with corresponding reagents. Among them, 2-bromo-1-fluoro-4-cyclopropylsulfurylbenzene was used to substitute 2-bromo-1-fluoro-4-methylsulfonylbenzene, and 2-oxa-6-aza-spiro[3.3]heptane hydrochloride was used to substitute 5-aza-spiro[2.4]heptane hydrochloride in the first step of the reaction, and Int. 8 was used to replace Int. 6 in the second step of the reaction, while other reaction reagents and conditions were completely consistent with those for synthesis of compound 24, and thus compound 67 was prepared.

MS: m/z 429.5 [M+H]$^+$.

$^1$H NMR (400 MHz, DMSO): δ 12.10 (s, 1H), 7.29 (t, J=2.5 Hz, 1H), 7.14-7.06 (m, 2H), 7.02 (d, J=2.5 Hz, 1H), 6.57 (d, J=8.7 Hz, 1H), 6.08 (s, 1H), 4.52 (s, 4H), 3.65 (s, 4H), 2.45 (m, 1H), 1.01-0.85 (m, 4H).

Synthesis of ethyl 6-(2-(6-trideuteromethyl-7-oxo-6,7-dihydro-1H-pyrrolo [2,3-c]pyridin-4-yl)-4-(methylsulfonyl)phenyl)-6-aza-spiro[2.5]octan-1-carboxylate (Compound 68)

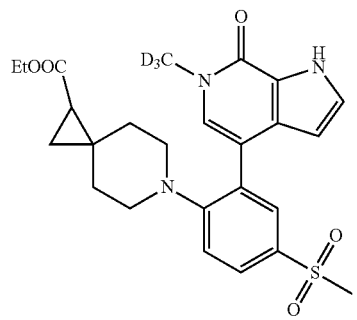

68

By the synthetic method and procedure of compound 24, the synthesis of compound 68 could be carried out with corresponding reagents. Among them, 1-ethyl formate-6-aza-spiro[2.5]octane hydrochloride was used to substitute 5-aza-spiro[2.4]heptane hydrochloride in the first step of the reaction, and Int. 8 was used to replace Int. 6 in the second step of the reaction, while other reaction reagents and conditions were completely consistent with those for synthesis of compound 24, and thus compound 68 was prepared.

MS: m/z 487.6 [M+H]⁺.

¹H NMR (400 MHz, DMSO) δ 12.03 (s, 1H), 7.78 (dd, J=8.5, 2.3 Hz, 1H), 7.71 (d, J=2.3 Hz, 1H), 7.44 (s, 1H), 7.29 (t, J=2.7 Hz, 1H), 7.24 (d, J=8.6 Hz, 1H), 6.14 (t, J=2.3 Hz, 1H), 4.05 (m, 2H), 3.19 (s, 3H), 3.05-2.82 (m, 4H), 1.50-1.36 (m, 3H), 1.23-1.09 (m, 5H), 0.93-0.73 (m, 2H).

Synthesis of 6-(2-(6-trideuteromethyl-7-oxo-6,7-dihydro-1H-pyrrolo[2,3-c] pyridin-4-yl)-4-(methylsulfonyl)phenyl)-6-aza-spiro[2.5]octan-1-carboxylic acid (Compound 69)

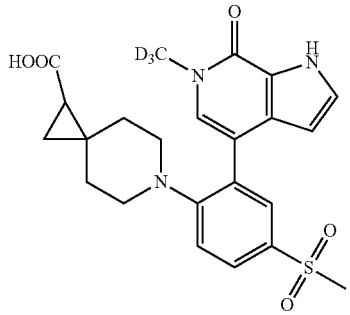

By the synthetic method and procedure of compound 24, the synthesis of compound 69 could be carried out with corresponding reagents. Among them, 1-formic acid-6-aza-spiro[2.5]octane hydrochloride was used to substitute 5-aza-spiro[2.4]heptane hydrochloride in the first step of the reaction, and Int. 8 was used to replace Int. 6 in the second step of the reaction, while other reaction reagents and conditions were completely consistent with those for synthesis of compound 24, and thus compound 69 was prepared.

MS: m/z 459.6 [M+H]⁺.

¹H NMR (400 MHz, DMSO) δ 12.03 (s, 1H), 7.78 (dd, J=8.5, 2.3 Hz, 1H), 7.71 (d, J=2.3 Hz, 1H), 7.44 (s, 1H), 7.29 (t, J=2.7 Hz, 1H), 7.24 (d, J=8.6 Hz, 1H), 6.14 (t, J=2.3 Hz, 1H), 3.19 (s, 3H), 3.05-2.82 (m, 4H), 1.50-1.36 (m, 3H), 1.23-1.09 (m, 2H), 0.93-0.73 (m, 2H).

Synthesis of N-(3-(6-methyl-7-oxo-6,7-dihydro-1H-pyrrolo[2,3-c]pyridin-4-yl)-4-(6-aza-spiro[2.5]octan-6-yl)phenyl)butyl-1-sulfonamide (Compound 70)

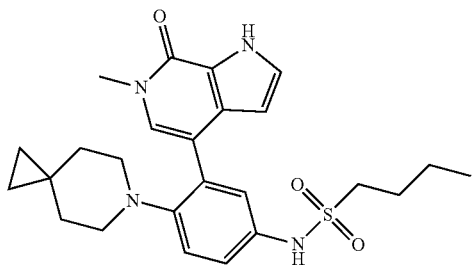

By the synthetic method and procedure of compound 7, the synthesis of compound 70 could be carried out with corresponding reagents. Among them, 6-aza-spiro[2.5]octane hydrochloride was used to substitute 5-aza-spiro[2.4]heptane hydrochloride in the first step of the reaction, and butanesulfonyl chloride was used to replace ethanesulfonyl chloride in the fourth step of the reaction, while other reaction reagents and conditions were completely consistent with those for synthesis of compound 7, and thus compound 70 was prepared.

MS: m/z 469.2 [M+H]⁺.

¹H NMR (400 MHz, DMSO) δ ppm 11.98 (s, 1H), 9.54 (s, 1H), 7.44 (s, 1H), 7.28 (s, 1H), 7.17-7.05 (m, 3H), 6.16 (s, 1H), 3.57 (s, 3H), 3.07-3.01 (m, 2H), 2.78 (s, 4H), 1.38-1.25 (m, 4H), 1.23-1.13 (m, 7H), 0.18 (s, 4H).

Synthesis of N-(3-(6-methyl-7-oxo-6,7-dihydro-1H-pyrrolo[2,3-c]pyridin-4-yl)-4-(5-aza-spiro[2.5]octan-5-yl)phenyl)methylsulfonamide (Compound 71)

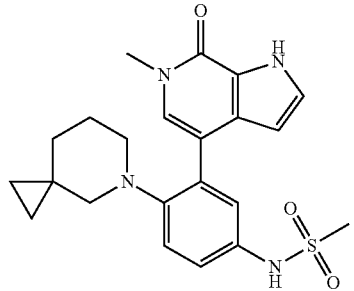

By the synthetic method and procedure of compound 7, the synthesis of compound 71 could be carried out with corresponding reagents. Among them, 5-aza-spiro[2.5]octane hydrochloride was used to substitute 5-aza-spiro[2.4]heptane hydrochloride in the first step of the reaction, and methanesulfonyl chloride was used to replace ethanesulfonyl chloride in the fourth step of the reaction, while other reaction reagents and conditions were completely consistent with those for synthesis of compound 7, and thus compound 71 was prepared.

MS: m/z 427.6 [M+H]⁺.

¹H NMR (400 MHz, DMSO) δ 12.01 (s, 1H), 9.55 (s, 1H), 7.46 (s, 1H), 7.29 (m, 1H), 7.19 (m, 1H), 7.15-7.09 (m, 1H), 7.03 (d, J=8.6 Hz, 1H), 6.22-6.12 (m, 1H), 3.57 (s, 3H), 3.32 (m, 1H), 2.97 (m, 1H), 2.93 (s, 3H), 2.77 (m, 1H), 2.47 (m, 1H), 1.51-1.34 (m, 2H), 1.32-1.08 (m, 2H), 0.85 (m, 1H), 0.71 (m, 1H), 0.14 (m, 1H), 0.04 (m, 1H).

Synthesis of 6-methyl-4-(5-(methylsulfonyl)-2-(2-oxa-7-aza-spiro[3.5] nonan-7-yl)phenyl)-1H-pyrrolo[2,3-c]pyridin-7(6H)-one (Compound 177)

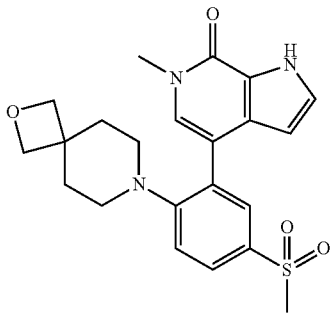
177

By the synthetic method and procedure of compound 24, the synthesis of compound 177 could be carried out with corresponding reagents. Among them, 2-oxa-7-aza-spiro[3.5]nonane was used to substitute 5-aza-spiro[2.4]heptane hydrochloride in the first step of the reaction, while other reaction reagents and conditions were completely consistent with those for synthesis of compound 24, and thus compound 177 was prepared.

MS: m/z 428.5 [M+H]$^+$.

$^1$H NMR (400 MHz, DMSO): δ 12.06 (s, 1H), 7.78 (dd, J=8.5, 2.3 Hz, 1H), 7.71 (d, J=2.3 Hz, 1H), 7.45 (s, 1H), 7.27 (d, J=2.7 Hz, 1H), 7.22 (d, J=8.6 Hz, 1H), 6.13 (d, J=2.7 Hz, 1H), 4.22 (s, 4H), 3.59 (s, 3H), 3.19 (s, 3H), 2.87 (s, 4H), 1.55 (s, 4H).

Synthesis of 4-(2-(1,1-difluoro-6-aza-spiro[2.5]octan-6-yl)-5-(methylsulfonyl)phenyl)-6-methyl-1H-pyrrolo[2,3-c]pyridin-7(6H)-one (Compound 178)

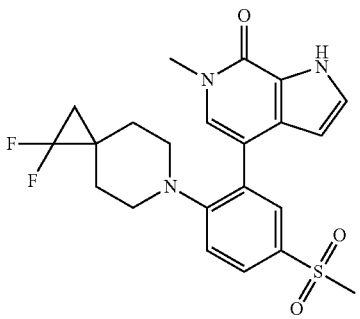
178

By the synthetic method and procedure of compound 24, the synthesis of compound 178 could be carried out with corresponding reagents. Among them, 1,1-difluoro-6-aza-spiro[2.5]octane hydrochloride was used to substitute 5-aza-spiro[2.4]heptane hydrochloride in the first step of the reaction, while other reaction reagents and conditions were completely consistent with those for synthesis of compound 24, and thus compound 178 was prepared.

MS: m/z 448.5 [M+H]$^+$.

$^1$H NMR (400 MHz, DMSO) δ 12.05 (s, 1H), 7.80 (dd, J=8.5, 2.1 Hz, 1H), 7.72 (d, J=2.2 Hz, 1H), 7.45 (s, 1H), 7.29 (s, 1H), 7.26 (d, J=8.6 Hz, 1H), 6.14 (s, 1H), 3.59 (s, 3H), 3.20 (s, 3H), 3.01-2.97 (m, 4H), 1.39-1.32 (m, 2H), 1.30-1.25 (m, 2H), 1.22-1.17 (m, 2H).

Synthesis of 4-(2-(1-(hydroxymethyl)-6-aza-spiro[2.5]octan-6-yl)-5-(methylsulfonyl)phenyl)-6-methyl-1H-pyrrolo[2,3-c]pyridin-7(6H)-one (Compound 179)

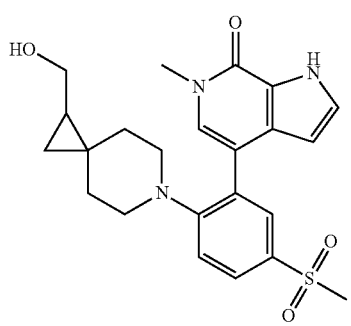
179

By the synthetic method and procedure of compound 24, the synthesis of compound 179 could be carried out with corresponding reagents. Among them, 1-(hydroxymethyl)-6-aza-spiro[2.5]octane hydrochloride was used to substitute 5-aza-spiro[2.4]heptane hydrochloride in the first step of the reaction, while other reaction reagents and conditions were completely consistent with those for synthesis of compound 24, and thus compound 179 was prepared.

MS: m/z 442.6 [M+H]$^+$.

$^1$H NMR (400 MHz, DMSO): δ 12.07 (s, 1H), 7.81 (dd, J=8.5, 2.4 Hz, 1H), 7.73 (d, J=2.4 Hz, 1H), 7.46 (s, 1H), 7.35-7.25 (m, 2H), 6.20-6.13 (m, 1H), 3.82 (s, 1H), 3.60 (s, 3H), 3.45 (m, 2H), 3.21 (s, 3H), 3.16-2.86 (m, 4H), 2.06-1.94 (m, 1H), 1.66-1.56 (m, 1H), 1.54-1.37 (m, 2H), 1.01-0.85 (m, 3H).

Synthesis of 6-(2-(6-methyl-7-oxo-6,7-dihydro-1H-pyrrolo[2,3-c]pyridin-4-yl)-4-(methylsulfonyl)phenyl)-6-aza-spiro[2.5]octan-1-formamide (Compound 180)

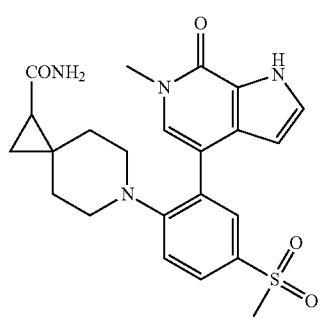
180

By the synthetic method and procedure of compound 24, the synthesis of compound 180 could be carried out with corresponding reagents. Among them, 1-formamide-6-aza-spiro[2.5]octane hydrochloride was used to substitute 5-aza-spiro[2.4]heptane hydrochloride in the first step of the reaction, while other reaction reagents and conditions were completely consistent with those for synthesis of compound 24, and thus compound 180 was prepared.

MS: m/z 455.5 [M+H]$^+$.

$^1$H NMR (400 MHz, DMSO): δ 12.07 (s, 1H), 8.21 (s, 2H), 7.81 (dd, J=8.5, 2.4 Hz, 1H), 7.73 (d, J=2.4 Hz, 1H), 7.46 (s, 1H), 7.35-7.25 (m, 2H), 6.20-6.13 (m, 1H), 3.60 (s, 3H), 3.21 (s, 3H), 3.16-2.86 (m, 4H), 2.06-1.94 (m, 1H), 1.66-1.56 (m, 1H), 1.54-1.37 (m, 2H), 1.01-0.85 (m, 3H).

Synthesis of 6-(2-(6-methyl-7-oxo-6,7-dihydro-1H-pyrrolo[2,3-c]pyridin-4-yl)-4-(methylsulfonyl)phenyl)-6-aza-spiro[2.5]octan-1-cyanide (Compound 181)

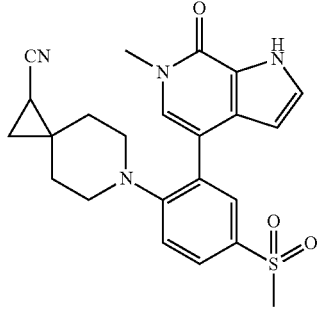

181

By the synthetic method and procedure of compound 24, the synthesis of compound 181 could be carried out with corresponding reagents. Among them, 1-cyano-6-aza-spiro[2.5]octane hydrochloride was used to substitute 5-aza-spiro[2.4]heptane hydrochloride in the first step of the reaction, while other reaction reagents and conditions were completely consistent with those for synthesis of compound 24, and thus compound 181 was prepared.

MS: m/z 437.5 [M+H]$^+$.

$^1$H NMR (400 MHz, DMSO): δ 12.07 (s, 1H), 7.81 (dd, J=8.5, 2.4 Hz, 1H), 7.73 (d, J=2.4 Hz, 1H), 7.46 (s, 1H), 7.35-7.25 (m, 2H), 6.20-6.13 (m, 1H), 3.60 (s, 3H), 3.21 (s, 3H), 3.16-2.86 (m, 4H), 2.06-1.94 (m, 1H), 1.66-1.56 (m, 1H), 1.54-1.37 (m, 2H), 1.01-0.85 (m, 3H).

Synthesis of 3,6-dimethyl-4-(5-(methylsulfonyl)-2-(6-aza-spiro[2.5]octan-6-yl)phenyl)-1H-pyrrolo[2,3-c]pyridin-7(6H)-one (Compound 182)

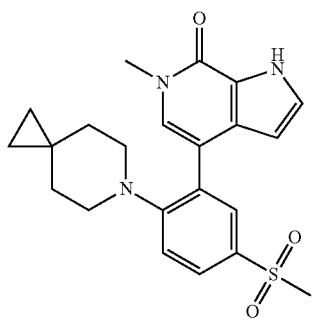

182

By the synthetic method and procedure of compound 24, the synthesis of compound 182 could be carried out with corresponding reagents. Among them, 6-aza-spiro[2.5]octane hydrochloride was used to substitute 5-aza-spiro[2.4]heptane hydrochloride in the first step of the reaction, and 3,6-dimethyl-4-(4,4,5,5-tetramethyl-1,3,2-dioxaborolan-2-yl)-1-p-tosyl-1H-pyrrolo[2,3-c] pyridin-7(6H)-one was used to replace Int. 6 in the second step of the reaction, while other reaction reagents and conditions were completely consistent with those for synthesis of compound 24, and thus compound 182 was prepared.

MS: m/z 426.5 [M+H]$^+$.

$^1$H NMR (400 MHz, DMSO): δ 11.77 (s, 1H), 7.80 (dd, J=8.6, 2.3 Hz, 1H), 7.62 (d, J=2.3 Hz, 1H), 7.20 (d, J=8.5 Hz, 2H), 7.08 (s, 1H), 3.55 (s, 3H), 3.19 (s, 3H), 3.15-3.03 (m, 2H), 2.96-2.84 (m, 2H), 1.69 (s, 3H), 1.15-1.03 (m, 2H), 1.02-0.89 (m, 2H), 0.19 (s, 4H).

Synthesis of 6-trideuteromethyl-4-(5-(methylsulfonyl)-2-(2-oxa-7-aza-spiro[3.5]nonan-7-yl)phenyl)-1H-pyrrolo[2,3-c]pyridin-7(6H)-one (Compound 183)

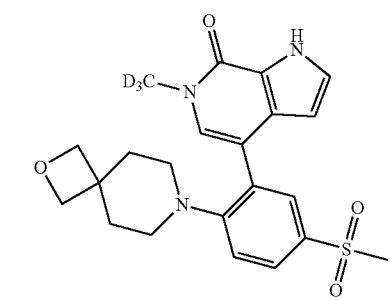

183

By the synthetic method and procedure of compound 24, the synthesis of compound 183 could be carried out with corresponding reagents. Among them, 2-oxa-7-aza-spiro[3.5]nonane hydrochloride was used to substitute 5-aza-spiro[2.4]heptane hydrochloride in the first step of the reaction, and Int. 8 was used to replace Int. 6 in the second step of the reaction, while other reaction reagents and conditions were completely consistent with those for synthesis of compound 24, and thus compound 183 was prepared.

MS: m/z 431.5 [M+H]$^+$.

$^1$H NMR (400 MHz, DMSO) δ 12.05 (s, 1H), 7.85-7.67 (m, 2H), 7.44 (s, 1H), 7.24 (m, 2H), 6.12 (s, 1H), 4.22 (s, 4H), 3.19 (s, 3H), 2.87 (s, 4H), 1.55 (s, 4H).

Synthesis of 4-(2-(1,1-difluoro-6-aza-spiro[2.5]octan-6-yl)-5-(methylsulfonyl)phenyl)-6-trideuteromethyl-1H-pyrrolo[2,3-c]pyridin-7(6H)-one (Compound 184)

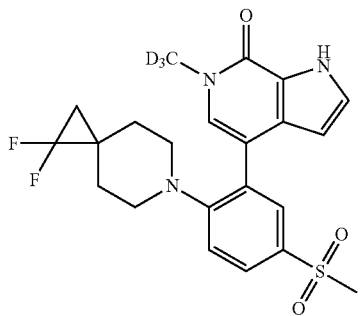

184

By the synthetic method and procedure of compound 24, the synthesis of compound 184 could be carried out with corresponding reagents. Among them, 1,1-difluoro-6-aza-spiro[2.5]octane hydrochloride was used to substitute 5-aza-spiro[2.4]heptane hydrochloride in the first step of the reaction, and Int. 8 was used to replace Int. 6 in the second step of the reaction, while other reaction reagents and conditions were completely consistent with those for synthesis of compound 24, and thus compound 184 was prepared.

MS: m/z 451.5 [M+H]⁺.

¹H NMR (400 MHz, DMSO) δ 12.05 (s, 1H), 7.79 (d, J=8.7 Hz, 1H), 7.72 (s, 1H), 7.45 (s, 1H), 7.32-7.23 (m, 2H), 6.14 (s, 1H), 3.20 (s, 3H), 2.99 (s, 4H), 1.30-1.16 (m, 6H)

Synthesis of 6-(2-(6-trideuteromethyl-7-oxo-6,7-dihydro-1H-pyrrolo[2,3-c] pyridin-4-yl)-4-(methylsulfonyl)phenyl)-6-aza-spiro[2.5]octan-1-formamide (Compound 185)

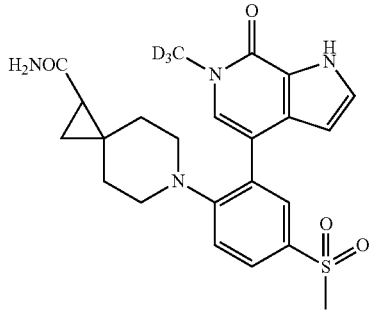

185

By the synthetic method and procedure of compound 24, the synthesis of compound 185 could be carried out with corresponding reagents. Among them, 1,1-formamide-6-aza-spiro[2.5]octane hydrochloride was used to substitute 5-aza-spiro[2.4]heptane hydrochloride in the first step of the reaction, and Int. 8 was used to replace Int. 6 in the second step of the reaction, while other reaction reagents and conditions were completely consistent with those for synthesis of compound 24, and thus compound 185 was prepared.

MS: m/z 458.5 [M+H]⁺.

¹H NMR (400 MHz, DMSO): δ 12.07 (s, 1H), 8.21 (s, 2H), 7.81 (dd, J=8.5, 2.4 Hz, 1H), 7.73 (d, J=2.4 Hz, 1H), 7.46 (s, 1H), 7.35-7.25 (m, 2H), 6.20-6.13 (m, 1H), 3.21 (s, 3H), 3.16-2.86 (m, 4H), 2.06-1.94 (m, 1H), 1.66-1.56 (m, 1H), 1.54-1.37 (m, 2H), 1.01-0.85 (m, 3H).

Synthesis of 4-(5(ethylsulfonyl)-2-(6-aza-spiro[2.5] octan-6-yl)pyridin-3-yl)-6-trideuteromethyl-1H-pyrrolo[2,3-c]pyridin-7(6H)-one (Compound 186)

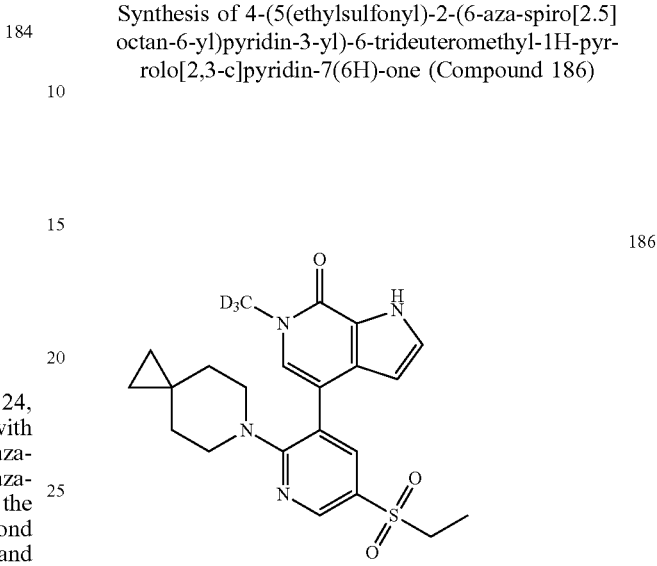

186

By the synthetic method and procedure of compound 24, the synthesis of compound 186 could be carried out with corresponding reagents. Among them, 6-aza-spiro[2.5]octane hydrochloride was used to substitute 5-aza-spiro[2.4]heptane hydrochloride, and 3-bromo-5-ethylsulfuryl-2-fluoropyridine was used to substitute 2-bromo-1-fluoro-4-methylsulfonylbenzene in the first step of the reaction, and Int. 8 was used to replace Int. 6 in the second step of the reaction, while other reaction reagents and conditions were completely consistent with those for synthesis of compound 24, and thus compound 186 was prepared.

MS: m/z 427.5 [M+H]⁺.

¹H NMR (400 MHz, DMSO) δ 12.16 (s, 1H), 8.51 (d, J=2.3 Hz, 1H), 7.87 (d, J=2.2 Hz, 1H), 7.43 (s, 1H), 7.34 (s, 1H), 6.13 (s, 1H), 3.34 (d, J=10.1 Hz, 4H), 3.25 (m, 2H), 1.25-1.20 (m, 3H), 1.15 (s, 4H), 0.22 (s, 4H).

Synthesis of 6-trideuteromethyl-4-(5(methylsulfonyl)-2-(6-aza-spiro[2.5] octan-6-yl)pyridin-3-yl)-1H-pyrrolo[2,3-c]pyridin-7(6H)-one (Compound 187)

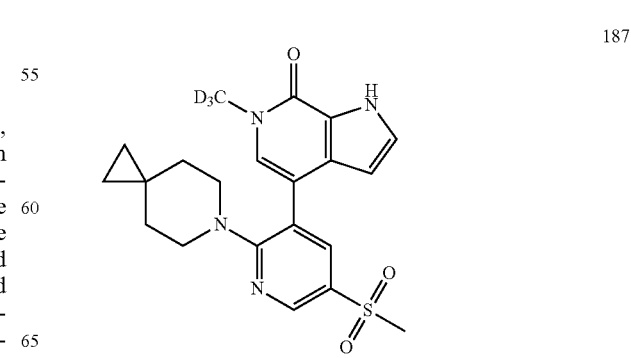

187

By the synthetic method and procedure of compound 24, the synthesis of compound 187 could be carried out with corresponding reagents. Among them, 6-aza-spiro[2.5]octane hydrochloride was used to substitute 5-aza-spiro[2.4]heptane hydrochloride, and 3-bromo-5-methylsulfuryl-2-fluoropyridine was used to substitute 2-bromo-1-fluoro-4-methylsulfonylbenzene in the first step of the reaction, and Int. 8 was used to replace Int. 6 in the second step of the reaction, while other reaction reagents and conditions were completely consistent with those for synthesis of compound 24, and thus compound 187 was prepared.

MS: m/z 416.5 [M+H]⁺.

¹H NMR (400 MHz, DMSO) δ 12.16 (s, 1H), 8.51 (d, J=2.3 Hz, 1H), 7.87 (d, J=2.2 Hz, 1H), 7.43 (s, 1H), 7.34 (s, 1H), 6.13 (s, 1H), 3.34 (d, J=10.1 Hz, 4H), 3.25-3.20 (m, 3H), 1.15 (s, 4H), 0.22 (s, 4H).

Synthesis of 4-(5-(isopropylsulfonyl)-2-(6-aza-spiro[2.5]octan-6-yl)pyridin-3-yl)-6-trideuteromethyl-1H-pyrrolo[2,3-c]pyridin-7(6H)-one (Compound 188)

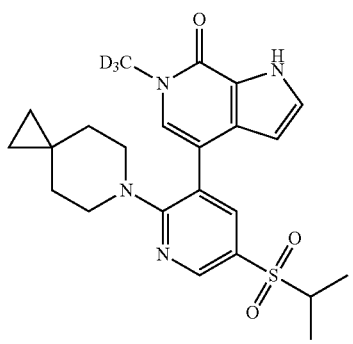

188

By the synthetic method and procedure of compound 24, the synthesis of compound 188 could be carried out with corresponding reagents. Among them, 6-aza-spiro[2.5]octane hydrochloride was used to substitute 5-aza-spiro[2.4]heptane hydrochloride, and 3-bromo-5-isopropylsulfuryl-2-fluoropyridine was used to substitute 2-bromo-1-fluoro-4-methylsulfonylbenzene in the first step of the reaction, and Int. 8 was used to replace Int. 6 in the second step of the reaction, while other reaction reagents and conditions were completely consistent with those for synthesis of compound 24, and thus compound 188 was prepared.

MS: m/z 444.6 [M+H]⁺.

¹H NMR (400 MHz, DMSO) δ 12.16 (s, 1H), 8.51 (d, J=2.3 Hz, 1H), 7.87 (d, J=2.2 Hz, 1H), 7.43 (s, 1H), 7.34 (s, 1H), 6.13 (s, 1H), 3.34 (d, J=10.1 Hz, 4H), 3.27-3.22 (m, 1H), 1.25-1.20 (m, 6H), 1.15 (s, 4H), 0.22 (s, 4H).

Synthesis of N-(3-(6-trideuteromethyl-7-oxo-6,7-dihydro-1H-pyrrolo[2,3-c] pyridin-4-yl)-4-(2-oxa-7-aza-spiro[3.5]nonan-7-yl)phenyl)methanesulfonamide (Compound 189)

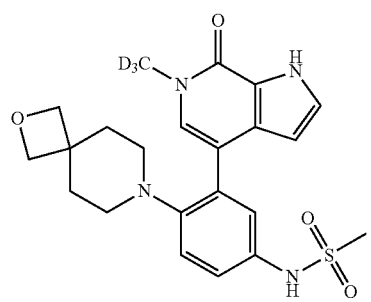

189

By the synthetic method and procedure of compound 7, the synthesis of compound 189 could be carried out with corresponding reagents. Among them, 2-oxa-7-aza-spiro[3.5]nonane hydrochloride was used to substitute 5-aza-spiro[2.4]heptane hydrochloride in the first step of the reaction, and Int. 8 was used to replace Int. 6 in the third step of the reaction, and methanesulfonyl chloride was used to take the place of ethanesulfonyl chloride in the fourth step of the reaction, while other reaction reagents and conditions were completely consistent with those for synthesis of compound 7, and thus compound 189 was prepared.

MS: m/z 446.6 [M+H]⁺.

¹H NMR (400 MHz, DMSO) δ 12.00 (s, 1H), 9.49 (s, 1H), 7.42 (s, 1H), 7.27 (t, J=2.6 Hz, 1H), 7.19-7.09 (m, 2H), 7.03 (d, J=8.6 Hz, 1H), 6.22-6.12 (m, 1H), 4.23 (s, 4H), 2.95 (s, 3H), 2.67 (s, 4H), 1.58 (s, 4H).

Synthesis of N-(4-(2-oxa-5-azabicyclo[2.2.1]heptan-5-yl)-3-(methyl-7-oxo-6,7-dihydro-1H-pyrrolo[2,3-c]pyridin-4-yl)phenyl)ethanesulfonamide (Compound 190)

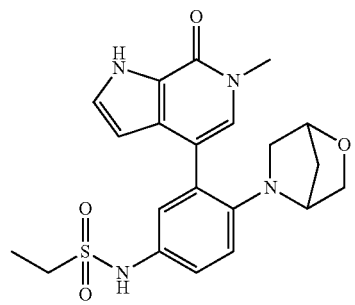

190

By the synthetic method and procedure of compound 7, the synthesis of compound 190 could be carried out with corresponding reagents. Among them, 2-oxa-5-azabicyclo[2.2.1]heptane hydrochloride was used to substitute 5-aza-spiro[2.4]heptane hydrochloride in the first step of the reaction, while other reaction reagents and conditions were completely consistent with those for synthesis of compound 7, and thus compound 190 was prepared.

MS: m/z 429.6 [M+H]⁺.

$^1$H NMR (400 MHz, DMSO) δ 12.01 (s, 1H), 9.55 (s, 1H), 7.42 (s, 1H), 7.27 (s, 1H), 7.15 (m, 2H), 7.02 (d, J=8.6 Hz, 1H), 6.15 (s, 1H), 4.08-3.91 (m, 3H), 3.65 (s, 3H), 3.04 (q, J=7.3 Hz, 2H), 3.01-2.80 (m, 3H), 2.01-1.91 (m, 2H), 1.21 (t, J=7.3 Hz, 3H).

Synthesis of N-(3-(6-methyl-7-O-6,7-dihydro-1H-pyrrolo[2,3-c]pyridin-4-yl)-4-(5-aza-spiro[2.4]heptan-2-yl)phenyl)oxetane-3-ylsulfonamide (Compound 191)

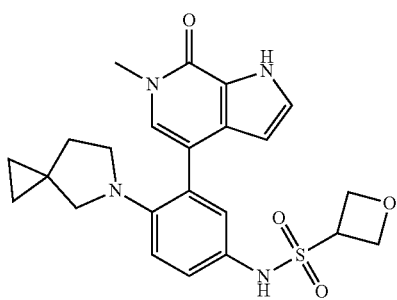

191

By the synthetic method and procedure of compound 7, the synthesis of compound 191 could be carried out with corresponding reagents. Among them, oxetane-3-sulfonyl chloride was used to substitute ethanesulfonyl chloride in the fourth step of the reaction, while other reaction reagents and conditions were completely consistent with those for synthesis of compound 7, and thus compound 191 was prepared.

MS: m/z 455.5 [M+H]$^+$.

$^1$H NMR (400 MHz, DMSO) δ 12.04 (s, 1H), 9.53 (s, 1H), 7.27 (t, J=2.7 Hz, 1H), 7.16 (s, 1H), 7.05 (dd, J=8.8, 2.6 Hz, 1H), 6.97 (d, J=2.6 Hz, 1H), 6.82 (d, J=8.8 Hz, 1H), 6.08-6.01 (m, 1H), 4.90-4.60 (m, 4H), 4.60-4.48 (m, 1H), 3.56 (s, 3H), 3.11 (t, J=6.6 Hz, 2H), 2.81 (s, 2H), 1.62 (t, J=6.6 Hz, 2H), 0.40 (m, 4H).

Synthesis of N-(4-(2-oxa-5-azabicyclo[2.2.1]heptan-5-yl)-3-(6-methyl-7-oxo-6,7-dihydro-1H-pyrrolo[2,3-c]pyridin-4-yl)phenyl)methanesulfonamide (Compound 192)

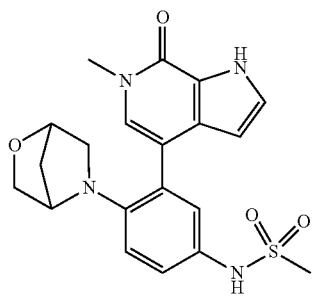

192

By the synthetic method and procedure of compound 7, the synthesis of compound 192 could be carried out with corresponding reagents. Among them, 2-oxa-5-azabicyclo[2.2.1]heptane hydrochloride was used to substitute 5-aza-spiro[2.4]heptane hydrochloride in the first step of the reaction, and methanesulfonyl chloride was used to replace ethanesulfonyl chloride in the fourth step of the reaction, while other reaction reagents and conditions were completely consistent with those for synthesis of compound 7, and thus compound 192 was prepared.

MS: m/z 415.5 [M+H]$^+$.

$^1$H NMR (400 MHz, DMSO) δ 12.01 (s, 1H), 9.55 (s, 1H), 7.42 (s, 1H), 7.27 (s, 1H), 7.15 (m, 2H), 7.02 (d, J=8.6 Hz, 1H), 6.15 (s, 1H), 4.08-3.91 (m, 3H), 3.65 (s, 3H), 3.04 (s, 3H), 3.01-2.80 (m, 3H), 2.01-1.91 (m, 2H).

Synthesis of N-(4-(1,1-difluoro-6-aza-spiro[2.5]octan-6-yl)-3-(6-methyl-7-oxo-6,7-dihydro-1H-pyrrolo[2,3-c]pyridin-4-yl)phenyl)ethanesulfonamide (Compound 193)

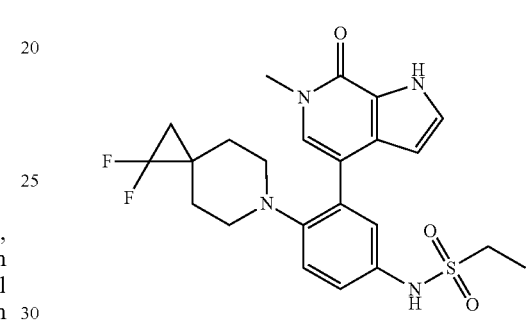

193

By the synthetic method and procedure of compound 7, the synthesis of compound 193 could be carried out with corresponding reagents. Among them, 1,1-difluoro-6-aza-spiro[2.5]octane hydrochloride was used to substitute 5-aza-spiro[2.4]heptane hydrochloride in the first step of the reaction, while other reaction reagents and conditions were completely consistent with those for synthesis of compound 7, and thus compound 193 was prepared.

MS: m/z 477.5 [M+H]$^+$.

$^1$H NMR (400 MHz, DMSO) δ 11.98 (s, 1H), 9.54 (s, 1H), 7.44 (s, 1H), 7.28 (s, 1H), 7.17 (s, 1H), 7.13 (d, J=7.8 Hz, 1H), 7.06 (d, J=8.4 Hz, 1H), 6.17 (s, 1H), 3.57 (s, 3H), 3.09-3.02 (m, 2H), 2.78 (s, 4H), 1.23-1.13 (m, 9H).

Synthesis of N-(3-(6-methyl-7-oxo-6,7-dihydro-1H-pyrrolo[2,3-c]pyridin-4-yl)-4-(2-oxa-7-aza-spiro[3.5]nonan-7-yl)phenyl)ethanesulfonamide (Compound 194)

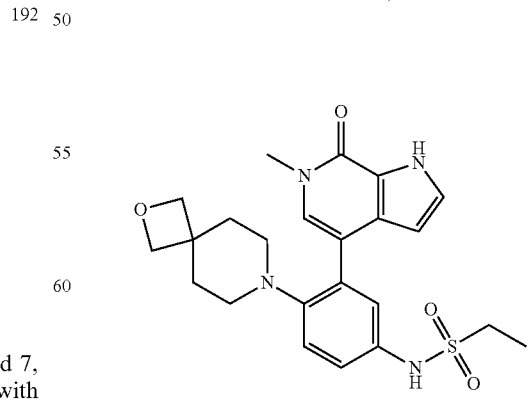

194

By the synthetic method and procedure of compound 7, the synthesis of compound 194 could be carried out with corresponding reagents. Among them, 2-oxa-7-aza-spiro[3.5]nonane hydrochloride was used to substitute 5-aza-spiro[2.4]heptane hydrochloride in the first step of the reaction, while other reaction reagents and conditions were completely consistent with those for synthesis of compound 7, and thus compound 194 was prepared.

MS: m/z 457.5 [M+H]⁺.

¹H NMR (400 MHz, DMSO) δ 12.01 (s, 1H), 9.55 (s, 1H), 7.42 (s, 1H), 7.27 (s, 1H), 7.15 (m, 2H), 7.02 (d, J=8.6 Hz, 1H), 6.15 (s, 1H), 4.28 (s, 4H), 3.60 (s, 3H), 3.04 (q, J=7.3 Hz, 2H), 2.66 (s, 4H), 1.58 (s, 4H), 1.21 (t, J=7.3 Hz, 3H).

Synthesis of N-(3-(6-methyl-7-oxo-6,7-dihydro-1H-pyrrolo[2,3-c]pyridin-4-yl)-4-(2-oxa-7-aza-spiro[3.5]nonan-7-yl)phenyl)methanesulfonamide (Compound 195)

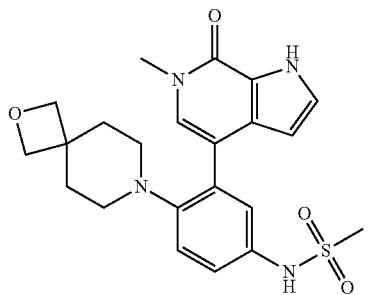

195

By the synthetic method and procedure of compound 7, the synthesis of compound 195 could be carried out with corresponding reagents. Among them, 2-oxa-7-aza-spiro[3.5]nonane hydrochloride was used to substitute 5-aza-spiro[2.4]heptane hydrochloride in the first step of the reaction, and methanesulfonyl chloride was used to replace ethanesulfonyl chloride in the fourth step of the reaction, while other reaction reagents and conditions were completely consistent with those for synthesis of compound 7, and thus compound 195 was prepared.

MS: m/z 443.5 [M+H]⁺.

¹H NMR (400 MHz, DMSO) δ 12.00 (s, 1H), 9.49 (s, 1H), 7.42 (s, 1H), 7.27 (t, J=2.6 Hz, 1H), 7.19-7.09 (m, 2H), 7.03 (d, J=8.6 Hz, 1H), 6.22-6.12 (m, 1H), 4.23 (s, 4H), 3.57 (s, 3H), 2.95 (s, 3H), 2.67 (s, 4H), 1.58 (s, 4H).

Synthesis of N-(3-(6-trideuteromethyl-7-oxo-6,7-dihydro-1H-pyrrolo[2,3-c] pyridin-4-yl)-4-(2-oxa-7-aza-spiro[3.5]nonan-7-yl)phenyl)ethanesulfonamide (Compound 196)

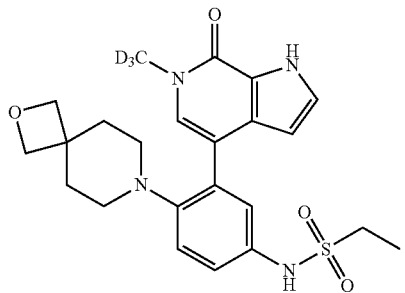

196

By the synthetic method and procedure of compound 7, the synthesis of compound 196 could be carried out with corresponding reagents. Among them, 2-oxa-7-aza-spiro[3.5]nonane hydrochloride was used to substitute 5-aza-spiro[2.4]heptane hydrochloride in the first step of the reaction, and Int. 8 was used to replace Int. 6 in the third step of the reaction, while other reaction reagents and conditions were completely consistent with those for synthesis of compound 7, and thus compound 196 was prepared.

MS: m/z 460.5 [M+H]⁺.

¹H NMR (400 MHz, DMSO) δ 12.01 (s, 1H), 9.55 (s, 1H), 7.42 (s, 1H), 7.27 (s, 1H), 7.15 (m, 2H), 7.02 (d, J=8.6 Hz, 1H), 6.15 (s, 1H), 4.28 (s, 4H), 3.04 (q, J=7.3 Hz, 2H), 2.66 (s, 4H), 1.58 (s, 4H), 1.21 (t, J=7.3 Hz, 3H).

Synthesis of N-ethyl-3-(6-trideuteromethyl-7-oxo-6,7-dihydro-1H-pyrrolo [2,3-c]pyridin-4-yl)-4-(6-aza-spiro[2.5]octan-6-yl)benzenesulfonamide (Compound 197)

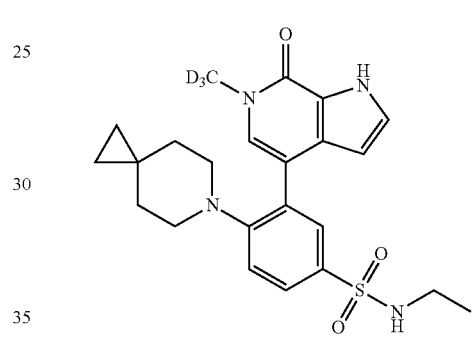

197

Synthesis of 3-bromo-N-ethyl-4-fluorobenzenesulfonamide (Int. 13)

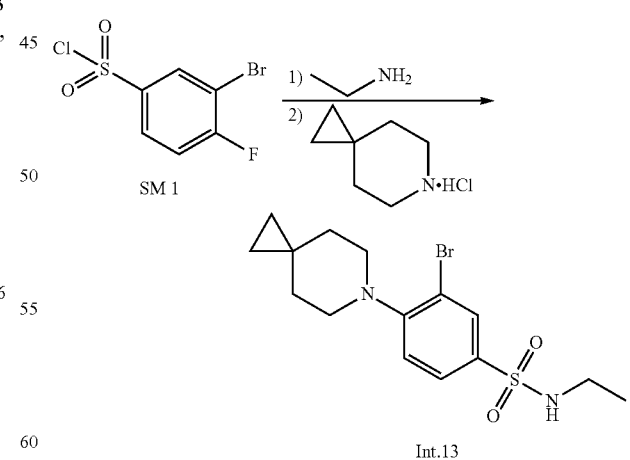

Int.13

Compound SM 1 (1.08 g, 4 mmol) and THF (10 mL) were added to a 50 mL reaction flask, and then 40% ethylamine aqueous solution (1 mL) was added to the system at room temperature, then the system was reacted at room temperature for 5 h. After completion of the reaction, the reaction solution was poured into 50 mL water, and extracted with 45 mL dichloromethane (15 mL×3). The organic phases were combined, dried over anhydrous sodium sulfate, and the solvent was rotatory evaporated to obtain a solid. DMSO (15 mL), 6-aza-spiro[2.5]octane hydrochloride (730 mg, 5 mmol), and sodium carbonate (1.27 g, 12 mmol) were added to the solid, and the system was reacted at 80° C. for 10 h. After the reaction was finished, the reaction solution was poured into 50 mL water, and extracted with 45 mL dichloromethane (15 mL×3). The organic phases were combined, dried over anhydrous sodium sulfate, and purified by column chromatography to obtain compound Int. 13 (1.4 g), with a yield of 93.7%. MS: m/z 373, 375 [M+H]⁺.

By the synthetic method and procedure of compound 24, the synthesis of compound 197 could be carried out with corresponding reagents. Among them, in the first step of the reaction, the conditions for synthesis of Int. 13 were used, and the solid intermediate obtained by the reaction of 3-bromo-4-fluorobenzene-1-sulfonyl chloride with 40% ethylamine aqueous solution was used to take the place of 2-bromo-1-fluoro-4-methylsulfonylbenzene, and 6-aza-spiro[2.5]octane hydrochloride was used to substitute 5-aza-spiro[2.4]heptane hydrochloride; and Int. 8 was used to replace Int. 6 in the second step of the reaction; while other reaction reagents and conditions were completely consistent with those for synthesis of compound 24, and thus compound 197 was prepared.

MS: m/z 444.6 [M+H]⁺.

¹H NMR (400 MHz, DMSO) δ ppm 11.98 (s, 1H), 9.54 (s, 1H), 7.44 (s, 1H), 7.28 (s, 1H), 7.17-7.05 (m, 3H), 6.16 (s, 1H), 3.07-3.01 (m, 2H), 2.78 (s, 4H), 1.23-1.13 (m, 7H), 0.19 (s, 4H).

Synthesis of 5-(6-trideuteromethyl-7-oxo-6,7-dihydro-1H-pyrrolo[2,3-c] pyridin-4-yl)-6-(5-aza-spiro[2.4]heptan-5-yl)pyridin-3-sulfonamide (Compound 198)

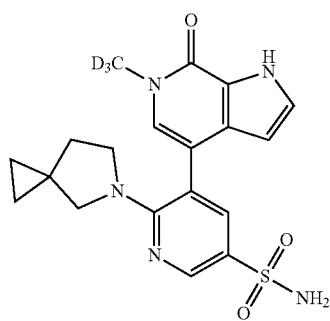

198

By the synthetic method and procedure of compound 197, the synthesis of compound 198 could be carried out with corresponding reagents. In the first step of the reaction, 5-bromo-6-fluoropyridin-3-sulfonyl chloride was used to substitute 3-bromo-4-fluorobenzenesulfonyl chloride, ammonia water was used to substitute ethylamine aqueous solution, and 5-aza-spiro[2.4]heptane hydrochloride was used to substitute 6-aza-spiro[2.5]octane hydrochloride, while other reaction reagents and conditions were completely consistent with those for synthesis of compound 197, and thus compound 198 was prepared.

MS: m/z 403.6 [M+H]⁺.

¹H NMR (400 MHz, DMSO) δ 12.18 (s, 1H), 8.46 (d, J=2.4 Hz, 1H), 7.75 (d, J=2.4 Hz, 1H), 7.33 (t, J=2.7 Hz, 1H), 7.26 (s, 1H), 7.20 (s, 2H), 6.09-5.98 (m, 1H), 3.35 (m, 2H), 3.18 (d, J=5.2 Hz, 2H), 1.64 (t, J=6.6 Hz, 2H), 0.46 (s, 4H).

Synthesis of 5-(6-trideuteromethyl-7-oxo-6,7-dihydro-1H-pyrrolo[2,3-c] pyridin-4-yl)-6-(6-aza-spiro[2.5]octan-6-yl)pyridin-3-sulfonamide (Compound 199)

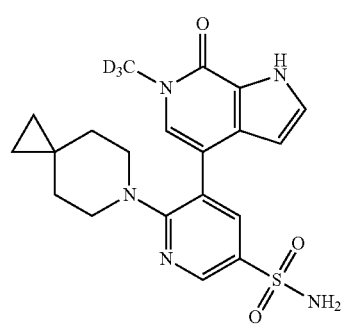

199

By the synthetic method and procedure of compound 197, the synthesis of compound 198 could be carried out with corresponding reagents. In the first step of the reaction, 5-bromo-6-fluoropyridin-3-sulfonyl chloride was used to substitute 3-bromo-4-fluorobenzenesulfonyl chloride, and ammonia water was used to substitute ethylamine aqueous solution, while other reaction reagents and conditions were completely consistent with those for synthesis of compound 197, and thus compound 199 was prepared.

MS: m/z 417.6 [M+H]⁺.

¹H NMR (400 MHz, DMSO) δ 12.16 (s, 1H), 8.51 (d, J=2.3 Hz, 1H), 7.87 (d, J=2.2 Hz, 1H), 7.43 (s, 1H), 7.34 (s, 1H), 7.30 (s, 2H), 6.13 (s, 1H), 3.34 (d, J=10.1 Hz, 4H), 1.15 (s, 4H), 0.22 (s, 4H).

Synthesis of 3-(6-trideuteromethyl-7-oxo-6,7-dihydro-1H-pyrrolo[2,3-c] pyridin-4-yl)-4-(5-aza-spiro[2.4]heptan-5-yl)benzensulfonamide (Compound 200)

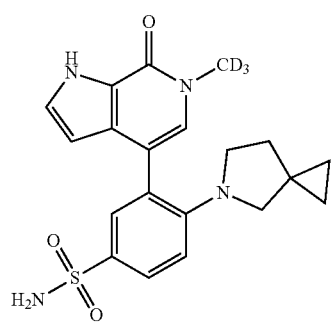

200

By the synthetic method and procedure of compound 197, the synthesis of compound 200 could be carried out with corresponding reagents. In the first step of the reaction, ammonia water was used to substitute ethylamine aqueous solution, and 5-aza-spiro[2.4]heptane hydrochloride was used to substitute 6-aza-spiro[2.5]octane hydrochloride, while other reaction reagents and conditions were completely consistent with those for synthesis of compound 197, and thus compound 200 was prepared.

MS: m/z 402.5 [M+H]$^+$.

$^1$H NMR (400 MHz, DMSO): δ 12.09 (s, 1H), 7.62 (dd, J=8.8, 2.4 Hz, 1H), 7.55 (d, J=2.4 Hz, 1H), 7.28 (d, J=2.7 Hz, 1H), 7.19 (s, 1H), 7.04 (s, 2H), 6.90 (d, J=8.8 Hz, 1H), 6.01 (d, J=2.7 Hz, 1H), 3.22 (t, J=6.6 Hz, 2H), 2.94 (s, 2H), 1.64 (t, J=6.5 Hz, 2H), 0.49-0.35 (m, 4H).

Synthesis of 3-(6-trideuteromethyl-7-oxo-6,7-dihydro-1H-pyrrolo[2,3-c] pyridin-4-yl)-4-(6-azaspiro[2.5]octan-6-yl)benzenesulfonamide (Compound 201)

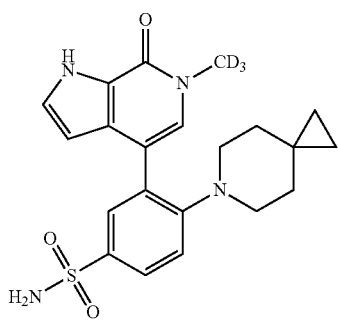

201

By the synthetic method and procedure of compound 197, the synthesis of compound 201 could be carried out with corresponding reagents. In the first step of the reaction, ammonia water was used to substitute ethylamine aqueous solution, while other reaction reagents and conditions were completely consistent with those for synthesis of compound 197, and thus compound 201 was prepared.

MS: m/z 416.6 [M+H]$^+$.

$^1$H NMR (400 MHz, DMSO) δ 11.85 (s, 1H), 7.46 (dd, J=8.5, 2.3 Hz, 1H), 7.42 (d, J=2.3 Hz, 1H), 7.26-7.19 (m, 2H), 7.10 (s, 1H), 7.00 (d, J=8.5 Hz, 1H), 5.92 (d, J=2.3 Hz, 1H), 2.79 (s, 4H), 0.99 (s, 4H), 0.22 (s, 4H).

Synthesis of N-methyl-3-(6-trideuteromethyl-7-oxo-6,7-dihydro-1H-pyrrolo [2,3-c]pyridin-4-yl)-4-(6-aza-spiro[2.5]octan-6-yl)benzenesulfonamide (Compound 202)

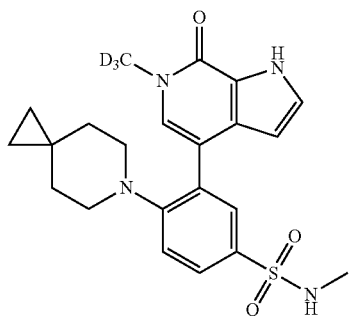

202

By the synthetic method and procedure of compound 197, the synthesis of compound 202 could be carried out with corresponding reagents. In the first step of the reaction, methylamine aqueous solution was used to substitute ethylamine aqueous solution, while other reaction reagents and conditions were completely consistent with those for synthesis of compound 197, and thus compound 202 was prepared.

MS: m/z 430.5 [M+H]$^+$.

$^1$H NMR (400 MHz, DMSO) δ 11.83 (s, 1H), 7.45 (d, J=8.4 Hz, 1H), 7.41 (s, 1H), 7.23 (s, 1H), 7.05 (dd, J=25.8, 10.0 Hz, 3H), 5.93 (s, 1H), 2.75 (s, 4H), 2.22 (d, J=3.8 Hz, 3H), 0.98 (d, J=46.2 Hz, 4H), 0.21 (s, 4H).

Synthesis of N,N-dimethyl-3-(6-trideuteromethyl-7-oxo-6,7-dihydro-1H-pyrrolo[2,3-c]pyridin-4-yl)-4-(6-aza-spiro[2.5]octan-6-yl)benzenesulfonamide (Compound 203)

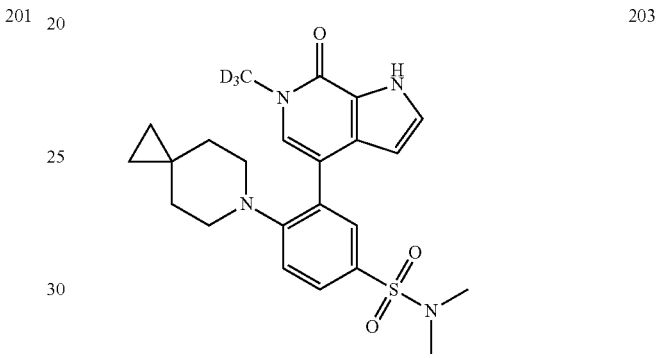

203

By the synthetic method and procedure of compound 197, the synthesis of compound 203 could be carried out with corresponding reagents. In the first step of the reaction, dimethylamine aqueous solution was used to substitute ethylamine aqueous solution, while other reaction reagents and conditions were completely consistent with those for synthesis of compound 197, and thus compound 203 was prepared.

MS: m/z 444.5 [M+H]$^+$.

$^1$H NMR (400 MHz, DMSO) δ 12.05 (s, 1H), 7.66-7.56 (m, 1H), 7.52 (d, J=1.9 Hz, 1H), 7.45 (s, 1H), 7.29 (s, 1H), 7.24 (d, J=8.6 Hz, 1H), 6.11 (s, 1H), 2.97 (s, 4H), 2.59 (d, J=18.4 Hz, 6H), 1.12 (s, 4H), 0.20 (s, 4H).

Synthesis of 4-(1,1-difluoro-6-aza-spiro[2.5]octan-6-yl)-N,N-dimethyl-3-(6-trideuteromethyl-7-oxo-6,7-dihydro-1H-pyrrolo[2,3-c]pyridin-4-yl)benzenesulfonamide (Compound 204)

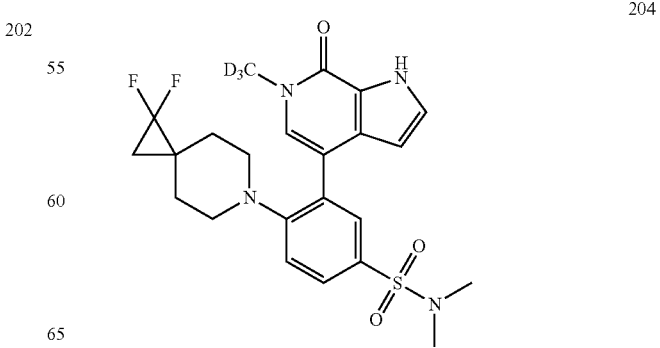

204

By the synthetic method and procedure of compound 197, the synthesis of compound 204 could be carried out with corresponding reagents. In the first step of the reaction, dimethylamine aqueous solution was used to substitute ethylamine aqueous solution, and 1,1-difluoro-6-aza-spiro[2.5]octane hydrochloride was used to replace 6-aza-spiro[2.5]octane hydrochloride, while other reaction reagents and conditions were completely consistent with those for synthesis of compound 197, and thus compound 204 was prepared.

MS: m/z 480.5 [M+H]$^+$.

$^1$H NMR (400 MHz, DMSO) δ 12.08 (s, 1H), 7.64 (dd, J=8.6, 2.3 Hz, 1H), 7.53 (d, J=2.2 Hz, 1H), 7.45 (s, 1H), 7.30 (t, J=2.6 Hz, 1H), 7.26 (d, J=8.6 Hz, 1H), 6.12 (s, 1H), 2.98 (s, 4H), 2.61 (s, 6H), 1.44-1.20 (m, 6H).

Synthesis of N-(2-hydroxyethyl)-3-(6-trideuteromethyl-7-oxo-6,7-dihydro-1H-pyrrolo[2,3-c]pyridin-4-yl)-4-(6-aza-spiro[2.5]octan-6-yl)benzenesulfonamide (Compound 205)

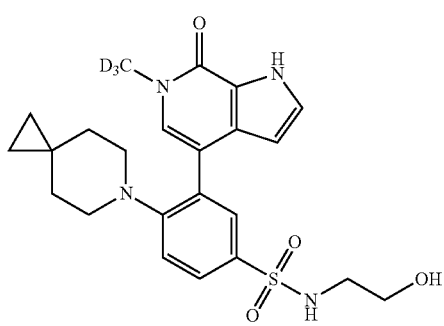

205

By the synthetic method and procedure of compound 197, the synthesis of compound 205 could be carried out with corresponding reagents. In the first step of the reaction, 2-hydroxyethylamine aqueous solution was used to substitute ethylamine aqueous solution, while other reaction reagents and conditions were completely consistent with those for synthesis of compound 197, and thus compound 205 was prepared.

MS: m/z 430.5 [M+H]$^+$.

$^1$H NMR (400 MHz, DMSO) δ 12.06 (s, 1H), 7.76-7.59 (m, 2H), 7.44 (s, 2H), 7.31 (s, 1H), 7.21 (d, J=8.5 Hz, 1H), 6.15 (s, 1H), 3.43-3.37 (m, 2H), 2.96 (m, 4H), 2.79 (m, 2H), 1.15 (m, 4H), 0.21 (s, 4H).

Synthesis of N-methyl-5-(6-trideuteromethyl-7-oxo-6,7-dihydro-1H-pyrrolo [2,3-c]pyridin-4-yl)-6-(6-aza-spiro[2.5]octan-6-yl)pyridin-3-sulfonamide (Compound 206)

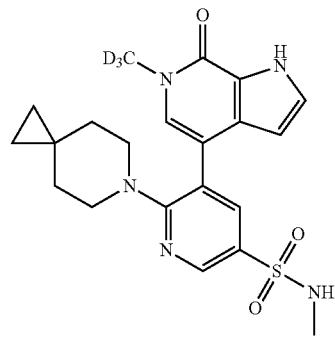

206

By the synthetic method and procedure of compound 197, the synthesis of compound 206 could be carried out with corresponding reagents. In the first step of the reaction, 5-bromo-6-fluoropyridin-3-sulfonyl chloride was used to replace 3-bromo-4-fluorobenzenesulfonyl chloride, and methylamine aqueous solution was used to substitute ethylamine aqueous solution, while other reaction reagents and conditions were completely consistent with those for synthesis of compound 197, and thus compound 206 was prepared.

MS: m/z 431.6 [M+H]$^+$.

$^1$H NMR (400 MHz, DMSO) δ 11.85 (s, 1H), 7.46 (dd, J=8.5, 2.3 Hz, 1H), 7.42 (d, J=2.3 Hz, 1H), 7.26-7.19 (m, 2H), 7.10 (s, 1H), 7.00 (d, J=8.5 Hz, 1H), 5.92 (d, J=2.3 Hz, 1H), 3.15 (s, 3H), 2.73 (br, 4H), 2.55 (s, 3H), 0.92 (br, 4H), 0.20 (br, 4H).

Synthesis of N-ethyl-5-(6-trideuteromethyl-7-oxo-6,7-dihydro-1H-pyrrolo [2,3-c]pyridin-4-yl)-6-(6-aza-spiro[2.5]octan-6-yl)pyridin-3-sulfonamide (Compound 207)

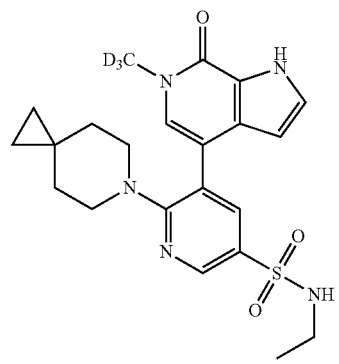

207

By the synthetic method and procedure of compound 197, the synthesis of compound 207 could be carried out with corresponding reagents. In the first step of the reaction, 5-bromo-6-fluoropyridin-3-sulfonyl chloride was used to replace 3-bromo-4-fluorobenzenesulfonyl chloride, while other reaction reagents and conditions were completely consistent with those for synthesis of compound 197, and thus compound 207 was prepared.

MS: m/z 445.6 [M+H]+.

1H NMR (400 MHz, DMSO) δ 11.85 (s, 1H), 7.46 (dd, J=8.5, 2.3 Hz, 1H), 7.42 (d, J=2.3 Hz, 1H), 7.26-7.19 (m, 2H), 7.10 (s, 1H), 7.00 (d, J=8.5 Hz, 1H), 5.92 (d, J=2.3 Hz, 1H), 2.75 (s, 4H), 2.57 (s, 2H), 0.92 (s, 4H), 0.78 (t, J=7.2 Hz, 3H), 0.18 (s, 4H).

Synthesis of N-isopropyl-5-(6-trideuteromethyl-7-oxo-6,7-dihydro-1H-pyrrolo[2,3-c]pyridin-4-yl)-6-(6-aza-spiro[2.5]octan-6-yl)pyridin-3-sulfonamide (Compound 208)

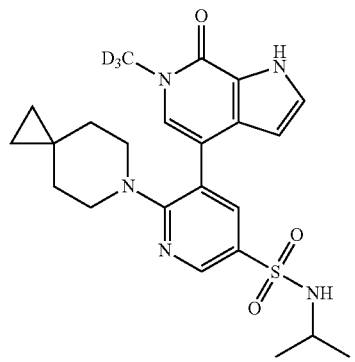

208

By the synthetic method and procedure of compound 197, the synthesis of compound 208 could be carried out with corresponding reagents. In the first step of the reaction, 5-bromo-6-fluoropyridin-3-sulfonyl chloride was used to replace 3-bromo-4-fluorobenzenesulfonyl chloride, and isopropylamine was used to substitute ethylamine aqueous solution, while other reaction reagents and conditions were completely consistent with those for synthesis of compound 197, and thus compound 208 was prepared.

MS: m/z 459.6 [M+H]+.

1H NMR (400 MHz, DMSO) δ 11.85 (s, 1H), 7.46 (dd, J=8.5, 2.3 Hz, 1H), 7.42 (d, J=2.3 Hz, 1H), 7.26-7.19 (m, 2H), 7.10 (s, 1H), 7.00 (d, J=8.5 Hz, 1H), 5.92 (d, J=2.3 Hz, 1H), 2.75-2.65 (m, 5H), 0.92 (s, 4H), 0.78 (d, J=7.2 Hz, 6H), 0.19 (s, 4H).

Synthesis of N,N-dimethyl-5-(6-trideuteromethyl-7-oxo-6,7-dihydro-1H-pyrrolo[2,3-c]pyridin-4-yl)-6-(6-aza-spiro[2.5]octan-6-yl)pyridin-3-sulfonamide (Compound 209)

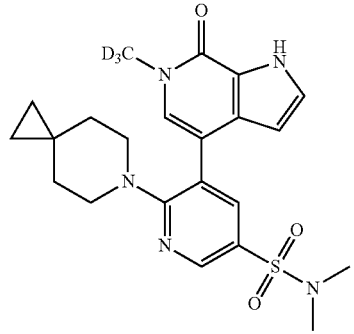

209

By the synthetic method and procedure of compound 197, the synthesis of compound 209 could be carried out with corresponding reagents. In the first step of the reaction, 5-bromo-6-fluoropyridin-3-sulfonyl chloride was used to replace 3-bromo-4-fluorobenzenesulfonyl chloride, and dimethylamine aqueous solution was used to substitute ethylamine aqueous solution, while other reaction reagents and conditions were completely consistent with those for synthesis of compound 197, and thus compound 209 was prepared.

MS: m/z 445.6 [M+H]+.

1H NMR (400 MHz, DMSO) δ 11.85 (s, 1H), 7.46 (dd, J=8.5, 2.3 Hz, 1H), 7.42 (d, J=2.3 Hz, 1H), 7.26-7.19 (m, 2H), 7.10 (s, 1H), 7.00 (d, J=8.5 Hz, 1H), 5.92 (d, J=2.3 Hz, 1H), 2.97 (s, 4H), 2.59 (d, J=18.4 Hz, 6H), 1.12 (s, 4H), 0.20 (s, 4H).

Synthesis of 4-(5-((3-hydroxylpyrrolidin-1-yl)sulfonyl)-2-(6-aza-spiro[2.5] octan-6-yl)pyridin-3-yl)-6-trideuteromethyl-1H-pyrrolo[2,3-c]pyridin-7(6H)-one (Compound 210)

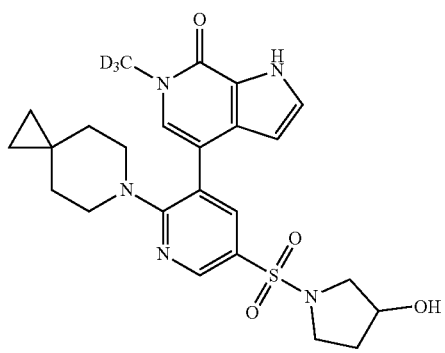

210

By the synthetic method and procedure of compound 197, the synthesis of compound 210 could be carried out with corresponding reagents. In the first step of the reaction, 5-bromo-6-fluoropyridin-3-sulfonyl chloride was used to replace 3-bromo-4-fluorobenzenesulfonyl chloride, and 3-hydroxylpyrrolidine was used to substitute ethylamine aqueous solution, while other reaction reagents and conditions were completely consistent with those for synthesis of compound 197, and thus compound 210 was prepared.

MS: m/z 487.2 [M+H]+.

1H NMR (400 MHz, DMSO) δ 11.85 (s, 1H), 7.46 (dd, J=8.5, 2.3 Hz, 1H), 7.42 (d, J=2.3 Hz, 1H), 7.26-7.19 (m, 2H), 7.10 (s, 1H), 7.00 (d, J=8.5 Hz, 1H), 5.92 (d, J=2.3 Hz, 1H), 2.75-2.65 (m, 4H), 2.45-2.1 (m, 5H), 0.92-0.78 (m, 6H), 0.20 (s, 4H).

Synthesis of 6-(1,1-difluoro-6-aza-spiro[2.5]octan-6-yl)-5-(6-trideuteromethyl-7-oxo-6,7-dihydro-1H-pyrrolo[2,3-c]pyridin-4-yl) pyridin-3-sulfonamide (Compound 211)

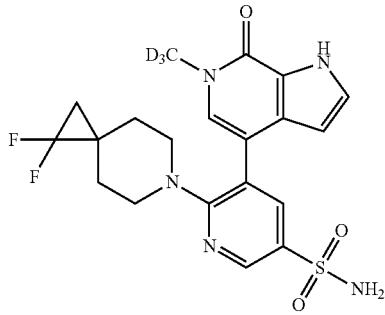

211

By the synthetic method and procedure of compound 197, the synthesis of compound 211 could be carried out with corresponding reagents. In the first step of the reaction, 5-bromo-6-fluoropyridin-3-sulfonyl chloride was used to substitute 3-bromo-4-fluorobenzenesulfonyl chloride, and ammonia water was used to substitute ethylamine aqueous solution, and 1,1-difluoro-6-aza-spiro[2.5]octane hydrochloride was used to replace 6-aza-spiro[2.5]octane hydrochloride, while other reaction reagents and conditions were completely consistent with those for synthesis of compound 197, and thus compound 211 was prepared.

MS: m/z 453.5 [M+H]+.

$^1$H NMR (400 MHz, DMSO) δ 11.85 (s, 1H), 7.46 (dd, J=8.5, 2.3 Hz, 1H), 7.42 (d, J=2.3 Hz, 1H), 7.26-7.19 (m, 2H), 7.10 (s, 1H), 7.00 (d, J=8.5 Hz, 1H), 5.92 (d, J=2.3 Hz, 1H), 2.99 (s, 4H), 1.30-1.16 (m, 6H).

Synthesis of 6-(1,1-difluoro-6-aza-spiro[2.5]octan-6-yl)-N-methyl-5-(6-trideuteromethyl-7-oxo-6,7-dihydro-1H-pyrrolo[2,3-c]pyridin-4-yl)pyridin-3-sulfonamide (Compound 212)

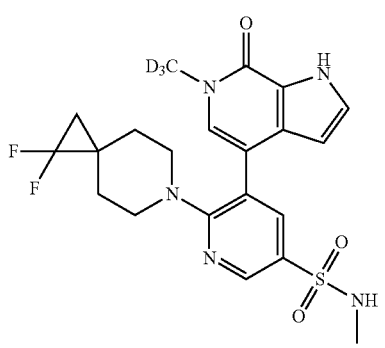

212

By the synthetic method and procedure of compound 197, the synthesis of compound 212 could be carried out with corresponding reagents. In the first step of the reaction, 5-bromo-6-fluoropyridin-3-sulfonyl chloride was used to substitute 3-bromo-4-fluorobenzenesulfonyl chloride, and methylamine aqueous solution was used to substitute ethylamine aqueous solution, and 1,1-difluoro-6-aza-spiro[2.5]octane hydrochloride was used to replace 6-aza-spiro[2.5]octane hydrochloride, while other reaction reagents and conditions were completely consistent with those for synthesis of compound 197, and thus compound 212 was prepared.

MS: m/z 467.5 [M+H]+.

$^1$H NMR (400 MHz, DMSO) δ 12.16 (s, 1H), 8.48 (d, J=2.4 Hz, 1H), 7.80 (d, J=2.4 Hz, 1H), 7.45 (s, 1H), 7.38 (d, J=5.1 Hz, 1H), 7.33 (t, J=2.7 Hz, 1H), 6.12 (d, J=2.3 Hz, 1H), 3.40 (d, J=13.3 Hz, 2H), 3.29-3.21 (m, 2H), 2.44 (d, J=5.1 Hz, 3H), 1.43 (d, J=8.1 Hz, 2H), 1.33 (s, 2H), 1.22 (t, J=8.1 Hz, 2H).

Synthesis of 6-(1,1-difluoro-6-aza-spiro[2.5]octan-6-yl)-N-trideuteromethyl-5-(6-trideuteromethyl-7-oxo-6,7-dihydro-1H-pyrrolo[2,3-c]pyridin-4-yl) pyridin-3-sulfonamide (Compound 213)

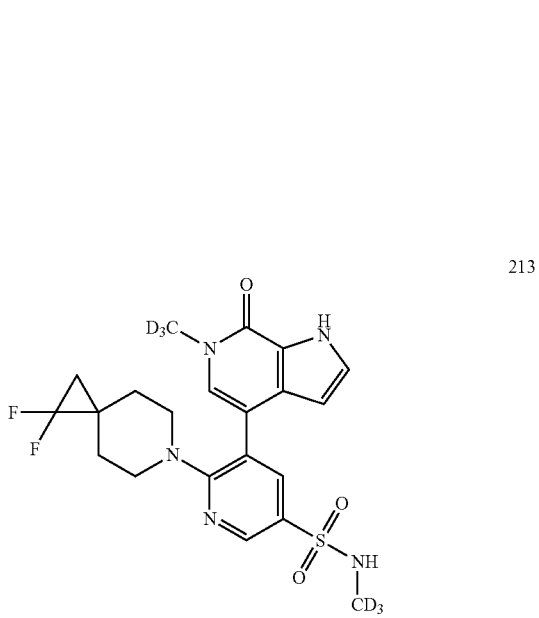 [SMILES: [2H]C([2H])([2H])NS(=O)(=O)c1cnc(N2CCC3(CC2)CC3(F)F)c(-c2cn(C([2H])([2H])[2H])c(=O)c3[nH]ccc23)c1]

213

By the synthetic method and procedure of compound 197, the synthesis of compound 213 could be carried out with corresponding reagents. In the first step of the reaction, 5-bromo-6-fluoropyridin-3-sulfonyl chloride was used to substitute 3-bromo-4-fluorobenzenesulfonyl chloride, and deuteromethylamine hydrochloride was used to substitute ethylamine aqueous solution, and 1,1-difluoro-6-aza-spiro[2.5]octane hydrochloride was used to replace 6-aza-spiro[2.5]octane hydrochloride, while other reaction reagents and conditions were completely consistent with those for synthesis of compound 197, and thus compound 213 was prepared.

MS: m/z 470.5 [M+H]+.

$^1$H NMR (400 MHz, DMSO) δ 11.85 (s, 1H), 7.46 (dd, J=8.5, 2.3 Hz, 1H), 7.42 (d, J=2.3 Hz, 1H), 7.26-7.19 (m, 2H), 7.10 (s, 1H), 7.00 (d, J=8.5 Hz, 1H), 5.92 (d, J=2.3 Hz, 1H), 2.99 (s, 4H), 1.30-1.16 (m, 6H).

Synthesis of 4-(2-(1,1-difluoro-6-aza-spiro[2.5]octan-6-yl)-5-(methylsulfonyl)pyridin-3-yl)-6-trideuteromethyl-1H-pyrrolo[2,3-c]pyridin-7(6H)-one (Compound 214)

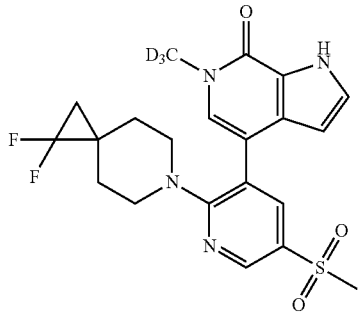

214

By the synthetic method and procedure of compound 24, the synthesis of compound 214 could be carried out with corresponding reagents. Among them, in the first step of the reaction, 1,1-difluoro-6-aza-spiro[2.5]octane hydrochloride was used to substitute 5-aza-spiro[2.4]heptane hydrochloride, and 3-bromo-5-methylsulfuryl-2-fluoropyridine was used to take the place of 2-bromo-1-fluoro-4-methylsulfonylbenzene; Int. 8 was used to replace Int. 6 in the second step of the reaction, while other reaction reagents and conditions were completely consistent with those for synthesis of compound 24, and thus compound 214 was prepared.

MS: m/z 452.5 [M+H]$^+$.

$^1$H NMR (400 MHz, DMSO) δ 11.85 (s, 1H), 7.46 (dd, J=8.5, 2.3 Hz, 1H), 7.42 (d, J=2.3 Hz, 1H), 7.26-7.19 (m, 2H), 7.10 (s, 1H), 7.00 (d, J=8.5 Hz, 1H), 5.92 (d, J=2.3 Hz, 1H), 3.20 (s, 3H), 2.99 (s, 4H), 1.30-1.16 (m, 6H).

Synthesis of 4-(2-(1,1-difluoro-6-aza-spiro[2.5]octan-6-yl)-5-(ethylsulfonyl) pyridin-3-yl)-6-trideuteromethyl-1H-pyrrolo[2,3-c]pyridin-7(6H)-one (Compound 215)

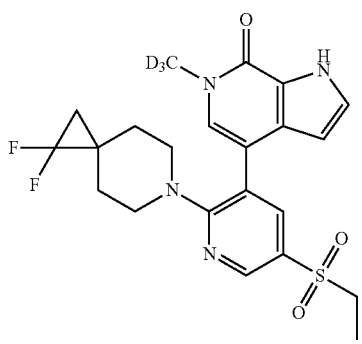

215

By the synthetic method and procedure of compound 24, the synthesis of compound 215 could be carried out with corresponding reagents. Among them, 1,1-difluoro-6-aza-spiro[2.5]octane hydrochloride was used to substitute 5-aza-spiro[2.4]heptane hydrochloride, and 3-bromo-5-ethylsulfuryl-2-fluoropyridine was used to take the place of 2-bromo-1-fluoro-4-methylsulfonylbenzene in the first step of the reaction; and Int. 8 was used to replace Int. 6 in the second step of the reaction, while other reaction reagents and conditions were completely consistent with those for synthesis of compound 24, and thus compound 215 was prepared.

MS: m/z 466.5 [M+H]$^+$.

$^1$H NMR (400 MHz, DMSO) δ 12.16 (s, 1H), 8.54 (d, J=2.4 Hz, 1H), 7.85 (d, J=2.4 Hz, 1H), 7.47 (s, 1H), 7.32 (t, J=2.7 Hz, 1H), 6.11 (d, J=2.2 Hz, 1H), 3.50-3.41 (m, 2H), 3.29 (dd, J=11.4, 7.5 Hz, 4H), 1.43 (d, J=8.6 Hz, 2H), 1.33 (s, 2H), 1.21 (dd, J=14.0, 5.5 Hz, 2H), 1.16 (dd, J=12.1, 4.8 Hz, 3H).

Synthesis of 4-(52-(1,1-difluoro-6-aza-spiro[2.5]octan-6-yl)-5-(isopropylsulfonyl)pyridin-3-yl)-6-trideuteromethyl-1H-pyrrolo[2,3-c]pyridin-7(6H)-one (Compound 216)

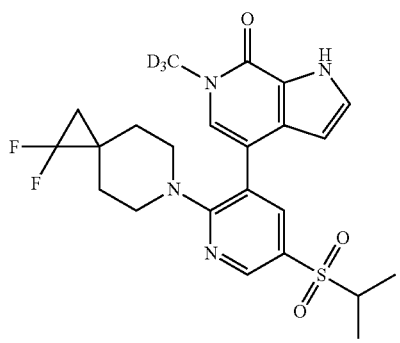

216

By the synthetic method and procedure of compound 24, the synthesis of compound 216 could be carried out with corresponding reagents. Among them, 1,1-difluoro-6-aza-spiro[2.5]octane hydrochloride was used to substitute 5-aza-spiro[2.4]heptane hydrochloride, and 3-bromo-5-isopropylsulfuryl-2-fluoropyridine was used to take the place of 2-bromo-1-fluoro-4-methylsulfonylbenzene in the first step of the reaction; and Int. 8 was used to replace Int. 6 in the second step of the reaction, while other reaction reagents and conditions were completely consistent with those for synthesis of compound 24, and thus compound 216 was prepared.

MS: m/z 480.5 [M+H]$^+$.

$^1$H NMR (400 MHz, DMSO) δ 11.85 (s, 1H), 7.46 (dd, J=8.5, 2.3 Hz, 1H), 7.42 (d, J=2.3 Hz, 1H), 7.26-7.19 (m, 2H), 7.10 (s, 1H), 7.00 (d, J=8.5 Hz, 1H), 5.92 (d, J=2.3 Hz, 1H), 3.10-3.01 (m, 1H), 2.99 (s, 4H), 2.77 (s, 3H), 1.30-1.16 (m, 6H), 0.99 (d, J=9.2 Hz, 6H).

Synthesis of 4-(1,1-difluoro-6-aza-spiro[2.5]octan-6-yl)-2-fluoro-5-(6-trideuteromethyl-7-oxo-6,7-dihydro-1H-pyrrolo[2,3-c]pyridin-4-yl)benzenesulfonamide (Compound 217)

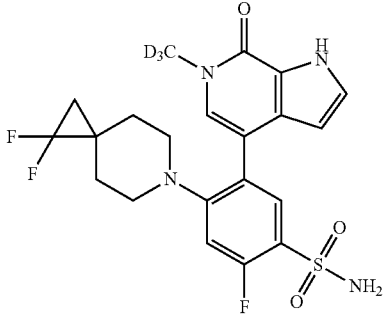

217

By the synthetic method and procedure of compound 197, the synthesis of compound 217 could be carried out with corresponding reagents. In the first step of the reaction, 2,4-difluoro-5-bromo-benzenesulfonyl chloride was used to substitute 3-bromo-4-fluorobenzenesulfonyl chloride, and ammonia water was used to take the place of ethylamine aqueous solution, and 1,1-difluoro-6-aza-spiro[2.5]octane hydrochloride was used to replace 6-aza-spiro[2.5]octane hydrochloride, while other reaction reagents and conditions were completely consistent with those for synthesis of compound 197, and thus compound 217 was prepared.

MS: m/z 470.5 [M+H]$^+$.

$^1$H NMR (400 MHz, DMSO) δ 12.06 (s, 1H), 7.59 (d, J=8.6 Hz, 1H), 7.49 (s, 2H), 7.35 (s, 1H), 7.29 (t, J=2.7 Hz, 1H), 7.04 (d, J=12.7 Hz, 1H), 6.12 (s, 1H), 2.97 (s, 4H), 1.43-1.07 (m, 6H).

Synthesis of 4-(2-(1,1-difluoro-6-aza-spiro[2.5]octan-6-yl)-5-(ethylsulfonyl)-4-fluorophenyl)-6-trideuteromethyl-1H-pyrrolo[2,3-c]pyridin-7(6H)-one (Compound 218)

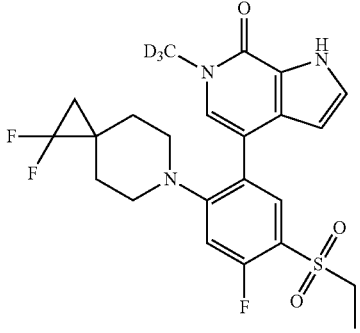

218

By the synthetic method and procedure of compound 24, the synthesis of compound 218 could be carried out with corresponding reagents. Among them, 1,1-difluoro-6-aza-spiro[2.5]octane hydrochloride was used to substitute 5-aza-spiro[2.4]heptane hydrochloride, and 2,4-difluoro-5-bromo-ethylsulfurylbenzene was used to take the place of 2-bromo-1-fluoro-4-methylsulfonylbenzene in the first step of the reaction; and Int. 8 was used to replace Int. 6 in the second step of the reaction, while other reaction reagents and conditions were completely consistent with those for synthesis of compound 24, and thus compound 218 was prepared.

MS: m/z 483.5 [M+H]$^+$.

$^1$H NMR (400 MHz, DMSO) δ 12.01 (s, 1H), 7.61 (d, J=8.6 Hz, 1H), 7.33 (s, 1H), 7.31 (t, J=2.7 Hz, 1H), 7.07 (d, J=12.7 Hz, 1H), 6.15 (s, 1H), 3.12 (q, J=9.8 Hz, 2H), 2.95 (s, 4H), 1.43-1.04 (m, 6H), 1.01 (t, J=9.8 Hz, 3H).

Synthesis of 4-(2-(1,1-difluoro-6-aza-spiro[2.5]octan-6-yl)-4-fluoro-5-(methylsulfonyl)phenyl)-6-trideuteromethyl-1H-pyrrolo[2,3-c]pyridin-7(6H)-one (Compound 219)

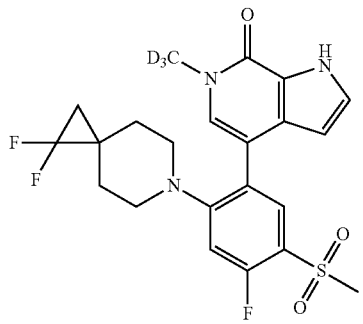

219

By the synthetic method and procedure of compound 24, the synthesis of compound 219 could be carried out with corresponding reagents. Among them, 1,1-difluoro-6-aza-spiro[2.5]octane hydrochloride was used to substitute 5-aza-spiro[2.4]heptane hydrochloride, and 2,4-difluoro-5-bromo (methylsulfuryl)benzene was used to take the place of 2-bromo-1-fluoro-4-(methylsulfonyl)benzene in the first step of the reaction; and Int. 8 was used to replace Int. 6 in the second step of the reaction, while other reaction reagents and conditions were completely consistent with those for synthesis of compound 24, and thus compound 219 was prepared.

MS: m/z 469.5 [M+H]$^+$.

$^1$H NMR (400 MHz, DMSO) δ 12.07 (s, 1H), 7.59 (d, J=8.5 Hz, 1H), 7.41 (s, 1H), 7.30 (t, J=2.7 Hz, 1H), 7.12 (d, J=13.0 Hz, 1H), 6.23-5.96 (m, 1H), 3.29 (s, 3H), 3.03 (m, 4H), 1.36 (m, 2H), 1.27 (m, 2H), 1.23-1.16 (m, 2H).

Synthesis of 3-(6-methyl-7-oxo-6,7-dihydro-1H-pyrrolo[2,3-c]pyridin-4-yl)-4-(6-aza-spiro[2.5]octan-6-yl)benzoic acid (Compound 220)

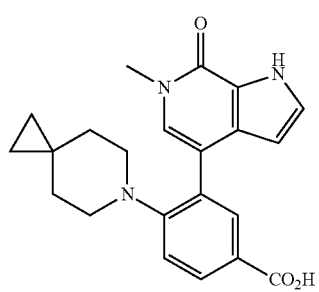

220

By the synthetic method and procedure of compound 24, the synthesis of compound 220 could be carried out with corresponding reagents. Among them, 6-aza-spiro[2.5]octane hydrochloride was used to substitute 5-aza-spiro[2.4]heptane hydrochloride, and 3-bromo-4-fluoro-benzoic acid was used to take the place of 2-bromo-1-fluoro-4-methylsulfonylbenzene in the first step of the reaction, while other reaction reagents and conditions were completely consistent with those for synthesis of compound 24, and thus compound 220 was prepared.

MS: m/z 378.5 [M+H]+.

1H NMR (400 MHz, DMSO) δ ppm 11.98 (s, 1H), 10.5 (s, 1H), 9.54 (s, 1H), 7.44 (s, 1H), 7.28 (s, 1H), 7.17-7.05 (m, 2H), 6.16 (s, 1H), 3.57 (s, 3H), 2.78 (s, 4H), 1.23-1.13 (m, 4H), 0.19 (s, 4H).

Synthesis of 3-(6-methyl-7-oxo-6,7-dihydro-1H-pyrrolo[2,3-c]pyridin-4-yl)-4-(6-aza-spiro[2.5]octan-6-yl)benzeneformamide (Compound 221)

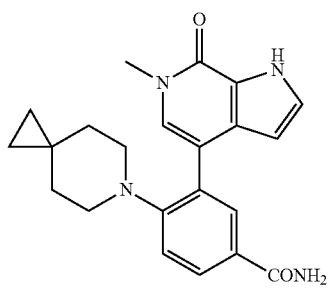

221

By the synthetic method and procedure of compound 24, the synthesis of compound 221 could be carried out with corresponding reagents. Among them, 6-aza-spiro[2.5]octane hydrochloride was used to substitute 5-aza-spiro[2.4]heptane hydrochloride, and 3-bromo-4-fluoro-benzeneformamide was used to take the place of 2-bromo-1-fluoro-4-methylsulfonylbenzene in the first step of the reaction, while other reaction reagents and conditions were completely consistent with those for synthesis of compound 24, and thus compound 221 was prepared.

MS: m/z 377.5 [M+H]+.

1H NMR (400 MHz, DMSO) δ 11.97 (s, 1H), 7.93-7.72 (m, 3H), 7.38 (s, 1H), 7.28 (s, 1H), 7.18 (s, 1H), 7.10 (d, J=8.6 Hz, 1H), 6.14 (s, 1H), 3.59 (s, 3H), 2.93 (s, 4H), 1.10 (s, 4H), 0.19 (s, 4H).

Synthesis of methyl 3-(6-methyl-7-oxo-6,7-dihydro-1H-pyrrolo[2,3-c]pyridin-4-yl)-4-(6-aza-spiro[2.5]octan-6-yl)benzoate (Compound 222)

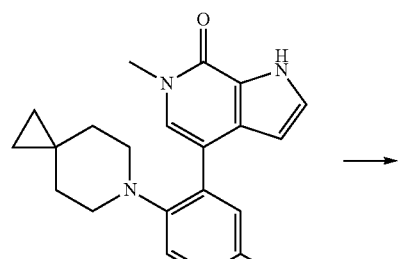

220

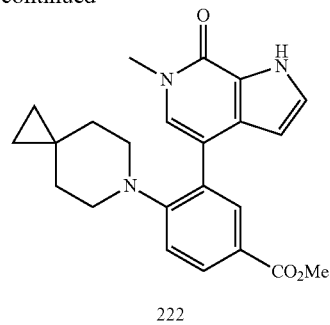

222

To a 50 mL reaction flask, were added 5 mL MeOH and compound 220 (75.6 mg, 0.2 mmol), to which was drop added 500 μL thionyl chloride at room temperature, and then the mixture was stirred overnight. After completion of the reaction, the solvent was rotatory evaporated, water was added, and then extracted with dichloromethane, followed by prep-TLC, to obtain methyl 3-(6-methyl-7-oxo-6,7-dihydro-1H-pyrrolo[2,3-c]pyridin-4-yl)-4-(6-aza-spiro[2.5]octan-6-yl)benzoate (compound 222, 65 mg), with a yield of 83%.

MS: m/z 392.5 [M+H]+.

1H NMR (400 MHz, DMSO) δ 11.92 (s, 1H), 7.78 (m, 2H), 7.36 (s, 1H), 7.27 (s, 1H), 7.06 (d, J=8.1 Hz, 1H), 6.05 (s, 1H), 4.11 (s, 3H), 3.61 (s, 3H), 2.91 (s, 4H), 1.12 (s, 4H), 0.21 (s, 4H).

Synthesis of 4-(5-acetyl-2-(6-aza-spiro[2.5]octan-6-yl)phenyl)-6-methyl-1H-pyrrolo[2,3-c]pyridin-7(6H)-one (Compound 223)

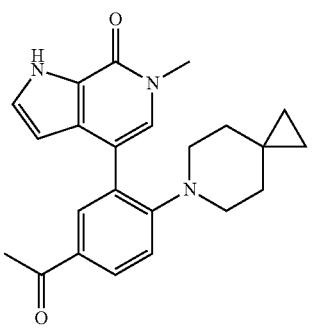

223

By the synthetic method and procedure of compound 24, the synthesis of compound 223 could be carried out with corresponding reagents. Among them, 6-aza-spiro[2.5]octane hydrochloride was used to substitute 5-aza-spiro[2.4]heptane hydrochloride, and 3-bromo-4-fluoro-acetophenone was used to take the place of 2-bromo-1-fluoro-4-methylsulfonylbenzene in the first step of the reaction, while other reaction reagents and conditions were completely consistent with those for synthesis of compound 24, and thus compound 223 was prepared.

MS: m/z 376.5 [M+H]+.

1H NMR (400 MHz, DMSO) δ 12.01 (s, 1H), 7.90 (dd, J=8.5, 2.0 Hz, 1H), 7.81 (d, J=2.1 Hz, 1H), 7.42 (s, 1H), 7.29 (d, J=2.6 Hz, 1H), 7.15 (d, J=8.5 Hz, 1H), 6.13 (s, 1H), 3.59 (s, 3H), 2.99 (s, 4H), 2.53 (s, 3H), 1.11 (s, 4H), 0.20 (s, 4H).

Synthesis of 4-(5-(1,1-dioxothiomorpholine-4-carbonyl)-2-(6-aza-spiro[2.5] octan-6-yl)phenyl)-6-methyl-1H-pyrrolo[2,3-c]pyridin-7(6H)-one (Compound 224)

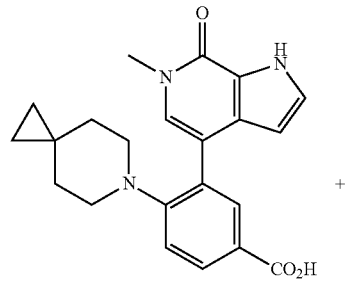

220

+

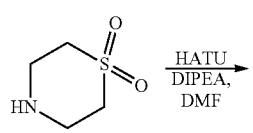

HATU
DIPEA,
DMF

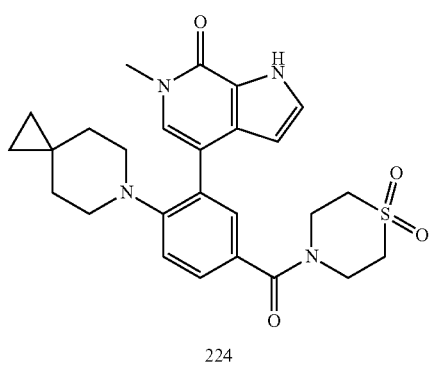

224

To a 50 mL reaction flask, were added 5 mL DMF, compound 220 (75.6 mg, 0.2 mmol), 1,1-dioxothiomorpholine (50 mg, 0.3 mmol), and HATU (100 mg, 0.4 mmol), then the mixture was stirred overnight at room temperature. After completion of the reaction, water was added, and then extracted with dichloromethane, followed by prep-TLC, to obtain compound 224 (60 mg), with a yield of 78%.

MS: m/z 495.6 [M+H]$^+$.

$^1$H NMR (400 MHz, DMSO) δ 12.01 (s, 1H), 7.48-7.37 (m, 3H), 7.29 (t, J=2.6 Hz, 1H), 7.13 (d, J=8.2 Hz, 1H), 6.21-6.14 (m, 1H), 3.92 (s, 4H), 3.58 (s, 3H), 3.26 (s, 4H), 2.91 (s, 4H), 1.13 (s, 4H), 0.20 (s, 4H).

Synthesis of 4-(5-(2-hydroxypropan-2-yl)-2-(6-azaspiro[2.5]octan-6-yl) phenyl)-6-methyl-1H-pyrrolo[2,3-c]pyridin-7(6H)-one (Compound 225)

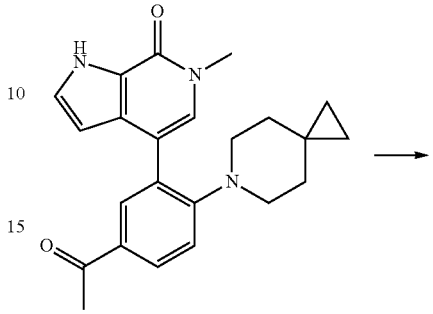

223

→

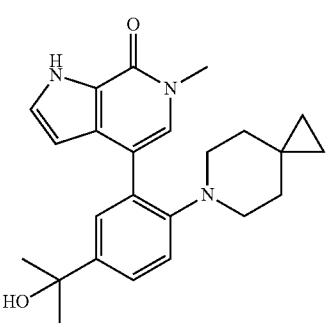

225

To a 50 mL reaction flask, were added THF (5 mL) and compound 223 (75 mg, 0.2 mmol), to which was drop added methyl Grignard reagent at room temperature, and then the mixture was stirred 5 h. After completion of the reaction, water was added, and then extracted with dichloromethane, followed by prep-TLC, to obtain compound 225 (45 mg), with a yield of 58%.

MS: m/z 392.5 [M+H]$^+$.

$^1$H NMR (400 MHz, DMSO) δ 11.98-11.92 (m, 1H), 7.38 (s, 3H), 7.29-7.25 (m, 1H), 7.06-7.00 (m, 1H), 6.19-6.15 (m, 1H), 4.95-4.89 (m, 1H), 3.59 (s, 3H), 2.82 (s, 4H), 1.44 (s, 6H), 1.13 (s, 4H), 0.20 (s, 4H).

Synthesis of Compound 226

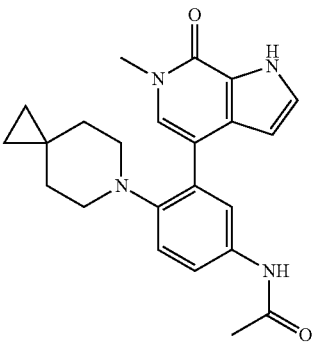

226

By the synthetic method and procedure of compound 7, the synthesis of compound 226 could be carried out with corresponding reagents. Among them, 6-aza-spiro[2.5]octane hydrochloride was used to substitute 5-aza-spiro[2.4]heptane hydrochloride in the first step of the reaction, and acetyl chloride was used to replace ethanesulfonyl chloride in the fourth step of the reaction, while other reaction reagents and conditions were completely consistent with those for synthesis of compound 7, and thus compound 226 was prepared.

MS: m/z 391.5 [M+H]$^+$.

$^1$H NMR (400 MHz, DMSO) δ ppm 11.98 (s, 1H), 9.54 (s, 1H), 7.44 (s, 1H), 7.28 (s, 1H), 7.17-7.05 (m, 3H), 6.16 (s, 1H), 3.57 (s, 3H), 2.78 (s, 4H), 2.06 (s, 3H), 1.23-1.13 (m, 4H), 0.19 (s, 4H).

Synthesis of N-(3-(6-trideuteromethyl-7-oxo-6,7-dihydro-1H-pyrrolo[2,3-c] pyridin-4-yl)-4-(6-aza-spiro[2.5]octan-6-yl)phenyl)acetylamine (Compound 227)

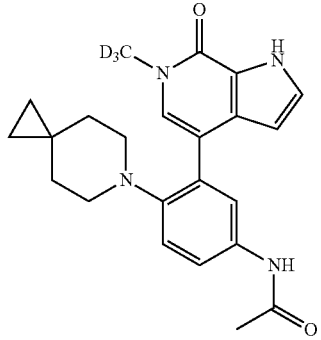

227

By the synthetic method and procedure of compound 7, the synthesis of compound 227 could be carried out with corresponding reagents. Among them, 6-aza-spiro[2.5]octane hydrochloride was used to substitute 5-aza-spiro[2.4]heptane hydrochloride in the first step of the reaction; Int. 8 was used to take the place of Int. 6; and acetyl chloride was used to replace ethanesulfonyl chloride in the fourth step of the reaction, while other reaction reagents and conditions were completely consistent with those for synthesis of compound 7, and thus compound 226 was prepared.

MS: m/z 394.5 [M+H]$^+$.

$^1$H NMR (400 MHz, DMSO) δ ppm 11.98 (s, 1H), 9.54 (s, 1H), 7.44 (s, 1H), 7.28 (s, 1H), 7.17-7.05 (m, 3H), 6.16 (s, 1H), 2.78 (s, 4H), 2.06 (s, 3H), 1.23-1.13 (m, 4H), 0.19 (s, 4H).

Example 3 Synthesis of 1-methyl-3-(3-(6-methyl-7-oxo-6,7-dihydro-1H-pyrrolo[2,3-c]pyridin-4-yl)-4-(6-aza-spiro[2.5]octan-6-yl)phenyl)urea (compound 228)

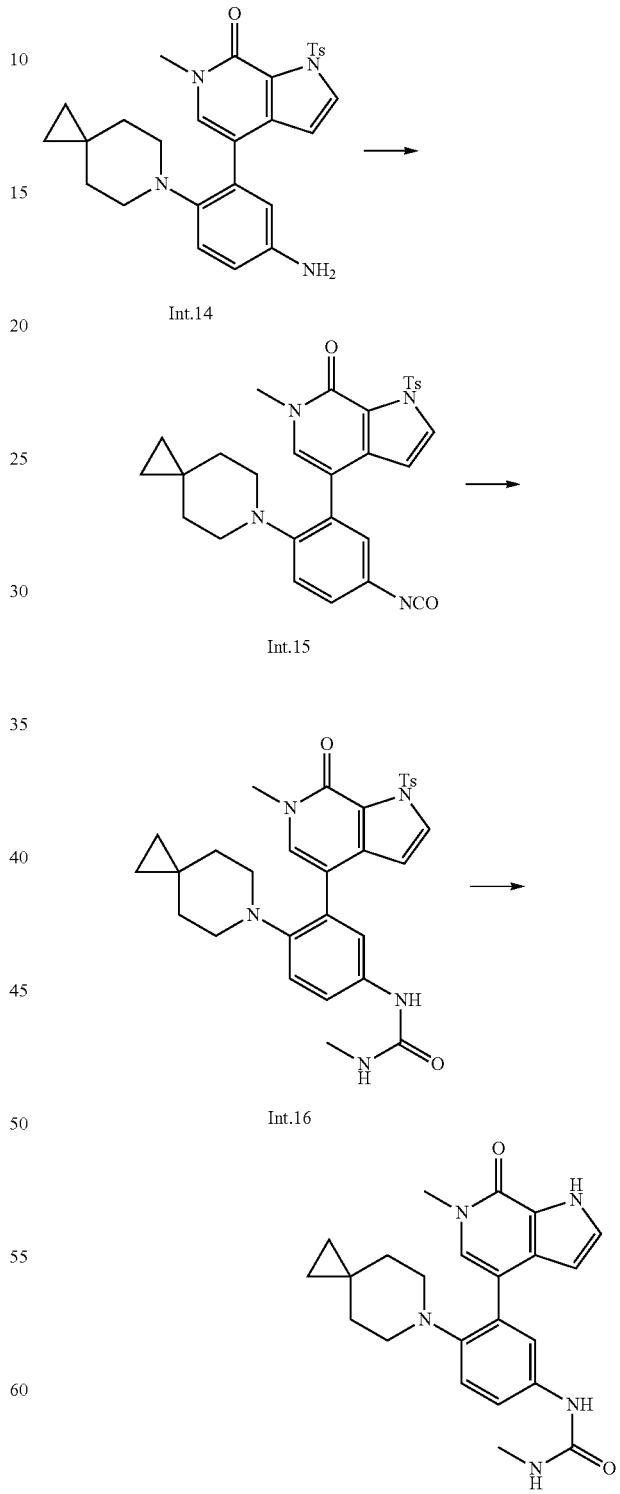

Synthesis of 4-(5-isocyanato-2-(6-aza-spiro[2.5]octan-6-yl)phenyl)-6-methyl-1-tosyl-1H-pyrrolo[2,3-c]pyridin-7(6H)-one (Int. 15)

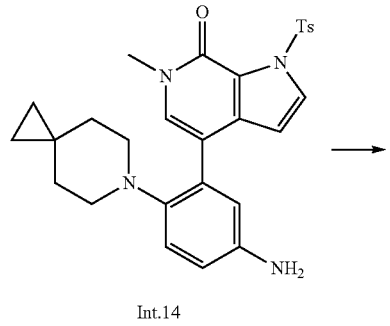
Int.14

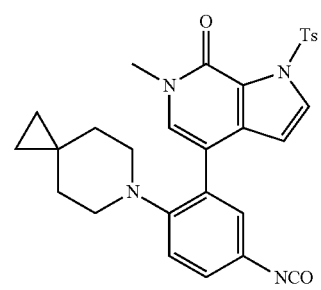
Int.15

To a 30 mL reaction flask, were added compound Int. 14 (450 mg, 0.9 mmol), dichloromethane (10 mL), and DIPEA (216 mg, 1.8 mmol), and then triphosgene (180 mg, 0.6 mmol) was added at 0° C. The system was allowed to react at 20° C. for 3 h, and after completion of the reaction, the solvent was rotatory evaporated, and the reaction was directly used in the next step.

Synthesis of 1-methyl-3-(3-(6-methyl-7-oxo-1-tosyl-6,7-dihydro-1H-pyrrolo[2,3-c]pyridin-4-yl)-4-(6-aza-spiro[2.5]octan-6-yl)phenyl)urea (Int. 16)

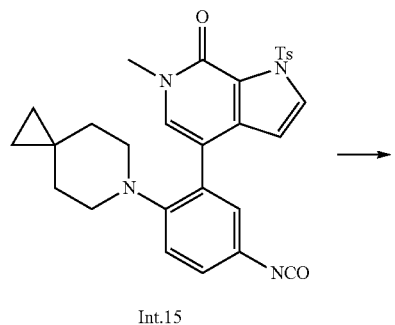
Int.15

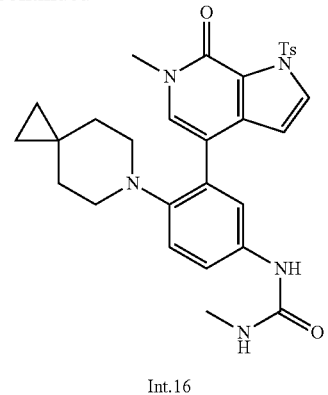
Int.16

To a 30 mL reaction flask, were added compound Int. 15 (158 mg, 0.3 mmol), dichloromethane (10 mL), and DIPEA (144 mg, 1.2 mmol), and then methylamine hydrochloride (40 mg, 0.6 mmol) was added at 0° C. The system was allowed to react at 20° C. for 3 h. After completion of the reaction, water was added, and then the mixture was extracted with dichloromethane, followed by prep-TLC, to obtain compound Int. 16 (132 mg), with a yield of 79%. MS: m/z 560.7 [M+H]$^+$.

Synthesis of 1-methyl-3-(3-(6-methyl-7-oxo-6,7-dihydro-1H-pyrrolo[2,3-c]pyridin-4-yl)-4-(6-aza-spiro[2.5]octan-6-yl)phenyl)urea (228)

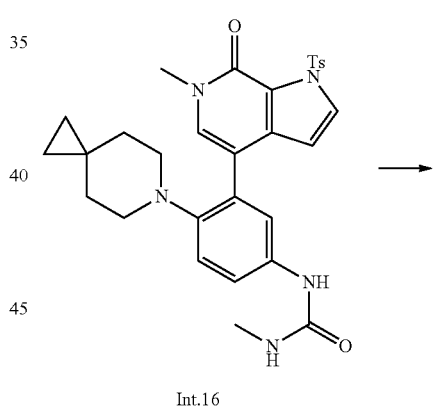
Int.16

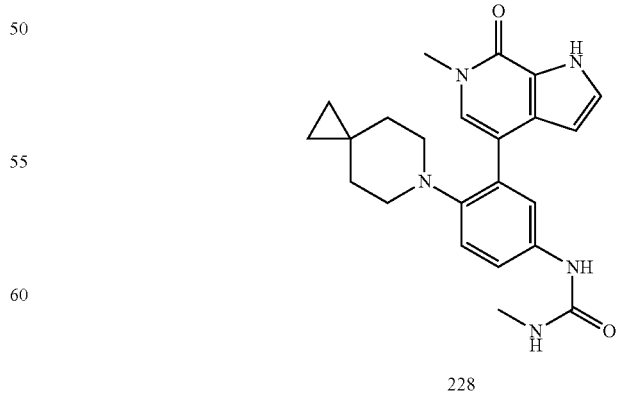
228

To a 50 mL reaction flask, were added THF (5 mL) and compound Int. 16 (112 mg, 0.2 mmol), and then potassium tert-butoxide (45 mg, 0.4 mmol) was added at room temperature. The mixture was stirred for 3 h. After completion of the reaction, water was added, and then the mixture was extracted with dichloromethane, followed by prep-TLC, to obtain compound 228 (60 mg), with a yield of 75%.

MS: m/z 406 [M+H]$^+$.

$^1$H NMR (400 MHz, DMSO) δ ppm 11.98 (s, 1H), 9.54 (s, 1H), 7.88 (s, 1H), 7.44 (s, 1H), 7.28 (s, 1H), 7.17-7.05 (m, 3H), 6.16 (s, 1H), 3.57 (s, 3H), 2.78 (s, 4H), 2.56 (s, 3H), 1.23-1.13 (m, 4H), 0.19 (s, 4H).

Synthesis of 1-(3-(6-methyl-7-oxo-6,7-dihydro-1H-pyrrolo[2,3-c]pyridin-4-yl)-4-(6-aza-spiro[2.5]octan-6-yl)phenyl)-3-phenylurea (Compound 229)

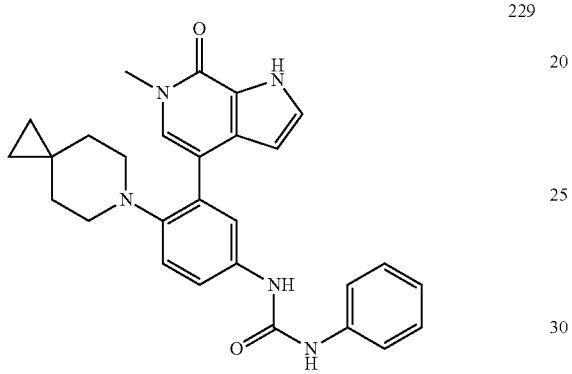

By the synthetic method and procedure of compound 228, the synthesis of compound 229 could be carried out with corresponding reagents. Phenylamine was used to substitute methylamine hydrochloride in the second step of the reaction, while other reaction reagents and conditions were completely consistent with those for synthesis of compound 228, and thus compound 229 was prepared.

MS: m/z 468.5 [M+H]$^+$ $^1$H NMR (400 MHz, DMSO) δ ppm 11.98 (s, 1H), 9.54 (s, 1H), 7.88 (s, 1H), 7.5-7.44 (m, 6H), 7.28 (s, 1H), 7.17-7.05 (m, 3H), 6.16 (s, 1H), 3.57 (s, 3H), 2.78 (s, 4H), 1.23-1.13 (m, 4H), 0.19 (s, 4H).

Synthesis of N-(3-(6-methyl-7-oxo-6,7-dihydro-1H-pyrrolo[2,3-c]pyridin-4-yl)-4-(2-oxa-7-azaspiro[2.5]nonan-7-yl)phenyl)acetylamine (Compound 230)

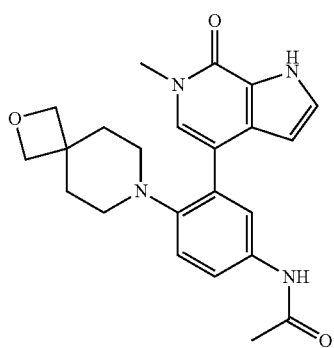

By the synthetic method and procedure of compound 7, the synthesis of compound 230 could be carried out with corresponding reagents. Among them, 2-oxa-7-aza-spiro[3.5]nonane hydrochloride was used to substitute 5-aza-spiro[2.4]heptane hydrochloride in the first step of the reaction; and acetyl chloride was used to replace ethanesulfonyl chloride in the fourth step of the reaction, while other reaction reagents and conditions were completely consistent with those for synthesis of compound 7, and thus compound 230 was prepared.

MS: m/z 407.5 [M+H]$^+$.

$^1$H NMR (400 MHz, DMSO) δ 11.97 (s, 1H), 9.84 (s, 1H), 7.54-7.45 (m, 2H), 7.39 (s, 1H), 7.26 (t, J=2.6 Hz, 1H), 6.99 (d, J=9.0 Hz, 1H), 6.16 (s, 1H), 4.23 (s, 4H), 3.56 (s, 3H), 2.66 (s, 4H), 2.01 (s, 3H), 1.57 (s, 4H).

Synthesis of 4-(2-(1,1-difluoro-6-aza-spiro[2.5]octan-6-yl)-5-(ethylsulfonyl) phenyl)-6-trideuteromethyl-1H-pyrrolo[2,3-c]pyridin-7(6H)-one (Compound 231)

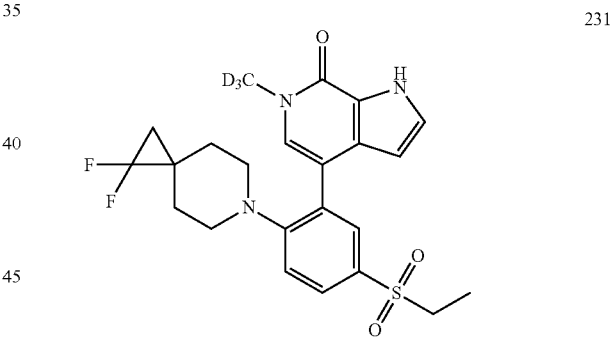

By the synthetic method and procedure of compound 24, the synthesis of compound 231 could be carried out with corresponding reagents. Among them, 1,1-difluoro-6-aza-spiro[2.5]octane hydrochloride was used to substitute 5-aza-spiro[2.4]heptane hydrochloride, and 2-bromo-1-fluoro-4-ethylsulfurylbenzene was used to substitute 2-bromo-1-fluoro-4-methylsulfonylbenzene in the first step of the reaction; and Int. 8 was used to replace Int. 6 in the second step of the reaction, while other reaction reagents and conditions were completely consistent with those for synthesis of compound 24, and thus compound 231 was prepared.

MS: m/z 465.5 [M+H]$^+$.

$^1$H NMR (400 MHz, DMSO) δ 11.98 (s, 1H), 9.54 (s, 1H), 7.44 (s, 1H), 7.28 (s, 1H), 7.17-7.05 (m, 2H), 6.16 (s, 1H), 3.10 (q, J=9.8 Hz, 2H), 2.99 (s, 4H), 2.77 (s, 3H), 1.30-1.16 (m, 6H), 0.99 (t, J=9.8 Hz, 3H).

Synthesis of 4-(5-(ethylsulfonyl)-2-(6-aza-spiro[2.5]octan-6-yl) phenyl)-6-trideuteromethyl-1H-pyrrolo[2,3-c]pyridin-7(6H)-one (Compound 232)

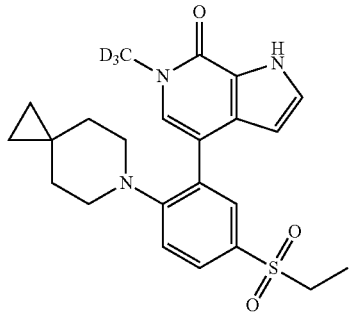

232

By the synthetic method and procedure of compound 24, the synthesis of compound 232 could be carried out with corresponding reagents. Among them, 6-aza-spiro[2.5]octane hydrochloride was used to substitute 5-aza-spiro[2.4]heptane hydrochloride, and 2-bromo-1-fluoro-4-ethylsulfurylbenzene was used to substitute 2-bromo-1-fluoro-4-methylsulfonylbenzene in the first step of the reaction; and Int. 8 was used to replace Int. 6 in the second step of the reaction, while other reaction reagents and conditions were completely consistent with those for synthesis of compound 24, and thus compound 232 was prepared.

MS: m/z 429.5 [M+H]⁺.

¹H NMR (400 MHz, DMSO) δ 11.98 (s, 1H), 9.54 (s, 1H), 7.44 (s, 1H), 7.28 (s, 1H), 7.17-7.05 (m, 2H), 6.16 (s, 1H), 3.10 (q, J=9.8 Hz, 2H), 2.78 (s, 4H), 1.23-1.13 (m, 4H), 0.99 (t, J=9.8 Hz, 3H), 0.19 (s, 4H).

Synthesis of 4-(2-(1,1-difluoro-6-aza-spiro[2.5]octan-6-yl)-5-(isopropylsulfonyl)phenyl)-6-trideuteromethyl-1H-pyrrolo[2,3-c]pyridin-7(6H)-one (Compound 233)

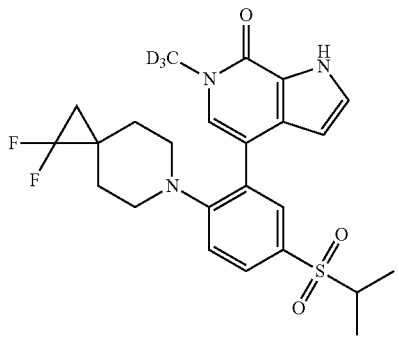

233

By the synthetic method and procedure of compound 24, the synthesis of compound 233 could be carried out with corresponding reagents. Among them, 1,1-difluoro-6-aza-spiro[2.5]octane hydrochloride was used to substitute 5-aza-spiro[2.4]heptane hydrochloride, and 2-bromo-1-fluoro-4-isopropylsulfurylbenzene was used to substitute 2-bromo-1-fluoro-4-methylsulfonylbenzene in the first step of the reaction; and Int. 8 was used to replace Int. 6 in the second step of the reaction, while other reaction reagents and conditions were completely consistent with those for synthesis of compound 24, and thus compound 233 was prepared.

MS: m/z 479.5 [M+H]⁺.

¹H NMR (400 MHz, DMSO) δ 11.98 (s, 1H), 9.54 (s, 1H), 7.44 (s, 1H), 7.28 (s, 1H), 7.17-7.05 (m, 2H), 6.16 (s, 1H), 3.20-3.15 (m, 1H), 2.99 (s, 4H), 2.77 (s, 3H), 1.30-1.16 (m, 6H), 1.33-1.31 (m, 6H).

Synthesis of 4-(5-(isopropylsulfonyl)-2-(6-aza-spiro[2.5]octan-6-yl)phenyl)-6-trideuteromethyl-1H-pyrrolo[2,3-c]pyridin-7(6H)-one (Compound 234)

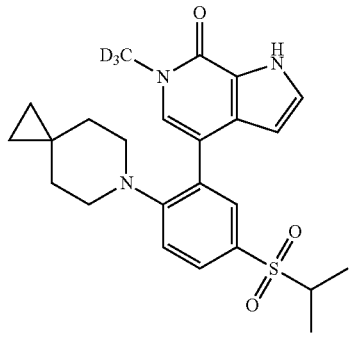

234

By the synthetic method and procedure of compound 24, the synthesis of compound 234 could be carried out with corresponding reagents. Among them, 6-aza-spiro[2.5]octane hydrochloride was used to substitute 5-aza-spiro[2.4]heptane hydrochloride, and 2-bromo-1-fluoro-4-isopropylsulfurylbenzene was used to substitute 2-bromo-1-fluoro-4-methylsulfonylbenzene in the first step of the reaction; and Int. 8 was used to replace Int. 6 in the second step of the reaction, while other reaction reagents and conditions were completely consistent with those for synthesis of compound 24, and thus compound 234 was prepared.

MS: m/z 443.5 [M+H]⁺.

¹H NMR (400 MHz, DMSO) δ 11.98 (s, 1H), 9.54 (s, 1H), 7.44 (s, 1H), 7.28 (s, 1H), 7.17-7.05 (m, 2H), 6.16 (s, 1H), 3.20-3.15 (m, 1H), 2.78 (s, 4H), 1.33-1.31 (m, 6H), 1.23-1.13 (m, 4H), 0.19 (s, 4H).

Synthesis of 2-((3-(6-trideuteromethyl-7-oxo-6,7-dihydro-1H-pyrrolo[2,3-c] pyridin-4-yl)-4-(6-aza-spiro[2.5]octan-6-yl)phenyl)sulfonyl)acetic acid (Compound 235)

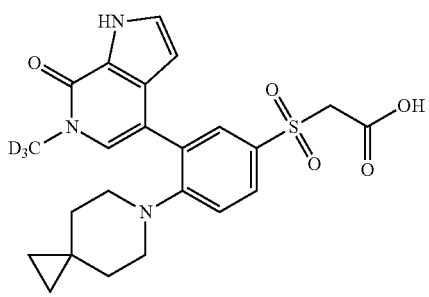

235

By the synthetic method and procedure of compound 24, the synthesis of compound 235 could be carried out with corresponding reagents. Among them, 6-aza-spiro[2.5]octane hydrochloride was used to substitute 5-aza-spiro[2.4]heptane hydrochloride, and 2-bromo-1-fluoro-4-carboxylmethylsulfurylbenzene was used to substitute 2-bromo-1-fluoro-4-methylsulfonylbenzene in the first step of the reaction; and Int. 8 was used to replace Int. 6 in the second step of the reaction, while other reaction reagents and conditions were completely consistent with those for synthesis of compound 24, and thus compound 235 was prepared.

MS: m/z 459.5 [M+H]⁺.

¹H NMR (400 MHz, DMSO) δ 13.42 (s, 1H), 11.91 (s, 1H), 9.54 (s, 1H), 7.44 (s, 1H), 7.28 (s, 1H), 7.17-7.05 (m, 2H), 6.16 (s, 1H), 5.98 (s, 2H), 2.81 (s, 4H), 1.24-1.13 (m, 4H), 0.18 (s, 4H).

Synthesis of 2-fluoro-5-(6-trideuteromethyl-7-oxo-6,7-dihydro-1H-pyrrolo [2,3-c]pyridin-4-yl)-4-(6-aza-spiro[2.5]octan-6-yl)benzenesulfonamide (Compound 236)

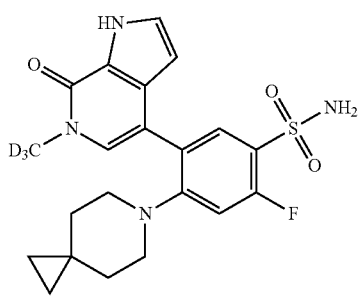

236

By the synthetic method and procedure of compound 197, the synthesis of compound 236 could be carried out with corresponding reagents. In the first step of the reaction, 2,4-difluoro-5-bromo-benzenesulfonyl chloride was used to substitute 3-bromo-4-fluorobenzenesulfonyl chloride, and ammonia water was used to take the place of ethylamine aqueous solution, while other reaction reagents and conditions were completely consistent with those for synthesis of compound 197, and thus compound 236 was prepared.

MS: m/z 434.5 [M+H]⁺.

¹H NMR (400 MHz, DMSO) δ 12.06 (s, 1H), 7.59 (d, J=8.6 Hz, 1H), 7.49 (s, 2H), 7.35 (s, 1H), 7.29 (t, J=2.7 Hz, 1H), 7.04 (d, J=12.7 Hz, 1H), 6.12 (s, 1H), 2.79 (s, 4H), 0.99 (s, 4H), 0.20 (s, 4H).

Synthesis of 4-(2-fluoro-5-(methanesulfonyl)-4-(6-aza-spiro[2.5]octan-6-yl) phenyl)-6-trideuteromethyl-1H-pyrrolo[2,3-c]pyridin-7(6H)-one (Compound 237)

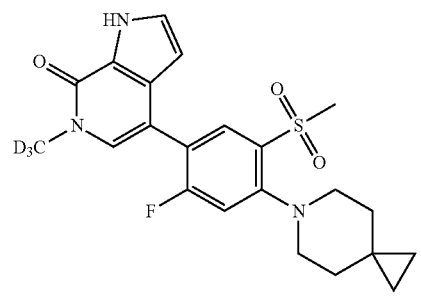

237

By the synthetic method and procedure of compound 24, the synthesis of compound 237 could be carried out with corresponding reagents. Among them, 6-aza-spiro[2.5]octane hydrochloride was used to substitute 5-aza-spiro[2.4]heptane hydrochloride, and 1-bromo-2,4-difluoro-5-methylsulfonylbenzene was used to substitute 2-bromo-1-fluoro-4-methylsulfonylbenzene in the first step of the reaction; and Int. 8 was used to replace Int. 6 in the second step of the reaction, while other reaction reagents and conditions were completely consistent with those for synthesis of compound 24, and thus compound 237 was prepared.

¹H NMR (400 MHz, DMSO) δ 12.02 (s, 1H), 7.55 (d, J=8.5 Hz, 1H), 7.43 (s, 1H), 7.34 (t, J=2.7 Hz, 1H), 7.22 (d, J=13.0 Hz, 1H), 6.24-5.86 (m, 1H), 3.29 (s, 3H), 2.79 (s, 4H), 0.99 (s, 4H), 0.19 (s, 4H).

Synthesis of 4-(4-fluoro-5-(methanesulfonyl)-2-(6-aza-spiro[2.5]octan-6-yl) phenyl)-6-trideuteromethyl-1H-pyrrolo[2,3-c]pyridin-7(6H)-one (Compound 238)

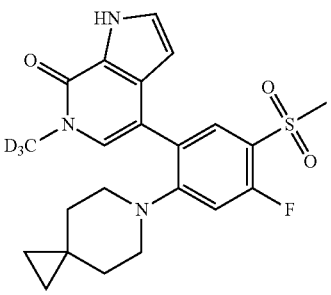

238

By the synthetic method and procedure of compound 24, the synthesis of compound 238 could be carried out with corresponding reagents. Among them, 6-aza-spiro[2.5]octane hydrochloride was used to substitute 5-aza-spiro[2.4]heptane hydrochloride, and 1-bromo-2,4-difluoro-5-methylsulfonylbenzene was used to substitute 2-bromo-1-fluoro-4-methylsulfonylbenzene in the first step of the reaction; and Int. 8 was used to replace Int. 6 in the second step of the reaction, while other reaction reagents and conditions were completely consistent with those for synthesis of compound 24, and thus compound 238 was prepared.

MS: m/z 433.5 [M+H]⁺.

¹H NMR (400 MHz, DMSO) δ 12.07 (s, 1H), 7.59 (d, J=8.5 Hz, 1H), 7.41 (s, 1H), 7.30 (t, J=2.7 Hz, 1H), 7.12 (d, J=13.0 Hz, 1H), 6.23-5.96 (m, 1H), 3.29 (s, 3H), 2.79 (s, 4H), 0.99 (s, 4H), 0.20 (s, 4H).

Synthesis of 2-((4-(1,1-difluoro-6-aza-spiro[2.5] octan-6-yl)-3-(6-trideuteromethyl-7-oxo-6,7-dihydro-1H-pyrrolo[2,3-c]pyridin-4-yl)phenyl)sulfonyl)-2-methylpropionic acid (Compound 239)

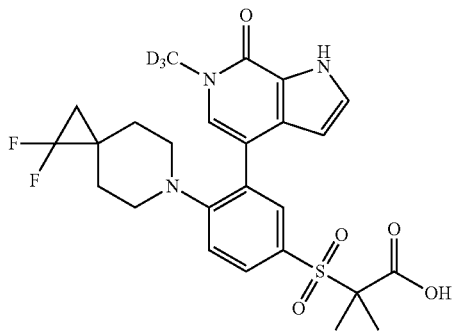

239

By the synthetic method and procedure of compound 24, the synthesis of compound 239 could be carried out with corresponding reagents. Among them, 1,1-difluoro-6-aza-spiro[2.5]octane hydrochloride was used to substitute 5-aza-spiro[2.4]heptane hydrochloride, and 2-bromo-1-fluoro-4-(2-methyl-2-carboxylethane-2-yl)sulfonylbenzene was used to substitute 2-bromo-1-fluoro-4-methylsulfonylbenzene in the first step of the reaction; and Int. 8 was used to replace Int. 6 in the second step of the reaction, while other reaction reagents and conditions were completely consistent with those for synthesis of compound 24, and thus compound 239 was prepared.

MS: m/z 523.5 [M+H]⁺.

¹H NMR (400 MHz, DMSO): δ 12.08 (s, 1H), 7.68 (dd, J=8.4, 2.4 Hz, 1H), 7.59 (d, J=2.0 Hz, 1H), 7.42 (s, 1H), 7.30 (t, J=2.4 Hz, 1H), 7.24 (d, J=8.4 Hz, 1H), 6.14 (t, J=2 Hz, 1H), 3.05-2.82 (t, J=4.4 Hz, 4H), 1.46 (s, 6H), 1.46-1.38 (m, 2H), 1.32-1.28 (m, 2H), 1.23-1.16 (m, 2H).

Synthesis of (R)-4-(2-(1,1-difluoro-6-aza-spiro[2.5] octan-6-yl)-5-((3-hydroxylpyrrolidin-1-yl)sulfonyl) phenyl)-6-trideuteromethyl-1H-pyrrolo[2,3-c]pyridin-7(6H)-one (Compound 240)

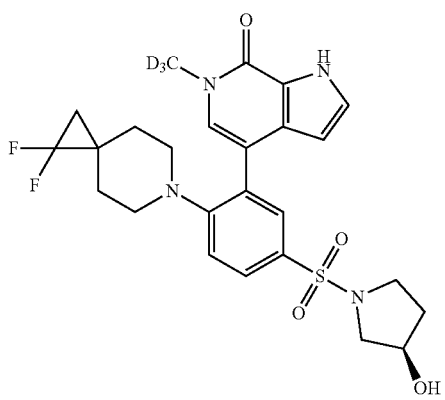

240

By the synthetic method and procedure of compound 197, the synthesis of compound 240 could be carried out with corresponding reagents. In the first step of the reaction, (R)-3-pyrrolidinol was used to take the place of ethylamine aqueous solution, and 1,1-difluoro-6-aza-spiro[2.5]octane hydrochloride was used to substitute 6-aza-spiro[2.5]octane hydrochloride, while other reaction reagents and conditions were completely consistent with those for synthesis of compound 197, and thus compound 240 was prepared.

MS: m/z 522.3 [M+H]⁺.

¹H NMR (400 MHz, DMSO) δ 12.08 (s, 1H), 7.69 (dd, J=8.5, 2.3 Hz, 1H), 7.60 (d, J=2.3 Hz, 1H), 7.45 (s, 1H), 7.31 (t, J=2.7 Hz, 1H), 7.25 (d, J=8.6 Hz, 1H), 6.22-6.09 (m, 1H), 4.96 (d, J=3.5 Hz, 1H), 4.20 (d, J=2.7 Hz, 1H), 3.35-3.17 (m, 4H), 3.06-2.93 (m, 4H), 1.85-1.73 (m, 1H), 1.72-1.60 (m, 1H), 1.48-1.35 (m, 2H), 1.30 (d, J=12.8 Hz, 2H), 1.21 (dd, J=11.1, 7.7 Hz, 2H).

Synthesis of (S)-4-(2-(1,1-difluoro-6-aza-spiro[2.5] octan-6-yl)-5-((3-hydroxylpyrrolidin-1-yl)sulfonyl) phenyl)-6-trideuteromethyl-1H-pyrrolo[2,3-c]pyridin-7(6H)-one (Compound 241)

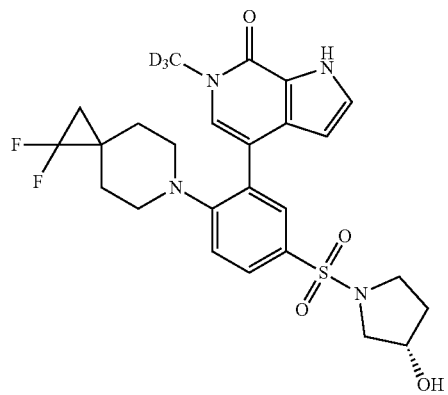

241

By the synthetic method and procedure of compound 197, the synthesis of compound 241 could be carried out with corresponding reagents. In the first step of the reaction, (S)-3-pyrrolidinol was used to take the place of ethylamine aqueous solution, and 1,1-difluoro-6-aza-spiro[2.5]octane hydrochloride was used to substitute 6-aza-spiro[2.5]octane hydrochloride, while other reaction reagents and conditions were completely consistent with those for synthesis of compound 197, and thus compound 241 was prepared.

MS: m/z 522.3 [M+H]⁺.

¹H NMR (400 MHz, DMSO) δ 12.08 (s, 1H), 7.69 (dd, J=8.5, 2.2 Hz, 1H), 7.60 (d, J=2.2 Hz, 1H), 7.51-7.39 (m, 1H), 7.31 (t, J=2.7 Hz, 1H), 7.24 (d, J=8.6 Hz, 1H), 6.14 (t, J=2.2 Hz, 1H), 4.97 (d, J=3.4 Hz, 1H), 4.20 (d, J=2.6 Hz, 1H), 3.31-3.16 (m, 3H), 3.07-2.90 (m, 5H), 1.87-1.72 (m, 1H), 1.72-1.59 (m, 1H), 1.47-1.35 (m, 2H), 1.30 (d, J=13.1 Hz, 2H), 1.24-1.19 (m, 2H).

Synthesis of (R)-4-(5-((3-hydroxylpyrrolidin-1-yl)sulfonyl)-2-(6-aza-spiro [2.5]octan-6-yl)phenyl)-6-trideuteromethyl-1H-pyrrolo[2,3-c]pyridin-7(6H)-one (Compound 242)

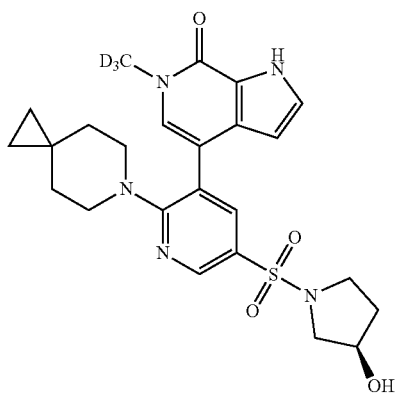

242

By the synthetic method and procedure of compound 197, the synthesis of compound 242 could be carried out with corresponding reagents. In the first step of the reaction, 5-bromo-6-fluoropyridin-3-sulfonyl chloride was used to substitute 3-bromo-4-fluorobenzenesulfonyl chloride, and (R)-3-pyrrolidinol was used to take the place of ethylamine aqueous solution, while other reaction reagents and conditions were completely consistent with those for synthesis of compound 197, and thus compound 242 was prepared.

MS: m/z 487.3 [M+H]$^+$.

$^1$H NMR (400 MHz, DMSO) δ 12.15 (s, 1H), 8.49 (d, J=2.3 Hz, 1H), 7.73 (t, J=14.5 Hz, 1H), 7.44 (s, 1H), 7.33 (t, J=2.5 Hz, 1H), 6.09 (d, J=26.1 Hz, 1H), 4.96 (d, J=3.2 Hz, 1H), 4.21 (s, 1H), 3.37-3.17 (m, 7H), 3.07 (d, J=10.7 Hz, 1H), 1.90-1.75 (m, 1H), 1.71 (d, J=3.1 Hz, 1H), 1.17 (dd, J=13.7, 6.0 Hz, 4H), 0.22 (s, 4H).

Synthesis of (S)-4-(5-((3-hydroxylpyrrolidin-1-yl)sulfonyl)-2-(6-aza-spiro [2.5]octan-6-yl)phenyl)-6-trideuteromethyl-1H-pyrrolo[2,3-c]pyridin-7(6H)-one (Compound 243)

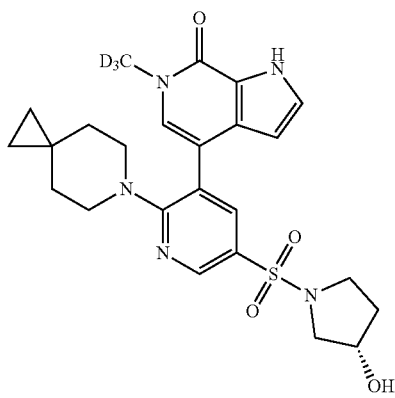

243

By the synthetic method and procedure of compound 197, the synthesis of compound 242 could be carried out with corresponding reagents. In the first step of the reaction, 5-bromo-6-fluoropyridin-3-sulfonyl chloride was used to substitute 3-bromo-4-fluorobenzenesulfonyl chloride, and (S)-3-pyrrolidinol was used to take the place of ethylamine aqueous solution, while other reaction reagents and conditions were completely consistent with those for synthesis of compound 197, and thus compound 243 was prepared.

MS: m/z 487.3 [M+H]$^+$.

$^1$H NMR (400 MHz, DMSO) δ 12.15 (s, 1H), 8.49 (d, J=2.3 Hz, 1H), 7.76 (d, J=2.3 Hz, 1H), 7.45 (s, 1H), 7.33 (s, 1H), 6.12 (s, 1H), 4.95 (d, J=3.2 Hz, 1H), 4.21 (s, 1H), 3.36-3.16 (m, 7H), 3.07 (d, J=10.8 Hz, 1H), 1.81 (dt, J=13.1, 10.9 Hz, 1H), 1.70 (d, J=2.9 Hz, 1H), 1.18 (dd, J=13.6, 6.1 Hz, 4H), 0.22 (s, 4H).

Synthesis of 1-((4-(1,1-difluoro-6-aza-spiro[2.5]octan-6-yl)-3-(6-trideuteromethyl-7-oxo-6,7-dihydro-1H-pyrrolo[2,3-c]pyridin-4-yl)phenyl)sulfonyl)pyrrolidin-2-carboxylic acid (Compound 244)

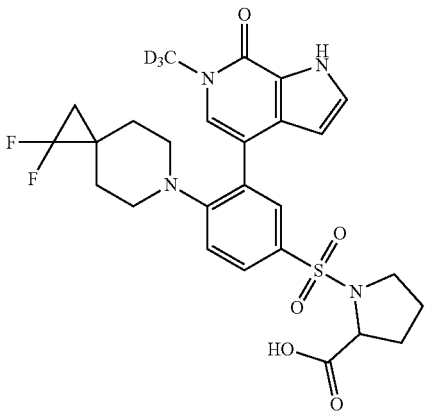

244

By the synthetic method and procedure of compound 197, the synthesis of compound 244 could be carried out with corresponding reagents. In the first step of the reaction, DL-proline was used to take the place of ethylamine aqueous solution, and 1,1-difluoro-6-aza-spiro[2.5]octane hydrochloride was used to substitute 6-aza-spiro[2.5]octane hydrochloride, while other reaction reagents and conditions were completely consistent with those for synthesis of compound 197, and thus compound 244 was prepared.

MS: m/z 550.6 [M+H]$^+$.

$^1$H NMR (400 MHz, DMSO) δ 12.03 (s, 1H), 7.74 (d, J=8.1 Hz, 1H), 7.65 (d, J=2.2 Hz, 1H), 7.45 (s, 1H), 7.29 (s, 1H), 7.19 (d, J=8.7 Hz, 1H), 6.17 (s, 1H), 4.87 (s, 1H), 4.26 (s, 1H), 3.94 (s, 1H), 2.95 (s, 4H), 1.97-1.85 (m, 2H), 1.31-1.14 (m, 8H).

Synthesis of 4-(5-amino-2-(6-aza-spiro[2.5]octan-6-yl)phenyl)-6-methyl-1H-pyrrolo[2,3-c]pyridin-7(6H)-one (Compound 245)

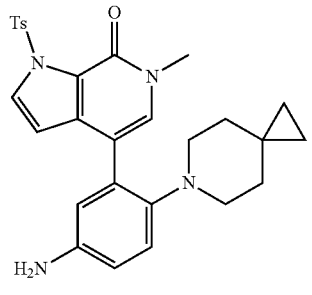

245-A

↓

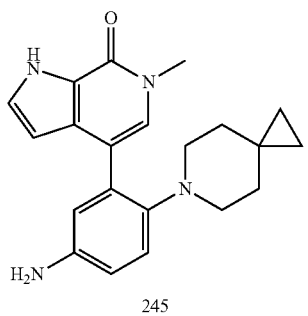

245

By the synthetic method and procedure of compound 5, the synthesis of compound 245-A could be carried out with corresponding reagents. In the first step of the reaction, 6-aza-spiro[2.5]octane hydrochloride was used to substitute 5-aza-spiro[2.4]heptane hydrochloride, while other reaction reagents and conditions were completely consistent with those for synthesis of compound 5, and thus compound 245-A was prepared.

To a 30 mL reaction flask, were added compound 245-A (75 mg, 0.15 mmol), THF (1 mL), and KOH (4 mL, 4M), and then the system was allowed to react at 80° C. for 3 h. After completion of the reaction, the reaction solution was poured into water (30 mL), and extracted with 30 mL dichloromethane (10 mL×3). The organic phases were combined, and dried with anhydrous Na$_2$SO$_4$, followed by purification with prep-TLC, to obtain compound 245 (39 mg), with a yield of 75%.

MS: m/z 349.5 [M+H]$^+$.

$^1$H NMR (400 MHz, DMSO) δ ppm 11.98 (s, 1H), 9.54 (s, 1H), 7.44 (s, 1H), 7.28 (s, 1H), 7.17-7.05 (m, 4H), 6.16 (s, 1H), 3.57 (s, 3H), 2.78 (s, 4H), 1.23-1.13 (m, 4H), 0.19 (s, 4H).

Synthesis of N-(3-(6-methyl-7-oxo-6,7-dihydro-1H-pyrrolo[2,3-c]pyridin-4-yl)-4-(5-aza-spiro[2.4]heptan-5-yl)phenyl)methanesulfonamide (Compound 246)

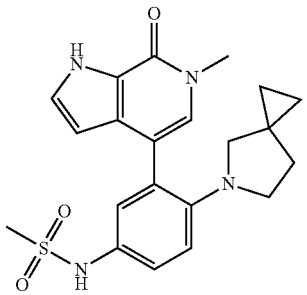

246

By the synthetic method and procedure of compound 7, the synthesis of compound 246 could be carried out with corresponding reagents. Among them, in the fourth step of the reaction, methanesulfonyl chloride was used to substitute ethanesulfonyl chloride, while other reaction reagents and conditions were completely consistent with those for synthesis of compound 7, and thus compound 246 was prepared.

MS: m/z 413.5 [M+H]$^+$.

$^1$H NMR (400 MHz, DMSO) δ 12.02 (s, 1H), 9.31 (s, 1H), 7.75-7.46 (m, 1H), 7.26 (t, J=2.7 Hz, 1H), 7.16 (s, 1H), 7.13-6.99 (m, 2H), 6.83 (d, J=8.8 Hz, 1H), 3.55 (s, 3H), 3.29 (s, 3H), 3.09 (t, J=6.6 Hz, 2H), 2.98 (q, J=7.3 Hz, 2H), 2.79 (s, 2H), 0.38 (m, 4H).

Synthesis of 4-((3-(6-methyl-7-oxo-6,7-dihydro-1H-pyrrolo[2,3-c]pyridin-4-yl)-4-(6-aza-spiro[2.5]octan-6-yl)phenyl)amino)-4-oxobutyric acid (Compound 247)

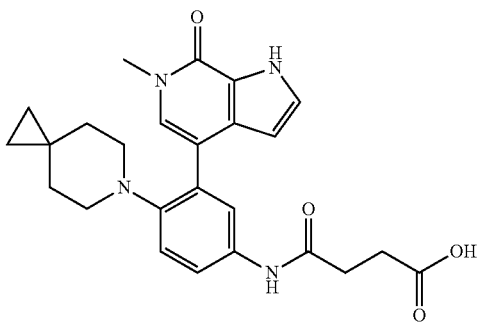

247

By the synthetic method and procedure of compound 7, the synthesis of compound 247 could be carried out with corresponding reagents. Among them, 6-aza-spiro[2.5]octane hydrochloride was used to substitute 5-aza-spiro[2.4]heptane hydrochloride in the first step of the reaction; and succinic anhydride was used to take the place of ethanesulfonyl chloride in the fourth step of the reaction, while other reaction reagents and conditions were completely consistent with those for synthesis of compound 7, and thus compound 247 was prepared.

MS: m/z 449.5 [M+H]$^+$.

¹H NMR (400 MHz, DMSO) δ ppm 13.12 (s, 1H), 11.98 (s, 1H), 9.54 (s, 1H), 7.44 (s, 1H), 7.28 (s, 1H), 7.17-7.05 (m, 3H), 6.16 (s, 1H), 3.57 (s, 3H), 2.78 (s, 4H), 2.35-2.06 m, 4H), 1.23-1.13 (m, 4H), 0.19 (s, 4H).

Synthesis of 1-(2-(6-methyl-7-oxo-6,7-dihydro-1H-pyrrolo[2,3-c]pyridin-4-yl)-4-(methanesulfonyl)phenyl)pyrrolidin-2-carboxylic acid (Compound 248)

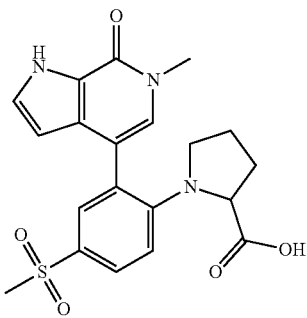

248

By the synthetic method and procedure of compound 24, the synthesis of compound 248 could be carried out with corresponding reagents. Among them, DL-proline was used to substitute 5-aza-spiro[2.4]heptane hydrochloride, while other reaction reagents and conditions were completely consistent with those for synthesis of compound 24, and thus compound 248 was prepared.

MS: m/z 416.5 [M+H]⁺.

¹H NMR (400 MHz, DMSO) δ 13.22 (s, 1H), 12.05 (s, 1H), 7.68 (dd, J=8.8, 2.3 Hz, 1H), 7.56 (d, J=2.4 Hz, 1H), 7.34-7.21 (m, 2H), 6.94 (d, J=8.9 Hz, 1H), 6.02 (d, J=2.7 Hz, 1H), 3.68 (s, 3H), 3.58 (m, 1H), 3.13 (s, 3H), 2.98 (m, 2H), 1.64-1.51 (m, 4H).

Synthesis of 4-(2-(2-(chloromethyl)pyrrolidin-1-yl)-5-(methanesulfonyl) phenyl)-6-methyl-1H-pyrrolo[2,3-c]pyridin-7(6H)-one (Compound 249)

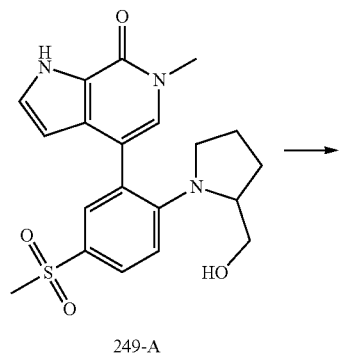

249-A

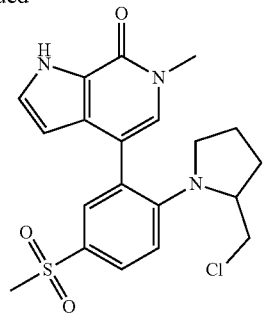

249

By the synthetic method and procedure of compound 24, the synthesis of compound 249-A could be carried out with corresponding reagents. Among them, pyrrolidin-2-methanol was used to substitute 5-aza-spiro[2.4]heptane hydrochloride, while other reaction reagents and conditions were completely consistent with those for synthesis of compound 24, and thus compound 249-A was prepared.

To a 25 mL reaction flask, were added compound 249-A (200 mg, 0.5 mmol), thionyl chloride (2 mL), and then the system was allowed to react at 50° C. for 3 h. After completion of the reaction, the reaction solution was poured into ice water (20 mL), and extracted with 30 mL dichloromethane (10 mL×3). The organic phases were combined, and dried with anhydrous Na₂SO₄, followed by purification with prep-TLC, to obtain compound 249 (163 mg), with a yield of 78%.

MS: m/z 420.5 [M+H]⁺.

¹H NMR (400 MHz, DMSO) δ 12.01 (s, 1H), 7.68 (dd, J=8.8, 2.3 Hz, 1H), 7.56 (d, J=2.4 Hz, 1H), 7.34-7.21 (m, 2H), 6.94 (d, J=8.9 Hz, 1H), 6.02 (d, J=2.7 Hz, 1H), 3.68 (s, 3H), 3.13 (s, 3H), 3.09-2.71 (m, 5H), 1.64-1.51 (m, 4H).

Synthesis of 4-(2-(1,1-difluoro-6-aza-spiro[2.5]octan-6-yl)-5-(ethylsulfonyl) phenyl)-6-trideuteromethyl-1H-pyrrolo[2,3-c]pyridin-7(6H)-one (Compound 250)

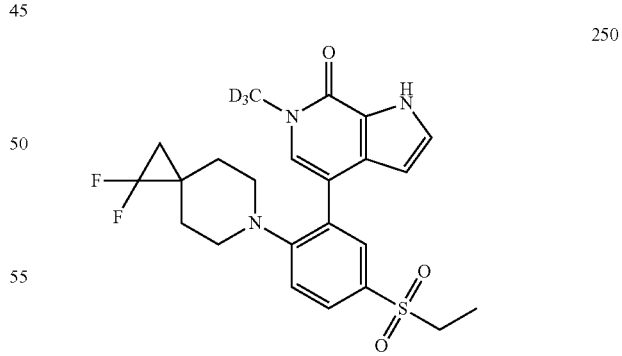

250

By the synthetic method and procedure of compound 24, the synthesis of compound 250 could be carried out with corresponding reagents. Among them, 2-bromo-1-fluoro-4-ethylsulfurylbenzene was used to replace 2-bromo-1-fluoro-4-methylsulfonylbenzene, and 1,1-difluoro-6-aza-spiro[2.5]octane hydrochloride was used to substitute 5-aza-spiro[2.4]heptane hydrochloride in the first step of the reaction; and Int. 8 was used to take the place of Int. 6 in the fourth step of the reaction, while other reaction reagents and conditions were completely consistent with those for synthesis of compound 24, and thus compound 250 was prepared.

MS: m/z 465.5 [M+H]⁺.

¹H NMR (400 MHz, DMSO) δ 12.06 (s, 1H), 7.75 (dd, J=8.5, 2.3 Hz, 1H), 7.67 (d, J=2.3 Hz, 1H), 7.45 (s, 1H), 7.33-7.23 (m, 2H), 6.17-6.05 (m, 1H), 3.27 (q, J=7.3 Hz, 2H), 3.00 (t, J=5.0 Hz, 4H), 1.38 (dd, J=12.0, 6.3 Hz, 2H), 1.28 (d, J=13.1 Hz, 2H), 1.24-1.15 (m, 2H), 1.13 (t, J=7.3 Hz, 3H).

Synthesis of 4-(1,1-difluoro-6-aza-spiro[2.5]octan-6-yl)-3-(6-trideuteromethyl-7-oxo-6,7-dihydro-1H-pyrrolo[2,3-c]pyridin-4-yl)benzenesulfonamide (Compound 251)

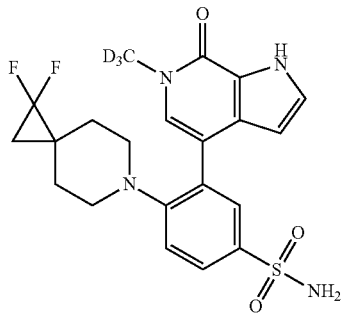

251

By the synthetic method and procedure of compound 197, the synthesis of compound 251 could be carried out with corresponding reagents. In the first step of the reaction, ammonia water was used to take the place of ethylamine aqueous solution, and 1,1-difluoro-6-aza-spiro[2.5]octane hydrochloride was used to substitute 6-aza-spiro[2.5]octane hydrochloride, while other reaction reagents and conditions were completely consistent with those for synthesis of compound 197, and thus compound 251 was prepared.

MS: m/z 452.5 [M+H]⁺.

¹H NMR (400 MHz, DMSO) δ 12.09 (s, 1H), 7.62 (dd, J=8.8, 2.4 Hz, 1H), 7.55 (d, J=2.4 Hz, 1H), 7.28 (d, J=2.7 Hz, 1H), 7.19 (s, 1H), 7.04 (s, 2H), 6.90 (d, J=8.8 Hz, 1H), 6.01 (d, J=2.7 Hz, 1H), 2.98 (s, 4H), 1.44-1.20 (m, 6H).

(2S,4R)-1-((4-(1,1-difluoro-6-aza-spiro[2.5]octan-6-yl)-3-(6-trideuteromethyl-7-oxo-6,7-dihydro-1H-pyrrolo[2,3-c]pyridin-4-yl)phenyl)sulfonyl)-4-hydroxylpyrrolidin-2-carboxylic acid (Compound 252)

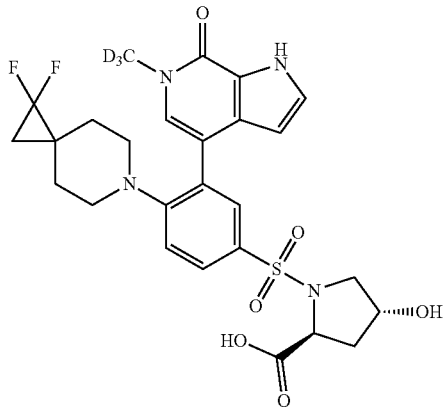

252

By the synthetic method and procedure of compound 197, the synthesis of compound 252 could be carried out with corresponding reagents. In the first step of the reaction, L-hydroxylproline was used to take the place of ethylamine aqueous solution, and 1,1-difluoro-6-aza-spiro[2.5]octane hydrochloride was used to substitute 6-aza-spiro[2.5]octane hydrochloride, while other reaction reagents and conditions were completely consistent with those for synthesis of compound 197, and thus compound 252 was prepared.

MS: m/z 566.5 [M+H]⁺.

¹H NMR (400 MHz, DMSO) δ 12.03 (s, 1H), 7.74 (d, J=8.1 Hz, 1H), 7.65 (d, J=2.2 Hz, 1H), 7.45 (s, 1H), 7.29 (s, 1H), 7.19 (d, J=8.7 Hz, 1H), 6.17 (s, 1H), 4.87 (s, 1H), 4.26 (s, 1H), 3.94 (s, 1H), 3.40 (m, 1H), 2.95 (s, 4H), 1.97-1.85 (m, 2H), 1.69 (s, 1H), 1.31-1.14 (m, 6H).

4-(4-(1,1-difluoro-6-aza-spiro[2.5]octan-6-yl)-2-fluoro-5-(methylsulfonyl) phenyl)-6-trideuteromethyl-1H-pyrrolo[2,3-c]pyridin-7(6H)-one (Compound 253)

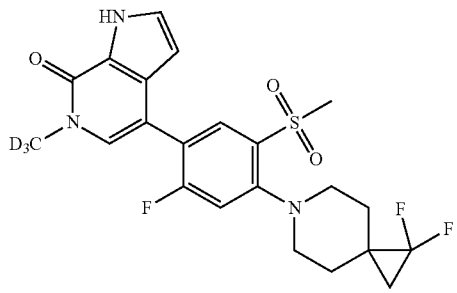

253

By the synthetic method and procedure of compound 24, the synthesis of compound 253 could be carried out with corresponding reagents. Among them, 1,1-difluoro-6-aza-spiro[2.5]octane hydrochloride was used to substitute 5-aza-spiro[2.4]heptane hydrochloride, and 2,4-difluoro-5-bromo-methylsulfonylbenzene was used to replace 2-bromo-1-fluoro-4-methylsulfonylbenzene in the first step of the reaction; and Int. 8 was used to take the place of Int. 6 in the second step of the reaction, while other reaction reagents and conditions were completely consistent with those for synthesis of compound 24, and thus compound 253 was prepared.

MS: m/z 469.5 [M+H]⁺.

¹H NMR (400 MHz, DMSO) δ 12.02 (s, 1H), 7.55 (d, J=8.5 Hz, 1H), 7.43 (s, 1H), 7.34 (t, J=2.7 Hz, 1H), 7.22 (d, J=13.0 Hz, 1H), 6.24-5.86 (m, 1H), 3.29 (s, 3H), 3.05-2.82 (t, J=4.4 Hz, 4H), 1.46-1.38 (m, 2H), 1.32-1.28 (m, 2H), 1.23-1.16 (m, 2H).

The beneficial effects of the present invention were illustrated by following experimental examples.

Abbreviations and Definitions of Terms mg milligram
mL milliliter
ug microgram
uL microliter
mM millimole
nM millimicromole
DMSO dimethylsulfoxide
Avg average value
SD standard deviation
DRC dose response curve Experimental Example 1 the Inhibitory Effect of the Compound According to the Present Invention on BRD 1. Experimental Objective Homogeneous time-resolved fluorescence technology (HTRF) was used to determine the binding effect of compounds on BRD4 (D1+D2) and BRDT (D1) proteins, as well as AlphaScreen method was used to detect the binding effect of compounds on BRD2 (D1+D2) and BRD3 (D1+D2) proteins.

2. Experimental Background

The compounds were screened in vitro, and each compound was serially diluted to 10 concentrations. Four proteins BRD4 (D1+D2), BRDT (D1), BRD2 (D1+D2) and BRD3 (D1+D2) were chosen to determine the $IC_{50}$ values of compounds (see Table 1).

3. Experimental Materials:
BRD2(1,2)(BPS, Cat. No. 31024)
BRD3(1,2)(BPS, Cat. No. 31035)
BRDT(D1)(Active Motif, Cat. No. 31450)
BRD4(1,2)(BPS, Cat. No. 31044)
(+)-JQ1(BPS, Cat. No. 27402)

4. Compound treatment: The test compound was dissolved in dimethyl sulfoxide (DMSO), and the storage concentration was 10 mM.

5. Steps for Homogeneous Time-Resolved Fluorescence Detection:

1) According to the arrangement of the detection plate, all compounds were diluted in Echo plate.

The final dilution concentration of DMSO is 0.1%.

2) The compound or DMSO was transferred to a 384-well detection plate with the Echo automatic sampler.

3) Two-fold concentration of the mixture of protein and peptide was added to the detection plate.

4) Two-fold concentration of mixed detection solution was added to the test plate, and shaken for 30 s.

5) Incubating for 2 h at room temperature.

6) Fluorescence signal was read on Envision multi-function microplate reader (excitation light wavelength being 340 nm, and emission light wavelength being 615 nm and 665 nm).

7) Curve fitting

The experimental data were recorded in an Excel file, and equation (1) was used to obtain the inhibition rate.

$$Inh\% = (Max - Signal) / (Max - Min) * 100 \quad \text{Equation (1):}$$

The obtained data was recorded in GraphPad software, and equation (2) was used to provide the $IC_{50}$ values.

$$Y = Bottom + (Top - Bottom) / (1 + 10\textasciicircum((Log\ IC50 - X) * Hill\ Slope)) \quad \text{Equation (2):}$$

Y axis was the inhibition rate, and X axis was the compound concentration.

6. AlphaScreen Detection Procedures:

1) Preparing One-Fold Concentration of Detection Buffer

One-fold concentration of detection buffer was prepared (Improved HEPES buffer)

2) Gradient Dilution of Compounds

Echo automatic sampler was used to transfer the compound to the detection plate for gradient dilution, so that the final concentration of dimethyl sulfoxide was 0.1%.

3) Preparation of Protein Solution

The protein was dissolved in one-fold concentration of detection buffer.

4) Preparation of Substrate Solution

The peptide was dissolved in one-fold concentration of detection buffer to prepare the substrate solution.

5) 5 µL protein solution was transferred to the detection plate, and one-fold concentration of detection buffer (5 µL) was placed in the negative control wells.

6) The plate was incubated for 15 min at room temperature.

7) 5 µL substrate solution was added to each well to start the reaction.

8) The plate was incubated for additional 60 min at room temperature.

9) Preparation of acceptor solution and donor solution in one-fold concentration of assay buffer Acceptor solution (15 µL) and donor solution (15 µL) were respectively added, and then incubated at room temperature for 60 min and protected against exposure to light.

10) The endpoint was read in EnSpire and Alpha mode.

11) Curve Fitting

The experimental data were recorded in an Excel file and equation (1) was used to get the inhibition rate.

$$Inh\% = (Max - Signal) / (Max - Min) * 100 \quad \text{Equation (1):}$$

The obtained data were input into GraphPad software, and equation (2) was used to obtain the $IC_{50}$ value.

$$Y = Bottom + (Top - Bottom) / (1 + 10\textasciicircum((Log\ IC50 - X) * Hill\ Slope)) \quad \text{Formula (2):}$$

Wherein, Y axis was the inhibition rate, and the X axis was the compound concentration.

7. Experimental Results:

As shown in Table 1, each compound of the present invention could effectively inhibit BRD protein, and the inhibitory effect was rather significant.

TABLE 1

The $IC_{50}$ values of compounds against BRD

| | BRD2(1,2) (uM) | BRD4(1,2) (uM) | BRD3(1,2) (uM) | BRDT(D1) (uM) |
|---|---|---|---|---|
| 213 | 0.0016 | 0.0041 | 0.0044 | 0.015 |
| 202 | 0.0016 | 0.0051 | 0.0045 | 0.016 |
| 240 | 0.0012 | 0.0064 | 0.0043 | 0.021 |
| 56 | 0.0011 | 0.0071 | 0.0043 | 0.021 |
| 215 | 0.0029 | 0.0053 | 0.0050 | 0.016 |
| 184 | 0.0020 | 0.0069 | 0.0047 | 0.019 |
| 204 | 0.0065 | 0.010 | 0.0074 | 0.019 |
| 243 | 0.0014 | 0.0089 | 0.0053 | 0.019 |
| 193 | 0.0027 | 0.014 | 0.0058 | 0.032 |
| 250 | 0.0015 | 0.0043 | 0.0041 | 0.015 |
| 41 | 0.0023 | 0.014 | 0.0052 | 0.030 |
| 219 | 0.0018 | 0.012 | 0.0067 | 0.040 |
| 241 | 0.0012 | 0.0058 | 0.0041 | 0.017 |
| 242 | 0.0015 | 0.0099 | 0.0053 | 0.019 |
| 217 | 0.0014 | 0.0062 | 0.0049 | 0.020 |
| 239 | 0.0030 | 0.014 | 0.0052 | 0.018 |
| 252 | 0.16 | 0.68 | 0.24 | 0.83 |
| 217 | 0.0015 | 0.0049 | 0.0045 | 0.019 |
| 212 | 0.0017 | 0.0043 | 0.0046 | 0.013 |
| 251 | 0.0012 | 0.0034 | 0.0039 | 0.013 |

Experimental Example 2 Biologically Determining the Inhibitory Effect of the Compound According to the Present Invention on the Proliferation of CWR22RV1 Cells 1. Experimental Materials
   CWR22RV1 cell line (Cell Bank of Chinese Academy of Sciences, TCHu100)
   FBS (Gibco, Cat. No. 10099-141)
   0.01M PBS (Biosharp, Cat. No. 162262)
   RIPM1640 (Hyclone, Cat. No. 308090.01)
   Penicillin-Streptomycin (Hyclone, Cat. No. SV30010)
   Cell counting kit-8 (Signalway Antibody, Cat. No. CP002)
   DMSO (Sigma, Cat. No. D5879)
   Centrifuge Tube, 15 ml (Excell Bio, Cat. No. CS015-0001)
   Cell Culture Dish, (Excell Bio, Cat. No. CS016-0128)
   96-well cell culture cluster (Corning, Cat. No. 3599)
2. Experimental method
(1) Preparation of Buffer

| Cell culture medium | PBS buffer |
|---|---|
| RIPM1640 media | PBS powder was dissolved in 2 L ultrapure water, and sterilized |
| 10% FBS | |
| 1% Pen Strep | |

(2) Experimental Procedures
   1) CWR22RV1 cells were subcultured in cell culture medium, and the cells in good growth condition were seeded in a 96-well plate, 80 μL for each well, thus the number of cells per well was 1500, then the plate was cultured overnight in a 37° C., 5% $CO_2$ cell incubator.
   2) The drug was prepared with dimethyl sulfoxide (DMSO) as a 30 mM stock solution. Prior to use, the solution was diluted 3 times with DMSO, and then diluted with a 3-fold gradient to obtain 9 concentration gradients. Then, each concentration of the compound was further diluted 200 times with the culture solution (to ensure that DMSO concentration in the culture system was 0.1%), 2 repeat wells for each concentration. The diluted solution of each compound (20 μL) was added to the cell culture well (with a final concentration of 10 μM, 3.3 μM, 1.1 μM . . . ), and shaken gently for mixing. In addition, three negative control wells containing only cells and three blank control wells containing only culture medium (20 μL DMSO diluted 200 times with culture medium being added to six wells) were included.
3. Result Detection:
   (1) After culturing for 6 days, 10 μL CCK-8 was added to each well and cultured for additional 2.5 h in a 37° C., 5% $CO_2$ cell incubator.
   (2) The absorbance (OD value) at 450 nm was measured with a multifunctional microplate reader.
   (3) The data was analyzed by the Dose-response-inhibition equation in the software GraphPad Prism6, and the $IC_{50}$ value was obtained.
   For inhibiting the activity of CWR22RV1, the $IC_{50}$ value (nM) of the compound according to the present invention was obtained, and the result was shown in Table 2.
4. Experimental Results:
   As shown in Table 2, each compound of the present invention could effectively inhibit CWR22RV1 cells.

TABLE 2

The $IC_{50}$ value of the compound according to the present invention for inhibition on the activity of CWR22RV1 (nM)

| Compound No. | $IC_{50}$ (nM) |
|---|---|
| 7 | 18 |
| 8 | 6 |
| 9 | 30 |
| 10 | 29 |
| 11 | 30 |
| 12 | 89 |
| 13 | 79 |
| 14 | 31 |
| 15 | 650 |
| 16 | 380 |
| 17 | 440 |
| 18 | 520 |
| 19 | 410 |
| 20 | 550 |
| 24 | 17 |
| 25 | 26 |
| 26 | 6 |
| 27 | 31 |
| 28 | 36 |
| 29 | 45 |
| 30 | 38 |
| 31 | 50 |
| 32 | 65 |
| 33 | 45 |
| 34 | 380 |
| 35 | 440 |
| 36 | 560 |
| 37 | 490 |
| 38 | 410 |
| 39 | 2410 |
| 40 | 15 |
| 41 | 5 |
| 42 | 30 |
| 43 | 50 |
| 44 | 45 |
| 45 | 110 |
| 46 | 130 |
| 47 | 50 |
| 48 | 400 |
| 49 | 420 |
| 50 | 510 |
| 51 | 490 |
| 52 | 520 |
| 53 | 550 |
| 54 | 18 |
| 55 | 21 |
| 56 | 3 |
| 57 | 25 |
| 58 | 50 |
| 59 | 65 |
| 60 | 39 |
| 61 | 105 |
| 62 | 130 |
| 63 | 60 |
| 64 | 380 |
| 65 | 410 |
| 66 | 520 |
| 67 | 490 |
| 68 | 530 |
| 69 | 570 |
| 70 | 130 |
| 71 | 94 |
| 176 | 18 |
| 177 | 17 |
| 178 | 5 |
| 179 | 51 |
| 180 | 460 |
| 181 | 90 |
| 182 | 40 |
| 183 | 63 |
| 184 | 8.1 |
| 185 | 1040 |
| 186 | 21 |

TABLE 2-continued

The IC$_{50}$ value of the compound according to the present invention for inhibition on the activity of CWR22RV1 (nM)

| Compound No. | IC$_{50}$ (nM) |
|---|---|
| 187 | 19 |
| 188 | 38 |
| 189 | 120 |
| 190 | 180 |
| 191 | 140 |
| 192 | 310 |
| 193 | 4 |
| 194 | 46 |
| 195 | 160 |
| 196 | 56 |
| 197 | 5 |
| 198 | 10 |
| 199 | 2 |
| 200 | 6.7 |
| 201 | 1.4 |
| 202 | 0.5 |
| 203 | 0.2 |
| 204 | 0.7 |
| 205 | 4.8 |
| 206 | |
| 207 | |
| 208 | |
| 209 | |
| 210 | |
| 211 | |
| 212 | |
| 213 | |
| 214 | |
| 215 | |
| 216 | |
| 217 | |
| 218 | |
| 219 | 7.1 |
| 220 | 530 |
| 221 | 130 |
| 222 | 350 |
| 223 | 110 |
| 224 | 62 |
| 225 | 130 |
| 226 | |
| 227 | |
| 228 | |
| 229 | |
| 230 | 250 |
| 231 | 1.8 |
| 232 | 0.6 |
| 233 | 1.3 |
| 234 | 0.9 |
| 235 | 1.7 |
| 236 | 3.2 |
| 237 | 4.2 |
| 238 | 8 |
| 239 | 7.8 |
| 240 | 4.8 |
| 241 | 1.7 |
| 242 | 2.2 |
| 243 | 1.3 |
| 244 | 81 |
| 245 | 230 |
| 246 | 30 |
| 247 | 670 |
| 248 | 7002 |
| 249 | 130 |
| 250 | 120 |

Experimental Example 3 Biologically Determining the Inhibitory Effect of the Compound According to the Present Invention on the Proliferation of BT474 Cells 1. Objective of test: The inhibitory effect of the compound on the proliferation of BT474 cells was determine.

2. Experimental Materials

BT474 cell line (Cell Bank of Chinese Academy of Sciences, TCHu143)

FBS (Gibco, Cat. No. 10099-141)

0.01M PBS (Biosharp, Cat. No. 162262)

RIPM1640 (Hyclone, Cat. No. 308090.01)

Penicillin-Streptomycin (Hyclone, Cat. No. SV30010)

Cell counting kit-8 (Signalway Antibody, Cat. No. CP002)

DMSO (Sigma, Cat. No. D5879)

Centrifuge Tube, 15 ml (Excell Bio, Cat. No. CS015-0001)

Cell Culture Dish (Excell Bio, Cat. No. CS016-0128)

96-well cell culture cluster (Corning, Cat. No. 3599)

3. Experimental Method (1) Preparation of Buffer

| Cell culture medium | PBS buffer |
|---|---|
| RIPM1640 media | PBS powder was |
| 10% FBS | dissolved in 2 L |
| 1% Pen Strep | ultrapure water, and sterilized |

(2) Experimental Procedures

1) BT474 cells were subcultured in cell culture media, and the cells in good growth condition were seeded in a 96-well plate, 80 μL for each well, thus the number of cells per well was 1500, then the plate was cultured overnight in a 37° C., 5% CO$_2$ cell incubator.

2) The drug was prepared with dimethyl sulfoxide (DMSO) as a 10 mM stock solution. Prior to use, the solution was diluted 3 times with DMSO, and then diluted with a 3-fold gradient to obtain 9 concentration gradients. Then, each concentration of the compound was further diluted 200 times with the culture media (to ensure that DMSO concentration in the culture system was 0.1%), 2 repeat wells for each concentration. The diluted solution of each compound (20 μL) was added to the cell culture well (with a final concentration of 10 μM, 3.3 μM, 1.1 and shaken gently for mixing. In addition, three negative control wells containing only cells and three blank control wells containing only culture medium (20 μL DMSO diluted 200 times with culture medium being added to six wells) were included.

4. Result Detection:

(1) After culturing for 6 days, 10 μL CCK-8 was added to each well and cultured for additional 2.5 h in a 37° C., 5% CO$_2$ cell incubator.

(2) The absorbance (OD value) at 450 nm was measured with a multifunctional microplate reader.

(3) The data was analyzed by the Dose-response-inhibition equation in the software GraphPad Prism6, and the IC$_{50}$ value was obtained.

For inhibiting the activity of BT474, the IC$_{50}$ value (nM) of the compound according to the present invention was obtained, and the result was shown in Table 3.

5. Experimental Results:

As shown in Table 3, the compound of the present invention, especially compounds 41 and 55, had an effective inhibitory action on BT474 cells.

TABLE 3

The $IC_{50}$ value of the compound for inhibition on the activity of BT474 (nM).

| Compound No. | $IC_{50}$ (nM) |
|---|---|
| 176 | 1500 |
| 55 | 130 |
| 41 | 330 |

Experimental Example 4 Biologically Determining the Inhibitory Effect of the Compound According to the Present Invention on the Proliferation of MCF-7 Cells 1. Objective of test: The inhibitory effect of the compound on the proliferation of MCF-7 cells was determine.
2. Experimental Materials
   MCF-7 cell line (Cell Bank of Chinese Academy of Sciences, TCHu74)
   FBS (Gibco, Cat. No. 10099-141)
   0.01M PBS (Biosharp, Cat. No. 162262)
   RIPM1640 (Hyclone, Cat. No. 308090.01)
   Penicillin-Streptomycin (Hyclone, Cat. No. SV30010)
   Cell counting kit-8 (Signalway Antibody, Cat. No. CP002)
   DMSO (Sigma, Cat. No. D5879)
   Centrifuge Tube, 15 ml (Excell Bio, Cat. No. CS015-0001)
   Cell Culture Dish, (Excell Bio, Cat. No. CS016-0128)
   96-well cell culture cluster (Corning, Cat. No. 3599)
3. Experimental Method
   (1) Preparation of Buffer

| Cell culture medium | PBS buffer |
|---|---|
| RIPM1640 media | PBS powder was dissolved in 2 L |
| 10% FBS | ultrapure water, and sterilized |
| 1% Pen Strep | |

(2) Experimental Procedures

1) MCF-7 cells were subcultured in cell culture media, and the cells in good growth condition were seeded in a 96-well plate, 80 µL for each well, thus the number of cells per well was 1000, then the plate was cultured overnight in a 37° C., 5% $CO_2$ cell incubator.

2) The drug was prepared with dimethyl sulfoxide (DMSO) as a 10 mM stock solution. Prior to use, the solution was diluted 3 times with DMSO, and then diluted with a 3-fold gradient to obtain 9 concentration gradients. Then, each concentration of the compound was further diluted 200 times with the culture media (to ensure that DMSO concentration in the culture system was 0.1%), 2 repeat wells for each concentration. The diluted solution of each compound (20 µL) was added to the cell culture well (with a final concentration of 10 µM, 3.3 µM, 1.1 µM . . . ), and shaken gently for mixing.

In addition, three negative control wells containing only cells and three blank control wells containing only culture medium (20 µL DMSO diluted 200 times with culture medium being added to six wells) were included.

4. Result Detection:

(1) After culturing for 6 days, 10 µL CCK-8 was added to each well and cultured for additional 2.5 h in a 37° C., 5% $CO_2$ cell incubator.

(2) The absorbance (OD value) at 450 nm was measured with a multifunctional microplate reader.

(3) The data was analyzed by the Dose-response-inhibition equation in the software GraphPad Prism6, and the $IC_{50}$ value was obtained.

For inhibiting the activity of MCF-7, the $IC_{50}$ value (nM) of the compound according to the present invention was obtained, and the result was shown in Table 4.

5. Experimental Results:

As shown in Table 4, the compound of the present invention, especially compounds 41, 184, and 178, had an effective inhibitory action on MCF-7 cells.

TABLE 4

The $IC_{50}$ value of the compound for inhibition on the activity of MCF-7 (nM).

| Compound No. | $IC_{50}$ (nM) |
|---|---|
| 176 | 580 |
| 55 | 100 |
| 41 | 54 |
| 184 | 14 |
| 178 | 29 |

Experimental Example 5 Biologically Determining the Inhibitory Effect of the Compound According to the Present Invention on the Proliferation of MDA-MB-231 Cells 1. Objective of test: The inhibitory effect of the compound on the proliferation of MDA-MB-231 cells was determine.
2. Experimental Materials
   MDA-MB-231 cell line (Cell Bank of Chinese Academy of Sciences, TCHu104)
   FBS (Gibco, Cat. No. 10099-141)
   0.01M PBS (Biosharp, Cat. No. 162262)
   RIPM1640 (Hyclone, Cat. No. 308090.01)
   Penicillin-Streptomycin (Hyclone, Cat. No. SV30010)
   Cell counting kit-8 (Signalway Antibody, Cat. No. CP002)
   DMSO (Sigma, Cat. No. D5879)
   Centrifuge Tube, 15 ml (Excell Bio, Cat. No. CS015-0001)
   Cell Culture Dish, (Excell Bio, Cat. No. CS016-0128)
   96-well cell culture cluster (Corning, Cat. No. 3599)
3. Experimental Method
   (1) Preparation of Buffer

| Cell culture medium | PBS buffer |
|---|---|
| RIPM1640 media | PBS powder was |
| 10% FBS | dissolved in 2 L |
| 1% Pen Strep | ultrapure water, and sterilized |

(2) Experimental Procedures

1) MDA-MB-231 cells were subcultured in cell culture media, and the cells in good growth condition were seeded in a 96-well plate, 80 µL for each well, thus the number of cells per well was 1500, then the plate was cultured overnight in a 37° C., 5% $CO_2$ cell incubator.

2) The drug was prepared with dimethyl sulfoxide (DMSO) as a 10 mM stock solution. Prior to use, the solution was diluted 3 times with DMSO, and then diluted with a 3-fold gradient to obtain 9 concentration gradients. Then, each concentration of the compound was further diluted 200 times with the culture media (to ensure that DMSO concentration in the culture system was 0.1%), 2 repeat wells for each concentration. The diluted solution of each compound (20 μL) was added to the cell culture well (with a final concentration of 10 μM, 3.3 μM, 1.1 μM . . . ), and shaken gently for mixing. In addition, three negative control wells containing only cells and three blank control wells containing only culture medium (20 μL DMSO diluted 200 times with culture medium being added to six wells) were included.

4. Result Detection:

(1) After culturing for 6 days, 10 μL CCK-8 was added to each well and cultured for additional 2.5 h in a 37° C., 5% $CO_2$ cell incubator.

(2) The absorbance (OD value) at 450 nm was measured with a multifunctional microplate reader.

(3) The data was analyzed by the Dose-response-inhibition equation in the software GraphPad Prism6, and the $IC_{50}$ value was obtained.

For inhibiting the activity of MDA-MB-231, the $IC_{50}$ value (nM) of the compound according to the present invention was obtained, and the result was shown in Table 5.

5. Experimental Results:

As shown in Table 5, the compound of the present invention, especially compounds 184 and 178, had an effective inhibitory action on MDA-MB-231 cells.

TABLE 5

The $IC_{50}$ value of the compound for inhibition on the activity of MDA-MB-231 (nM).

| Compound No. | IC50 (nM) |
|---|---|
| 176 | 4500 |
| 55 | 749 |
| 41 | 7540 |
| 184 | 26 |
| 178 | 39 |

Experimental Example 6 Biologically Determining the Inhibitory Effect of the Compound According to the Present Invention on the Proliferation of MDA-MB-453 Cells 1. Objective of test: The inhibitory effect of the compound on the proliferation of MDA-MB-453 cells was determine.
2. Experimental Materials
MDA-MB-453 cell line (Cell Bank of Chinese Academy of Sciences, TCHu35)
FBS (Gibco, Cat. No. 10099-141)
0.01M PBS (Biosharp, Cat. No. 162262)
RIPM1640 (Hyclone, Cat. No. 308090.01)
Penicillin-Streptomycin (Hyclone, Cat. No. SV30010)
Cell counting kit-8 (Signalway Antibody, Cat. No. CP002)
DMSO (Sigma, Cat. No. D5879)
Centrifuge Tube, 15 ml (Excell Bio, Cat. No. CS015-0001)
Cell Culture Dish, (Excell Bio, Cat. No. CS016-0128)
96-well cell culture cluster (Corning, Cat. No. 3599)

3. Experimental Method (1) Preparation of Buffer

| Cell culture medium | PBS buffer |
|---|---|
| RIPM1640 media | PBS powder was |
| 10% FBS | dissolved in 2 L |
| 1% Pen Strep | ultrapure water, and sterilized |

(2) Experimental Procedures

1) MDA-MB-453 cells were subcultured in cell culture media, and the cells in good growth condition were seeded in a 96-well plate, 80 μL for each well, thus the number of cells per well was 1500, then the plate was cultured overnight in a 37° C., 5% $CO_2$ cell incubator.

2) The drug was prepared with dimethyl sulfoxide (DMSO) as a 10 mM stock solution. Prior to use, the solution was diluted 3 times with DMSO, and then diluted with a 3-fold gradient to obtain 9 concentration gradients. Then, each concentration of the compound was further diluted 200 times with the culture media (to ensure that DMSO concentration in the culture system was 0.1%), 2 repeat wells for each concentration. The diluted solution of each compound (20 μL) was added to the cell culture well (with a final concentration of 10 μM, 3.3 μM, 1.1 μM . . . ), and shaken gently for mixing. In addition, three negative control wells containing only cells and three blank control wells containing only culture medium (20 μL DMSO diluted 200 times with culture medium being added to six wells) were included.

4. Result Detection:

(1) After culturing for 6 days, 10 μL CCK-8 was added to each well and cultured for additional 2.5 h in a 37° C., 5% $CO_2$ cell incubator.

(2) The absorbance (OD value) at 450 nm was measured with a multifunctional microplate reader.

(3) The data was analyzed by the Dose-response-inhibition equation in the software GraphPad Prism6, and the $IC_{50}$ value was obtained.

For inhibiting the activity of MDA-MB-453, the $IC_{50}$ value (nM) of the compound according to the present invention was obtained, and the result was shown in Table 6.

5. Experimental Results:

As shown in Table 6, the compound of the present invention, especially compounds 55 and 41, had an effective inhibitory action on MDA-MB-453 cells.

TABLE 6

The $IC_{50}$ value of the compound for inhibition on the activity of MDA-MB-453 (nM).

| Compound No. | IC50 (nM) |
|---|---|
| 176 | 1080 |
| 55 | 48 |
| 41 | 89 |
| 184 | 440 |
| 178 | 720 |

Experimental Example 7 Biologically Determining the Inhibitory Effect of the Compound According to the Present Invention on the Proliferation of Vcap Cells 1. Experimental Materials
   Vcap cell line (Cell Bank of Chinese Academy of Sciences, TCHu220)
   FBS (Gibco, Cat. No. 10099-141)
   0.01M PBS (Biosharp, Cat. No. 162262)
   DMEM HIGH Glucose (Hyclone, Cat. No. SH30243.01)
   Penicillin-Streptomycin (Hyclone, Cat. No. SV30010)
   Cell counting kit-8 (Signalway Antibody, Cat. No. CP002)
   DMSO (Sigma, Cat. No. D5879)
   Centrifuge Tube, 15 ml (Excell Bio, Cat. No. CS015-0001)
   Cell Culture Dish, (Excell Bio, Cat. No. CS016-0128)
   96-well cell culture cluster (Corning, Cat. No. 3599)
2. Experimental Method
   (1) Preparation of Buffer

| Cell culture medium | PBS buffer |
|---|---|
| RIPM1640 media | PBS powder was |
| 10% FBS | dissolved in 2 L |
| 1% Pen Strep | ultrapure water, and sterilized |

(2) Experimental Procedures

1) Vcap cells were subcultured in cell culture media, and the cells in good growth condition were seeded in a 96-well plate, 80 μL for each well, thus the number of cells per well was 10000, then the plate was cultured overnight in a 37° C., 5% $CO_2$ cell incubator.

2) The drug was prepared with dimethyl sulfoxide (DMSO) as a 10 mM stock solution. Prior to use, the solution was diluted 3 times with DMSO, and then diluted with a 3-fold gradient to obtain 9 concentration gradients. Then, each concentration of the compound was further diluted 200 times with the culture media (to ensure that DMSO concentration in the culture system was 0.1%), 2 repeat wells for each concentration. The diluted solution of each compound (20 μL) was added to the cell culture well (with a final concentration of 10 μM, 3.3 μM, 1.1 μM . . . ), and shaken gently for mixing. In addition, three negative control wells containing only cells and three blank control wells containing only culture medium (20 μL DMSO diluted 200 times with culture medium being added to six wells) were included.

3. Result Detection:
   (1) After culturing for 6 days, 10 μL CCK-8 was added to each well and cultured for additional 2.5 h in a 37° C., 5% $CO_2$ cell incubator.
   (2) The absorbance (OD value) at 450 nm was measured with a multifunctional microplate reader.
   (3) The data was analyzed by the Dose-response-inhibition equation in the software GraphPad Prism6, and the $IC_{50}$ value was obtained.

For inhibiting the activity of Vcap, the $IC_{50}$ value (nM) of the compound according to the present invention was obtained, and the result was shown in Table 7.

4. Experimental Results:
   As shown in Table 7, the compound of the present invention, especially compounds 184, 231, and 219, had an effective inhibitory action on Vcap cells.

TABLE 7

The $IC_{50}$ value of the compound according to the present invention for inhibition on the activity of Vcap (nM).

| Compound No. | IC50 (nM) |
|---|---|
| 184 | 15 |
| 231 | 3.9 |
| 219 | 17.6 |

Experimental Example 8 Biologically Determining the Inhibitory Effect of the Compound According to the Present Invention in Combination with Androgen Receptor Inhibitor HC-1119 (Deuterated Enzalutamide) on the Proliferation of CWR22RV1 Cells Objective of test: The inhibitory effect of the compound in combination with HC-1119 on the proliferation of CWR22RV1 cells was determine.

Experimental Materials
   CWR22RV1 cell line (Cell Bank of Chinese Academy of Sciences, TCHu100)
   FBS (Gibco, Cat. No. 10099-141)
   0.01M PBS (Biosharp, Cat. No. 162262)
   RIPM1640 (Hyclone, Cat. No. 308090.01)
   Penicillin-Streptomycin (Hyclone, Cat. No. SV30010)
   Cell counting kit-8 (Signalway Antibody, Cat. No. CP002)
   DMSO (Sigma, Cat. No. D5879)
   Centrifuge Tube, 15 ml (Excell Bio, Cat. No. CS015-0001)
   Cell Culture Dish, (Excell Bio, Cat. No. CS016-0128)
   96-well cell culture cluster (Corning, Cat. No. 3599)
Experimental Method:
   1. Preparation of Buffer

| Cell culture medium | PBS buffer |
|---|---|
| RIPM1640 media | PBS powder was |
| 10% FBS | dissolved in 2 L |
| 1% Pen Strep | ultrapure water, and sterilized |

2. Experimental Procedures:

1) CWR22RV1 cells were subcultured in cell culture media, and the cells in good growth condition were seeded in a 96-well plate, 60 μL for each well, thus the number of cells per well was 2000, then the plate was cultured overnight in a 37° C., 5% $CO_2$ cell incubator.

2) The drug was prepared with dimethyl sulfoxide (DMSO) as a 10 mM stock solution. Prior to use, the solution was diluted 3 times with DMSO, and then diluted with a 3-fold gradient to obtain 9 concentration gradients. Then, each concentration of the compound was further diluted 200 times with the culture media (to ensure that DMSO concentration in the culture system was 0.1%), 2 repeat wells for each concentration. The diluted solution of each compound (20 μL) was added to the cell culture well (with a final concentration of 10 μM, 3.3 μM, 1.1 μM . . . ); while the solution of HC-1119 was diluted with culture media to the concentrations of 50 μM and 15 μM, respectively, and the diluted solution of HC-1119 was added to the corresponding cell culture well (with a final concentration of 10 μM, 3 μM), then shaken gently for mixing. In addition, three negative control wells containing only cells and three blank control wells containing only culture media (20 μL DMSO diluted 200 times with culture media being added to six wells) were included.

3. Result Detection:

(1) After culturing for 6 days, 10 μL CCK-8 was added to each well and cultured for additional 2.5 h in a 37° C., 5% $CO_2$ cell incubator.

(2) The absorbance (OD value) at 450 nm was measured with a multifunctional microplate reader.

(3) The data was analyzed by the Dose-response-inhibition equation in the software GraphPad Prism6, and the $IC_{50}$ value was obtained.

For inhibiting the activity of CWR22RV1, the $IC_{50}$ value (nM) of the compound according to the present invention was obtained, and the result was shown in Table 8.

4. Experimental Results:

As shown in Table 8, the compounds 184 and 231 according to the present invention, in combination with androgen receptor inhibitor HC-1119 respectively, could improve the inhibitory action on CWR22RV1 cells, and the inhibitory effect enhanced as the increase of concentration.

TABLE 8

The $IC_{50}$ value of the compound for inhibition on the activity of CWR22RV1 (nM).

| Compound No. | IC50 (nM) |
| --- | --- |
| 184 | 8.1 |
| 10 μM HC-1119 + 184 | 1.5 |
| 3 μM HC-1119 + 184 | 2.0 |
| 231 | 1.8 |
| 10 μM HC-1119 + 231 | 0.51 |
| 3 μM HC-1119 + 231 | 0.65 |

Experimental Example 9 Biologically Determining the Inhibitory Effect of the Compound According to the Present Invention in Combination with Androgen Receptor Inhibitor HC-1119 (Deuterated Enzalutamide) on the Proliferation of Vcap Cells Objective of test: The inhibitory effect of the compound in combination with HC-1119 on the proliferation of Vcap cells was determine.

1. Experimental Materials

Vcap cell line (Cell Bank of Chinese Academy of Sciences, TCHu220)
FBS (Gibco, Cat. No. 10099-141)
0.01M PBS (Biosharp, Cat. No. 162262)
DMEM HIGH Glucose (Hyclone, Cat. No. SH30243.01)
Penicillin-Streptomycin (Hyclone, Cat. No. SV30010)
Cell counting kit-8 (Signalway Antibody, Cat. No. CP002)
DMSO (Sigma, Cat. No. D5879)
Centrifuge Tube, 15 ml (Excell Bio, Cat. No. CS015-0001)
Cell Culture Dish (Excell Bio, Cat. No. CS016-0128)
96-well cell culture cluster (Corning, Cat. No. 3599)

2. Experimental Method (1) Preparation of Buffer

| Cell culture medium | PBS buffer |
| --- | --- |
| DMEM media | PBS powder was |
| 10% FBS | dissolved in 2 L |
| 1% Pen Strep | ultrapure water, and sterilized |

(2) Experimental Procedures

1) Vcap cells were subcultured in cell culture media, and the cells in good growth condition were seeded in a 96-well plate, 60 μL for each well, thus the number of cells per well was 10000, then the plate was cultured overnight in a 37° C., 5% $CO_2$ cell incubator.

2) The drug was prepared with dimethyl sulfoxide (DMSO) as a 10 mM stock solution. Prior to use, the solution was diluted 3 times with DMSO, and then diluted with a 3-fold gradient to obtain 9 concentration gradients. Then, each concentration of the compound was further diluted 200 times with the culture media (to ensure that DMSO concentration in the culture system was 0.1%), 2 repeat wells for each concentration. The diluted solution of each compound (20 μL) was added to the cell culture well (with a final concentration of 10 μM, 3.3 μM, 1.1 μM . . . ); while the solution of HC-1119 was diluted with culture media to the concentrations of 50 μM and 15 μM, respectively, and the diluted solution of HC-1119 was added to the corresponding cell culture well (with a final concentration of 10 μM, 1 μM), then shaken gently for mixing. In addition, three negative control wells containing only cells and three blank control wells containing only culture media (20 μL DMSO diluted 200 times with culture media being added to six wells) were included.

3. Result Detection:

(1) After culturing for 6 days, 10 μL CCK-8 was added to each well and cultured for additional 2.5 h in a 37° C., 5% $CO_2$ cell incubator.

(2) The absorbance (OD value) at 450 nm was measured with a multifunctional microplate reader.

(3) The data was analyzed by the Dose-response-inhibition equation in the software GraphPad Prism6, and the $IC_{50}$ value was obtained.

For inhibiting the activity of Vcap, the $IC_{50}$ value (nM) of the compound according to the present invention in combination with HC-1119 was obtained, and the result was shown in Table 9.

4. Experimental Results:

As shown in Table 9, the compounds 184, 231, and 219 according to the present invention, in combination with androgen receptor inhibitor HC-1119 respectively, could improve the inhibitory action on Vcap cells, and the inhibitory effect enhanced as the increase of concentration.

TABLE 9

The $IC_{50}$ value of the compound according to the present invention in combination with HC-1119 for inhibition on the activity of Vcap (nM).

| Compound No. | $IC_{50}$ (nM) |
| --- | --- |
| 184 | 15 |
| 10 μM HC-1119 + 184 | 0.13 |
| 1 μM HC-1119 + 184 | 0.33 |
| 231 | 3.9 |
| 10 μM HC-1119 + 231 | 0.027 |
| 1 μM HC-1119 + 231 | 0.076 |
| 219 | 17.6 |
| 10 μM HC-1119 + 219 | 0.18 |
| 1 μM HC-1119 + 219 | 0.55 |

In summary, the compounds provided in the present invention had a good inhibitory effect on the proliferation of a variety of human prostate cancer cells (CWR22RV1 and Vcap) and breast cancer cells (BT474, MCF-7, MDA-MB-231, MDA-MB-453); moreover, the compound of the present invention combined with the androgen receptor inhibitor HC-1119 could significantly enhance the inhibitory effect on prostate cancer cells, and the inhibitory effect improved as the increase of concentration. It was shown that the compound of the present invention could not only be used alone to prepare anti-tumor drugs, but also could be combined with other anti-tumor drugs, such as androgen receptor inhibitors, other targeted drugs, etc., to prepare anti-tumor drugs with better therapeutic effects, especially those for treatment of prostate cancer and breast cancer.

The invention claimed is:

1. A compound of formula (I), or a pharmaceutically acceptable salt, solvate or hydrate thereof:

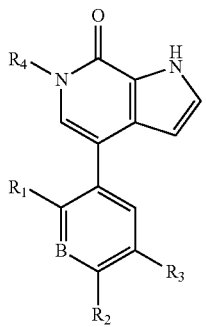

(I)

wherein, $R_1$ is selected from

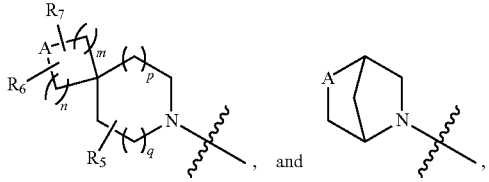

, and $R_2$ is selected from H, halogen, $C_1$-$C_8$ alkyl, $C_1$-$C_8$ haloalkyl, $C_1$-$C_8$ alkoxy, substituted aryl, substituted heteroaryl,

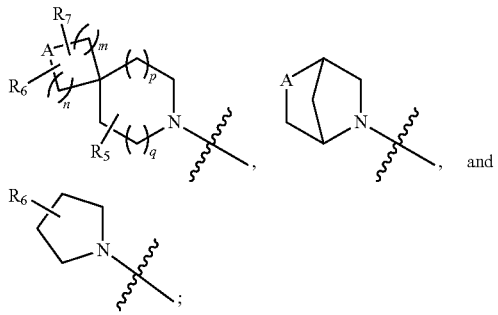

$R_3$ is selected from —NHSO$_2$R$_8$, —SO$_2$R$_8$, —SO$_2$NR$_8$R$_9$, $C_1$-$C_8$ alkyl, carboxyl, —CONHR$_8$, —COOR$_8$, —COR$_8$, hydroxyl-substituted $C_1$-$C_8$ alkyl, —NHCOR$_8$, —NHCONHR$_8$, amino, and

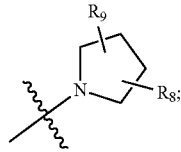

$R_4$ is selected from H, $C_1$-$C_8$ alkyl, $C_1$-$C_8$ haloalkyl, and $C_1$-$C_8$ deuterated alkyl;
A is selected from CH$_2$, NH, O, S, SO, and SO$_2$;
B CH or N;
m, n, p, q=0, 1, or 2;
$R_6$, is selected from halogen, hydroxyl, cyano, CONH$_2$, $C_1$-$C_8$ alkyl, $C_1$-$C_8$ alkoxy, $C_3$-$C_8$ cycloalkyl, $C_3$-$C_8$ heterocycloalkyl, hydroxyl or carboxyl-substituted $C_3$-$C_8$ heterocycloalkyl, —COOR$_{10}$, hydroxyl or carboxyl-substituted $C_1$-$C_8$ alkyl, $C_1$-$C_8$ haloalkyl, $C_1$-$C_8$ deuterated alkyl, aryl, and heteroaryl;
$R_5$, $R_7$, $R_8$, and $R_9$ are each independently selected from H, halogen, hydroxyl, cyano, CONH$_2$, $C_1$-$C_8$ alkyl, $C_1$-$C_8$ alkoxy, $C_3$-$C_8$ cycloalkyl, $C_3$-$C_8$ heterocycloalkyl, hydroxyl or carboxyl-substituted $C_3$-$C_8$ heterocycloalkyl, —COOR$_{10}$, hydroxyl or carboxyl-substituted $C_1$-$C_8$ alkyl, $C_1$-$C_8$ haloalkyl, $C_1$-$C_8$ deuterated alkyl, aryl, and heteroaryl; and
$R_{10}$ is H or $C_1$-$C_8$ alkyl.

2. The compound according to claim 1, or a pharmaceutically acceptable salt, solvate or hydrate thereof, wherein said $R_4$ is selected from $C_1$-$C_8$ alkyl and $C_1$-$C_8$ deuterated alkyl.

3. The compound according to claim 2, or a pharmaceutically acceptable salt, solvate or hydrate thereof, wherein said $R_4$ is methyl or deuterated methyl.

4. The compound according to claim 1, or a pharmaceutically acceptable salt, solvate or hydrate thereof, wherein said $R_{10}$ is H or ethyl.

5. The compound according to claim 1, or a pharmaceutically acceptable salt, solvate or hydrate thereof, wherein said compound of formula (I) has a structure of formula (II):

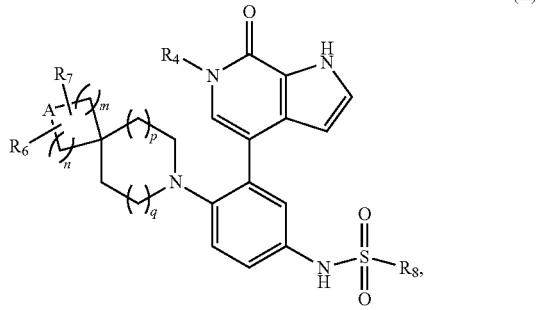

(II)

wherein, $R_6$ and $R_7$ are each independently selected from H, halogen, and COOR$_{10}$; $R_8$ is selected from $C_1$-$C_8$ alkyl, $C_3$-$C_8$ cycloalkyl, and $C_3$-$C_8$ heterocycloalkyl; $R_4$ is selected from methyl and deuterated methyl; A is selected from CH$_2$, O, and S; and m, n, p, q=0, 1, or 2.

6. The compound according to claim 1, or a pharmaceutically acceptable salt, solvate or hydrate thereof, wherein said compound of formula (I) has a structure of formula (III)-1 or (III)-2:

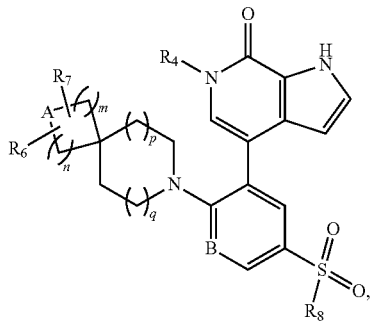

(III)-1

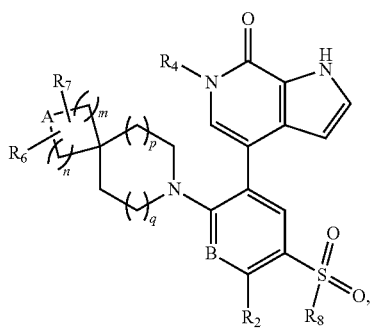

(III)-2 wherein, B is CH or N; $R_6$ and $R_7$ are each independently selected from H, halogen, cyano, $COOR_{10}$, $CONH_2$, and hydroxyl-substituted $C_1$-$C_8$ alkyl; $R_8$ is selected from $C_1$-$C_8$ alkyl, hydroxyl or carboxyl-substituted $C_1$-$C_8$ alkyl, $C_3$-$C_8$ cycloalkyl, $C_3$-$C_8$ heterocycloalkyl, and hydroxyl or carboxyl-substituted $C_3$-$C_8$ heterocycloalkyl; $R_4$ is selected from methyl and deuterated methyl; A is selected from $CH_2$, O or S; m, n, p, q=0, 1, or 2; and $R_2$ is halogen.

7. The compound according to claim 1, or a pharmaceutically acceptable salt, solvate or hydrate thereof, wherein said compound of formula (I) has a structure of formula (IV):

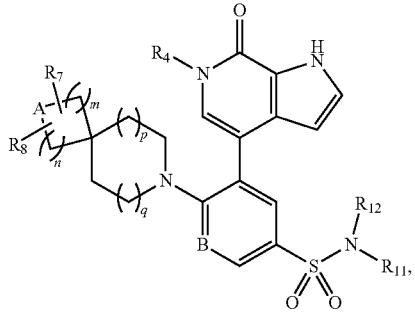

(IV)

wherein, B is CH or N; $R_6$ and $R_7$ are each independently selected from H and halogen;

$R_{12}$ and $R_{11}$ are each independently selected from H, $C_1$-$C_8$ alkyl, hydroxyl or carboxyl-substituted $C_1$-$C_8$ alkyl, and $C_1$-$C_8$ deuterated alkyl; or $R_{12}$ and $R_{11}$ are linked to form a five-membered ring; $R_4$ is selected from methyl and deuterated methyl; A is selected from $CH_2$, O, and S; m, n, p, q=0, 1, or 2.

8. The compound according to claim 1, or a pharmaceutically acceptable salt, solvate or hydrate thereof, wherein said compound of formula (I) has a structure of formula (V):

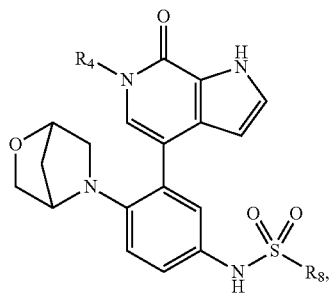

(V)

wherein, $R_8$ is a $C_1$-$C_8$ alkyl; and $R_4$ is selected from methyl and deuterated methyl.

9. The compound according to claim 1, or a pharmaceutically acceptable salt, solvate or hydrate thereof, wherein said compound of formula (I) is one selected from the following compounds:

7

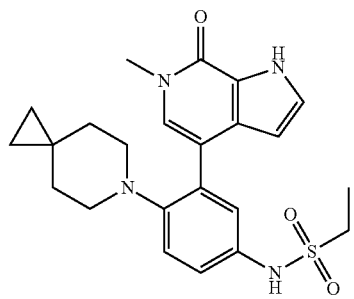

8

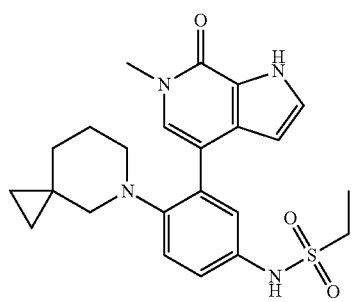

9

159
-continued
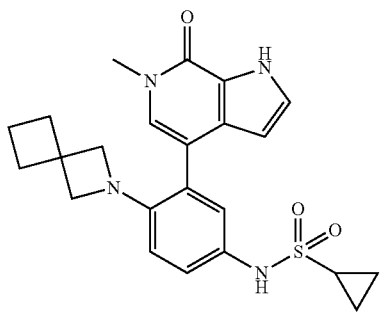
10
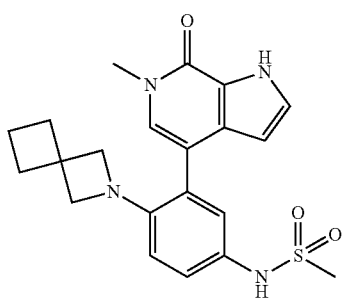
11
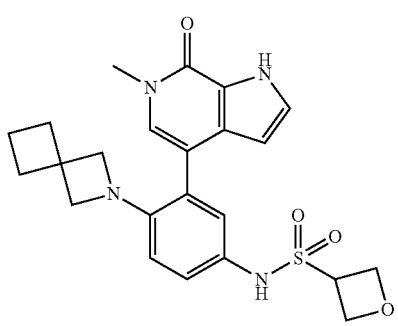
12
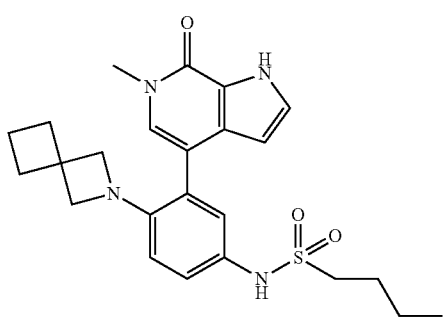
13
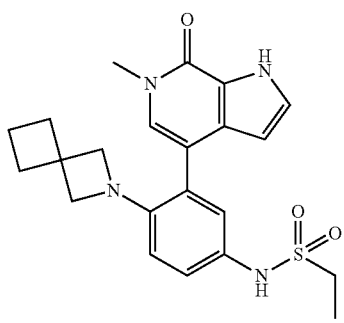
14
160
-continued
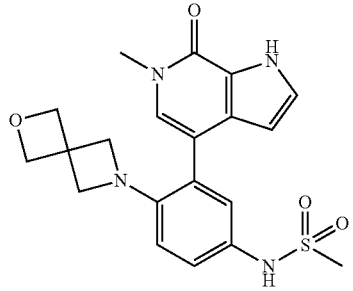
15
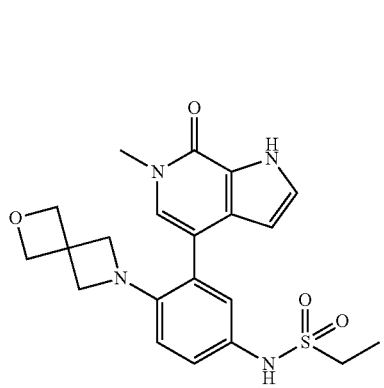
16
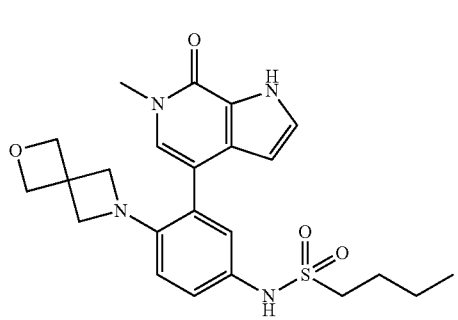
17
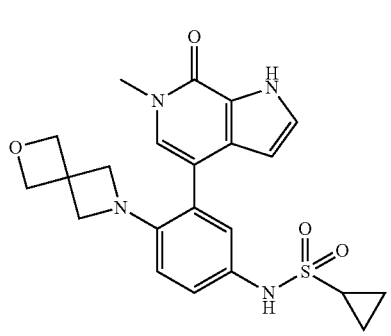
18
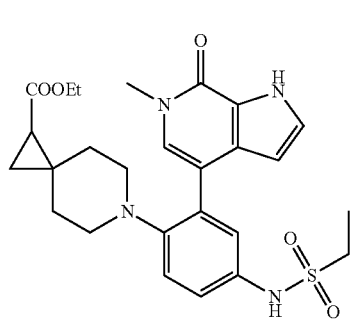
19

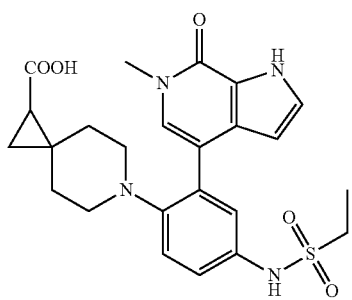
20
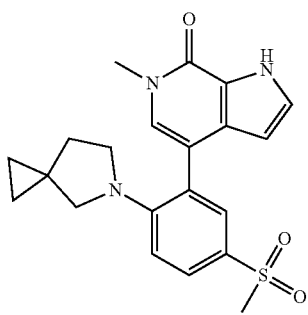
24
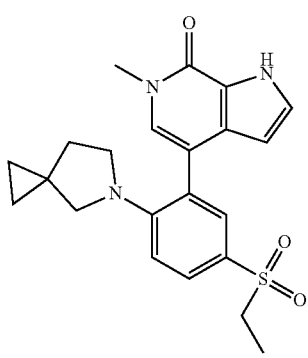
25
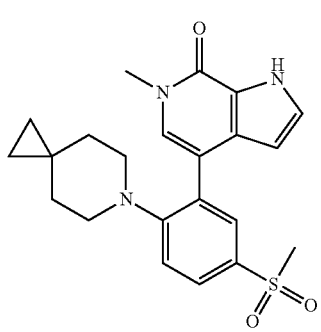
26
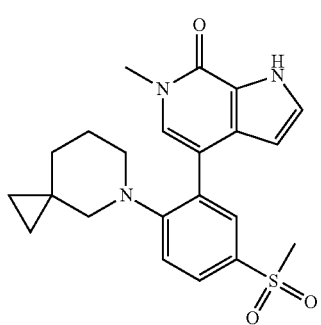
27
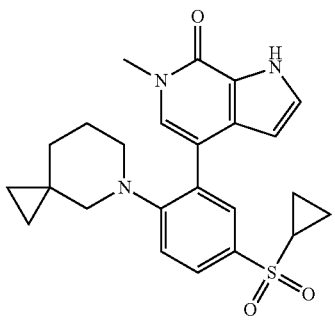
28
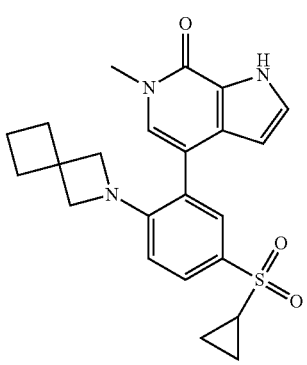
29
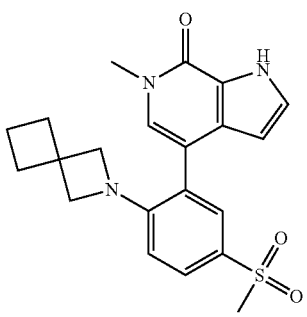
30
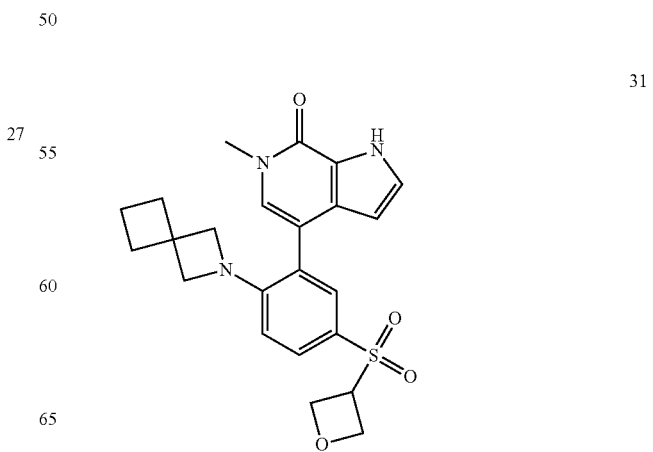
31

32
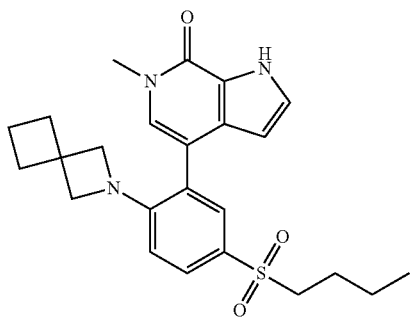
33
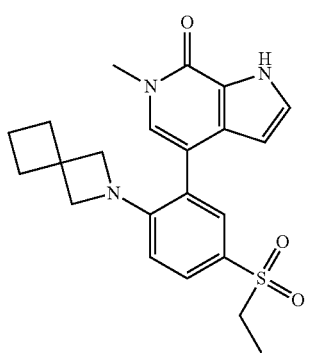
34
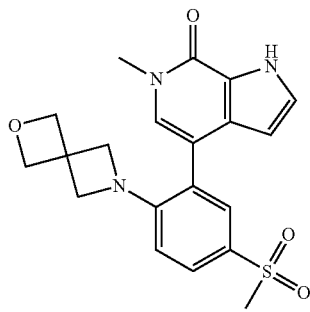
35
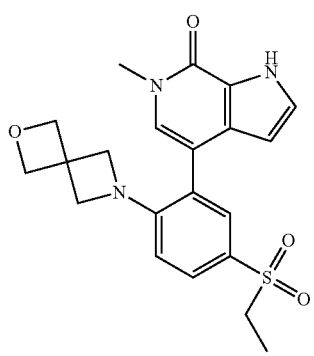
36
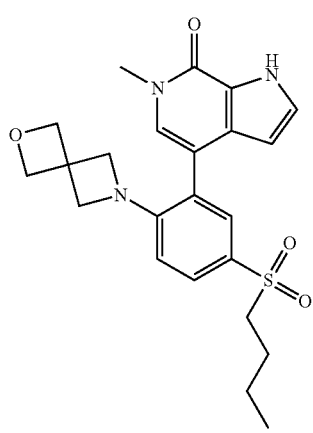
37
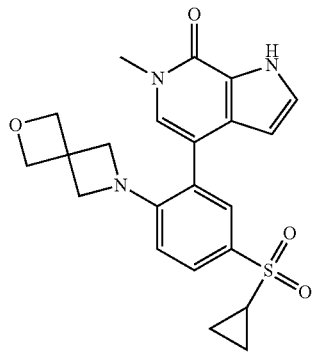
38
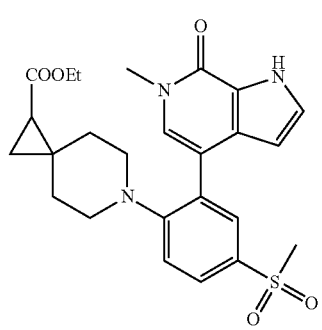
39
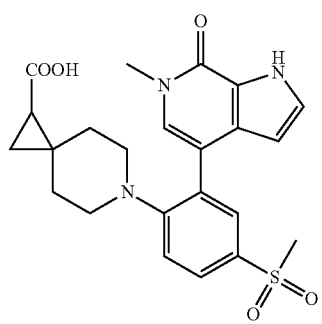

40
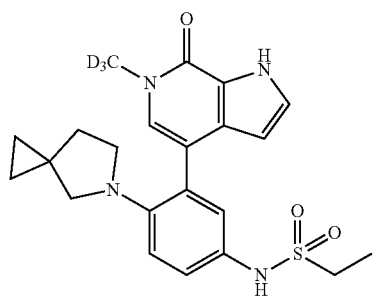
41
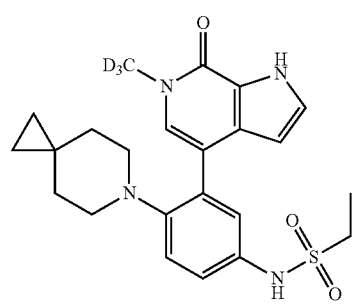
42
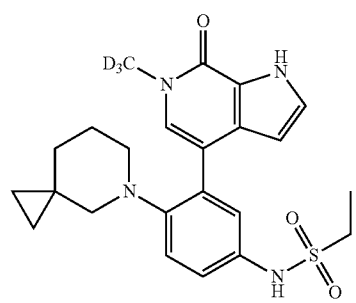
43
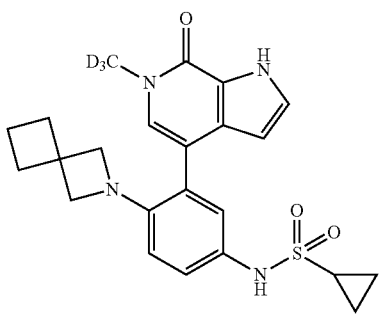
44
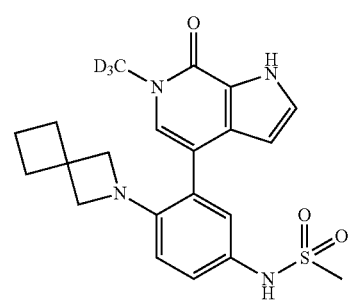
45
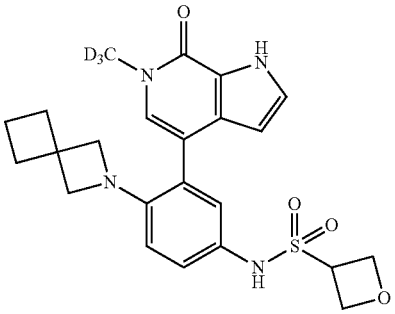
46
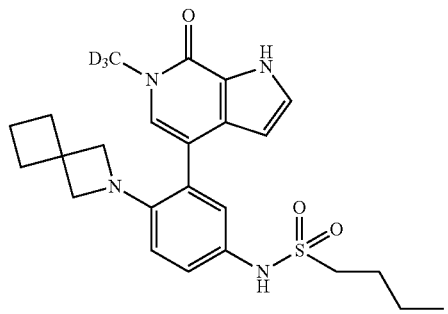
47
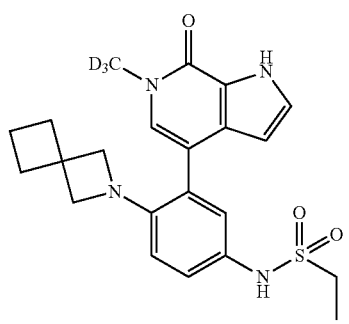
48
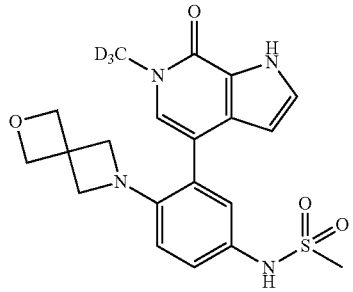
49
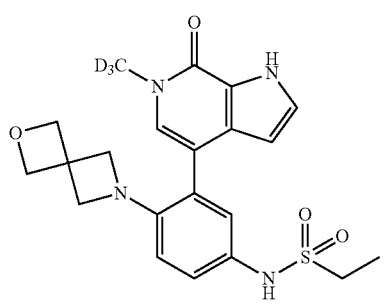

50
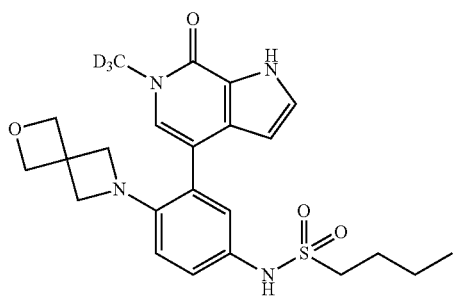
51
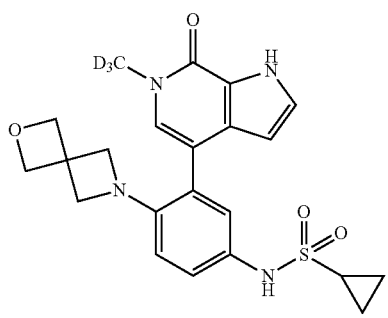
52
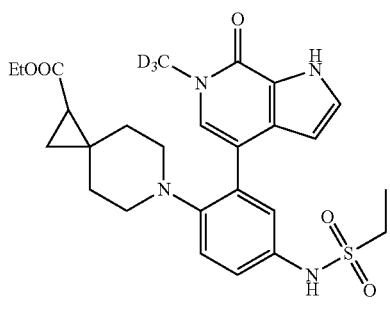
53
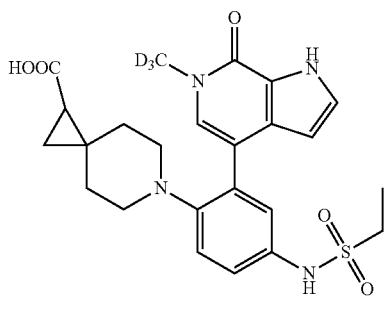
54
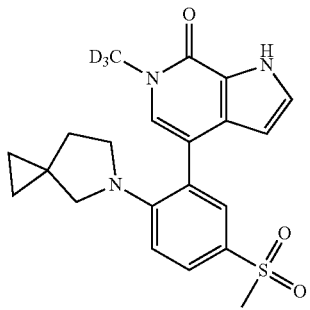
55
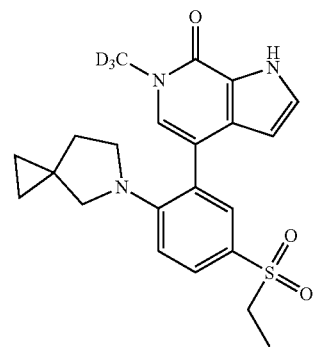
56
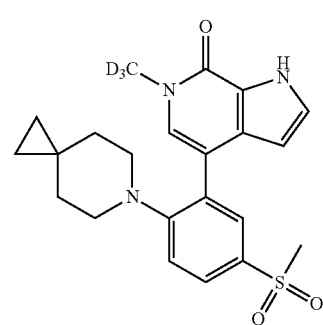
57
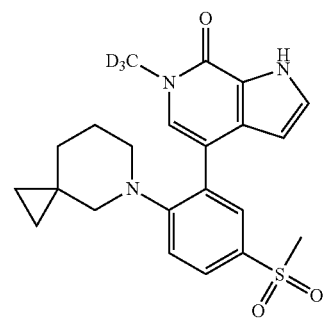
58
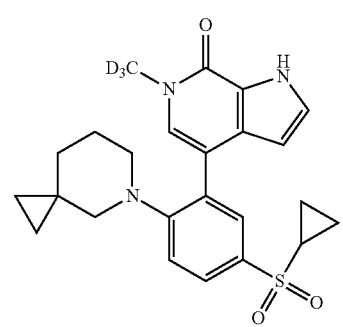

-continued
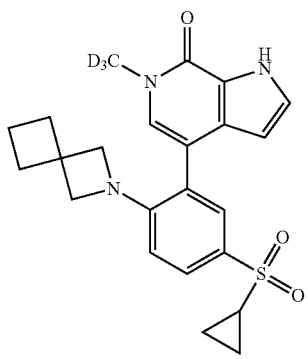
59
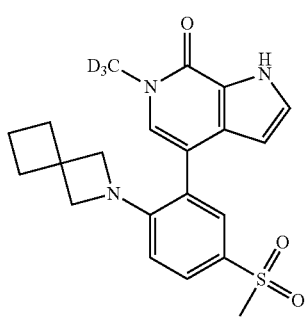
60
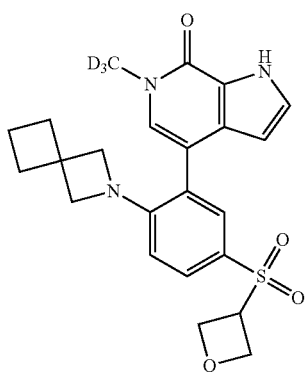
61
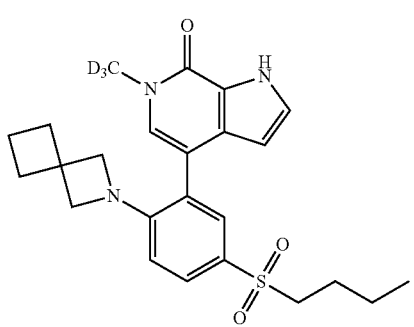
62
-continued
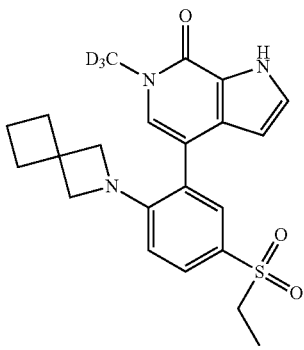
63
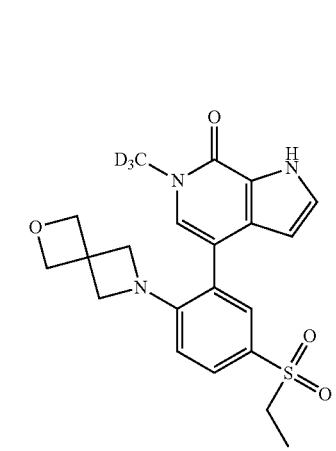
64
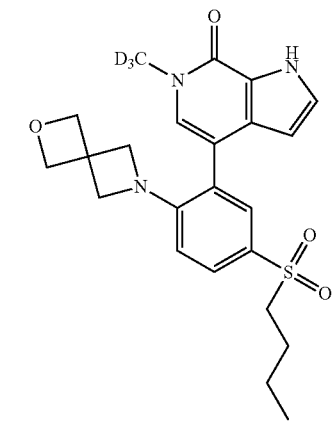
65

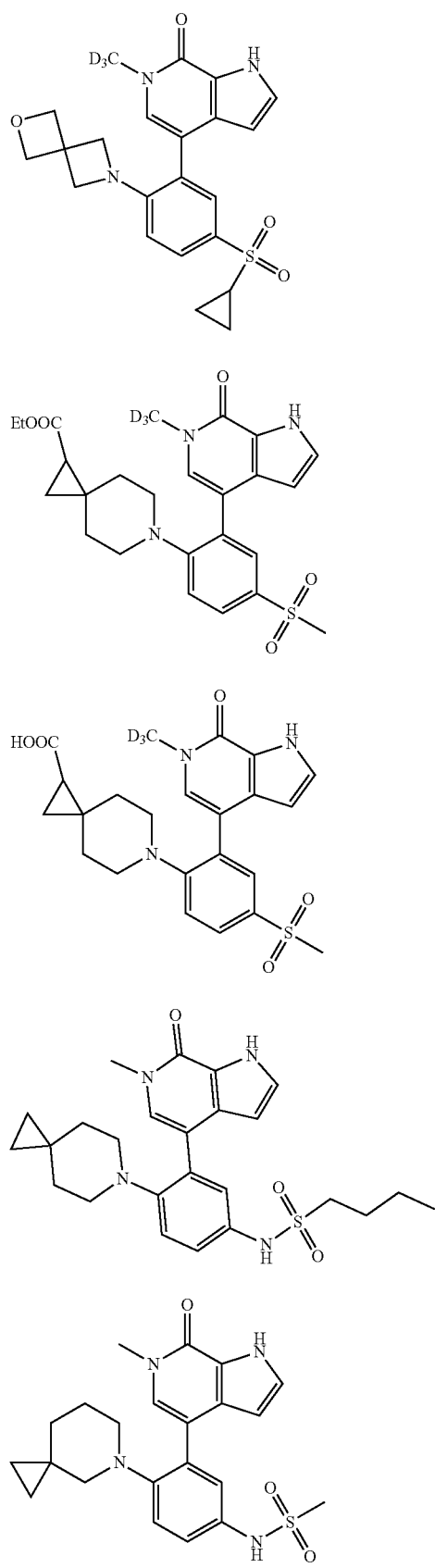
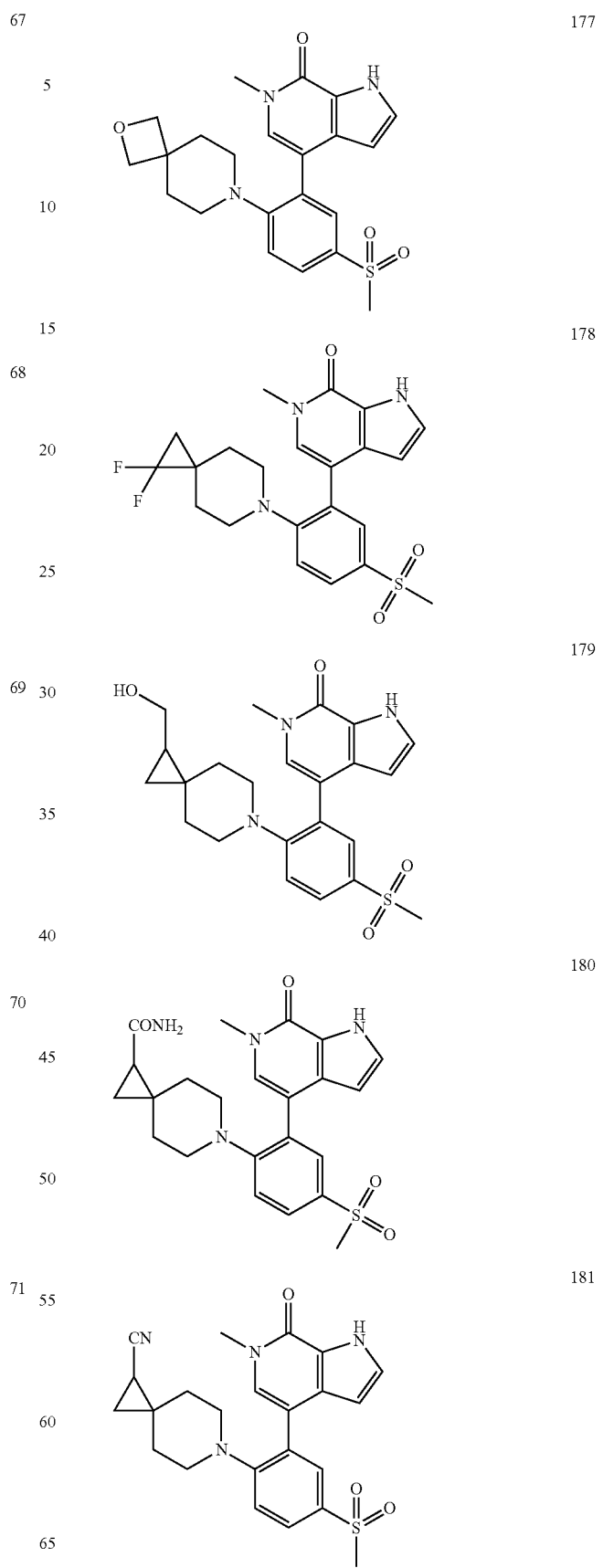

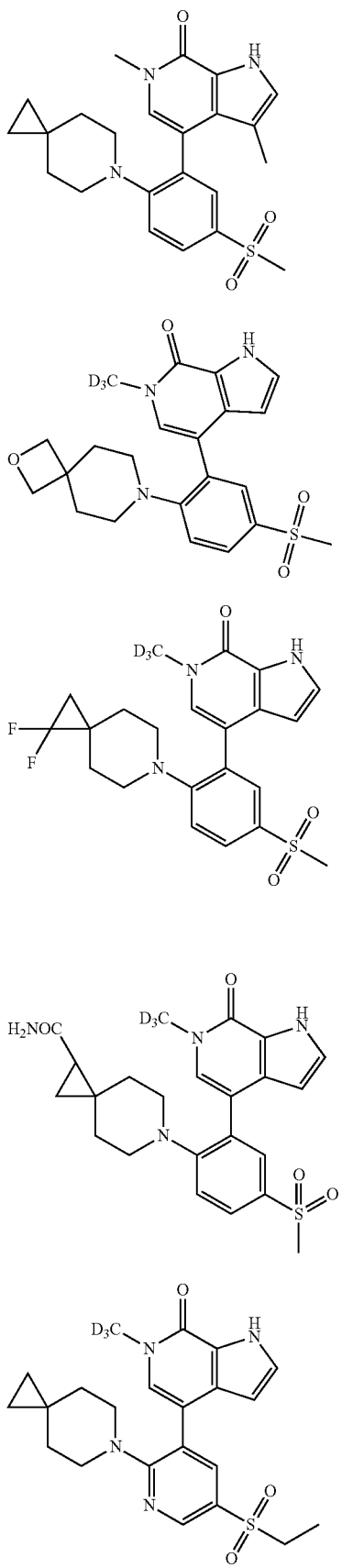
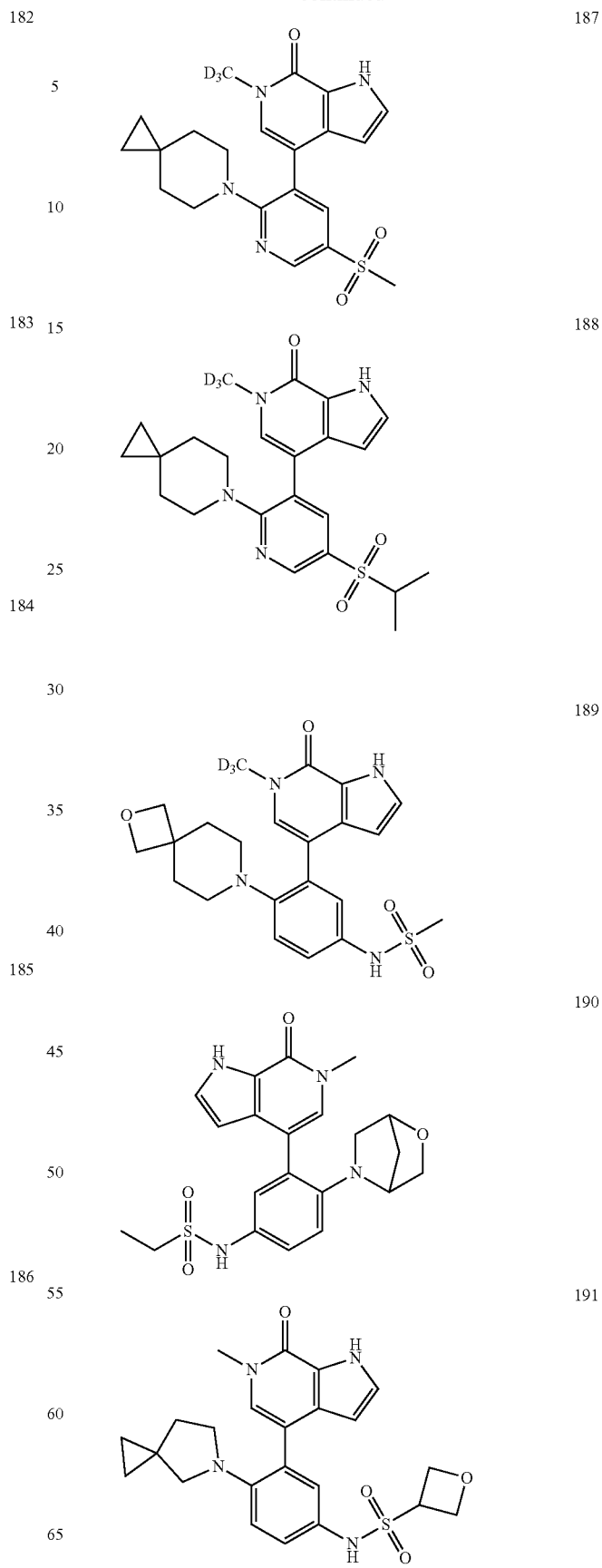

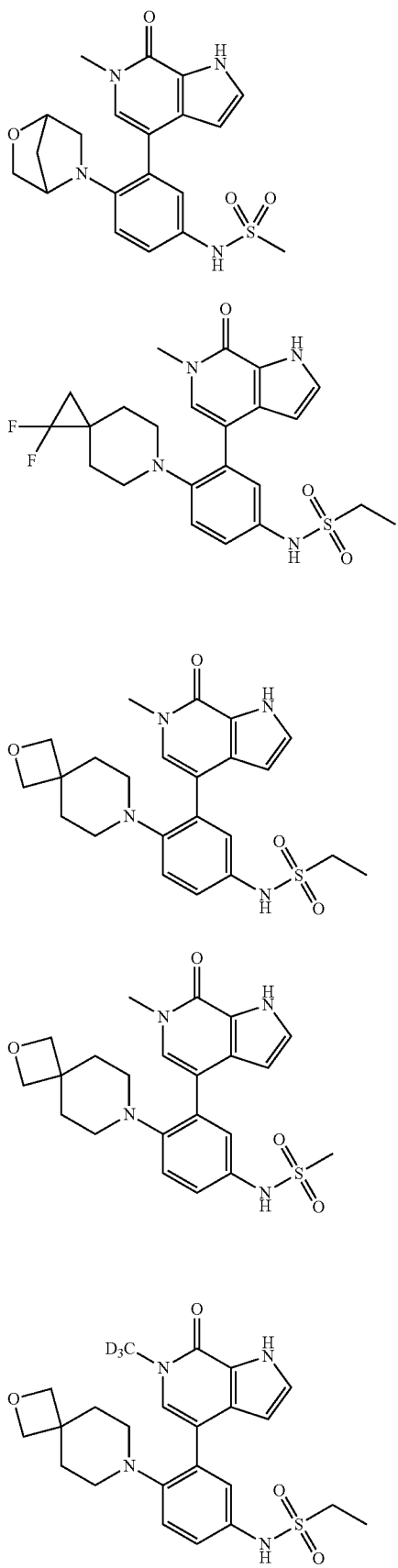
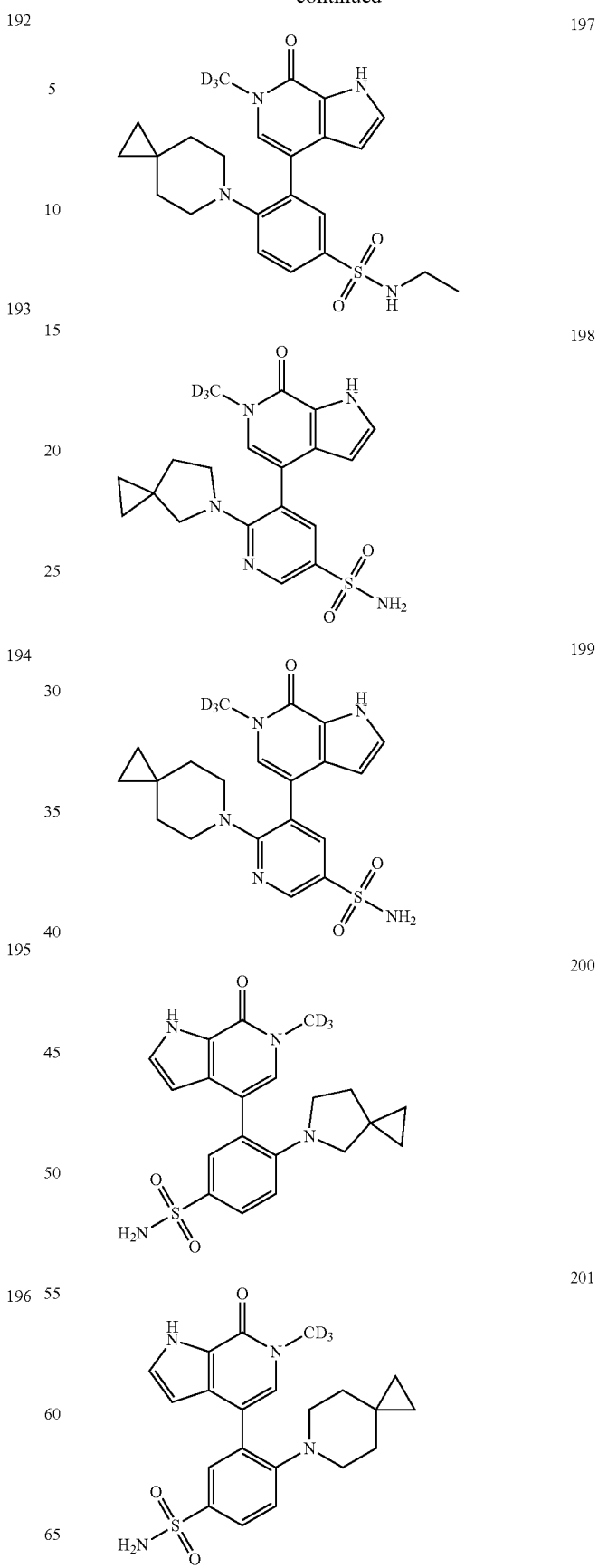

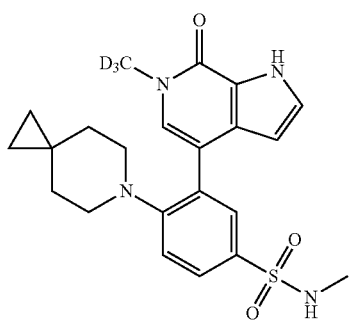
202
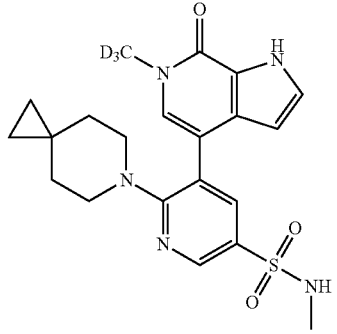
203
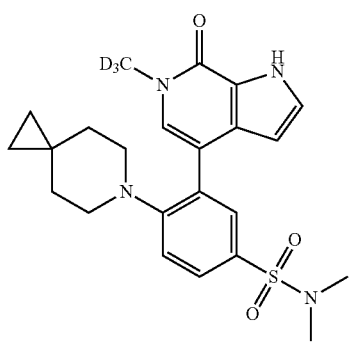
206
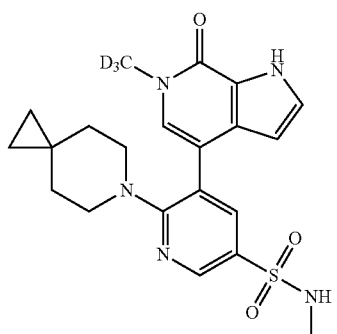
207
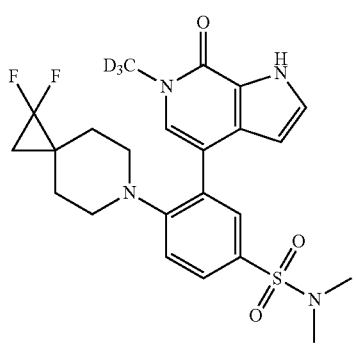
204
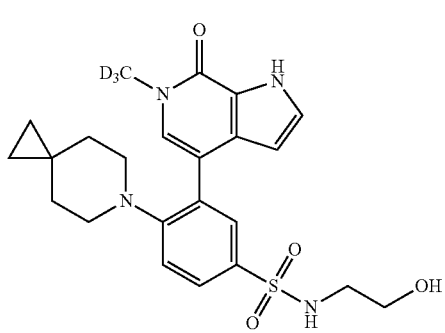
205
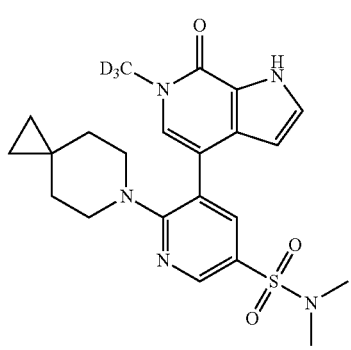
208
209

210 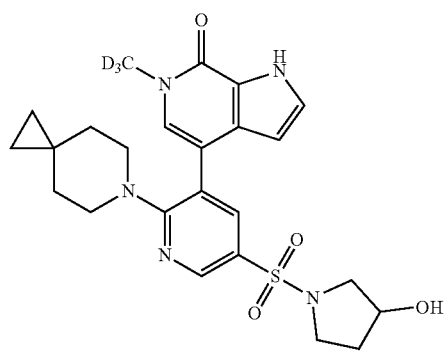
211 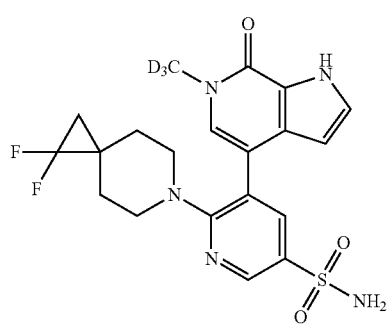
212 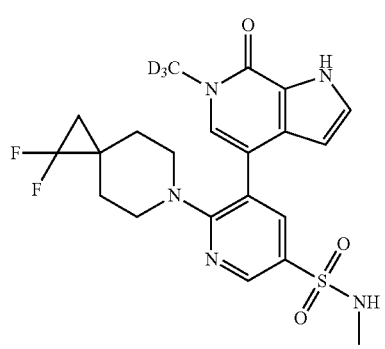
213 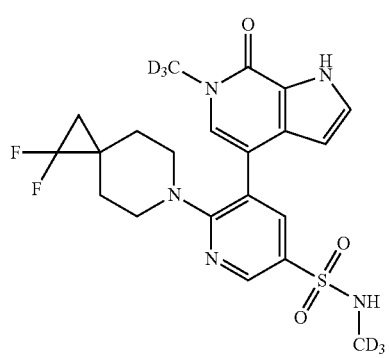
214 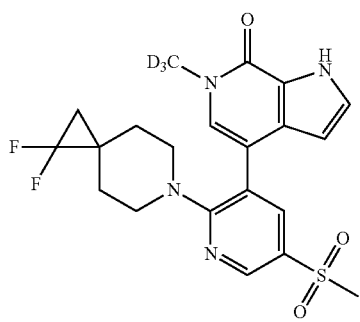
215 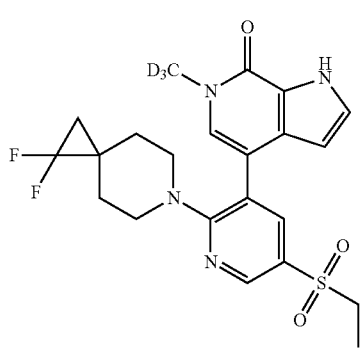
216 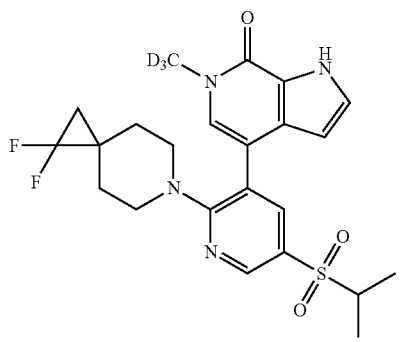
217 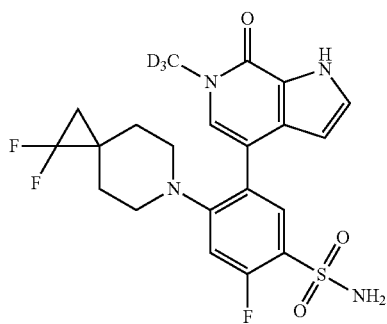

| | |
|---|---|
| 218 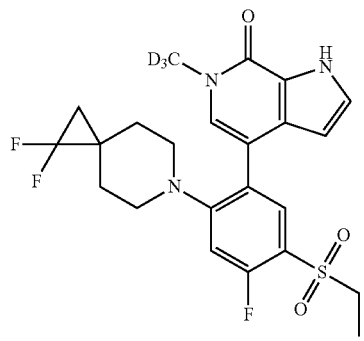 | 223 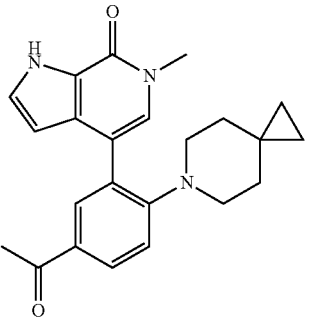 |
| 219 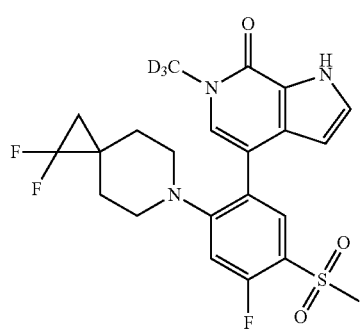 | 224 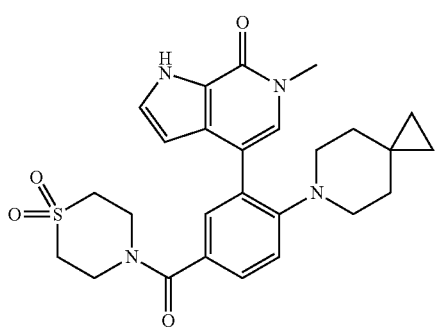 |
| 220 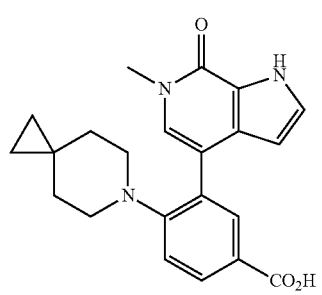 | 225 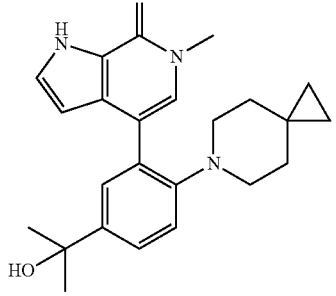 |
| 221 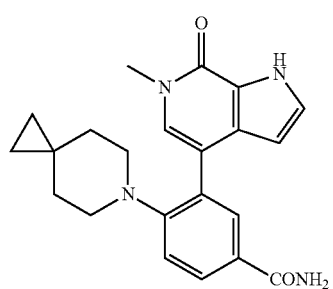 | 226 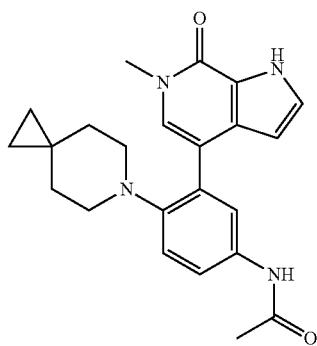 |
| 222 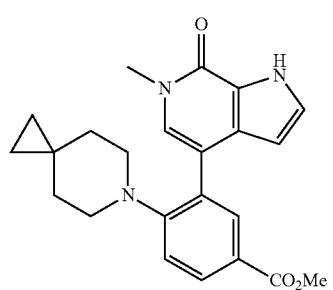 | |

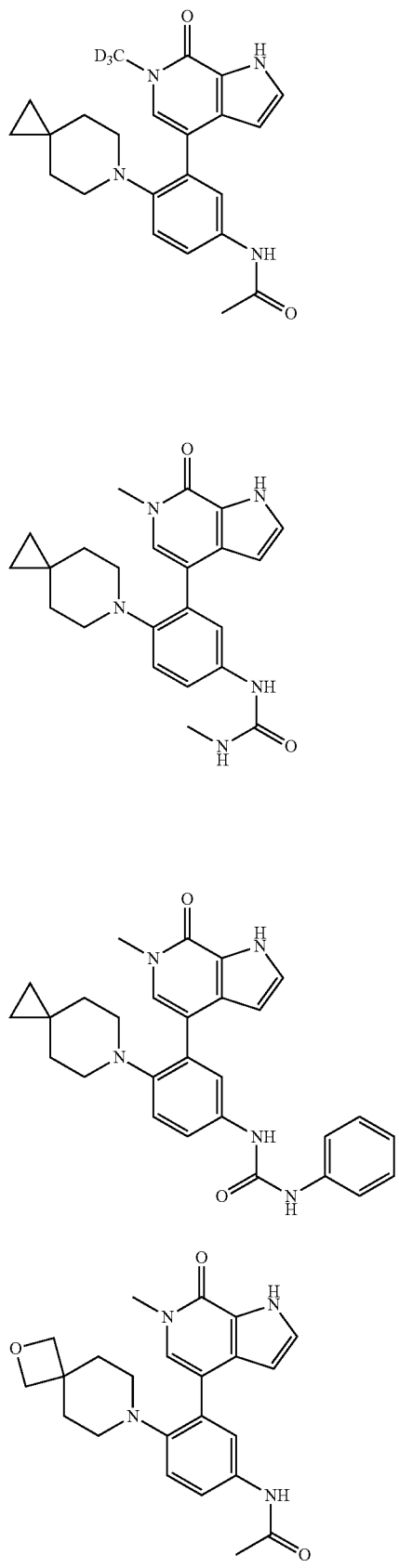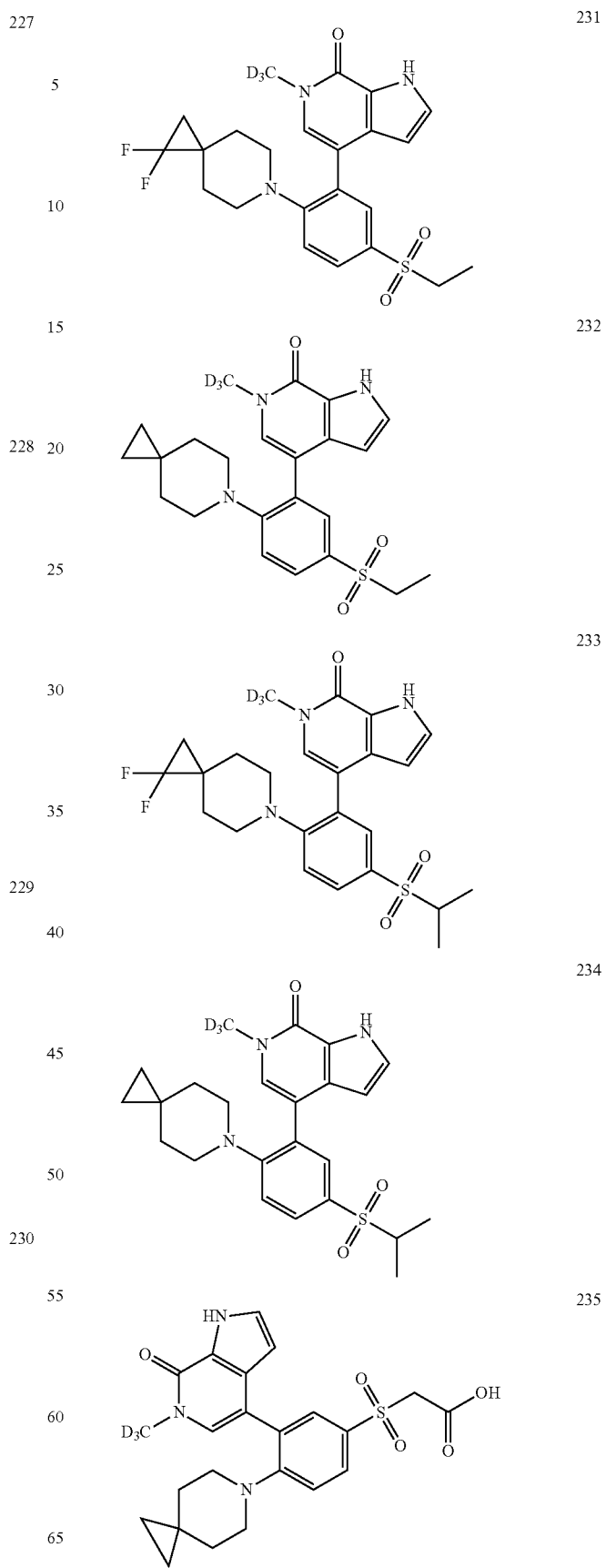

236
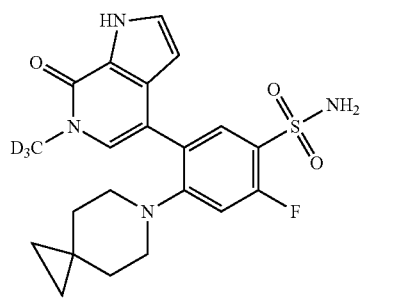
237
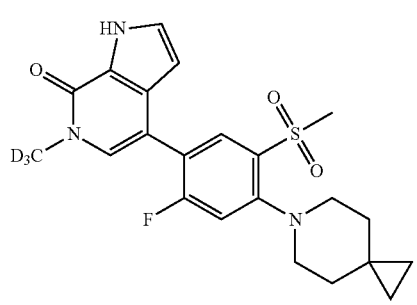
238
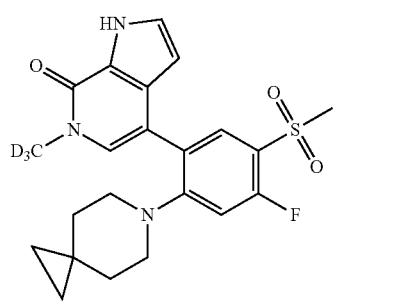
239
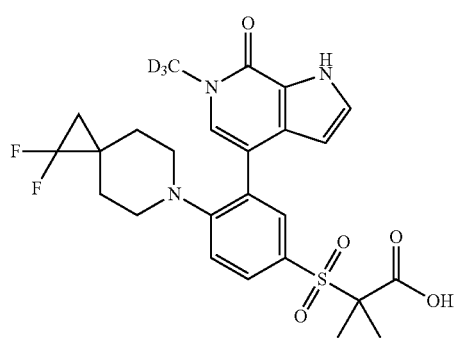
240
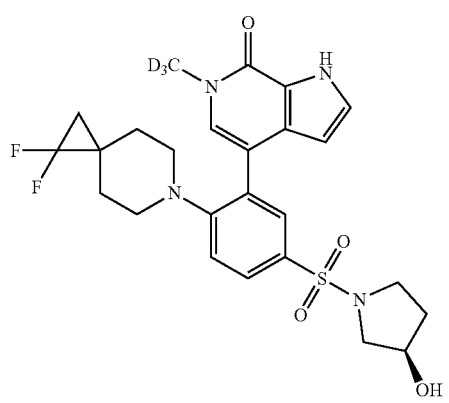
241
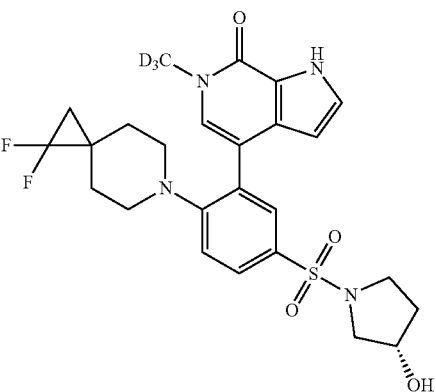
242
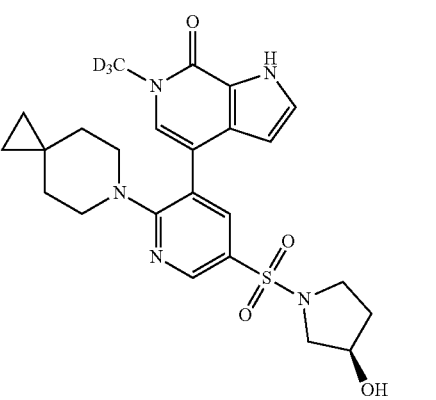
243
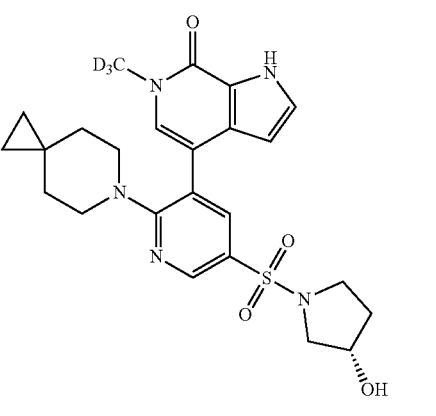
244
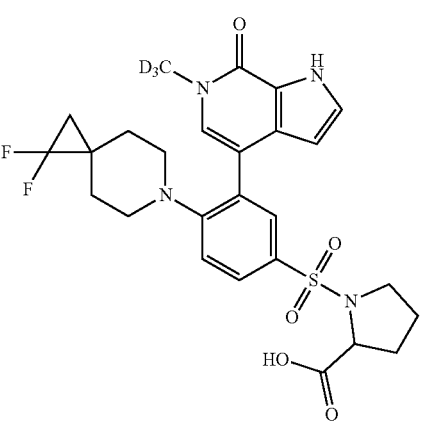

245 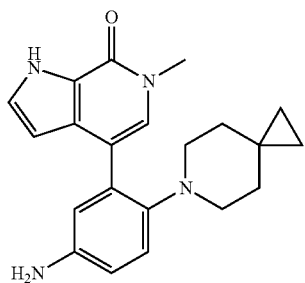
246 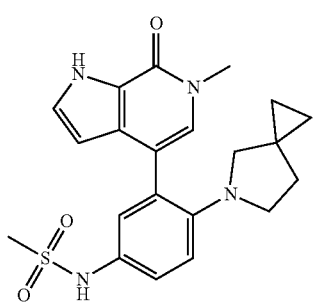
247 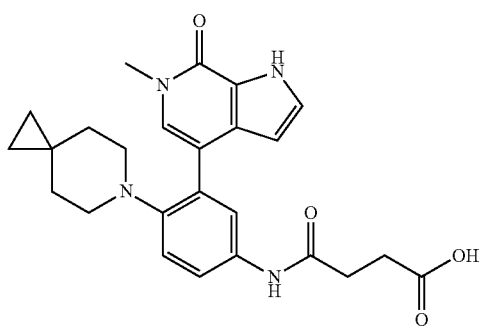
250 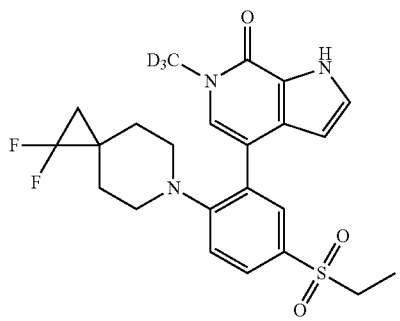
251 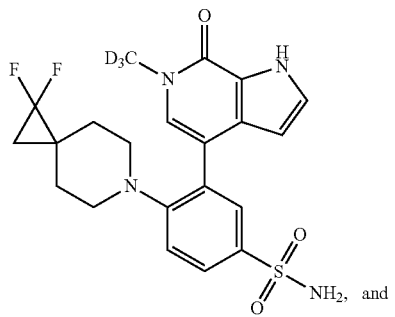
, and
252 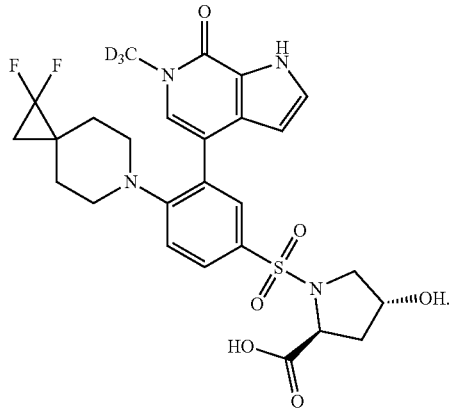
10. A method for preparation of the compound according to claim 1, comprising the following steps:
Scheme 1
or
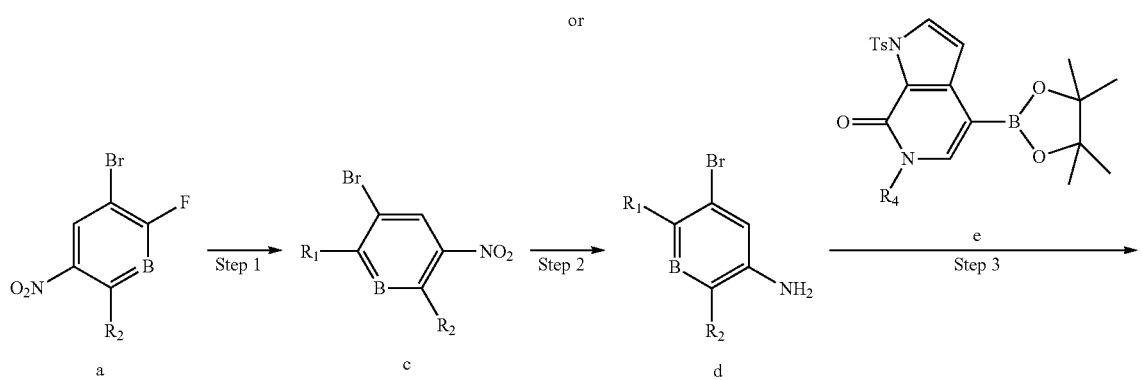

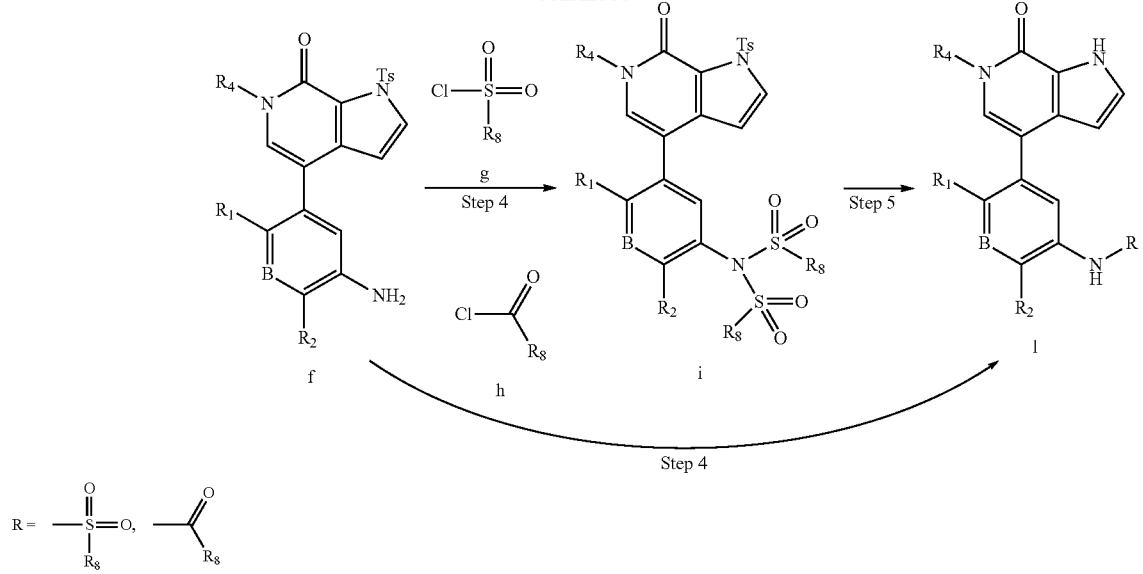

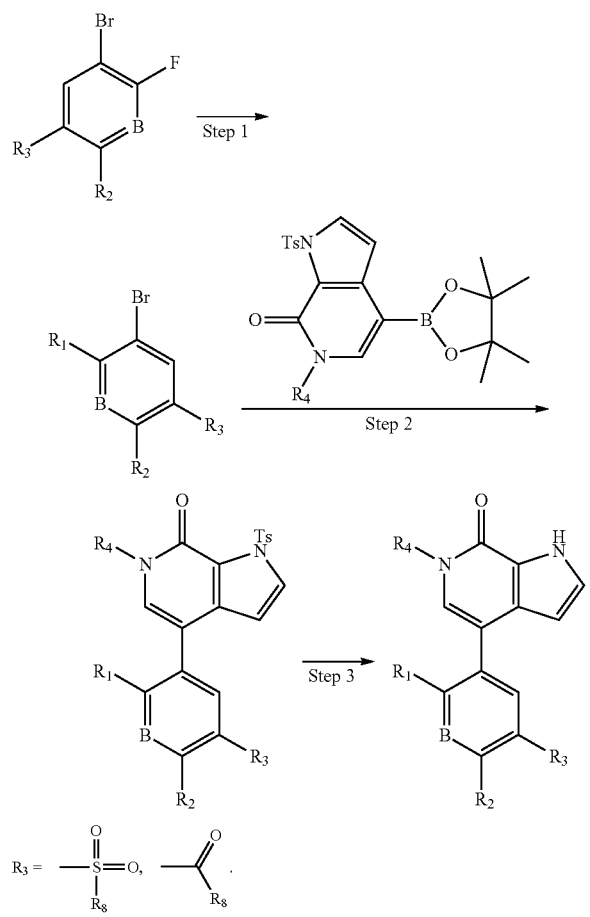

Scheme 2

11. A method for treatment of diseases or symptoms related to BET protein, comprising administering an effective amount of a composition to a subject in need thereof, wherein the composition comprises the compound according to claim 1, or a pharmaceutically acceptable salt, solvate or hydrate thereof.

12. The method according to claim 11, wherein the diseases or symptoms related to BET protein are tumors, autoimmune or inflammatory diseases, and viral infections.

13. The method according to claim 12, wherein the tumors are breast cancer, brain cancer, cervical cancer, colorectal cancer, gastrointestinal cancer, esophageal cancer, liver cancer, lung cancer, pancreatic cancer, endometrial cancer, nasopharyngeal cancer, ovarian cancer, prostate cancer, and hematopoietic system tumors.

14. The method according to claim 13, wherein the tumors are breast cancer and prostate cancer.

15. The method according to claim 12, wherein the autoimmune or inflammatory diseases are allergy, allergic rhinitis, arthritis, asthma, chronic obstructive pulmonary disease, degenerative arthritis, skin disease, organ rejection, eczema, hepatitis, inflammatory bowel disease, multiple sclerosis, myasthenia gravis, psoriasis, sepsis, systemic lupus erythematosus, tissue transplant rejection, and type 1 diabetes.

16. The method according to claim 12, wherein the viral infections are infections caused by: adenovirus, hepatitis B virus, hepatitis C virus, herpes virus, human immunodeficiency virus, or human papilloma virus.

17. A pharmaceutical composition, comprising the compound according to claim 1 or a pharmaceutically acceptable salt, solvate or hydrate thereof as an active ingredient, and one or more pharmaceutically acceptable excipients or auxiliary components.

18. A drug combination with anti-tumor efficacy, comprising the compound according to claim 1 or a pharmaceutically acceptable salt, solvate or hydrate thereof, and one or more drugs with anti-tumor effects, and one or more pharmaceutically acceptable carriers in units of the same or different specifications for simultaneous or separated administration.

19. The drug combination according to claim 18, wherein said one or more drugs with anti-tumor effects are chemotherapeutic drugs.

20. The drug combination according to claim 19, wherein said chemotherapeutic drugs are targeted drug selected from one or more of androgen receptor inhibitors.

\* \* \* \* \*